United States Patent
Lepifre et al.

(10) Patent No.: US 9,777,015 B2
(45) Date of Patent: Oct. 3, 2017

(54) USEFUL THIOPHENE DERIVATIVES IN THE TREATMENT OF DIABETES

(71) Applicant: METABRAIN RESEARCH, Chilly Mazarin (FR)

(72) Inventors: Franck F. Lepifre, Saclay (FR); Gersande R. Lena, Julienas (FR); Valerie Autier, Gif sur Yvette (FR); Micheline R. Kergoat, Bures sur Yvette (FR); Lauren R. Faveriel, Longjumeau (FR); Christine G. Charon, Gometz le Chatel (FR); Sophie N. Raynal, Paris (FR); Annick M. Audet, Leudeville (FR)

(73) Assignee: METABRAIN RESEARCH, Chilly Mazarin (FR)

(*) Notice: Subject to any disclaimer, the term of this patent is extended or adjusted under 35 U.S.C. 154(b) by 0 days.

(21) Appl. No.: 14/415,988

(22) PCT Filed: Jul. 16, 2013

(86) PCT No.: PCT/FR2013/051702
§ 371 (c)(1),
(2) Date: Jan. 20, 2015

(87) PCT Pub. No.: WO2014/013181
PCT Pub. Date: Jan. 23, 2014

(65) Prior Publication Data
US 2015/0197530 A1    Jul. 16, 2015

(30) Foreign Application Priority Data

Jul. 20, 2012  (FR) ..................... 12 57079

(51) Int. Cl.
| | | |
|---|---|---|
| *A61K 31/4025* | (2006.01) | |
| *C07D 493/14* | (2006.01) | |
| *C07D 333/24* | (2006.01) | |
| *C07D 333/34* | (2006.01) | |
| *C07D 333/38* | (2006.01) | |
| *C07D 333/40* | (2006.01) | |
| *C07H 9/04* | (2006.01) | |
| *C07D 409/04* | (2006.01) | |
| *C07D 409/06* | (2006.01) | |
| *C07D 409/12* | (2006.01) | |
| *C07D 409/14* | (2006.01) | |
| *C07D 417/06* | (2006.01) | |
| *A61K 31/381* | (2006.01) | |
| *A61K 31/4436* | (2006.01) | |
| *A61K 31/5377* | (2006.01) | |
| *A61K 45/06* | (2006.01) | |

(52) U.S. Cl.
CPC .......... *C07D 493/14* (2013.01); *A61K 31/381* (2013.01); *A61K 31/4025* (2013.01); *A61K 31/4436* (2013.01); *A61K 31/5377* (2013.01); *A61K 45/06* (2013.01); *C07D 333/24* (2013.01); *C07D 333/34* (2013.01); *C07D 333/38* (2013.01); *C07D 333/40* (2013.01); *C07D 409/04* (2013.01); *C07D 409/06* (2013.01); *C07D 409/12* (2013.01); *C07D 409/14* (2013.01); *C07D 417/06* (2013.01); *C07H 9/04* (2013.01)

(58) Field of Classification Search
CPC .................................................. A61K 31/4025
See application file for complete search history.

(56) References Cited

U.S. PATENT DOCUMENTS

| | | | |
|---|---|---|---|
| 7,067,507 B2 * | 6/2006 | Pulley .................. | C07D 273/02 514/183 |
| 2006/0135597 A1 | 6/2006 | Hosaka et al. | |
| 2009/0163545 A1 | 6/2009 | Goldfarb | |

(Continued)

FOREIGN PATENT DOCUMENTS

| | | | |
|---|---|---|---|
| JP | 201451463 | * | 3/2014 |
| WO | 02095361 | | 11/2002 |

(Continued)

OTHER PUBLICATIONS

Centers for Disease Control and Prevention. "Primary Prevention of Type 2 Diabetes Mellitus by Lifestyle Intervention: Implications for Health Policy." Ann Intern Med. © 2004, vol. 140, pp. 951-957.*

(Continued)

*Primary Examiner* — Noble Jarrell
*Assistant Examiner* — John S Kenyon
(74) *Attorney, Agent, or Firm* — Hamre, Schumann, Mueller & Larson, P.C.

(57) ABSTRACT

The present invention relates to a thiophene derivative of the following general formula I

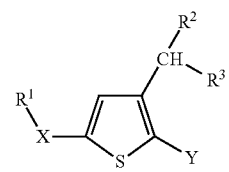

or an enantiomer, diastereoisomer, hydrate, solvate, tautomer, racemic mixture or pharmaceutically acceptable salt thereof or to its use as a drug in particular intended for treating and/or preventing diabetes, its complications and/or associated pathologies, advantageously diabetes of type II and hyperglycemia.

20 Claims, No Drawings

(56) References Cited

U.S. PATENT DOCUMENTS

2010/0260778 A1    10/2010   Pang et al.
2012/0114696 A1     5/2012   Pang et al.

FOREIGN PATENT DOCUMENTS

WO     2004035570     4/2004
WO     2008051197     5/2008

OTHER PUBLICATIONS

Mayo Clinic. "Diabetes." © 2014. Available from: < http://www.mayoclinic.org/diseases-conditions/diabetes/basics/prevention/con-20033091?p=1 >.*

Mayo Clinic. "Parkinson's disease." © 2016. Available from: < http://www.mayoclinic.org/diseases-conditions/parkinsons-disease/basics/prevention/con-20028488?p=1 >.*

Park et al.: "Serotype-selective, small molecule inhibitors of the zinc endopeptidase of botulinum neurotoxin serotype A"; Bioorganic & Medicinal Chemistry, 2006, vol. 14(2), pp. 395-408.

Shengwu Jishu Tongxun: "Hologram quantitative structure-activity relationship study of botulinum neurotoxin A inhibitors"; 2007, vol. 18(4), 625-627, (English abstract only).

Floquet et al.: "Discovering new inhibitors of bacterial glucosamine-6P synthase (GlmS) by docking simulations"; Bioorganic & Medicinal Chemistry Letters, 2007, 17(7), pp. 1966-1970.

I. N Fedorova et al. "Synthesis and antimicrobial activity of substituted 5-hydroxynaphtho[1,2-b]thiophenes and 4-hydroxybenzo[2,1-b:3,4-b']dithiophenes"; Khimiko-Farmatsevticheskii Zhurnal, 1987, vol. 21(11), pp. 1320-1326 (English abstract only).

Pang et al.: "Computer-Aided Lead Optimization: Improved Small-Molecule INhiitor of the Zinc Endopeptidase of Botulinum Neurotoxin Serotype A"; PLoS ONE, 2010, 5(4), pp. 1-8.

Merino et al.: "Bi-imidazoles as molecular probes for peripheral sites of the zinc endopeptidase of botulinum neurotoxin serotype A"; Bioorganic & Medicinal Chemistry, 2006, vol. 14(2), pp. 3583-3591.

Pang et al.: "Potent New Small-Molecule Inhibitor of Botulinum Neurotoxin Serotype A Endopeptidase Developed by Synthesis-Based Computer-Aided Molecular Design"; PLoS ONE, 2009, vol. 4(11), pp. 1-18.

Portha et al.: "Diabetogenic Effect of Streptozotocin in the Rat During the Perinatal Period"; Diabetes, vol. 23, 1974, pp. 889-895.

Giroix et al.: "Glocuse Insensitivity and Amino-acid Hypersensitivity of Insulin Release in Rats with Non-insulin dependent Diabetes"; Diabetes, 1983, vol. 32, pp. 445-451.

Assan et al.: "Diphasic Glucagon Release Induced by Arginine in the Perfused Rat Pancreas"; Nature New Biology, 1972, vol. 239, pp. 125-126.

Sussman et al.: "An in Vitro Method for Studying Insulin Secretion in the Perfused Isolated Rat Pancreas"; Diabetes, 1966, vol. 15, pp. 466-472.

Goto et al.: "Spontaneous Diabetes Produced by Selective Breeding of Normal Wistar Rats"; Proc. Japan Acad., 1975, vol. 51, pp. 80-85.

Portha et al.: "The GK rat beta-cell: A prototype for the diseased human beta-cell in type 2 diabetes?"; Molecular and Cellular Endocrinology, 2009, vol. 297, pp. 73-85.

International search report for International application No. PCT/FR2013/051702, dated Sep. 16, 2013 (5 pages).

Asfari et al.: "Establishment of 2-Mercaptoethanol-Dependent Differentiated Insulin-Secreting Cell Lines"; The Endocrine Society, 1992, vol. 130, pp. 167-178.

Fedorova et al.: "Synthesis and antimicrobial of susbtituted 5-hydroxynaphtho[1,2-b]thiophenes and 4-hydroxybenzo[2,1-b:3,4-b']dithiophenes" Khimiko-Farmatsevticheskii Zhurnal, 1987, vol. 21(11), pp. 1320-1326.

* cited by examiner

USEFUL THIOPHENE DERIVATIVES IN THE TREATMENT OF DIABETES

DESCRIPTION OF THE INVENTION

The present invention relates to thiophene derivatives useful in treating pathologies associated with the metabolic syndrome, in particular treating or preventing diabetes.

Diabetes mellitus represents a very heterogenous group of diseases all having in common a certain number of features: hyperglycemia, functional and quantitative abnormalities of pancreatic beta cells, tissue insulin-resistance and an increased risk of developing complications in the long term, in particular cardiovascular complications.

Diabetes of type II has become a major problem of public health. Its prevalence is sharply increasing in most industrialized countries but even more in countries with a fully expanding economy. Today, this can be referred to as an epidemic for this disease which causes substantial complications which may become very invalidating or even lethal inter alia because of kidney failure, myocardial infarction or cardiovascular strokes. A few figures on diabetes (WHO data):

More than 220 million persons are diabetic worldwide.
Diabetes multiplies the risks of stroke by 3.
Diabetes is the first cause of blindness and of kidney failure in the western world.
According to estimations, diabetes has killed 1.1 million persons in 2005.
According to projections from the WHO, the number of deaths by diabetes will double between 2005 and 2030.

In France, care and treatment of diabetics is a great burden on the budget of State Health Insurance. Considering the alarming figures of the number of diabetic patients in the world from now to 2030, many pharmaceutical and biotechnological companies intensely invest in R&D in the field of metabolism and more particularly in that of type II diabetes in order to put on the market, novel drug alternatives.

At the present time, no treatment of type II diabetes is capable of re-establishing normal glycemic equilibrium over 24 hours and is not without secondary effects. None of them take into account the complete pathology of the disease and only aim at correcting one or the other deficiency. Antidiabetics which have been put on the market quite recently have not shown any greater improvement in glycemic control than the one observed with pre-existing treatments and have caused undesirable secondary effects, which leaves space for novel potential treatments. Therefore there exists a need for novel molecules useful in treating or preventing diabetes, or its complications and/or associated pathologies, advantageously diabetes of type II.

The inventors have surprisingly discovered that certain thiophene derivatives have an inhibitory activity on liver production of glucose and an activity for secreting insulin in response to glucose and in particular which may be used as products for pharmaceutical use in patients which are in need thereof, notably for preventing and/or treating diabetes and its complications and/or associated pathologies (obesity, hypertension, etc. . . . ), advantageously diabetes of type II.

DETAILED DESCRIPTION OF THE INVENTION

The present invention therefore relates to thiophene derivatives of the following general formula I:

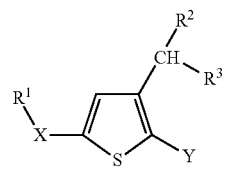

(I)

wherein:
Y represents an aryl group, advantageously a phenyl (Ph), a heteroaryl group, advantageously a furyl, or a benzo-1,3-dioxole group, the aryl or heteroaryl group being optionally substituted with one or more groups selected from —CN; a halogen atom, advantageously selected from Cl or F; —O($C_1$-$C_6$ alkyl), advantageously —OMe, the alkyl group being optionally substituted with one or more halogen atoms, advantageously F, such as for example —OCF$_3$ or —OCHF$_2$, or with a —O($C_1$-$C_6$ alkyl) group, advantageously —OMe; $C_1$-$C_6$ alkyl, advantageously methyl, substituted with one or more halogen atoms, advantageously F, such as for example —CF$_3$, or with an —O($C_1$-$C_6$ alkyl) group, advantageously —OMe, such as for example CH$_2$OMe, or with an —OH group such as for example —CH$_2$OH; —SO$_2$($C_1$-$C_6$ alkyl), advantageously —SO$_2$Me; —CONRaRb wherein Ra represents a hydrogen atom or a $C_1$-$C_6$ alkyl group, advantageously methyl and Rb represents a $C_1$-$C_6$ alkyl group; or —OH; examples of an optionally substituted aryl group are Ph, 4-F-Ph, 2,3-(F)2-Ph, 2-F-4-Cl-Ph, 4-Cl-Ph, 3,4-(Cl)2-Ph, 3-NC-Ph, 4-NC-Ph, 3-MeO-Ph, 4-MeO-Ph, 2-MeO-3-F-Ph and 2-OH-3-F-Ph;
X represents a —SO$_2$ group or a

group, advantageously a

group, wherein
⟋⟋ represents a bond and W represents an oxygen atom or the —NOR$^4$ group, wherein R$^4$ represents a hydrogen atom, a $C_1$-$C_6$ alkyl group or a ($C_1$-$C_6$ alkyl)aryl group, the aryl group being optionally substituted with one or more groups selected from —CN; a halogen atom, advantageously selected from Cl or F; —O($C_1$-$C_6$ alkyl), advantageously —OMe, the alkyl group being optionally substituted with one or more halogen atoms, advantageously F, or with an —O($C_1$-$C_6$ alkyl) group, advantageously —OMe; a $C_1$-$C_6$ alkyl substituted with one or more halogen atoms, advantageously F, or with an —O($C_1$-$C_6$ alkyl) group, advantageously —OMe or with a —OH group; —SO$_2$($C_1$-$C_6$ alkyl); —CONRa'Rb' in which Ra' represents a hydrogen atom or a $C_1$-$C_6$ alkyl group and Rb' represents a $C_1$-$C_6$ alkyl group, or —OH or
⟋⟋ is absent and W represents —OH;
R$^1$ represents
a $C_1$-$C_6$ alkyl group, advantageously methyl or ethyl, the alkyl group being optionally substituted with a halogen atom, advantageously Cl, such as for example —(CH$_2$)$_2$Cl;

a $C_3$-$C_6$ cycloalkyl group, advantageously cyclopropyl or cyclohexyl;

a ($C_1$-$C_6$ alkyl)O($C_1$-$C_6$ alkyl) group;

a ($C_1$-$C_6$ alkyl)NR($C_1$-$C_6$ alkyl) group in which R represents a hydrogen atom or a $C_1$-$C_6$ alkyl group, advantageously methyl;

an aryl group, advantageously a phenyl (Ph), the aryl group being optionally substituted with one or more groups selected from —CN; a halogen atom, advantageously selected from Cl or F; —O($C_1$-$C_6$ alkyl), advantageously —OMe, the alkyl group being optionally substituted with one or more halogen atoms, advantageously F, such as for example —OCF$_3$ or —OCHF$_2$, or with an —O($C_1$-$C_6$ alkyl) group, advantageously —OMe; —SO$_2$($C_1$-$C_6$ alkyl) advantageously —SO$_2$Me; —CONRa"Rb" wherein Ra" represents a hydrogen atom or a $C_1$-$C_6$ alkyl group, advantageously methyl and Rb" represents a $C_1$-$C_6$ alkyl group, advantageously methyl; or $C_1$-$C_6$ alkyl group, advantageously methyl, the alkyl group being optionally substituted with one or more halogen atoms, advantageously F, such as for example —CF$_3$, or with a —O($C_1$-$C_6$ alkyl) group, advantageously —OMe, such as for example —CH$_2$OMe, or with an —OH group such as for example —CH$_2$OH; optionally substituted aryl group examples are Ph, 2-F-Ph, 3-F-Ph, 4-F-Ph, 2,3-(F)2-Ph, 2,4-(F)2-Ph, 2,5-(F)2-Ph, 3,5-(F)2-Ph, 3-Cl-Ph, 2,4-(Cl)2-Ph, 3,4-(Cl)2-Ph, 4-NC-Ph, 2-MeO-Ph, 4-MeO-Ph, 3-MeO-Ph, 3-F-4-MeO-Ph and 3-Me-4-F-Ph;

a ($C_1$-$C_6$ alkyl)aryl group; advantageously ($C_1$-$C_6$ alkyl)phenyl, in particular benzyl or (CH$_2$)$_2$phenyl, the aryl group being optionally substituted with one or more groups selected from —CN; a halogen atom, advantageously selected from F or Cl, in particular F; —O($C_1$-$C_6$ alkyl) advantageously —OMe; or $C_1$-$C_6$ alkyl, advantageously methyl; optionally substituted examples of a ($C_1$-$C_6$ alkyl)aryl group are CH$_2$Ph, CH$_2$-4-F-Ph and (CH$_2$)2Ph;

an —NH-aryl group, advantageously —NH-phenyl, the aryl group being optionally substituted with one or more groups selected from —CN; a halogen atom, advantageously F or Cl; —O($C_1$-$C_6$ alkyl), advantageously —OMe; or $C_1$-$C_6$ alkyl, advantageously methyl; optionally substituted examples of a —NH-aryl group are NH-4-Br-Ph, NH-3-MeO-Ph and NH-4-MeO-Ph;

an —NH($C_1$-$C_6$ alkyl)aryl group, advantageously —NH($C_1$-$C_6$ alkyl)phenyl, in particular —NH(CH$_2$)phenyl, the aryl group being optionally substituted with one or more groups selected from —CN; a halogen atom; —O($C_1$-$C_6$ alkyl), advantageously —OMe; or $C_1$-$C_6$ alkyl, advantageously methyl; examples of an optionally substituted —NH($C_1$-$C_6$ alkyl)aryl group are —NHCH$_2$-3-MeO-Ph and NHCH$_2$-4-MeO-Ph;

a heteroaryl group, advantageously furyl, pyridyl or thiazolyl, optionally substituted with a halogen atom, in particular —Cl (preferably it is not substituted);

an —OH group;

a morpholine group; or an N-phenylpiperazine group;

an NH—NH—CO-aryl group wherein the aryl group is optionally substituted with one or more groups selected from a halogen atom, advantageously Cl and an —O($C_1$-$C_6$ alkyl) group, advantageously —OMe;

a NH—NH—CO-heteroaryl group, advantageously NH—NH—CO-pyridyl.

$R^2$ represents a hydrogen atom; a $C_1$-$C_6$ alkyl group, advantageously a methyl group; a ($C_1$-$C_6$ alkyl)aryl group, advantageously a ($C_1$-$C_6$ alkyl)phenyl group, in particular a benzyl group; or a ($C_1$-$C_6$ alkyl)O($C_1$-$C_6$ alkyl) group, advantageously a —CH$_2$OCH$_3$ group; advantageously $R^2$ represents a hydrogen atom;

$R^3$ represents a —COOR$^5$ group, wherein R$^5$ represents a hydrogen atom, a $C_1$-$C_6$ alkyl group, such as for example a methyl, ethyl, isopropyl and t-butyl group, or the glucopyranose group;

a —COSR$^6$ group, wherein R$^6$ represents a hydrogen atom or a $C_1$-$C_6$ alkyl group;

a —CONR$^7$R$^8$ group, wherein R$^7$ represents a hydrogen atom or a $C_1$-$C_6$ alkyl group, such as a methyl group, and R$^8$ represents a hydrogen atom; a $C_1$-$C_6$ alkyl group, advantageously ethyl or methyl, optionally substituted with an —OH group, such as for example —(CH$_2$)$_2$OH; an —OH group; an —O($C_1$-$C_6$ alkyl) group, advantageously —Oethyl; a group —NH$_2$; a group —($C_1$-$C_6$ alkyl)NR$^9$R$^{10}$, advantageously —(CH$_2$)$_2$NR$^9$R$^{10}$, wherein R$^9$ and R$^{10}$ both represent a $C_1$-$C_6$ alkyl group, advantageously a methyl or ethyl group; a group —($C_1$-$C_6$ alkyl)COOH advantageously —CH$_2$COOH; a group —($C_1$-$C_6$alkyl)COO($C_1$-$C_6$ alkyl) advantageously —CH$_2$COOethyl; an aryl group advantageously a phenyl (Ph); or a heteroaryl group; examples of a —CONR$^7$R$^8$ group are CONH$_2$, CONHEt, CONHOH, CONHOEt, CONHNH$_2$, CONH(CH$_2$)$_2$OH, CONH(CH$_2$)$_2$NMe$_2$, CONH(CH$_2$)$_2$NEt$_2$, CONMeCH$_2$COOH, CONMeCH$_2$COOEt, CONMeOMe, CONHPh and CONHheteroaryl;

a —CSNR$^{11}$R$^{12}$ group wherein R$^{11}$ and R$^{12}$ represent independently of each other a hydrogen atom or a $C_1$-$C_6$ alkyl group, such as for example an ethyl group, advantageously R$^{11}$ represents a hydrogen atom and R$^{12}$ represents a $C_1$-$C_6$ alkyl group, such as for example an ethyl group;

a —CN group;

a —C(=NH)NHOH group;

a —COmorpholine group;

a —Copyrolidine group;

a —CON-Me-piperazine group;

a —COguanidine or —COguanidine-BOC group;

a tetrazole group; or an oxadiazolone group;

or an enantiomer, diastereoisomer, hydrate, solvate, tautomer, racemic mixture or a pharmaceutically acceptable salt thereof, except for the compounds (a) to (z1) of the following formulae:

(a)

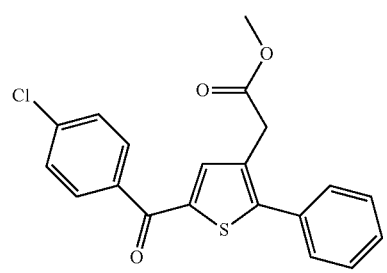

-continued (b)

(c)

(d)

(e)

(f)

(g)

-continued (h)

(i)

(j)

(k)

(l)

(m)

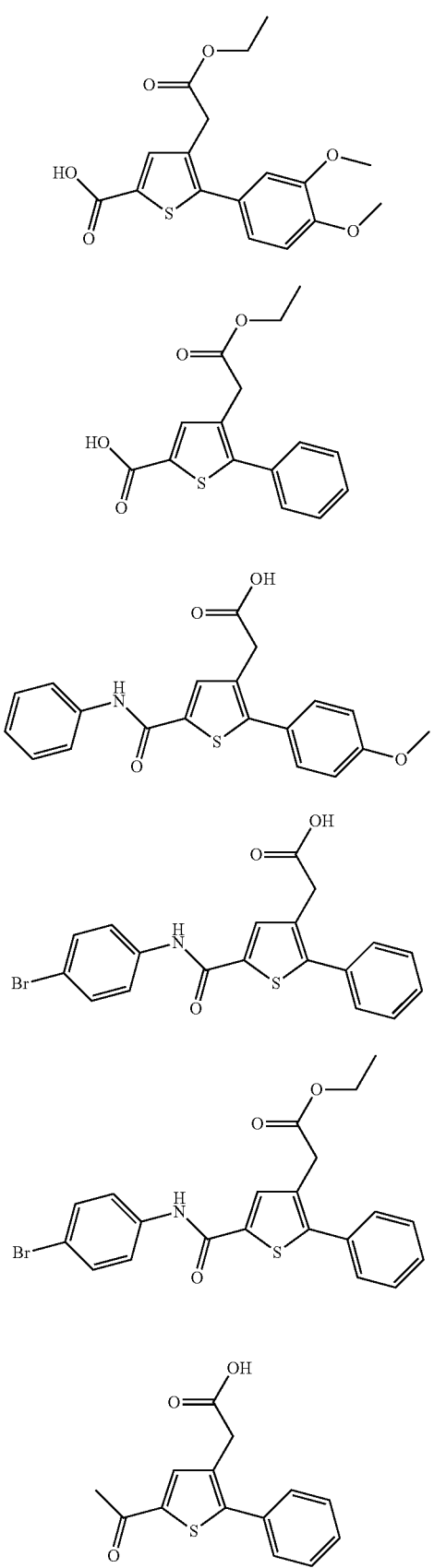
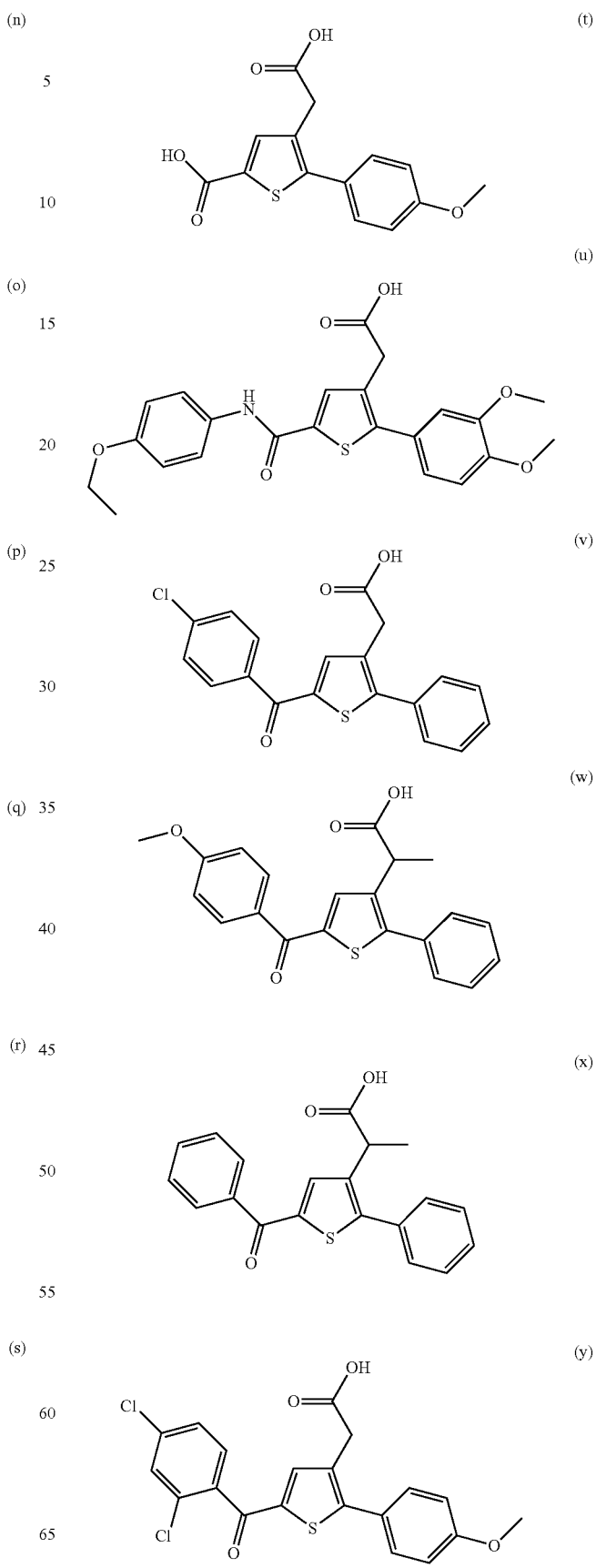

-continued

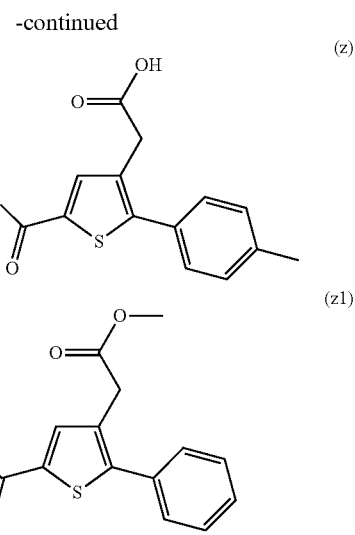

Documents [1] to [9] disclose 11 compounds of structures covered by the general formula (I) (compounds (a) to (e), (q), (t), (v) to (x) and (z1) above) without however describing any antidiabetic activity. They are therefore excluded from the products of formula (I) but not from the use of these products in treating or preventing diabetes.

Moreover 16 compounds with structures covered by the general formula (I) (compounds (f) to (p), (r), (s), (u), (y) and (z) above) are commercially available without however any therapeutic activity being disclosed. They are therefore excluded from the products of formula (I) but not from the use of these products as a drug and in particular in treating or preventing diabetes.

Within the scope of the present invention, by <<aryl group>>, is meant an aromatic ring having 5 to 8 carbon atoms or several fused aromatic rings having 5 to 14 carbon atoms. In particular, the aryl groups may be monocyclic or bicyclic groups, preferably phenyl or naphthyl groups. Advantageously this is a phenyl group (Ph).

Within the scope of the present invention, by <<heteroaryl group>> is meant any hydrocarbon aromatic group with 3 to 9 atoms containing one or more heteroatoms, such as for example sulfur, nitrogen or oxygen atoms. The heteroaryl according to present invention may be formed with one or more fused rings. Examples of heteroaryl groups are furyl, isoxazyl, pyridyl, thiazolyl, pyrimidyl, benzimidazole, benzoxazole, benzothiazole groups. Advantageously, the heteroaryl group is selected from furyl, pyridyl and thiazolyl groups, advantageously this is the furyl group.

Within the scope of the present invention, by <<halogen atom>> is meant any halogen atom, advantageously selected from Cl, Br, I or F, in particular selected from F, Cl or Br, in particular F or Cl.

Within the scope of the present invention, by <<$C_1$-$C_6$ alkyl group>> is meant any alkyl group with 1 to 6 carbon atoms, either linear or branched, in particular, the methyl, ethyl, n-propyl, iso-propyl, n-butyl, iso-butyl, sec-butyl, t-butyl, n-pentyl, n-hexyl groups. Advantageously, this is a methyl, ethyl, iso-propyl or t-butyl group, in particular a methyl or ethyl group, more particularly a methyl group.

Within the scope of the present invention, by <<$C_3$-$C_6$ cycloalkyl group>> is meant any saturated and hydrocarbon ring comprising from 3 to 6 carbon atoms, in particular, the cyclopropyl, cyclobutyl, cyclopentyl or cyclohexyl group. Advantageously, this is a cyclopropyl or cyclohexyl group.

Within the scope of the present invention, by <<($C_1$-$C_6$ alkyl)aryl group>> is meant any aryl group as defined above, bound via a $C_1$-$C_6$ alkyl group as defined above. In particular an example of a ($C_1$-$C_6$ alkyl)aryl group is a benzyl group or —(CH$_2$)$_2$phenyl group.

Within the scope of the present invention, by <<pharmaceutically acceptable>> is meant what is useful in the preparation of a pharmaceutical composition which is generally safe, non-toxic and neither undesirable biologically nor otherwise and which is acceptable for veterinary use as well as in human pharmaceutics.

Within the scope of the present invention, by <<pharmaceutically acceptable salts of a compound>> are meant salts which are pharmaceutically acceptable, as defined here, and which have the desired pharmacological activity of the parent compound. Such salts comprise:

(1) acid addition salts formed with mineral acids such as hydrochloric acid, hydrobromic acid, sulfuric acid, nitric acid, phosphoric acid and the like; or formed with organic acids such as acetic acid, benzene-sulfonic acid, benzoic acid, camphor sulfonic acid, citric acid, ethane-sulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid and the like; or (2) the salts formed when an acid proton present in the parent compound is either replaced with a metal ion, for example an alkaline metal ion, an earth alkaline metal ion or an aluminium ion; or is coordinated with an organic or inorganic base. The acceptable organic bases comprise diethanolamine, ethanolamine, N-methylglucamine, triethanolamine, tromethamine and the like. The acceptable inorganic bases comprise aluminium hydroxide, calcium hydroxide, potassium hydroxide, sodium carbonate and sodium hydroxide.

Within the scope of the present invention, by <<solvate of a compound>>, is meant any compound obtained by adding an inert solvent molecule onto the compound according to the invention, the solvate forming because of their mutual attraction force. Solvates are for example alcoholates of the compound. A hydrate is a solvate in which the inert solvent used is water. It may be a mono-, di- or tri-hydrate.

Within the scope of the present invention, by <<tautomer>> is meant any isomer for making up the compounds according to the present invention which are interconvertible by the reversible chemical reaction called tautomerization. In most cases, the reaction occurs by migration of a hydrogen atom accompanied by a change in localization of a double bond. In a solution of a compound capable of tautomerization, an equilibrium between 2 tautomers is generated. The ratio between tautomers is then dependent on the solvent, on the temperature and on the pH. Tautomery is therefore the transformation of a functional group into another, most often by concomitant displacement of a hydrogen atom and of a n bond (double or triple bond). Common tautomers are for example the aldehyde/ketones—alcohols or more specifically enols pairs; amides—imidic acids; lactams—lactims; imines—enamines; enamines—enamines. In particular, it may include a cycle-chain tautomery which occurs when the movement of the proton is accompanied by the transformation of an open structure into one ring.

In an advantageously embodiment of the present invention, ⌒ represents a bond and W represents an oxygen atom or the —NOR$^4$ group, wherein R$^4$ represents a hydrogen atom, a $C_1$-$C_6$ alkyl group such as for example a methyl or ethyl group, or a ($C_1$-$C_6$ alkyl)aryl group such as for example a ($C_1$-$C_6$ alkyl)phenyl group, in particular a benzyl group, the aryl group, advantageously phenyl, being optionally substituted with one or more groups selected from —CN; a halogen atom, advantageously selected from Cl or F; —O($C_1$-$C_6$ alkyl) advantageously —OMe, the alkyl group being optionally substituted with one or more halogen atoms, advantageously F, or with an —O($C_1$-$C_6$ alkyl) group, advantageously —OMe; a $C_1$-$C_6$ alkyl substituted with one or more halogen atoms, advantageously F, or with a —O($C_1$-$C_6$ alkyl) group, advantageously —OMe or with —OH group; —SO$_2$($C_1$-$C_6$ alkyl); —CONRa'Rb' wherein Ra' represents a hydrogen atom or a $C_1$-$C_6$ alkyl group and Rb' represents a $C_1$-$C_6$ alkyl group, or —OH. Advantageously ⌒ represents a bond and W represents an oxygen atom or the —NOR$^4$ group, wherein R$^4$ represents a hydrogen atom or a $C_1$-$C_6$ alkyl group such as for example a methyl or ethyl group, still more advantageously W represents an oxygen atom.

In another advantageous embodiment of the present invention, Y represents an aryl, advantageously phenyl, a heteroaryl group, advantageously furyl, or a benzo-1,3-dioxole group, the aryl group being optionally substituted with one or more groups selected from —CN; a halogen atom, advantageously selected from Cl or F; —O($C_1$-$C_6$ alkyl), advantageously —OMe; or —OH; advantageously Y represents an aryl group, advantageously a phenyl, the aryl group being optionally substituted with one or more groups selected from —CN; a halogen atom, advantageously selected from Cl or F, in particular Cl; or —O($C_1$-$C_6$ alkyl), advantageously —OMe. Advantageously, the substitution on the phenyl group is found in the ortho and/or meta and/or para position. Still more advantageously Y represents a substituted phenyl group, advantageously in the ortho and/or meta and/or para positions, with one or more halogen atoms, advantageously Cl and/or F, in particular Cl.

In still another advantageous embodiment of the present invention, R$^1$ represents a $C_3$-$C_6$ cycloalkyl group, advantageously cyclopropyl or cyclohexyl; an aryl group, advantageously a phenyl, the aryl group being optionally substituted with one or more groups selected from —CN; a halogen atom, advantageously selected from Cl or F; —O($C_1$-$C_6$ alkyl), advantageously —OMe; or $C_1$-$C_6$ alkyl, advantageously methyl; a heteroaryl group, advantageously a furanyl, pyridyl or thiazolyl, the furanyl group being optionally substituted with a halogen atom, in particular Cl (preferably it is not substituted); or a morpholine group. Advantageously R$^1$ represents a phenyl group (Ph), the phenyl group being optionally substituted with one or more groups selected from a halogen atom, advantageously selected from Cl or F, in particular Cl, and —O($C_1$-$C_6$ alkyl), advantageously —OMe, in particular the phenyl group is optionally substituted with one or more groups —O($C_1$-$C_6$ alkyl), advantageously —OMe; or a furanyl, pyridyl or thiazolyl group, the furanyl group being optionally substituted with a halogen atom, in particular Cl, (preferably it is not substituted).

In another embodiment of the present invention, R$^2$ represents a hydrogen atom, a $C_1$-$C_6$ alkyl group, advantageously a methyl group, or a ($C_1$-$C_6$ alkyl)O($C_1$-$C_6$ alkyl) group, in particular a hydrogen atom.

In still another advantageous embodiment of the present invention, R$^3$ represents a —COguanidine group, a —COOR$^5$ group, wherein R$^5$ represents a hydrogen atom or a $C_1$-$C_6$ alkyl group, such as for example a methyl, ethyl, isopropyl and t-butyl group; a —CONR$^7$R$^8$ group, wherein R$^7$ represents a hydrogen atom and R$^8$ represents a hydrogen atom; a $C_1$-$C_6$ alkyl group, advantageously an ethyl or methyl, optionally substituted with an —OH group, such as for example —(CH$_2$)$_2$OH; an —OH group; an —O($C_1$-$C_6$ alkyl) group, advantageously —Oethyl; or a —($C_1$-$C_6$ alkyl)NR$^9$R$^{10}$ group wherein R$^9$ and R$^{10}$ both represent a $C_1$-$C_6$ alkyl group, advantageously a methyl or ethyl group; or a —COmorpholine group; advantageously, R$^3$ represents a —CONHOH group, a —COguanidine group or a —COOR$^5$ group, wherein R$^5$ represents a hydrogen atom or a $C_1$-$C_6$ alkyl group, such as for example a methyl, ethyl, isopropyl and t-butyl group. Still more advantageously, R$^3$ represents a —COOR$^5$ group, wherein R$^5$ represents a hydrogen atom or a $C_1$-$C_6$ alkyl group, such as for example a methyl, ethyl, isopropyl and t-butyl group. More advantageously, R$^3$ represents a —COOH or COOEt group, in particular COOH.

In a particularly interesting embodiment of the present invention, the thiophene derivatives are selected from the compounds of formulae 1 to 187 as indicated in Table 1 hereafter.

In another still more interesting embodiment, the thiophene derivatives are selected from the 102 compounds numbered as 3, 5, 6, 10-15, 18, 19, 21, 22, 24-27, 29-33, 35, 39, 40, 43, 44, 46, 48-52, 56, 58-61, 63-65, 67, 68, 70-78, 81, 83, 84, 86, 89, 91, 93, 95, 96, 98, 100, 102, 104, 106, 108-110, 114, 123-125, 127, 128, 130, 133, 136, 137, 139, 140, 142-144, 148, 149, 154, 155, 156-159, 165-167, 175, 176 and 182-187, as indicated in Table 1 hereafter.

Still more advantageously, these are the compounds 10, 13, 49, 56, 58, 60, 63, 100, 104, 110, 124, 127, 128, 130, 136, 143, 148, 149, 156, 157-159, 167, 175, 176, 184 and 185, as indicated in Table 1 hereafter.

The present invention further relates to a pharmaceutical composition comprising a thiophene derivative according to the present invention and a pharmaceutically acceptable excipient.

These compositions may be formulated for administration to mammals, including humans. The dosage varies according to the treatment and according to the relevant disease. These pharmaceutical compositions are adapted for administration via any suitable route, for example orally (including the buccal and sublingual routes), via a rectal, nasal, topical (including transdermal), vaginal, intraocular or parenteral (including subcutaneous, intramuscular or intravenous) route. Advantageously, the pharmaceutical compositions are adapted for oral administration. These formulations may be prepared by using all the methods known to one skilled in the art combining the active ingredients with suitable pharmaceutically acceptable excipients.

The suitable dosage unit forms orally comprise tablets, gelatin capsules, powders, granules and oral solutions or suspensions in aqueous or non-aqueous liquids, edible or food foams, or water-in-oil or oil-in-water liquid emulsions. When a solid composition is prepared as a tablet, the main active ingredient is advantageously mixed as a powder, with a suitable pharmaceutical excipient such as gelatin, starch, lactose, magnesium stearate, talcum, gum arabic or the like. It is possible to coat the tablets with saccharose or with other suitable materials or further they may be treated so that they have a prolonged or delayed activity and they release continuously a predetermined amount of active ingredient.

A preparation in gelatin capsules is obtained by mixing the active ingredients, advantageously as a powder, with a diluent and by pouring the obtained mixture in soft or hard gelatin capsules, in particular gelatin capsules. Lubricants such as for example talc, magnesium stearate, calcium stearate or polyethylene glycol in solid form may be added into the composition before putting it into gelatin capsules. A disintegrator or a solubilizer such as for example calcium carbonate or sodium carbonate may also be added in order to improve the availability of the drug after having taken the gelatin capsule.

Further, if necessary it is possible to add into the mixture, binders, lubricants and suitable disintegrators as well as coloring agents. The suitable binders may for example be starch, gelatin, natural sugars such as for example glucose or beta-lactose, sweetening agents made from maize, a synthetic or natural rubber such as for example acacia or sodium alginate, carboxymethylcellulose, polyethylene glycol, waxes and the like. The lubricants which may be used in these dosage forms include sodium oleate, sodium stearate, magnesium stearate, sodium benzoate, sodium acetate, sodium chloride and the like. The disintegrators include starch, methylcellulose, agar, bentonite, xanthan gum and the like. The tablets are formulated for example by preparing a mixture of powder, granulation or dry pressing of the mixture, addition of a lubricant and of a disintegrator and pressing of the mixture in order to obtain the tablets. A mixture of powder is prepared by mixing the active ingredient suitably added with a diluent or a base and optionally with a binder such as for example carboxymethylcellulose, alginate, gelatin or polyvinylpyrrolidone, a dissolution retardant such as for example paraffin, an absorption accelerator such as for example a quaternary salt and/or an absorbant such as for example bentonite, kaolin or dicalcium phosphate. The mixtures of powders may be granulated by wetting with a binder such as for example a syrup, a paste of starch, acacia mucilage or cellulose solutions or polymeric materials and pressing through a sieve. The granules may be lubricated by adding stearic acid, a stearate salt, talc or a mineral oil so as to avoid their sticking to the moulds allowing the manufacturing of the tablets. The lubricated mixture is then pressed for obtaining the tablets. An opaque or transparent protective layer consisting in a shellac layer, a sugar layer or of polymeric materials is optionally present. Coloring agents may be added to these coatings so as to differentiate them from the other tablets.

A preparation as a syrup or an elixir may contain the active ingredient together with a sweetener, an antiseptic, as well as an agent giving taste and a suitable coloring agent. Generally, the syrup preparations are obtained by dissolving the compound in an aqueous solution with a suitable agent giving taste while the elixirs are prepared by using a non-toxic alcoholic carrier.

The powders or the granules which may be dispersed in water may contain the active ingredients mixed with dispersion agents or with wetting agents, or with suspending agents, such as for example ethoxylated isostearyl alcohols and polyoxyethylene sorbitol ethers, and just as with flavor enhancers or sweeteners.

For rectal administration, one resorts to suppositories which are prepared with binders which melt at the rectal temperature, for example cocoa butter or polyethylene glycols.

For parenteral, intranasal or intraocular administration, aqueous suspensions, isotonic saline solutions or sterile and injectable solutions are used which contain pharmacologically compatible dispersion agents and/or wetting agents.

The active ingredient may also be formulated in the form of microcapsules, optionally with one or more additive supports.

The pharmaceutical compositions adapted for administration via a topical route may be formulated as a cream, an ointment, a suspension, a lotion, a powder, a solution, a paste, a gel, a spray, aerosols or oils.

Pharmaceutical compositions adapted for administration via a nasal route in which the supporting excipient is in the solid state comprise powders having particle sizes for example in the range from 20 to 500 microns, administered by inhalation from a container containing the powder positioned near the nose.

The pharmaceutical formulations adapted for administration via a vaginal route may quite be administered as a buffer, cream, gel, paste, foam or spray.

In an advantageous embodiment, the pharmaceutical composition according to the present invention further comprises another active agent, advantageously having a complementary or synergistic effect. In particular, this active agent is another antidiabetic agent, advantageously selected from insulin, sulfonylureas, glinides, biguanides, thiazolidinediones, GLP-1R agonists, DPP-IV inhibitors, SGLT-2 inhibitors, advantageously selected from insulin, glibenclamide, gliclazide, glipizide, glimepiride, repaglinide, nateglinide, metformin, troglitazone, rosiglitazone, pioglitazone, exenatide, liraglutide, sitagliptin, vildagliptin, saxagliptin, alogliptin, dapagliflozin. More particularly, this is metformin. This second active agent may be administered in the same pharmaceutical composition as the thiophene derivative of the present invention. It may also be administered separately, i.e. at the same moment or in a way spread out in time. Advantageously, this second active agent is administered orally.

The present invention further relates to a thiophene derivative according to the present invention or selected from the compounds of formulae (f) to (p), (r), (s), (u), (y) and (z) as defined above for use as a drug. Indeed, as indicated above, the compounds (f) to (p), (r), (s), (u), (y) and (z) are available commercially, without any therapeutic activity being associated with them. Thus, therefore, they have never been disclosed as a drug.

The present invention also relates to the use of a thiophene derivative according to the present invention or selected from the compounds of formulae (f) to (p), (r), (s), (u), (y) and (z) as defined above for preparing a drug.

According to the present invention, the compounds of formula (I) have an antihyperglycemic activity. They may reduce the hyperglycemia, more particularly hyperglycemia of diabetes type II. Notably, the compounds of the invention have an antihyperglycemic activity and are therefore useful in treating and/or preventing diabetes, its complications and/or its associated pathologies, such as for example the pathologies associated with metabolic syndrome, advantageously diabetes of type II or hyperglycemia. These drugs are particularly active in elderly persons. By <<elderly persons>> are meant persons, men or women, 65 years old or more.

The term of <<resistance to insulin>> as used within the scope of the present invention, refers to a condition where a normal amount of insulin is unable to produce a physiological or normal molecular response.

The present invention therefore relates to a thiophene derivative according to the invention or selected from the compounds of formulae (a) to (z1), as defined above for use as a drug intended for treating and/or preventing diabetes, its complications and/or associated pathologies, advantageously of diabetes type II and of hyperglycemia. Indeed, as indicated above, the compounds of formulae (a) to (z1) have never been disclosed as antidiabetic agents.

The inventors have discovered that the derivatives according to the present invention gave the possibility of stimulating insulin secretion by INS1 cells and of inhibiting liver production of glucose at isolated rat hepatocytes.

Advantageously, diabetes is selected from early, belated, pediatric diabetes, elderly and gestational persons, in particular elderly persons. Advantageously, the deficiencies of diabetes and the complications and/or pathologies associated with diabetes are selected from hyperglycemia, functional and quantitative abnormalities of endocrine pancreatic cells, insulin resistance, diabetic neuropathy, diabetic nephropathy, diabetic retinopathy, inflammation, obesity, hypertension, cardiovascular, microvascular, neurological problems and wound-healing problems. Advantageously, this is hyperglycemia, functional and quantitative abnormalities of endocrine pancreatic cells, insulin resistance and inflammation.

Advantageously, the treated patient has risk factors associated with diabetes, i.e. a disease rate directly or indirectly associated with the occurrence of diabetes. In particular, this comprises family history, gestational diabetes, weight excess, obesity, insufficient physical exercise, hypertension, a high level of triglycerides, inflammation and hyperlipidemia.

The present invention further relates to the use of a thiophene derivative according to the invention or selected from compounds of formulae (a) to (z1) as defined above for making a drug intended for treating and/or preventing diabetes, its complications and/or associated pathologies, notably of diabetes of type II and of hyperglycemia.

Finally, it relates to a treatment and/or preventive and/or prophylactic treatment method and/or for retarding occurrence of diabetes, of its complications and/or associated pathologies, advantageously of diabetes of type II and hyperglycemia, comprising the administration of an efficient amount of a thiophene derivative according to the invention or selected from the compounds of formulae (a) to (z1), as defined above, to a patient in need thereof.

The efficient amount will be adapted depending on the nature and the severity of the pathology to be treated, the administration route and also the weight and the age of the patient. Generally, the dose unit will vary between 0.5 mg and 2,000 mg daily, in one or more takings, advantageously between 1 and 1,000 mg.

The thiophene derivatives according to the invention are made by methods well known to one skilled in the art and partly by methods as described hereafter.

The invention will be better understood upon reading the description and the examples which follow which are given as a non-limiting indication.

Description of the Synthesis and General Schemes

The compounds of general formula (I) may be prepared by applying or adapting any method known per se of one skilled in the art and/or within reach of one skilled in the art, notably those described by Larock in Comprehensive Organic Transformations, VCH Pub., 1989, or by applying or adapting methods described in the procedures which follow.

The synthesis of the molecules of general formula (I) is close, sometimes identical, with what has been described in documents [2], [5], [9], [10], [11] and [12] without this list of references being able to be considered as exhaustive.

The different groups $R^1$ to $R^8$ and Y of schemes 1 to 13 refer to the definitions given earlier.

Scheme 1:

The formation of the thiophene ring may be achieved in 3 steps from a properly substituted 4-phenyl-4-oxo butanoic acid, the acid function is esterified under standard conditions, chloroformylation is achieved in a step before cyclization in the presence of sulfur. The major product of this reaction is the intermediate 1.4, the formation of which is accompanied by the production of a byproduct 1.5. 1.4 is then acylated or sulfonylated according to Friedel-Craft type conditions; with saponification of the ester function, it is possible to result in products of type 1.7 and 1.9 respectively.

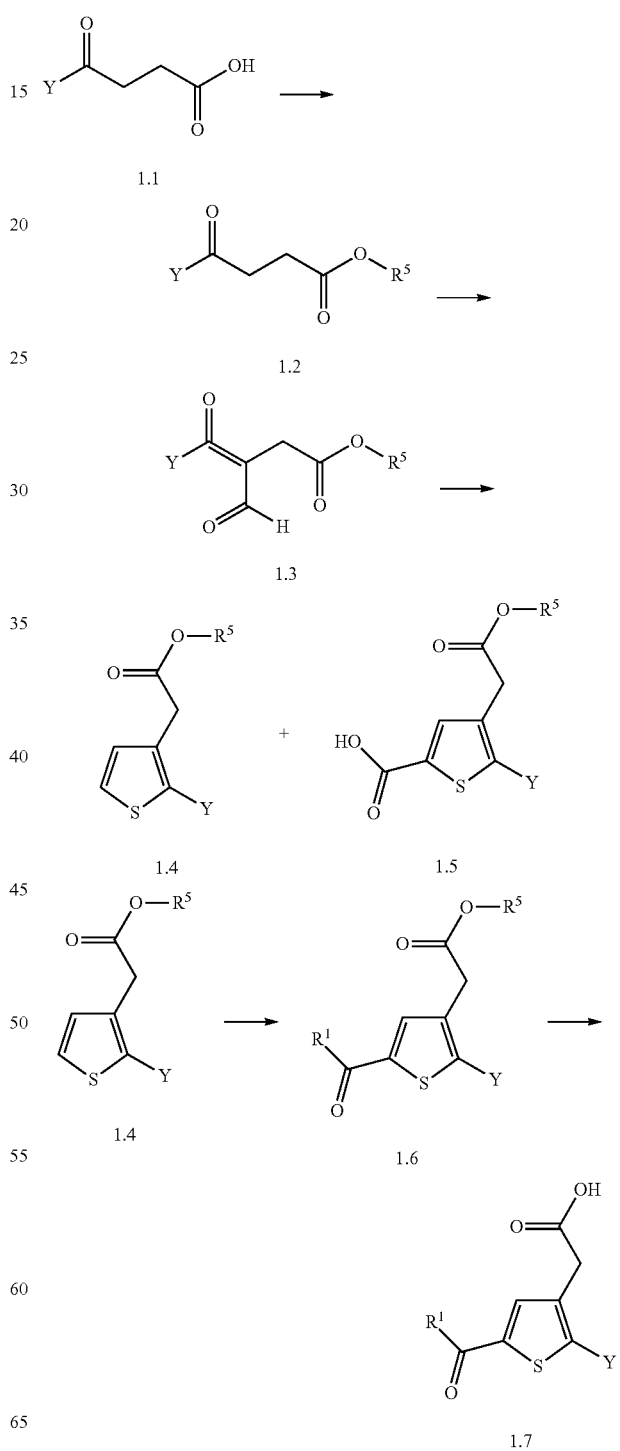

-continued

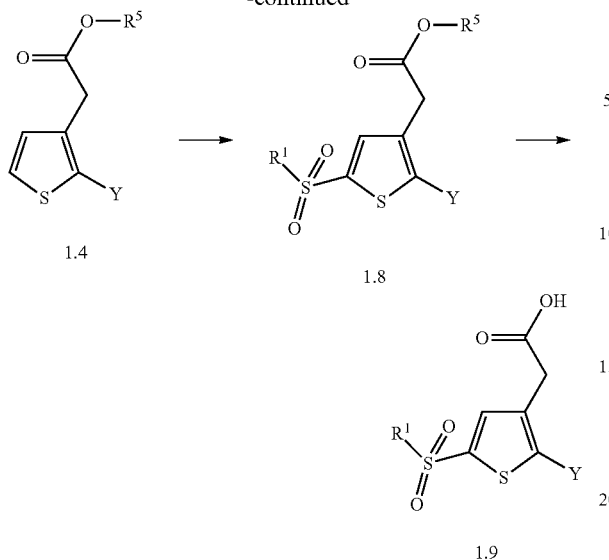

1.4
1.8
1.9

The preparation of complex esters may be envisioned from the acids 1.7 or 1.9 according to standard esterification conditions or by preparing an intermediate acid chloride followed by an acylation reaction. Trans-esterification reactions from derivatives of type 1.6 or 1.8 may also be conducted according to standard conditions.

Scheme 2:

The preparation of amides of type 2.1 was able to be achieved from derivatives 1.7 by passing through an intermediate acid chloride and by conducting an acylation reaction on an amine, or else under peptide coupling conditions such as

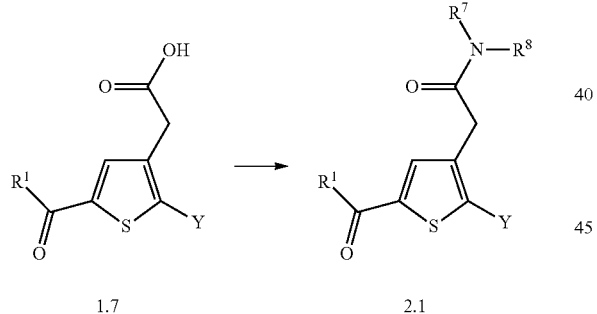

1.7
2.1

Scheme 3:

The reduction of the ketone was achieved under standard reduction conditions which proved to be selective.

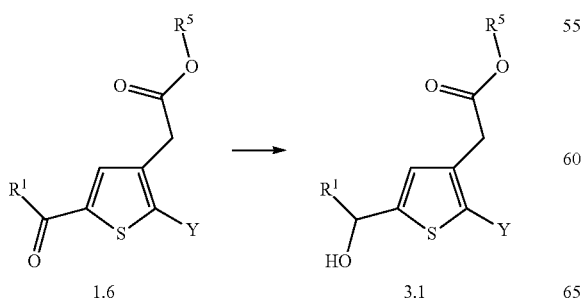

1.6
3.1

Scheme 4:

The preparation of oximes was achieved from derivatives 1.6.

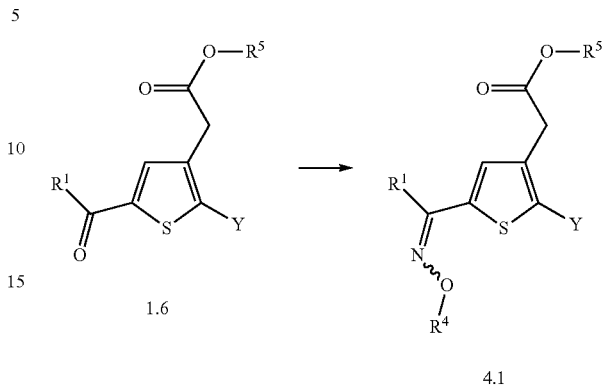

1.6
4.1

Scheme 5:

Derivatives of formula 1.5 were used for preparing amides by passing through the intermediate formation of an acid chloride and by conducting an acylation reaction on an amine, or else under peptide coupling conditions such as EDC.HCl, HOBt or further PyBOP. A represents an aryl group, a ($C_1$-$C_6$ alkyl)aryl group or further an arylCONH group.

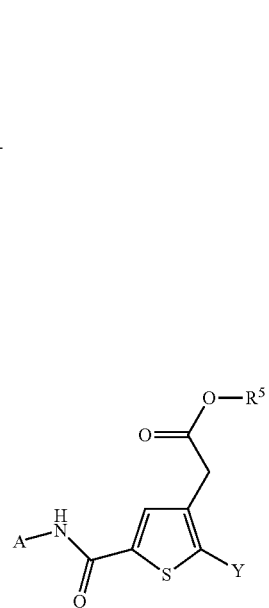

1.5

5.1

Scheme 6:

Alpha-substituted derivatives of the acid were prepared by deprotonation under basic conditions followed by addition of an electrophilic reagent. In the case when the electrophilic reagent is bromo(methoxy)methane, according to the operation conditions, the reaction may lead to the formation of the acrylate of type 6.2.

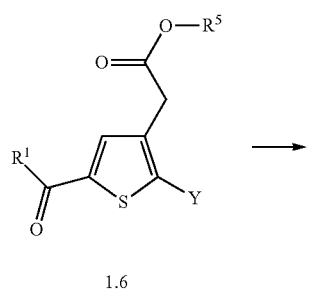

1.6

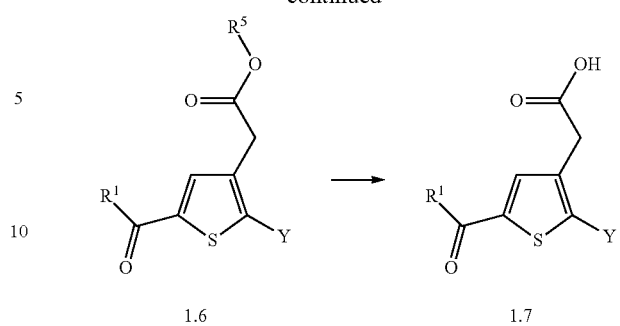

1.6   1.7

Hal: represents a halogen atom, advantageously bromine.

Scheme 8:

Simplification of this procedure may be contemplated in certain cases, derivatives of type 8.1 were prepared by acylation of derivatives of type 7.2 and were engaged in arylation reactions catalyzed with palladium involving iodophenyl derivatives in order to obtain the derivatives of type 1.6.

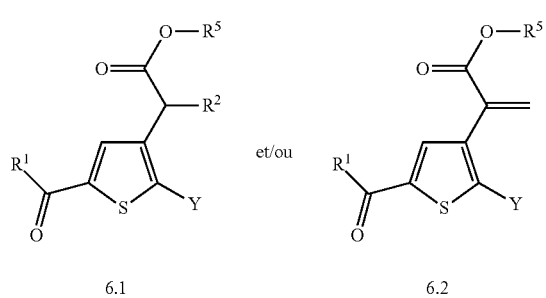

6.1   et/ou   6.2

Scheme 7:

Specific introduction of certain groups was possible by using an alternative synthesis method to the one described in scheme 1. Starting with a thiophene acetic acid, an esterification reaction was conducted, followed by halogenation, the introduction of aryl or heteroaryl substituents is allowed by applying transformations of the Suzuki type, in order to obtain derivatives of type 1.4, which are then worked upon in the same way as earlier, i.e., engaged in an acylation reaction of the Friedel-Craft type and then saponification in order to obtain the derivatives 1.7.

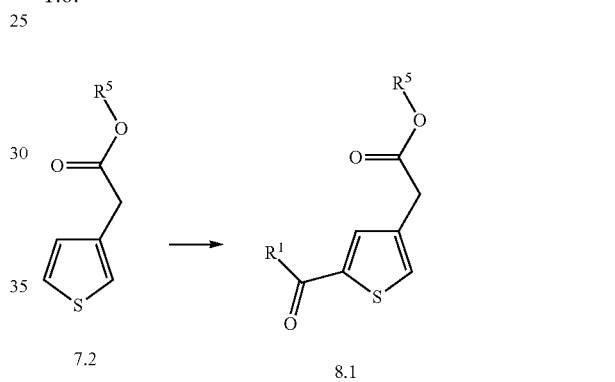

7.2   8.1

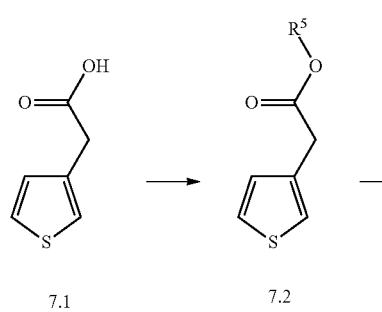

7.1   7.2

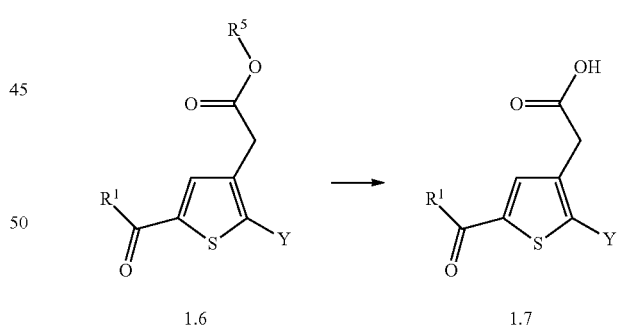

1.6   1.7

Scheme 9:

An alternative method for preparing the compounds of formula I resorts to a 2-boronate-3-methylthiophene derivative which is engaged in a reaction of the Suzuki type. The derivatives of type 9.2 are acylated according to Friedel-Craft conditions. Obtaining derivatives 1.6 is ensured by halogenation, cyanation and then alcoholic hydrolysis of derivatives 9.3

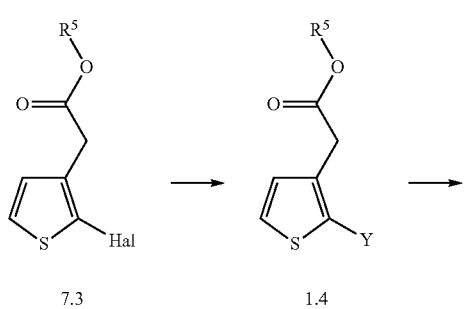

7.3   1.4

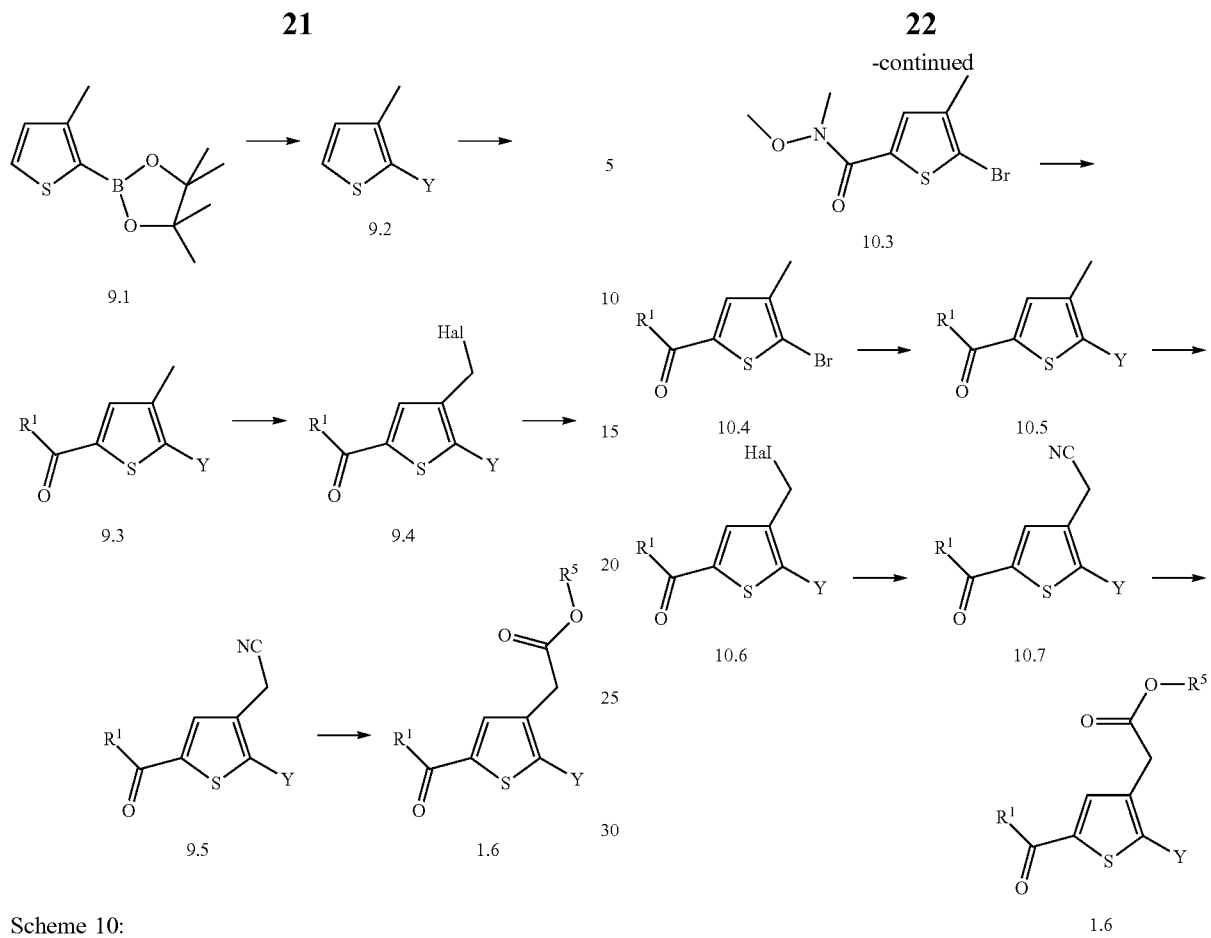

Scheme 10:

With the purpose of allowing introduction of specific groups, another alternative synthesis method to the methods described earlier was developed. Starting with methyl 5-bromo-4-methylthiophene-2-carboxylate, a saponification reaction was conducted in order to obtain the corresponding acid and to be able to prepare a Weinreb amide. In the presence of an organometal of the halogen-magnesium type, the derivatives of type 10.3 gave the possibility of obtaining derivatives of type 10.4, which were then engaged into a reaction of the Suzuki type, followed by halogenation and then cyanation in order to obtain derivatives of type 10.7.

The latter were engaged in alcohol hydrolysis reactions in order to obtain esters of the type 1.6.

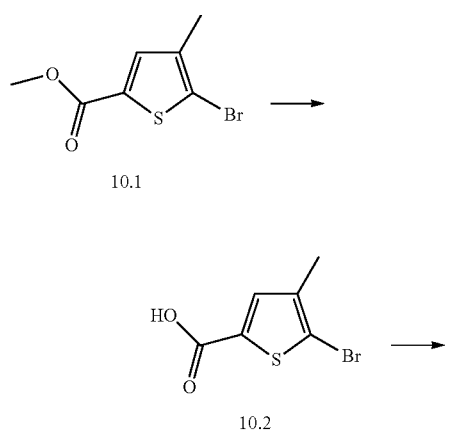

Scheme 11:

Introducing substituents to the acid function required another synthesis method, which resorts to a 2-(thiophen-3-yl)acetonitrile as a starting product, this product was engaged in a halogenation reaction followed by coupling catalyzed by palladium of the Suzuki type in order to obtain the derivatives of type 11.3, these products were acylated according to Friedel-Craft conditions in order to obtain the derivatives of type 10.7.

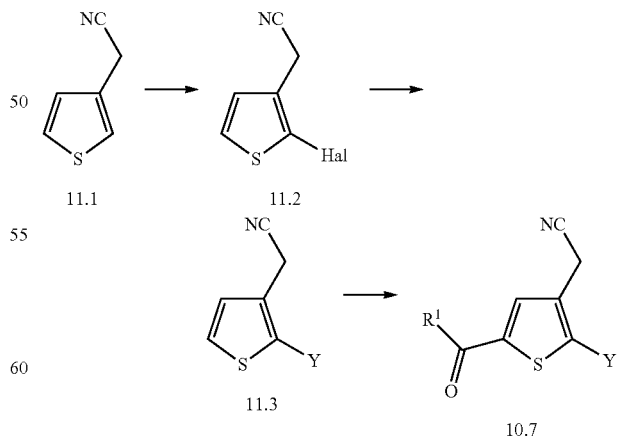

Scheme 12:

The derivatives of type 10.7 were subject to a treatment with an azide in order to form the tetrazole derivatives 12.1.

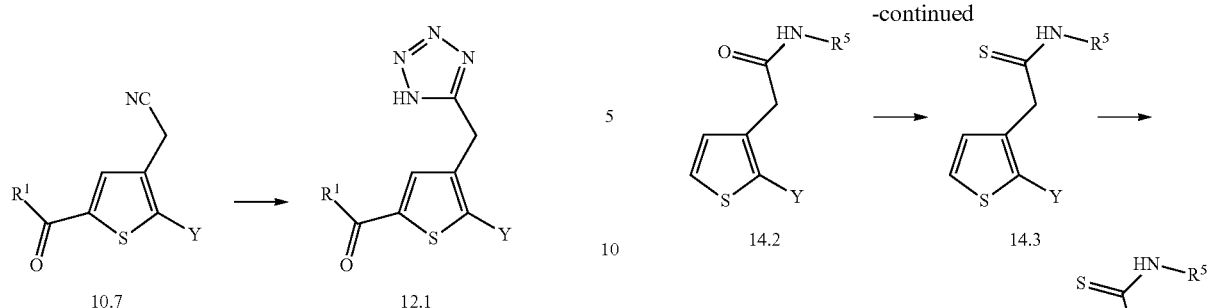

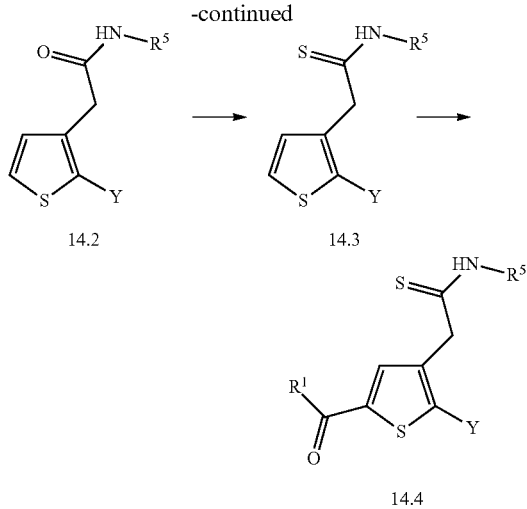

Scheme 13:

The derivatives of type 10.7 were subject to a treatment with a hydroxylamine in order to obtain the open derivatives of type 13.1 which were then engaged into carbonylation reactions in the presence of carbonyl diimidazole in order to obtain oxadiazolones of the type 13.2.

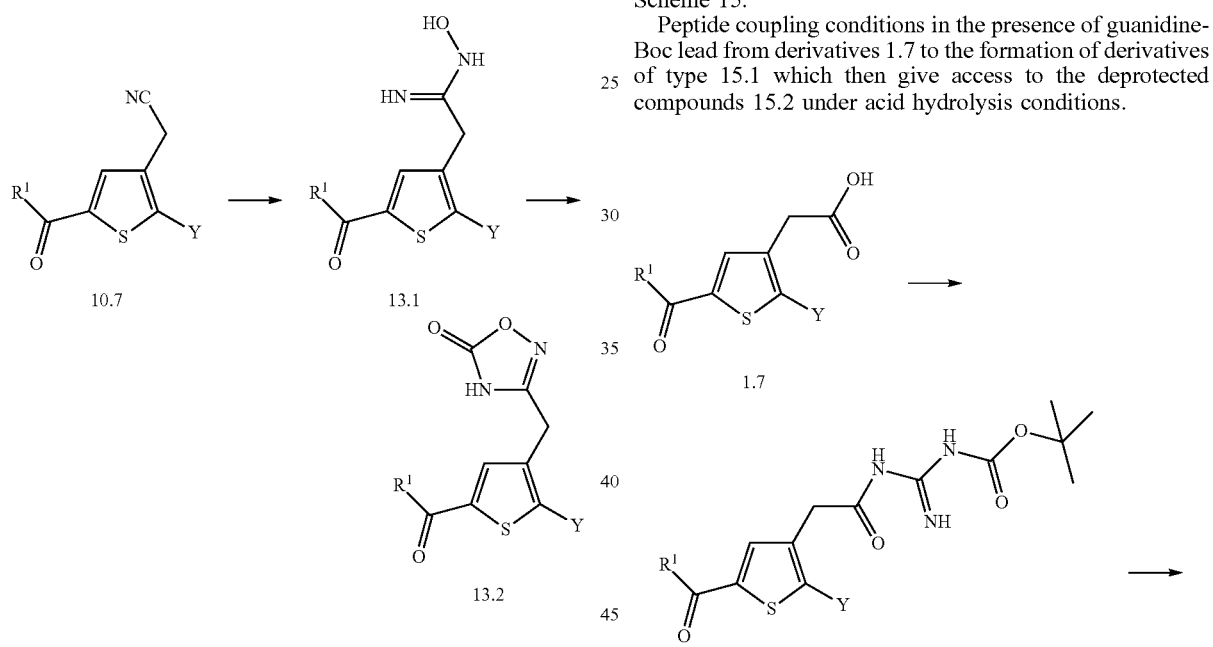

Scheme 14:

The derivatives of type 1.4 were subject to hydrolysis under basic conditions in order to obtain intermediate acid derivatives of type 14.1 which were then engaged into peptide coupling reactions with which derivatives of type 14.2 may be obtained. The latter treated by Lawesson's reagent form the corresponding thioamides 14.3. Finally, a Friedel-Craft acylation reaction gives access to the compounds of type 14.4.

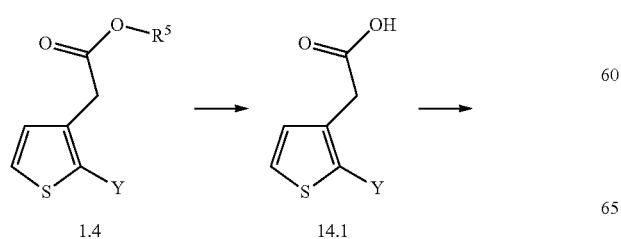

Scheme 15:

Peptide coupling conditions in the presence of guanidine-Boc lead from derivatives 1.7 to the formation of derivatives of type 15.1 which then give access to the deprotected compounds 15.2 under acid hydrolysis conditions.

EXAMPLES

Equipment and Method

Proton ($^1$H) nuclear magnetic resonance (NMR) spectra are obtained on a Bruker Avance DPX300 (300.16 MHz) apparatus. The chemical shifts (δ) are measured in parts per million (ppm). The spectra are calibrated by the chemical shift of the deuterated solvent used. The coupling constants (J) are expressed in Hertz (Hz) and the multiplicity is represented in the following way, singlet (s), doublet (d), doublet-doublet (dd), triplet (t), triplet-doublet (td), quadruplet (q), multiplet (m). The mass spectra (MS) are obtained with a spectrometer Agilent Technologies MSD, type G1946A, the samples are ionized by an "Atmospheric pressure chemical ionization" (APCI) source.

Abbreviations

AIBN azoisobutyronitrile
EDC N-(3-dimethylaminopropyl)-N-ethylcarbodiimide
HOBt 1-hydroxybenzotriazole
CDCl$_3$ deuterated chloroform
DMSO deuterated dimethylsulfoxyde
PyBOP (benzotriazol-1-yl-oxytripyrrolidinophosphonium hexafluorophosphate)
DMPU 1,3-dimethyl-3,4,5,6-tetrahydro-2(1H)-pyrimidinone
DMF dimethylformamide
Boc tert-butoxycarbonyl
mmol millimole(s)
μM micromolar
ml milliliter(s)
g gram(s)
M mol/liter
N normal
nm nanometer(s)
min minute(s)
h hour(s)
d day(s)
r.t. room temperature
UV ultraviolet
ctrl control
HGP Hepatic Glucose Production The list of the examples below is used for illustrating the scope of this invention and not for limiting the field of application thereof.

TABLE 1

List of the molecules for which the synthesis is exemplified

| No. | Chemical structure | Chemical name |
|---|---|---|
| 1 | 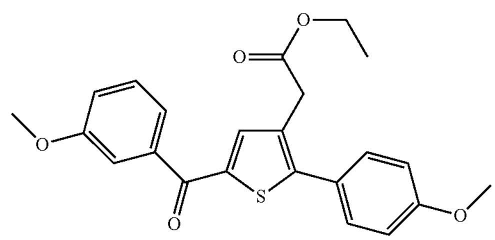 | ethyl 2-(5-(4-methoxybenzoyl)-2-(4-methoxyphenyl)thiophen-3-yl)acetate |
| 2 | 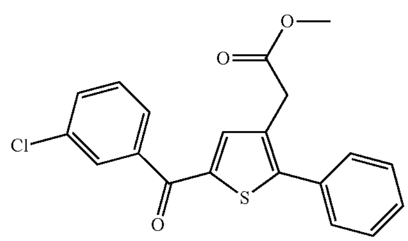 [SMILES: COC(=O)Cc1cc(C(=O)c2cccc(Cl)c2)sc1-c1ccccc1] | methyl 2-(5-(3-chlorobenzoyl)-2-phenylthiophen-3-yl)acetate |
| 3 | 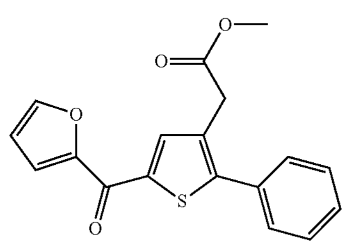 [SMILES: COC(=O)Cc1cc(C(=O)c2ccco2)sc1-c1ccccc1] | methyl 2-(5-(furan-2-carbonyl)-2-phenylthiophen-3-yl)acetate |
| 4 | 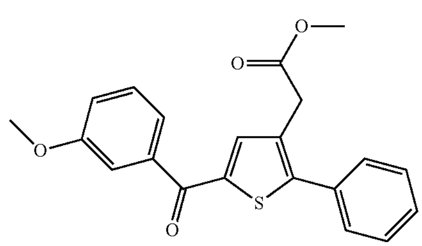 [SMILES: COC(=O)Cc1cc(C(=O)c2cccc(OC)c2)sc1-c1ccccc1] | methyl 2-(5-(3-methoxybenzoyl)-2-phenylthiophen-3-yl)acetate |

TABLE 1-continued

List of the molecules for which the synthesis is exemplified

| No. | Chemical structure | Chemical name |
|---|---|---|
| 5 | 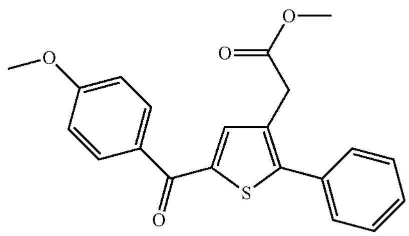 [SMILES: COC(=O)Cc1cc(C(=O)c2ccc(OC)cc2)sc1-c1ccccc1] | methyl 2-(5-(4-methoxybenzoyl)-2-phenylthiophen-3-yl)acetate |
| 6 | 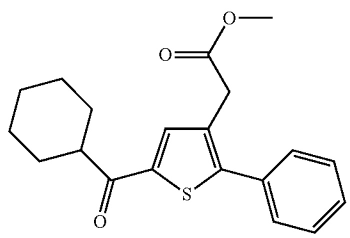 [SMILES: COC(=O)Cc1cc(C(=O)C2CCCCC2)sc1-c1ccccc1] | methyl 2-(5-(cyclohexanecarbonyl)-2-phenylthiophen-3-yl)acetate |
| 7 | 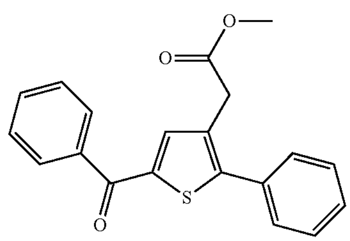 [SMILES: COC(=O)Cc1cc(C(=O)c2ccccc2)sc1-c1ccccc1] | methyl 2-(5-benzoyl-2-phenyl-thiophen-3-yl)acetate |
| 8 | 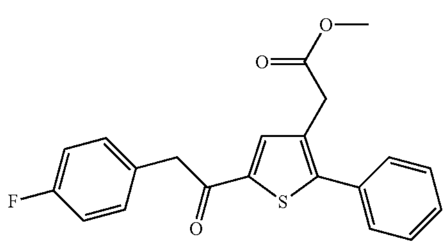 [SMILES: COC(=O)Cc1cc(C(=O)Cc2ccc(F)cc2)sc1-c1ccccc1] | methyl 2-(5-(2-(4-fluoro-phenyl)acetyl)-2-phenylthiophen-3-yl)acetate |
| 9 | 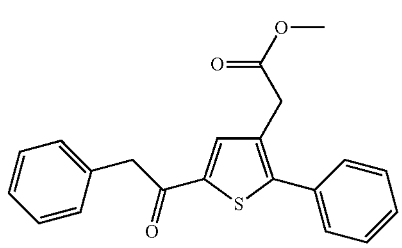 [SMILES: COC(=O)Cc1cc(C(=O)Cc2ccccc2)sc1-c1ccccc1] | methyl 2-(2-phenyl-5-(2-phenyl-acetyl)thiophen-3-yl)acetate |
| 10 | 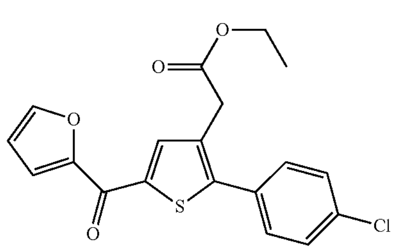 [SMILES: CCOC(=O)Cc1cc(C(=O)c2ccco2)sc1-c1ccc(Cl)cc1] | ethyl 2-(2-(4-chlorophenyl)-5-(furan-2-carbonyl)thiophen-3-yl)acetate |

TABLE 1-continued

List of the molecules for which the synthesis is exemplified

| No. | Chemical structure | Chemical name |
|---|---|---|
| 11 | 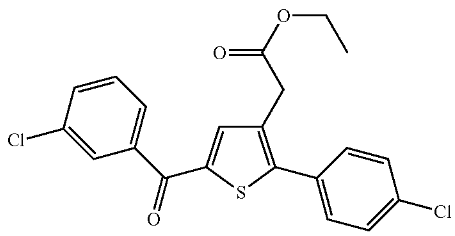 [SMILES: CCOC(=O)Cc1cc(C(=O)c2cccc(Cl)c2)sc1-c1ccc(Cl)cc1] | ethyl 2-(5-(3-chlorobenzoyl)-2-(4-chlorophenyl)thiophen-3-yl)acetate |
| 12 | 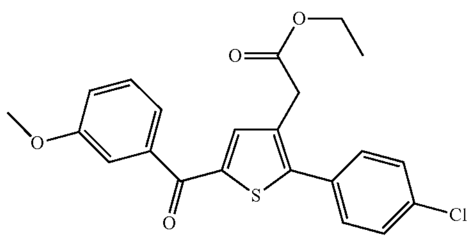 [SMILES: CCOC(=O)Cc1cc(C(=O)c2cccc(OC)c2)sc1-c1ccc(Cl)cc1] | ethyl 2-(2-(4-chlorophenyl)-5-(3-methoxybenzoyl)thiophen-3-yl)acetate |
| 13 | 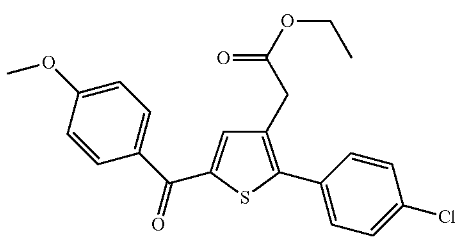 [SMILES: CCOC(=O)Cc1cc(C(=O)c2ccc(OC)cc2)sc1-c1ccc(Cl)cc1] | ethyl 2-(2-(4-chlorophenyl)-5-(4-methoxybenzoyl)thiophen-3-yl)acetate |
| 14 | 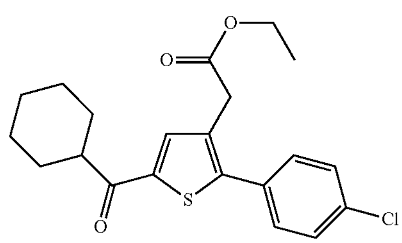 [SMILES: CCOC(=O)Cc1cc(C(=O)C2CCCCC2)sc1-c1ccc(Cl)cc1] | ethyl 2-(2-(4-chlorophenyl)-5-(cyclohexanecarbonyl)thiophen-3-yl)acetate |
| 15 | 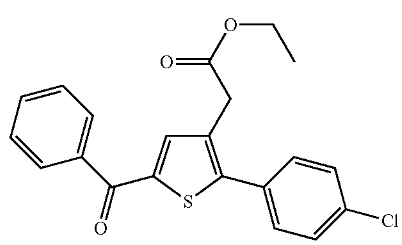 [SMILES: CCOC(=O)Cc1cc(C(=O)c2ccccc2)sc1-c1ccc(Cl)cc1] | ethyl 2-(5-benzoyl-2-(4-chlorophenyl)thiophen-3-yl)acetate |
| 16 | 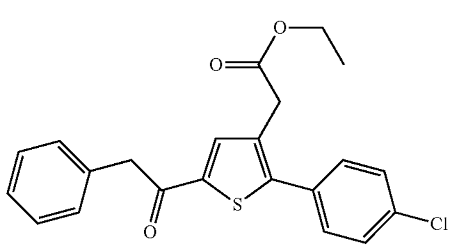 [SMILES: CCOC(=O)Cc1cc(C(=O)Cc2ccccc2)sc1-c1ccc(Cl)cc1] | ethyl 2-(2-(4-chlorophenyl)-5-(2-phenylacetyl)thiophen-3-yl)acetate |

TABLE 1-continued

List of the molecules for which the synthesis is exemplified

| No. | Chemical structure | Chemical name |
|-----|-------------------|---------------|
| 17 | 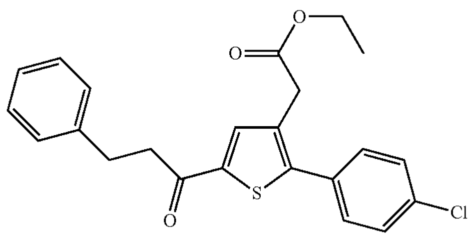 [SMILES: CCOC(=O)Cc1cc(C(=O)CCc2ccccc2)sc1-c1ccc(Cl)cc1] | ethyl 2-(2-(4-chlorophenyl)-5-(3-phenylpropanoyl)thiophen-3-yl)acetate |
| 18 | 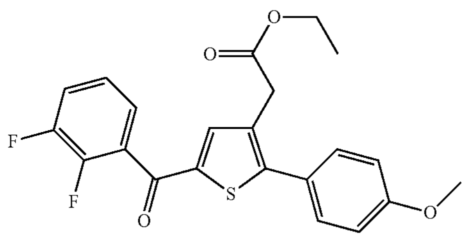 [SMILES: CCOC(=O)Cc1cc(C(=O)c2cccc(F)c2F)sc1-c1ccc(OC)cc1] | ethyl 2-(5-(2,3-difluorobenzoyl)-2-(4-methoxyphenyl)thiophen-3-yl)acetate |
| 19 | 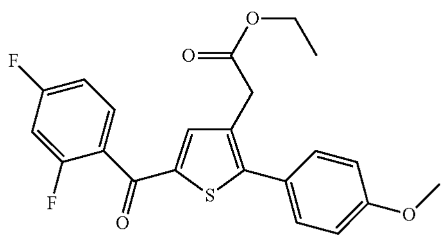 [SMILES: CCOC(=O)Cc1cc(C(=O)c2ccc(F)cc2F)sc1-c1ccc(OC)cc1] | ethyl 2-(5-(2,4-difluorobenzoyl)-2-(4-methoxyphenyl)thiophen-3-yl)acetate |
| 20 | 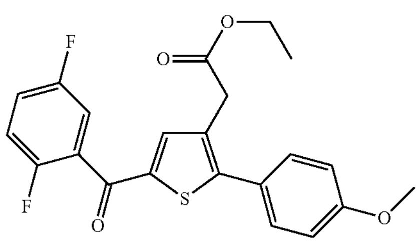 [SMILES: CCOC(=O)Cc1cc(C(=O)c2cc(F)ccc2F)sc1-c1ccc(OC)cc1] | ethyl 2-(5-(2,5-difluorobenzoyl)-2-(4-methoxyphenyl)thiophen-3-yl)acetate |
| 21 | 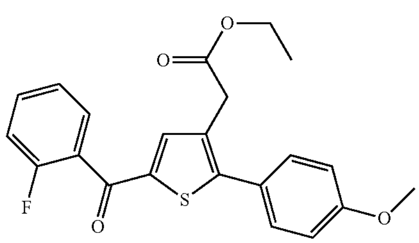 [SMILES: CCOC(=O)Cc1cc(C(=O)c2ccccc2F)sc1-c1ccc(OC)cc1] | ethyl 2-(5-(2-fluorobenzoyl)-2-(4-methoxyphenyl)thiophen-3-yl)acetate |
| 22 | 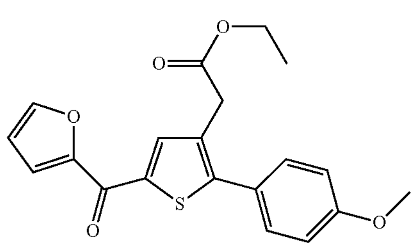 [SMILES: CCOC(=O)Cc1cc(C(=O)c2ccco2)sc1-c1ccc(OC)cc1] | ethyl 2-(5-(furan-2-carbonyl)-2-(4-methoxyphenyl)thiophen-3-yl)acetate |

TABLE 1-continued

List of the molecules for which the synthesis is exemplified

| No. | Chemical structure | Chemical name |
| --- | --- | --- |
| 23 | 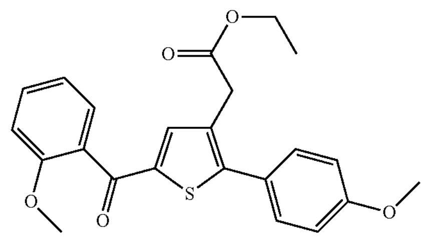 [SMILES: CCOC(=O)Cc1cc(C(=O)c2ccccc2OC)sc1-c1ccc(OC)cc1] | ethyl 2-(5-(2-methoxybenzoyl)-2-(4-methoxyphenyl)thiophen-3-yl)acetate |
| 24 | 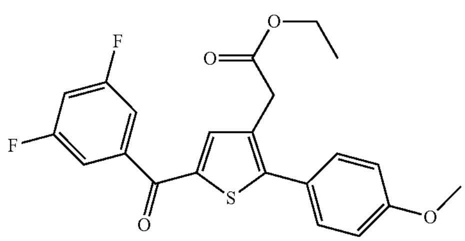 [SMILES: CCOC(=O)Cc1cc(C(=O)c2cc(F)cc(F)c2)sc1-c1ccc(OC)cc1] | ethyl 2-(5-(3,5-difluorobenzoyl)-2-(4-methoxyphenyl)thiophen-3-yl)acetate |
| 25 | 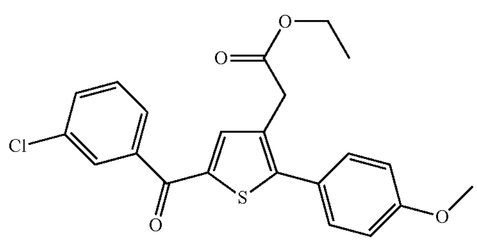 [SMILES: CCOC(=O)Cc1cc(C(=O)c2cccc(Cl)c2)sc1-c1ccc(OC)cc1] | ethyl 2-(5-(3-chlorobenzoyl)-2-(4-methoxyphenyl)thiophen-3-yl)acetate |
| 26 | 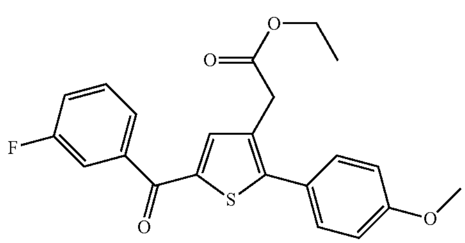 [SMILES: CCOC(=O)Cc1cc(C(=O)c2cccc(F)c2)sc1-c1ccc(OC)cc1] | ethyl 2-(5-(3-fluorobenzoyl)-2-(4-methoxyphenyl)thiophen-3-yl)acetate |
| 27 | 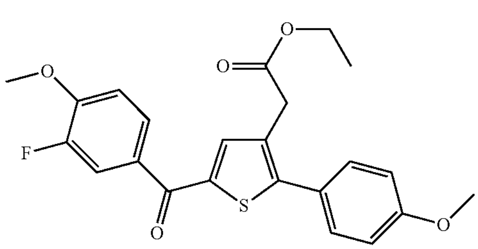 | ethyl 2-(5-(3-fluoro-4-methoxybenzoyl)-2-(4-methoxyphenyl)thiophen-3-yl)acetate |
| 28 | 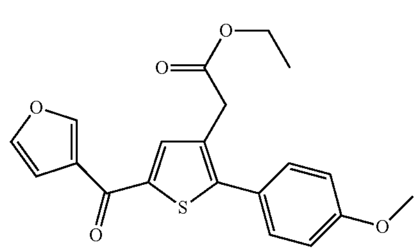 [SMILES: CCOC(=O)Cc1cc(C(=O)c2ccoc2)sc1-c1ccc(OC)cc1] | ethyl 2-(5-(furan-3-carbonyl)-2-(4-methoxyphenyl)thiophen-3-yl)acetate |

TABLE 1-continued

List of the molecules for which the synthesis is exemplified

| No. | Chemical structure | Chemical name |
| --- | --- | --- |
| 29 | 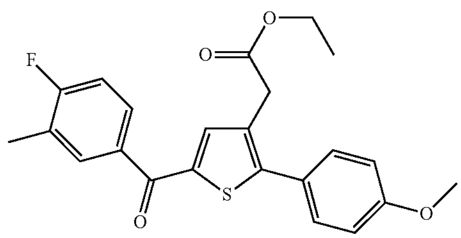 | ethyl 2-(5-(4-fluoro-3-methyl-benzoyl)-2-(4-methoxyphenyl)thiophen-3-yl)acetate |
| 30 | 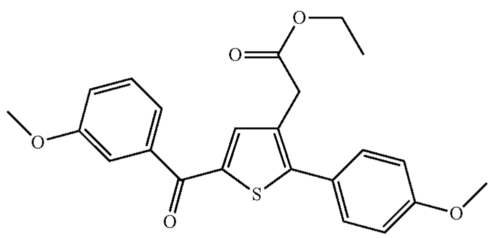 | ethyl 2-(5-(3-methoxybenzoyl)-2-(4-methoxyphenyl)thiophen-3-yl)acetate |
| 31 | 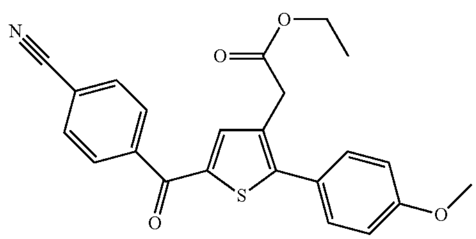 [SMILES: CCOC(=O)Cc1cc(C(=O)c2ccc(C#N)cc2)sc1-c1ccc(OC)cc1] | ethyl 2-(5-(4-cyanobenzoyl)-2-(4-methoxyphenyl)thiophen-3-yl)acetate |
| 32 | 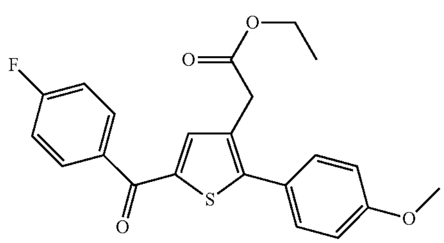 [SMILES: CCOC(=O)Cc1cc(C(=O)c2ccc(F)cc2)sc1-c1ccc(OC)cc1] | ethyl 2-(5-(4-fluorobenzoyl)-2-(4-methoxyphenyl)thiophen-3-yl)acetate |
| 33 | 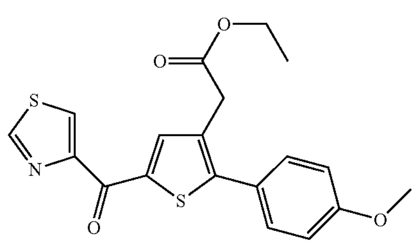 [SMILES: CCOC(=O)Cc1cc(C(=O)c2cscn2)sc1-c1ccc(OC)cc1] | ethyl 2-(2-(4-methoxyphenyl)-5-(thiazole-4-carbonyl)thiophen-3-yl)acetate |
| 34 | 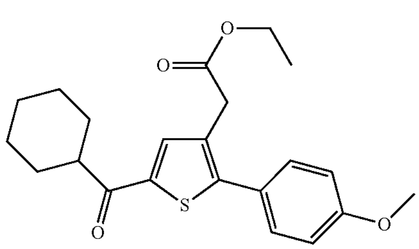 [SMILES: CCOC(=O)Cc1cc(C(=O)C2CCCCC2)sc1-c1ccc(OC)cc1] | ethyl 2-(5-(cyclohexanecarbonyl)-2-(4-methoxyphenyl)thiophen-3-yl)acetate |

TABLE 1-continued

List of the molecules for which the synthesis is exemplified

| No. | Chemical structure | Chemical name |
|---|---|---|
| 35 | 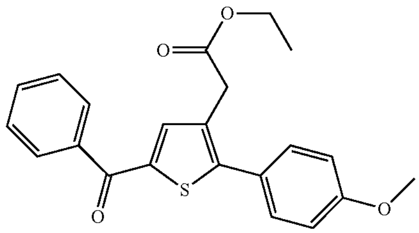 [SMILES: CCOC(=O)Cc1cc(C(=O)c2ccccc2)sc1-c1ccc(OC)cc1] | ethyl 2-(5-benzoyl-2-(4-methoxy-phenyl)thiophen-3-yl)acetate |
| 36 | 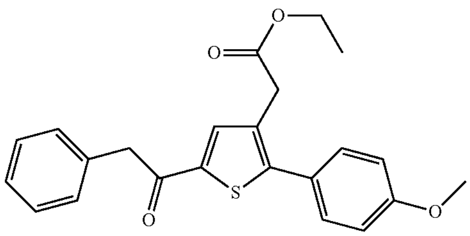 [SMILES: CCOC(=O)Cc1cc(C(=O)Cc2ccccc2)sc1-c1ccc(OC)cc1] | ethyl 2-(2-(4-methoxyphenyl)-5-(2-phenylacetyl)thiophen-3-yl)acetate |
| 37 | 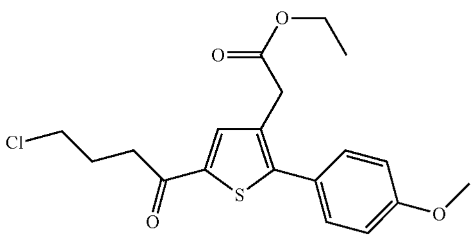 [SMILES: CCOC(=O)Cc1cc(C(=O)CCCCl)sc1-c1ccc(OC)cc1] | ethyl 2-(5-(4-chlorobutanoyl)-2-(4-methoxyphenyl)thiophen-3-yl)acetate |
| 38 | 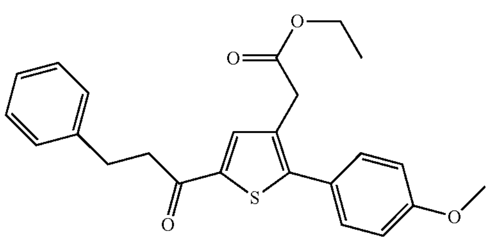 [SMILES: CCOC(=O)Cc1cc(C(=O)CCc2ccccc2)sc1-c1ccc(OC)cc1] | ethyl 2-(2-(4-methoxyphenyl)-5-(3-phenylpropanoyl)thiophen-3-yl)acetate |
| 39 | 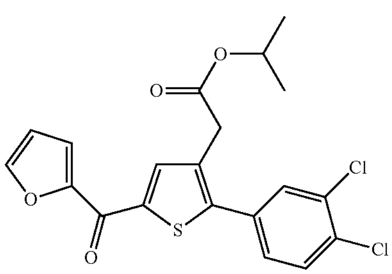 [SMILES: CC(C)OC(=O)Cc1cc(C(=O)c2ccco2)sc1-c1ccc(Cl)c(Cl)c1] | isopropyl 2-(2-(3,4-dichlorophenyl)-5-(furan-2-carbonyl)thiophen-3-yl)acetate |
| 40 | 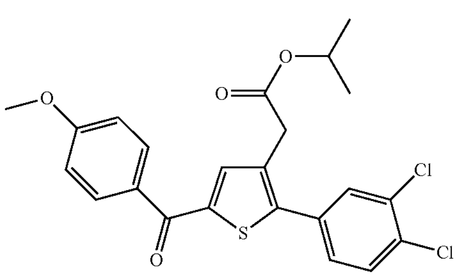 [SMILES: COc1ccc(C(=O)c2cc(CC(=O)OC(C)C)c(-c3ccc(Cl)c(Cl)c3)s2)cc1] | isopropyl 2-(2-(3,4-dichlorophenyl)-5-(4-methoxybenzoyl)thiophen-3-yl)acetate |

TABLE 1-continued

List of the molecules for which the synthesis is exemplified

| No. | Chemical structure | Chemical name |
| --- | --- | --- |
| 41 | 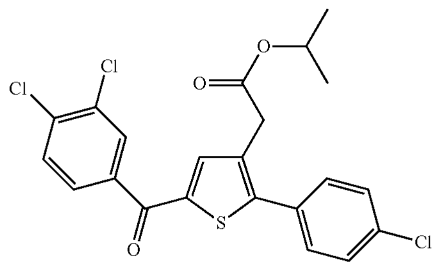 [SMILES: CC(C)OC(=O)Cc1cc(C(=O)c2ccc(Cl)c(Cl)c2)sc1-c1ccc(Cl)cc1] | isopropyl 2-(2-(4-chlorophenyl)-5-(3,4-dichlorobenzoyl)thiophen-3-yl)acetate |
| 42 | 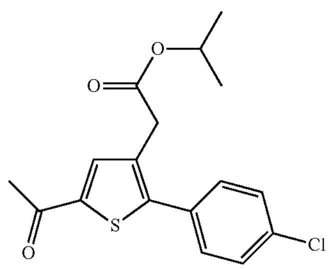 [SMILES: CC(=O)c1cc(CC(=O)OC(C)C)c(-c2ccc(Cl)cc2)s1] | isopropyl 2-(5-acetyl-2-(4-chlorophenyl)thiophen-3-yl)acetate |
| 43 | 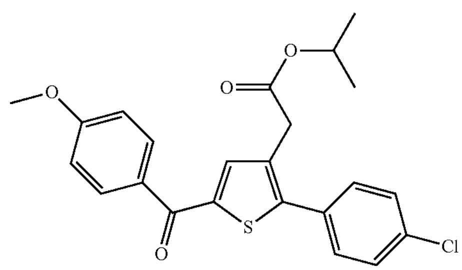 [SMILES: COc1ccc(C(=O)c2cc(CC(=O)OC(C)C)c(-c3ccc(Cl)cc3)s2)cc1] | isopropyl 2-(2-(4-chlorophenyl)-5-(4-methoxybenzoyl)thiophen-3-yl)acetate |
| 44 | 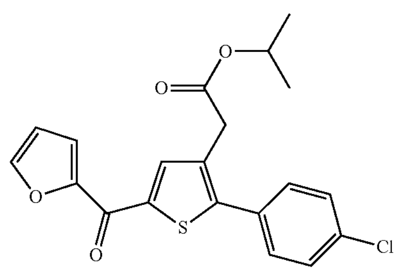 [SMILES: CC(C)OC(=O)Cc1cc(C(=O)c2ccco2)sc1-c1ccc(Cl)cc1] | isopropyl 2-(2-(4-chlorophenyl)-5-(furan-2-carbonyl)thiophen-3-yl)acetate |
| 45 | 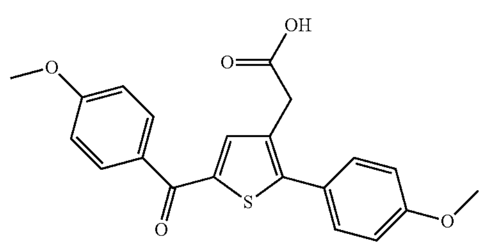 | 2-(5-(4-methoxybenzoyl)-2-(4-methoxyphenyl)thiophen-3-yl)acetic acid |
| 46 | 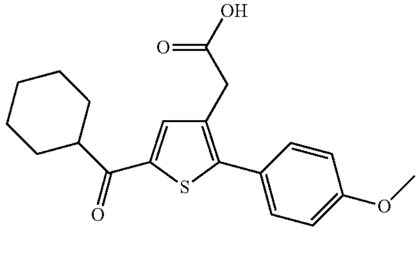 [SMILES: COc1ccc(-c2sc(C(=O)C3CCCCC3)cc2CC(=O)O)cc1] | 2-(5-(cyclohexanecarbonyl)-2-(4-methoxyphenyl)thiophen-3-yl)acetic acid |

TABLE 1-continued

List of the molecules for which the synthesis is exemplified

| No. | Chemical structure | Chemical name |
| --- | --- | --- |
| 47 | 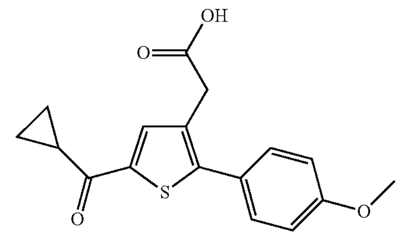 [SMILES: COc1ccc(-c2sc(C(=O)C3CC3)cc2CC(=O)O)cc1] | 2-(5-(cyclopropanecarbonyl)-2-(4-methoxyphenyl)thiophen-3-yl)acetic acid |
| 48 | 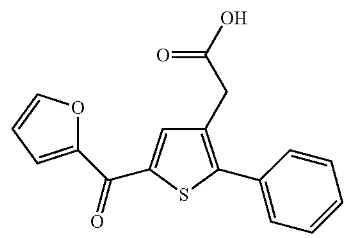 [SMILES: O=C(O)Cc1cc(C(=O)c2ccco2)sc1-c1ccccc1] | 2-(5-(furan-2-carbonyl)-2-phenyl-thiophen-3-yl)acetic acid |
| 49 | 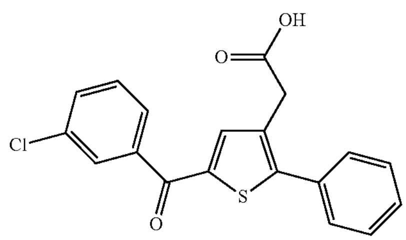 [SMILES: O=C(O)Cc1cc(C(=O)c2cccc(Cl)c2)sc1-c1ccccc1] | 2-(5-(3-chlorobenzoyl)-2-phenyl-thiophen-3-yl)acetic acid |
| 50 | 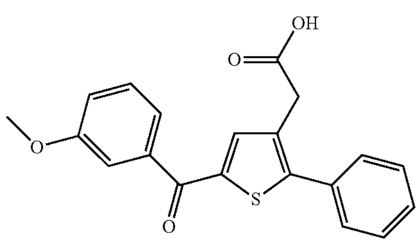 [SMILES: COc1cccc(C(=O)c2cc(CC(=O)O)c(-c3ccccc3)s2)c1] | 2-(5-(3-methoxybenzoyl)-2-phenylthiophen-3-yl)acetic acid |
| 51 | 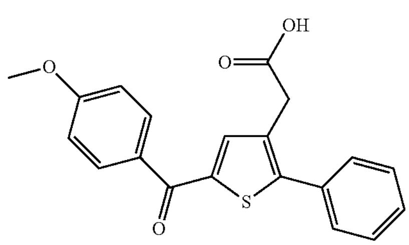 [SMILES: COc1ccc(C(=O)c2cc(CC(=O)O)c(-c3ccccc3)s2)cc1] | 2-(5-(4-methoxybenzoyl)-2-phenylthiophen-3-yl)acetic acid |
| 52 | 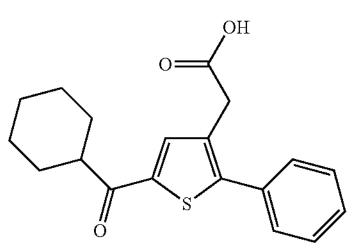 [SMILES: O=C(O)Cc1cc(C(=O)C2CCCCC2)sc1-c1ccccc1] | 2-(5-(cyclohexanecarbonyl)-2-phenylthiophen-3-yl)acetic acid |

TABLE 1-continued

List of the molecules for which the synthesis is exemplified

| No. | Chemical structure | Chemical name |
|---|---|---|
| 53 | 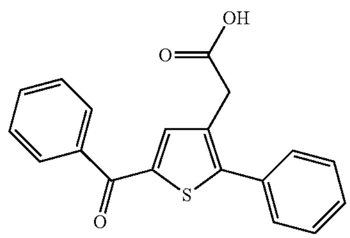 [SMILES: O=C(O)Cc1cc(C(=O)c2ccccc2)sc1-c1ccccc1] | 2-(5-benzoyl-2-phenylthiophen-3-yl) acetic acid |
| 54 | 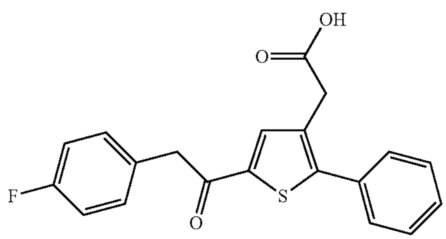 [SMILES: O=C(O)Cc1cc(C(=O)Cc2ccc(F)cc2)sc1-c1ccccc1] | 2-(5-(2-(4-fluorophenyl)acetyl)-2-phenylthiophen-3-yl)acetic acid |
| 55 | 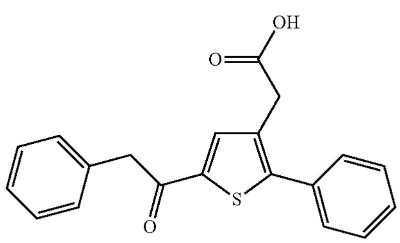 [SMILES: O=C(O)Cc1cc(C(=O)Cc2ccccc2)sc1-c1ccccc1] | 2-(2-phenyl-5-(2-phenyl-acetyl)thiophen-3-yl)acetic acid |
| 56 | 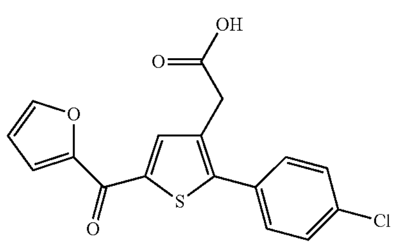 [SMILES: O=C(O)Cc1cc(C(=O)c2ccco2)sc1-c1ccc(Cl)cc1] | 2-(2-(4-chlorophenyl)-5-(furan-2-carbonyl)thiophen-3-yl)acetic acid |
| 57 | 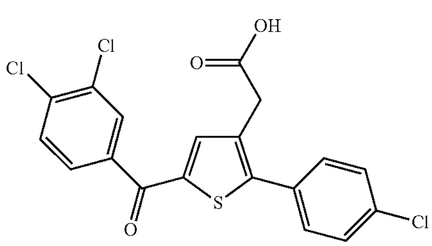 [SMILES: O=C(O)Cc1cc(C(=O)c2ccc(Cl)c(Cl)c2)sc1-c1ccc(Cl)cc1] | 2-(2-(4-chlorophenyl)-5-(3,4-dichlorobenzoyl)thiophen-3-yl)acetic acid |
| 58 | 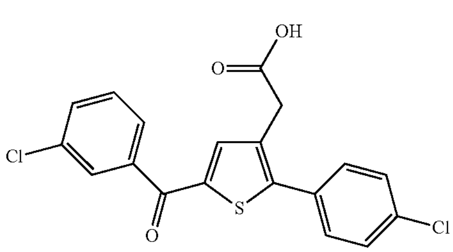 [SMILES: O=C(O)Cc1cc(C(=O)c2cccc(Cl)c2)sc1-c1ccc(Cl)cc1] | 2-(5-(3-chlorobenzoyl)-2-(4-chlorophenyl)thiophen-3-yl)acetic acid |

TABLE 1-continued

List of the molecules for which the synthesis is exemplified

| No. | Chemical structure | Chemical name |
|---|---|---|
| 59 | 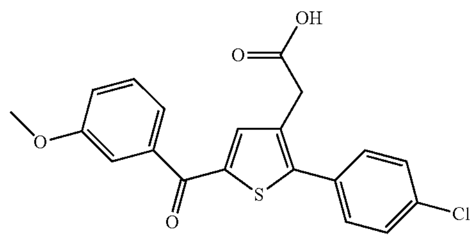 [SMILES: COc1cccc(C(=O)c2cc(CC(=O)O)c(-c3ccc(Cl)cc3)s2)c1] | 2-(2-(4-chlorophenyl)-5-(3-methoxybenzoyl)thiophen-3-yl)acetic acid |
| 60 | 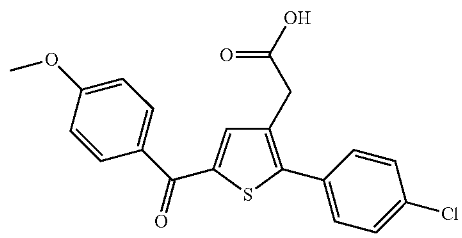 [SMILES: COc1ccc(C(=O)c2cc(CC(=O)O)c(-c3ccc(Cl)cc3)s2)cc1] | 2-(2-(4-chlorophenyl)-5-(4-methoxybenzoyl)thiophen-3-yl)acetic acid |
| 61 | 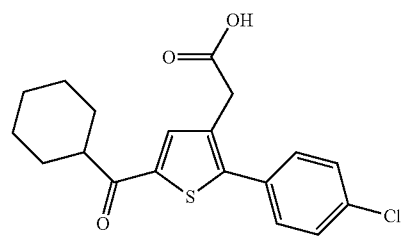 [SMILES: O=C(O)Cc1cc(C(=O)C2CCCCC2)sc1-c1ccc(Cl)cc1] | 2-(2-(4-chlorophenyl)-5-(cyclohexanecarbonyl)thiophen-3-yl)acetic acid |
| 62 | 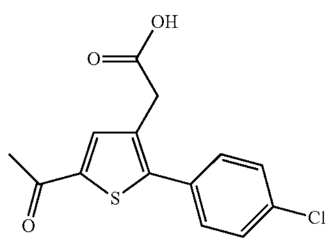 [SMILES: CC(=O)c1cc(CC(=O)O)c(-c2ccc(Cl)cc2)s1] | 2-(5-acetyl-2-(4-chlorophenyl)thiophen-3-yl)acetic acid |
| 63 | 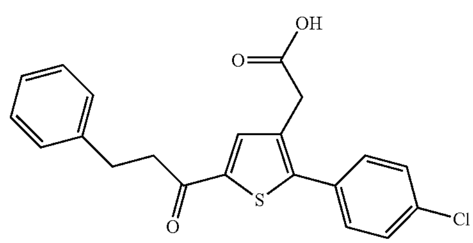 [SMILES: O=C(O)Cc1cc(C(=O)CCc2ccccc2)sc1-c1ccc(Cl)cc1] | 2-(2-(4-chlorophenyl)-5-(3-phenylpropanoyl)thiophen-3-yl)acetic acid |
| 64 | 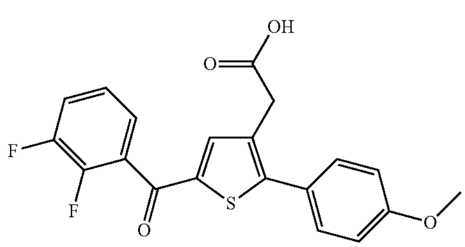 [SMILES: COc1ccc(-c2sc(C(=O)c3cccc(F)c3F)cc2CC(=O)O)cc1] | 2-(5-(2,3-difluorobenzoyl)-2-(4-methoxyphenyl)thiophen-3-yl)acetic acid |

TABLE 1-continued

List of the molecules for which the synthesis is exemplified

| No. | Chemical structure | Chemical name |
|-----|--------------------|---------------|
| 65 | 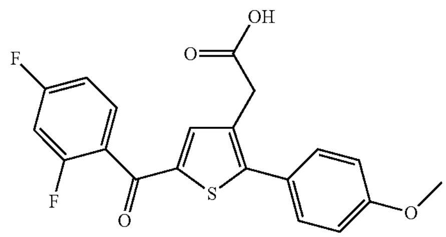 [SMILES: COc1ccc(-c2sc(C(=O)c3ccc(F)cc3F)cc2CC(=O)O)cc1] | 2-(5-(2,4-difluorobenzoyl)-2-(4-methoxyphenyl)thiophen-3-yl)acetic acid |
| 66 | 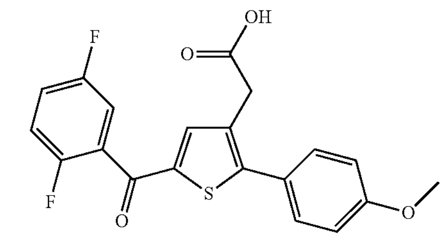 [SMILES: COc1ccc(-c2sc(C(=O)c3cc(F)ccc3F)cc2CC(=O)O)cc1] | 2-(5-(2,5-difluorobenzoyl)-2-(4-methoxyphenyl)thiophen-3-yl)acetic acid |
| 67 | 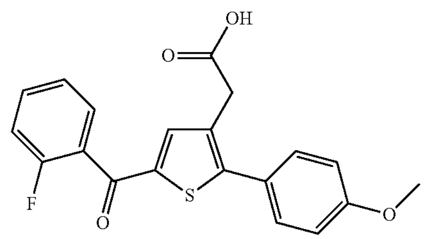 [SMILES: COc1ccc(-c2sc(C(=O)c3ccccc3F)cc2CC(=O)O)cc1] | 2-(5-(2-fluorobenzoyl)-2-(4-methoxyphenyl)thiophen-3-yl)acetic acid |
| 68 | 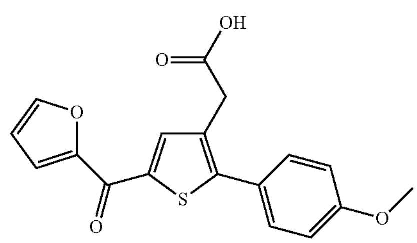 [SMILES: COc1ccc(-c2sc(C(=O)c3ccco3)cc2CC(=O)O)cc1] | 2-(5-(furan-2-carbonyl)-2-(4-methoxyphenyl)thiophen-3-yl)acetic acid |
| 69 | 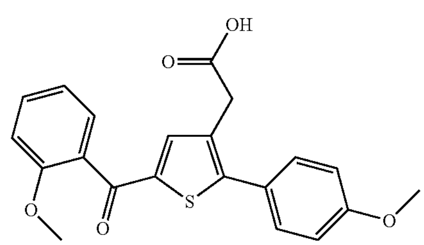 [SMILES: COc1ccc(-c2sc(C(=O)c3ccccc3OC)cc2CC(=O)O)cc1] | 2-(5-(2-methoxybenzoyl)-2-(4-methoxyphenyl)thiophen-3-yl)acetic acid |
| 70 | 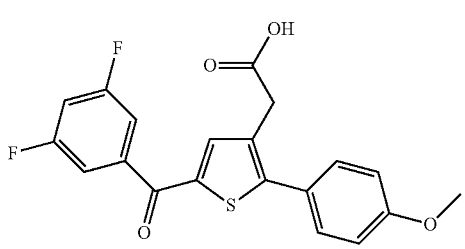 [SMILES: COc1ccc(-c2sc(C(=O)c3cc(F)cc(F)c3)cc2CC(=O)O)cc1] | 2-(5-(3,5-difluorobenzoyl)-2-(4-methoxyphenyl)thiophen-3-yl)acetic acid |

TABLE 1-continued

List of the molecules for which the synthesis is exemplified

| No. | Chemical structure | Chemical name |
|---|---|---|
| 71 | 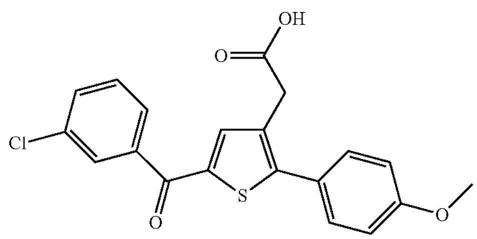 [SMILES: COc1ccc(-c2sc(C(=O)c3cccc(Cl)c3)cc2CC(=O)O)cc1] | 2-(5-(3-chlorobenzoyl)-2-(4-methoxyphenyl)thiophen-3-yl)acetic acid |
| 72 | 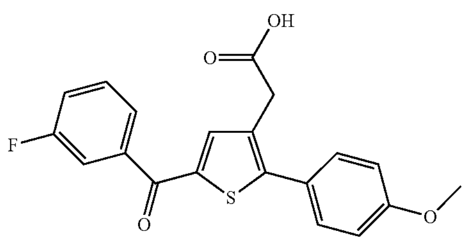 [SMILES: COc1ccc(-c2sc(C(=O)c3cccc(F)c3)cc2CC(=O)O)cc1] | 2-(5-(3-fluorobenzoyl)-2-(4-methoxyphenyl)thiophen-3-yl)acetic acid |
| 73 | 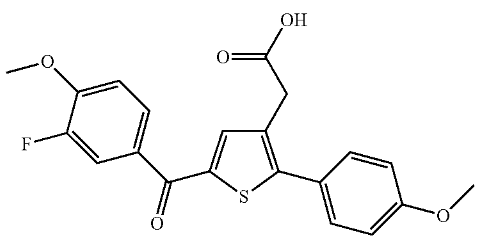 | 2-(5-(3-fluoro-4-methoxybenzoyl)-2-(4-methoxyphenyl)thiophen-3-yl) acetic acid |
| 74 | 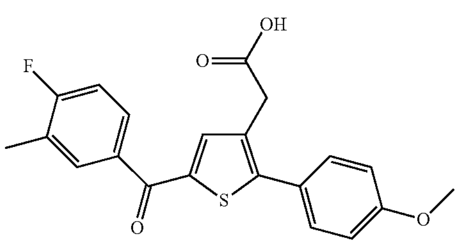 | 2-(5-(4-fluoro-3-methylbenzoyl)-2-(4-methoxyphenyl)thiophen-3-yl)acetic acid |
| 75 | 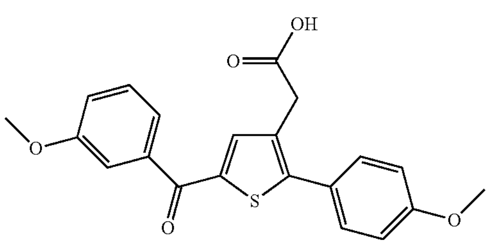 | 2-(5-(3-methoxybenzoyl)-2-(4-methoxyphenyl)thiophen-3-yl)acetic acid |
| 76 | 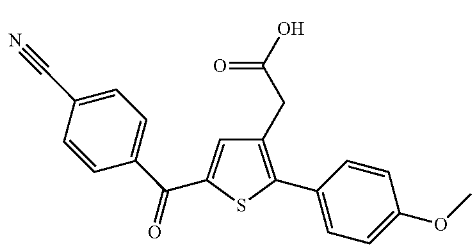 [SMILES: COc1ccc(-c2sc(C(=O)c3ccc(C#N)cc3)cc2CC(=O)O)cc1] | 2-(5-(4-cyanobenzoyl)-2-(4-methoxyphenyl)thiophen-3-yl)acetic acid |

TABLE 1-continued

List of the molecules for which the synthesis is exemplified

| No. | Chemical structure | Chemical name |
|---|---|---|
| 77 | 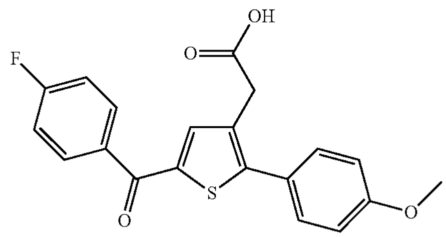 [SMILES: COc1ccc(-c2sc(C(=O)c3ccc(F)cc3)cc2CC(=O)O)cc1] | 2-(5-(4-fluorobenzoyl)-2-(4-methoxyphenyl)thiophen-3-yl)acetic acid |
| 78 | 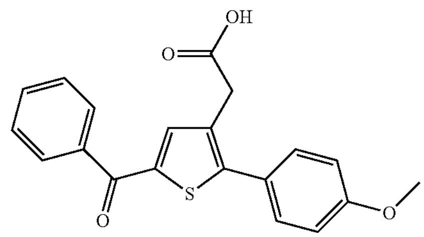 [SMILES: COc1ccc(-c2sc(C(=O)c3ccccc3)cc2CC(=O)O)cc1] | 2-(5-benzoyl-2-(4-methoxyphenyl)thiophen-3-yl)acetic acid |
| 79 | 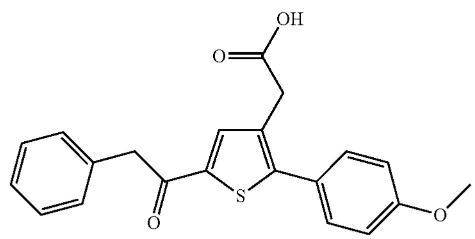 [SMILES: COc1ccc(-c2sc(C(=O)Cc3ccccc3)cc2CC(=O)O)cc1] | 2-(2-(4-methoxyphenyl)-5-(2-phenylacetyl)thiophen-3-yl)acetic acid |
| 80 | 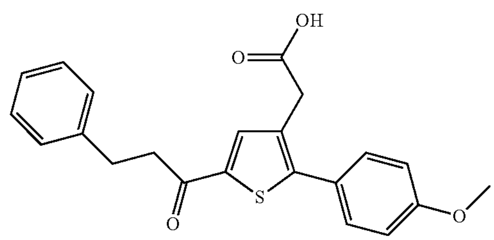 [SMILES: COc1ccc(-c2sc(C(=O)CCc3ccccc3)cc2CC(=O)O)cc1] | 2-(2-(4-methoxyphenyl)-5-(3-phenylpropanoyl)thiophen-3-yl)ace acetic acid |
| 81 | 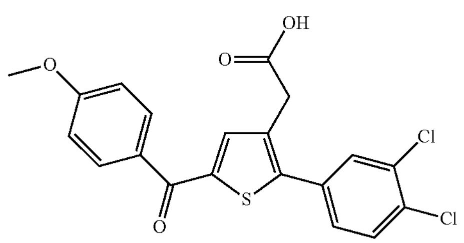 [SMILES: COc1ccc(C(=O)c2cc(CC(=O)O)c(-c3ccc(Cl)c(Cl)c3)s2)cc1] | 2-(2-(3,4-dichlorophenyl)-5-(4-methoxybenzoyl)thiophen-3-yl)acetic acid |
| 82 | 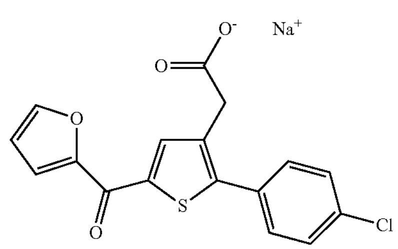 [SMILES: O=C([O-])Cc1cc(C(=O)c2ccco2)sc1-c1ccc(Cl)cc1 ; [Na+]] | sodium 2-(2-(4-chlorophenyl)-5-(furan-2-carbonyl)thiophen-3-yl)acetate |

TABLE 1-continued

List of the molecules for which the synthesis is exemplified

| No. | Chemical structure | Chemical name |
|---|---|---|
| 83 | 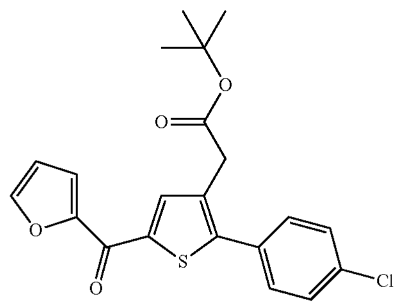 [SMILES: CC(C)(C)OC(=O)Cc1cc(C(=O)c2ccco2)sc1-c1ccc(Cl)cc1] | tert-butyl 2-(2-(4-chlorophenyl)-5-(furan-2-carbonyl)thiophen-3-yl)acetate |
| 84 | 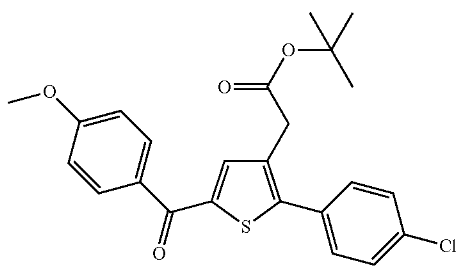 [SMILES: COc1ccc(C(=O)c2cc(CC(=O)OC(C)(C)C)c(-c3ccc(Cl)cc3)s2)cc1] | tert-butyl 2-(2-(4-chlorophenyl)-5-(4-methoxybenzoyl)thiophen-3-yl)acetate |
| 85 | 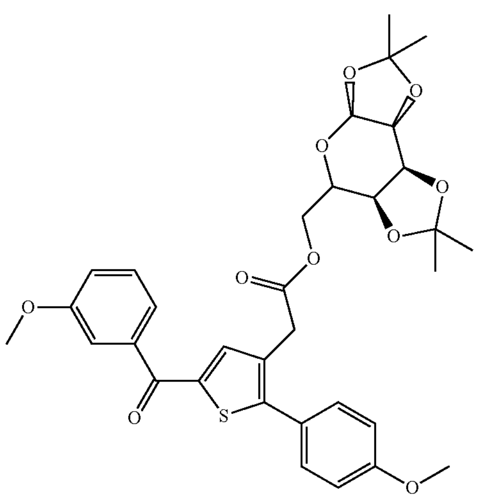 | ((3aS,5aS,8aS,8bS)-2,2,7,7-tetramethyltetrahydro-3aH-bis([1,3]dioxolo)[4,5-b:4',5'-d]pyran-5-yl)methyl 2-(5-(3-methoxy-benzoyl)-2-(4-methoxy-phenyl)thiophen-3-yl)acetate |
| 86 | 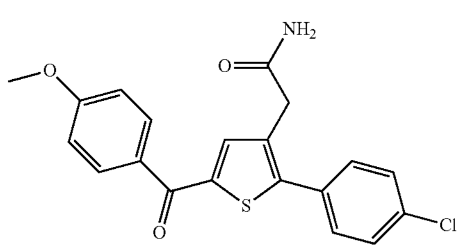 [SMILES: COc1ccc(C(=O)c2cc(CC(N)=O)c(-c3ccc(Cl)cc3)s2)cc1] | 2-(2-(4-chlorophenyl)-5-(4-methoxybenzoyl)thiophen-3-yl)acetamide |

TABLE 1-continued

List of the molecules for which the synthesis is exemplified

| No. | Chemical structure | Chemical name |
|---|---|---|
| 87 | 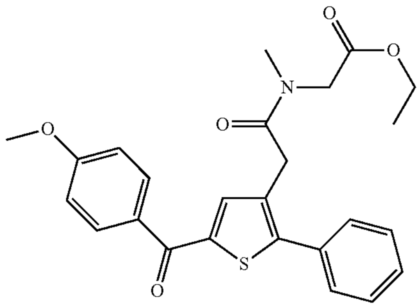 [SMILES: CCOC(=O)CN(C)C(=O)Cc1cc(C(=O)c2ccc(OC)cc2)sc1-c1ccccc1] | ethyl 2-(2-(5-(4-methoxybenzoyl)-2-phenylthiophen-3-yl)-N-methylacetamido)acetate |
| 88 | 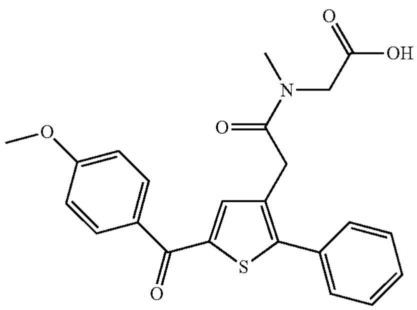 [SMILES: COc1ccc(C(=O)c2cc(CC(=O)N(C)CC(=O)O)c(-c3ccccc3)s2)cc1] | 2-(2-(5-(4-methoxybenzoyl)-2-phenylthiophen-3-yl)-N-methylacetamido)acetic acid |
| 89 | 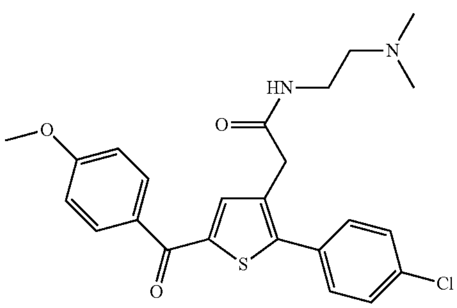 [SMILES: COc1ccc(C(=O)c2cc(CC(=O)NCCN(C)C)c(-c3ccc(Cl)cc3)s2)cc1] | 2-(2-(4-chlorophenyl)-5-(4-methoxybenzoyl)thiophen-3-yl)-N-(2-(dimethylamino)ethyl)acetamide |
| 90 | 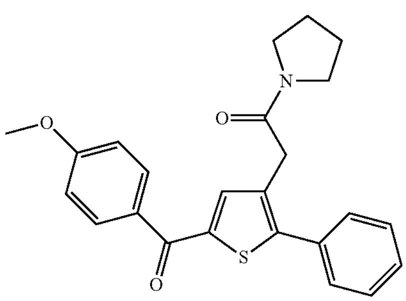 [SMILES: COc1ccc(C(=O)c2cc(CC(=O)N3CCCC3)c(-c3ccccc3)s2)cc1] | 2-(5-(4-methoxybenzoyl)-2-phenylthiophen-3-yl)-1-(pyrrolidin-1-yl)ethanone |
| 91 | 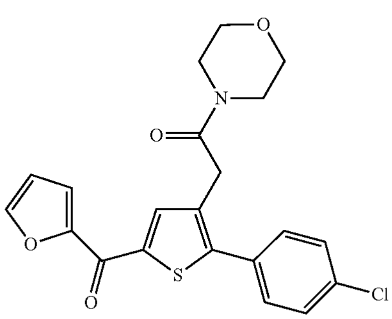 [SMILES: O=C(c1ccco1)c1cc(CC(=O)N2CCOCC2)c(-c2ccc(Cl)cc2)s1] | 2-(2-(4-chlorophenyl)-5-(furan-2-carbonyl)thiophen-3-yl)-1-morpholino ethanone |

TABLE 1-continued

List of the molecules for which the synthesis is exemplified

| No. | Chemical structure | Chemical name |
|---|---|---|
| 92 | 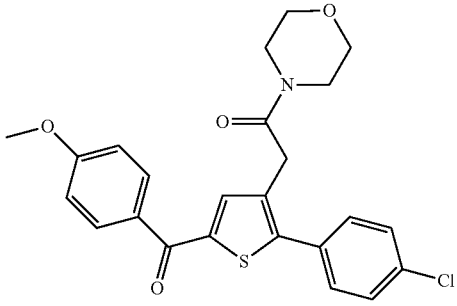 [SMILES: COc1ccc(C(=O)c2cc(CC(=O)N3CCOCC3)c(-c3ccc(Cl)cc3)s2)cc1] | 2-(2-(4-chlorophenyl)-5-(4-methoxybenzoyl)thiophen-3-yl)-1-morpholinoethanone |
| 93 | 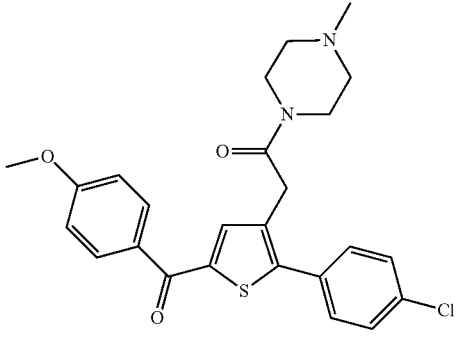 [SMILES: COc1ccc(C(=O)c2cc(CC(=O)N3CCN(C)CC3)c(-c3ccc(Cl)cc3)s2)cc1] | 2-(2-(4-chlorophenyl)-5-(4-methoxybenzoyl)thiophen-3-yl)-1-(4-methylpiperazin-1-yl)ethanone |
| 94 | 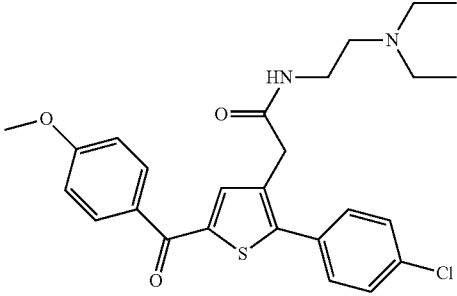 [SMILES: CCN(CC)CCNC(=O)Cc1cc(C(=O)c2ccc(OC)cc2)sc1-c1ccc(Cl)cc1] | 2-(2-(4-chlorophenyl)-5-(4-methoxybenzoyl)thiophen-3-yl)-N-(2-(diethylamino)ethyl)acetamide |
| 95 | 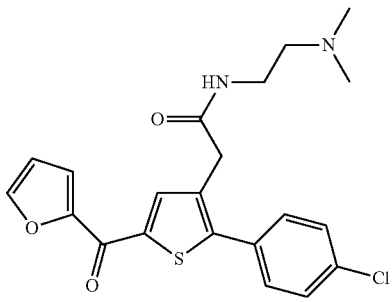 [SMILES: CN(C)CCNC(=O)Cc1cc(C(=O)c2ccco2)sc1-c1ccc(Cl)cc1] | 2-(2-(4-chlorophenyl)-5-(furan-2-carbonyl)thiophen-3-yl)-N-(2-(dimethylamino)ethyl)acetamide |
| 96 | 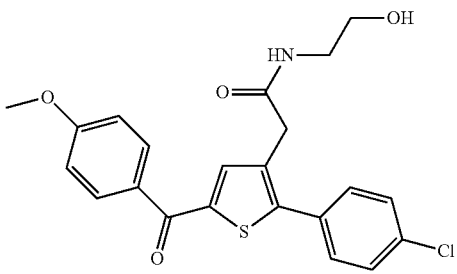 [SMILES: COc1ccc(C(=O)c2cc(CC(=O)NCCO)c(-c3ccc(Cl)cc3)s2)cc1] | 2-(2-(4-chlorophenyl)-5-(4-methoxybenzoyl)thiophen-3-yl)-N-(2-hydroxyethyl)acetamide |

TABLE 1-continued

List of the molecules for which the synthesis is exemplified

| No. | Chemical structure | Chemical name |
|---|---|---|
| 97 | 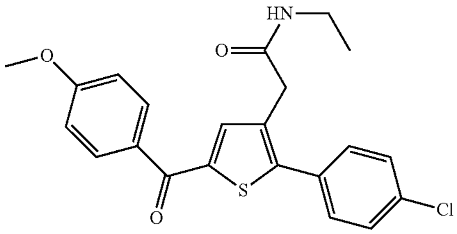 | 2-(2-(4-chlorophenyl)-5-(4-methoxybenzoyl)thiophen-3-yl)-N-ethylacetamide |
| 98 | 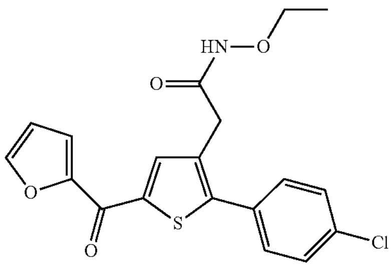 [SMILES: CCONC(=O)Cc1cc(C(=O)c2ccco2)sc1-c1ccc(Cl)cc1] | 2-(2-(4-chlorophenyl)-5-(furan-2-carbonyl)thiophen-3-yl)-N-ethoxyacetamide |
| 99 | 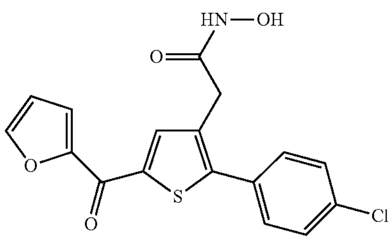 [SMILES: O=C(Cc1cc(C(=O)c2ccco2)sc1-c1ccc(Cl)cc1)NO] | 2-(2-(4-chlorophenyl)-5-(furan-2-carbonyl)thiophen-3-yl)-N-hydroxyacetamide |
| 100 | 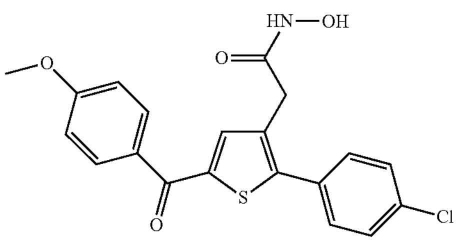 [SMILES: COc1ccc(C(=O)c2cc(CC(=O)NO)c(-c3ccc(Cl)cc3)s2)cc1] | 2-(2-(4-chlorophenyl)-5-(4-methoxybenzoyl)thiophen-3-yl)-N-hydroxyacetamide |
| 101 | 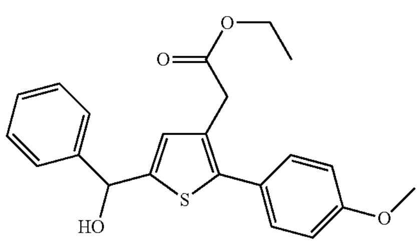 [SMILES: CCOC(=O)Cc1cc(C(O)c2ccccc2)sc1-c1ccc(OC)cc1] | ethyl 2-(5-(hydroxy(phenyl)methyl)-2-(4-methoxyphenyl)thiophen-3-yl)acetate |
| 102 | 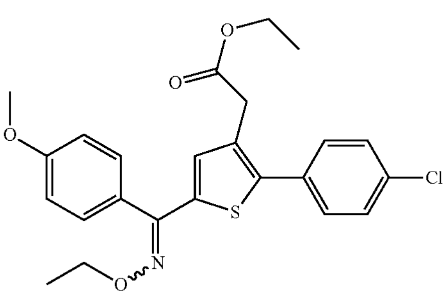 [SMILES: CCON=C(c1ccc(OC)cc1)c1cc(CC(=O)OCC)c(-c2ccc(Cl)cc2)s1] | ethyl 2-(2-(4-chlorophenyl)-5-((ethoxyimino)(4-methoxyphenyl)methyl)thiophen-3-yl)acetate |

TABLE 1-continued

List of the molecules for which the synthesis is exemplified

| No. | Chemical structure | Chemical name |
|---|---|---|
| 103 | 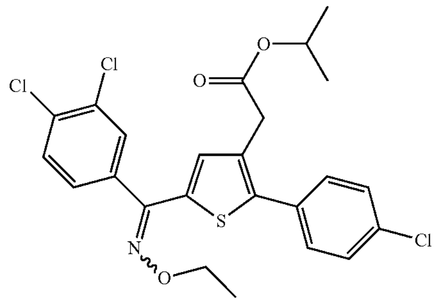 [SMILES: CCON=C(c1ccc(Cl)c(Cl)c1)c1cc(CC(=O)OC(C)C)c(-c2ccc(Cl)cc2)s1] | isopropyl 2-(2-(4-chlorophenyl)-5-((3,4-dichlorophenyl)-(ethoxyimino)methyl)thiophen-3-yl)acetate |
| 104 | 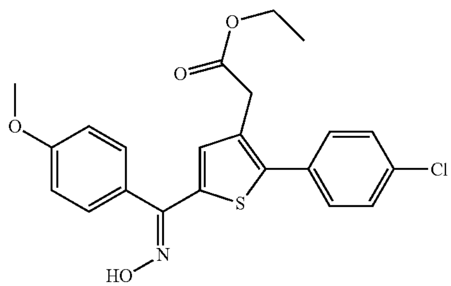 [SMILES: CCOC(=O)Cc1cc(/C(=N/O)c2ccc(OC)cc2)sc1-c1ccc(Cl)cc1] | ethyl 2-(2-(4-chlorophenyl)-5-((hydroxyimino)(4-methoxyphenyl)methyl)thiophen-3-yl)acetate |
| 105 | 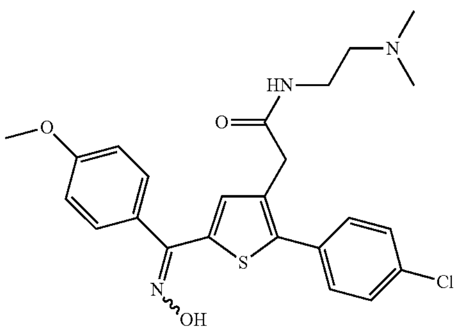 [SMILES: COc1ccc(C(=NO)c2cc(CC(=O)NCCN(C)C)c(-c3ccc(Cl)cc3)s2)cc1] | 2-(2-(4-chlorophenyl)-5-((hydroxyimino)(4-methoxyphenyl)methyl)thiophen-3-yl)-N-(2-(dimethylamino)ethyl)acetamide |
| 106 | 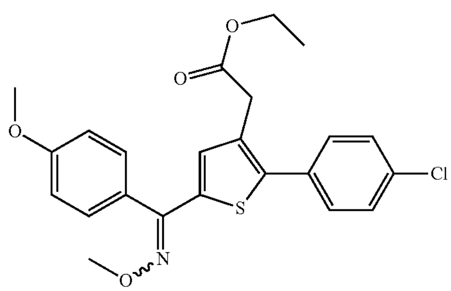 [SMILES: CCOC(=O)Cc1cc(C(=NOC)c2ccc(OC)cc2)sc1-c1ccc(Cl)cc1] | ethyl 2-(2-(4-chlorophenyl)-5-((methoxyimino)(4-methoxyphenyl)methyl)thiophen-3-yl)acetate |
| 107 | 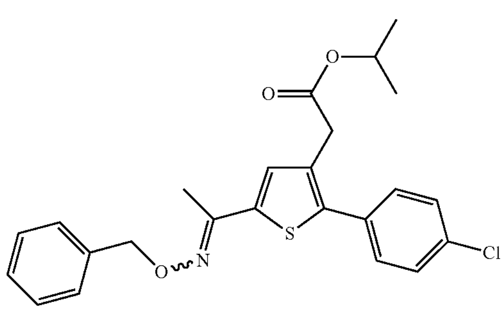 [SMILES: CC(=NOCc1ccccc1)c1cc(CC(=O)OC(C)C)c(-c2ccc(Cl)cc2)s1] | isopropyl 2-(5-(1-((benzyloxy)imino)ethyl)-2-(4-chlorophenyl)thiophen-3-yl)acetate |

TABLE 1-continued

List of the molecules for which the synthesis is exemplified

| No. | Chemical structure | Chemical name |
|---|---|---|
| 108 | 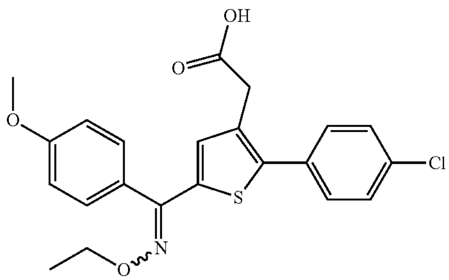 [SMILES: CCON=C(c1ccc(OC)cc1)c1cc(CC(=O)O)c(-c2ccc(Cl)cc2)s1] | 2-(2-(4-chlorophenyl)-5-((ethoxyimino)(4-methoxyphenyl)methyl)thiophen-3-yl)acetic acid |
| 109 | 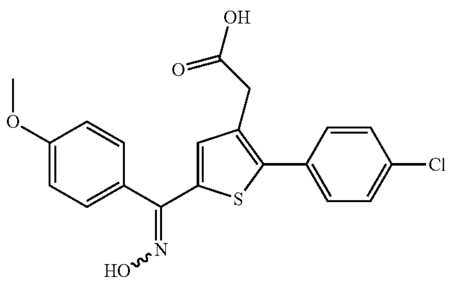 [SMILES: COc1ccc(C(=NO)c2cc(CC(=O)O)c(-c3ccc(Cl)cc3)s2)cc1] | 2-(2-(4-chlorophenyl)-5-((hydroxyimino)(4-methoxyphenyl)methyl)thiophen-3-yl)acetic acid |
| 110 | 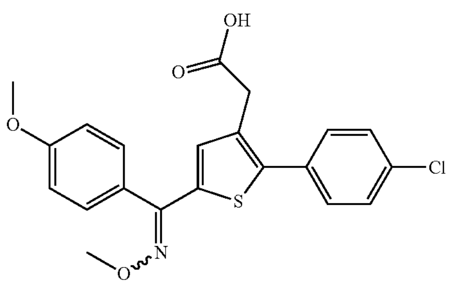 [SMILES: CON=C(c1ccc(OC)cc1)c1cc(CC(=O)O)c(-c2ccc(Cl)cc2)s1] | 2-(2-(4-chlorophenyl)-5-((methoxyimino)(4-methoxyphenyl)methyl)thiophen-3-yl)acetic acid |
| 111 | 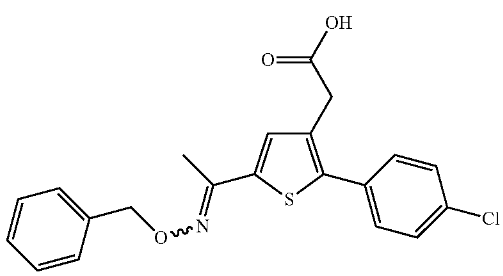 [SMILES: CC(=NOCc1ccccc1)c1cc(CC(=O)O)c(-c2ccc(Cl)cc2)s1] | 2-(5-(1-((benzyloxy)imino)ethyl)-2-(4-chlorophenyl)thiophen-3-yl)acetic acid |
| 112 | 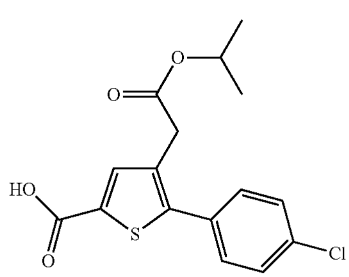 [SMILES: CC(C)OC(=O)Cc1cc(C(=O)O)sc1-c1ccc(Cl)cc1] | 5-(4-chlorophenyl)-4-(2-isopropoxy-2-oxoethyl)thiophene-2-carboxylic acid |

TABLE 1-continued

List of the molecules for which the synthesis is exemplified

| No. | Chemical structure | Chemical name |
|---|---|---|
| 113 | 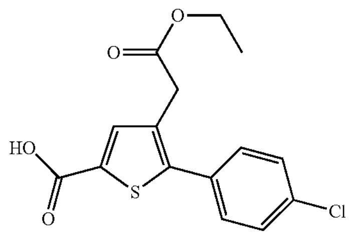 [SMILES: CCOC(=O)Cc1cc(C(=O)O)sc1-c1ccc(Cl)cc1] | 5-(4-chlorophenyl)-4-(2-ethoxy-2-oxoethyl)thiophene-2-carboxylic acid |
| 114 | 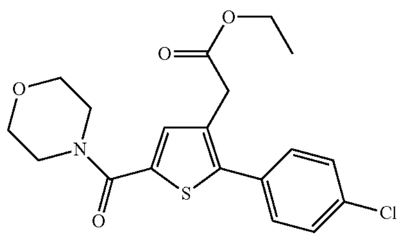 [SMILES: CCOC(=O)Cc1cc(C(=O)N2CCOCC2)sc1-c1ccc(Cl)cc1] | ethyl 2-(2-(4-chlorophenyl)-5-(morpholine-4-carbonyl)thiophen-3-yl)acetate |
| 115 | 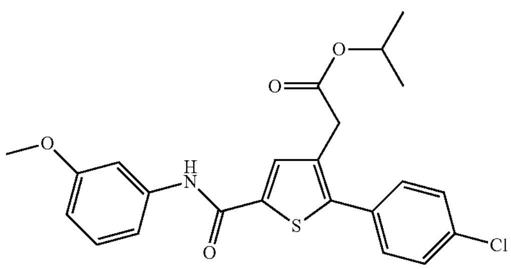 [SMILES: COc1cccc(NC(=O)c2cc(CC(=O)OC(C)C)c(-c3ccc(Cl)cc3)s2)c1] | isopropyl 2-(2-(4-chlorophenyl)-5-((3-methoxyphenyl)-carbamoyl)thiophen-3-yl)acetate |
| 116 | 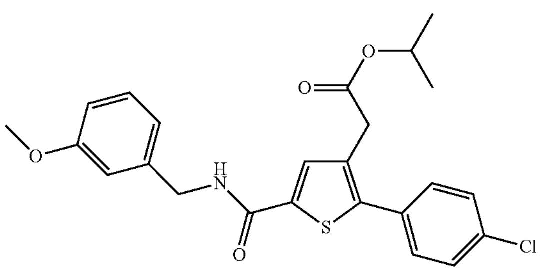 [SMILES: COc1cccc(CNC(=O)c2cc(CC(=O)OC(C)C)c(-c3ccc(Cl)cc3)s2)c1] | isopropyl 2-(2-(4-chlorophenyl)-5-((3-methoxybenzyl)-carbamoyl)thiophen-3-yl)acetate |
| 117 | 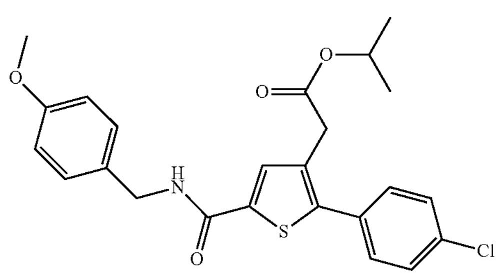 [SMILES: COc1ccc(CNC(=O)c2cc(CC(=O)OC(C)C)c(-c3ccc(Cl)cc3)s2)cc1] | isopropyl 2-(2-(4-chlorophenyl)-5-((4-methoxybenzyl)-carbamoyl)thiophen-3-yl)acetate |
| 118 | 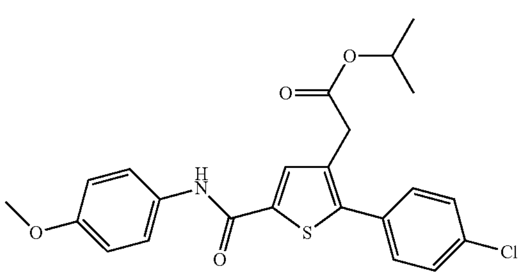 [SMILES: COc1ccc(NC(=O)c2cc(CC(=O)OC(C)C)c(-c3ccc(Cl)cc3)s2)cc1] | isopropyl 2-(2-(4-chlorophenyl)-5-((4-methoxyphenyl)-carbamoyl)thiophen-3-yl)acetate |

TABLE 1-continued

List of the molecules for which the synthesis is exemplified

| No. | Chemical structure | Chemical name |
|---|---|---|
| 119 | 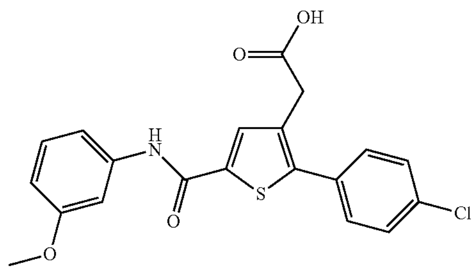 [SMILES: COc1cccc(NC(=O)c2cc(CC(=O)O)c(-c3ccc(Cl)cc3)s2)c1] | 2-(2-(4-chlorophenyl)-5-((3-methoxyphenyl)carbamoyl)thiophen-3-yl)acetic acid |
| 120 | 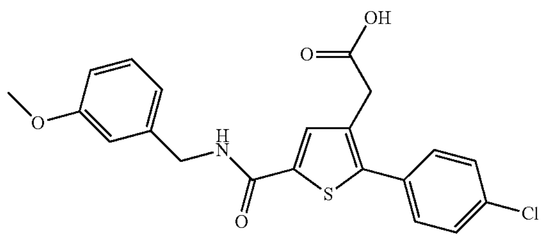 [SMILES: COc1cccc(CNC(=O)c2cc(CC(=O)O)c(-c3ccc(Cl)cc3)s2)c1] | 2-(2-(4-chlorophenyl)-5-((3-methoxybenzyl)carbamoyl)thiophen-3-yl)acetic acid |
| 121 | 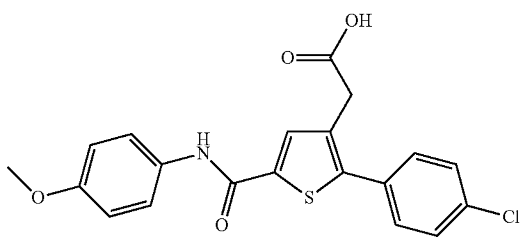 [SMILES: COc1ccc(NC(=O)c2cc(CC(=O)O)c(-c3ccc(Cl)cc3)s2)cc1] | 2-(2-(4-chlorophenyl)-5-((4-methoxyphenyl)carbamoyl)thiophen-3-yl)acetic acid |
| 122 | 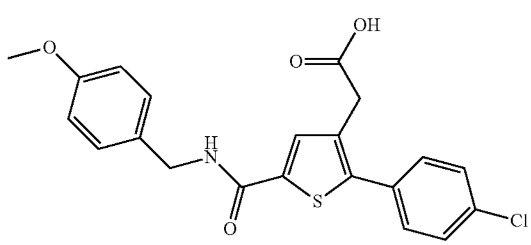 [SMILES: COc1ccc(CNC(=O)c2cc(CC(=O)O)c(-c3ccc(Cl)cc3)s2)cc1] | 2-(2-(4-chlorophenyl)-5-((4-methoxybenzyl)carbamoyl)thiophen-3-yl)acetic acid |
| 123 | 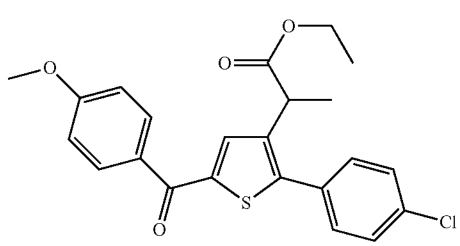 [SMILES: CCOC(=O)C(C)c1cc(C(=O)c2ccc(OC)cc2)sc1-c1ccc(Cl)cc1] | ethyl 2-(2-(4-chlorophenyl)-5-(4-methoxybenzoyl)thiophen-3-yl)propanoate |
| 124 | 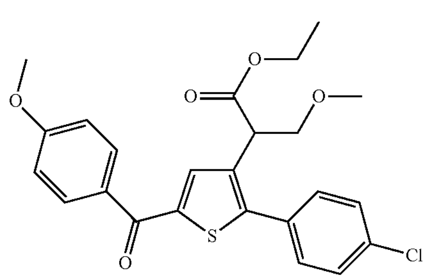 [SMILES: CCOC(=O)C(COC)c1cc(C(=O)c2ccc(OC)cc2)sc1-c1ccc(Cl)cc1] | ethyl 2-(2-(4-chlorophenyl)-5-(4-methoxybenzoyl)thiophen-3-yl)-3-methoxypropanoate |

TABLE 1-continued

List of the molecules for which the synthesis is exemplified

| No. | Chemical structure | Chemical name |
| --- | --- | --- |
| 125 | 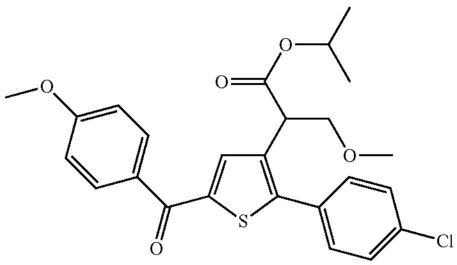 [SMILES: COCC(C(=O)OC(C)C)c1cc(C(=O)c2ccc(OC)cc2)sc1-c1ccc(Cl)cc1] | isopropyl 2-(2-(4-chlorophenyl)-5-(4-methoxybenzoyl)thiophen-3-yl)-3-methoxypropanoate |
| 126 | 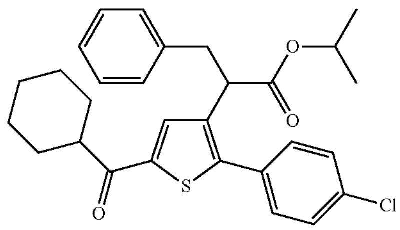 [SMILES: CC(C)OC(=O)C(Cc1ccccc1)c1cc(C(=O)C2CCCCC2)sc1-c1ccc(Cl)cc1] | isopropyl 2-(2-(4-chlorophenyl)-5-(cyclohexanecarbonyl)thiophen-3-yl)-3-phenylpropanoate |
| 127 | 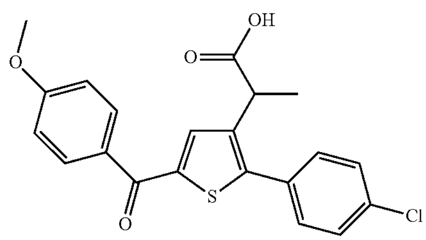 [SMILES: COc1ccc(C(=O)c2cc(C(C)C(=O)O)c(-c3ccc(Cl)cc3)s2)cc1] | 2-(2-(4-chlorophenyl)-5-(4-methoxybenzoyl)thiophen-3-yl) propanoic acid |
| 128 | 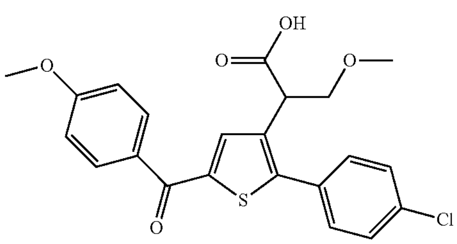 [SMILES: COCC(C(=O)O)c1cc(C(=O)c2ccc(OC)cc2)sc1-c1ccc(Cl)cc1] | 2-(2-(4-chlorophenyl)-5-(4-methoxybenzoyl)thiophen-3-yl)-3-methoxypropanoic acid |
| 129 | 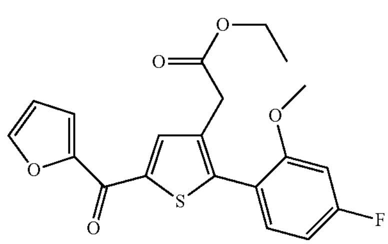 [SMILES: CCOC(=O)Cc1cc(C(=O)c2ccco2)sc1-c1ccc(F)cc1OC] | ethyl 2-(2-(4-fluoro-2-methoxyphenyl)-5-(furan-2-carbonyl)-thiophen-3-yl)acetate |
| 130 | 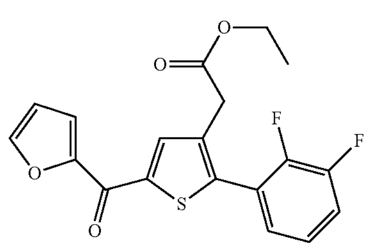 [SMILES: CCOC(=O)Cc1cc(C(=O)c2ccco2)sc1-c1cccc(F)c1F] | ethyl 2-(2-(2,3-difluorophenyl)-5-(furan-2-carbonyl)thiophen-3-yl)acetate |

TABLE 1-continued

List of the molecules for which the synthesis is exemplified

| No. | Chemical structure | Chemical name |
| --- | --- | --- |
| 131 | 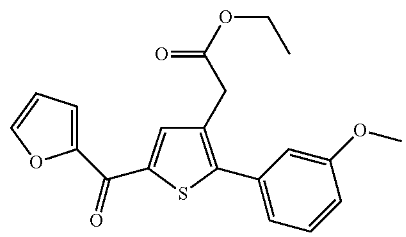 [SMILES: CCOC(=O)Cc1cc(C(=O)c2ccco2)sc1-c1cccc(OC)c1] | ethyl 2-(5-(furan-2-carbonyl)-2-(3-methoxyphenyl)thiophen-3-yl)acetate |
| 132 | 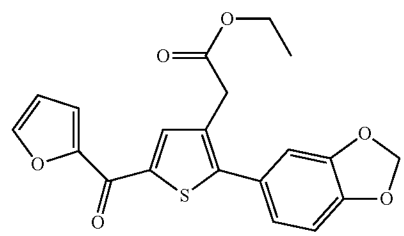 [SMILES: CCOC(=O)Cc1cc(C(=O)c2ccco2)sc1-c1ccc2c(c1)OCO2] | ethyl 2-(2-(benzo[d][1,3]dioxol-5-yl)-5-(furan-2-carbonyl)thiophen-3-yl)acetate |
| 133 | 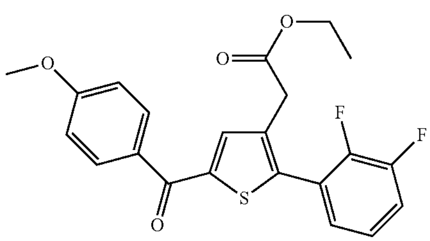 [SMILES: CCOC(=O)Cc1cc(C(=O)c2ccc(OC)cc2)sc1-c1cccc(F)c1F] | ethyl 2-(2-(2,3-difluorophenyl)-5-(4-methoxybenzoyl)thiophen-3-yl)acetate |
| 134 | 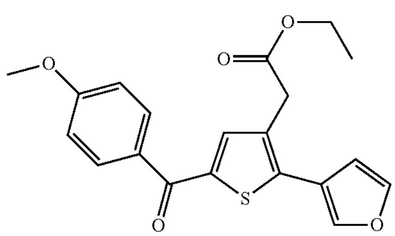 [SMILES: CCOC(=O)Cc1cc(C(=O)c2ccc(OC)cc2)sc1-c1ccoc1] | ethyl 2-(2-(furan-3-yl)-5-(4-methoxy-benzoyl)thiophen-3-yl)acetate |
| 135 | 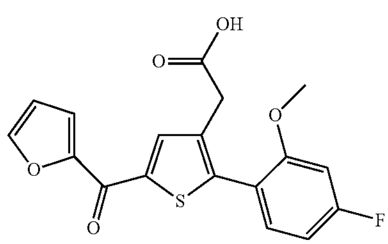 [SMILES: COc1cc(F)ccc1-c1sc(C(=O)c2ccco2)cc1CC(=O)O] | 2-(2-(4-fluoro-2-methoxyphenyl)-5-(furan-2-carbonyl)thiophen-3-yl)acetic acid |
| 136 | 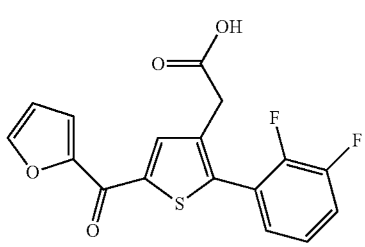 [SMILES: O=C(O)Cc1cc(C(=O)c2ccco2)sc1-c1cccc(F)c1F] | 2-(2-(2,3-difluorophenyl)-5-(furan-2-carbonyl)thiophen-3-yl)acetic acid |

TABLE 1-continued

List of the molecules for which the synthesis is exemplified

| No. | Chemical structure | Chemical name |
|---|---|---|
| 137 | 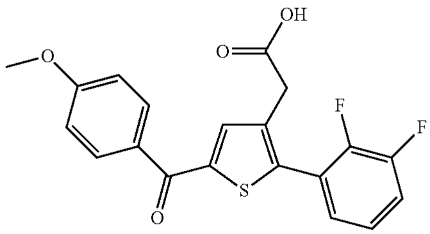 [SMILES: COc1ccc(C(=O)c2cc(CC(=O)O)c(-c3cccc(F)c3F)s2)cc1] | 2-(2-(2,3-difluorophenyl)-5-(4-methoxybenzoyl)thiophen-3-yl)acetic acid |
| 138 | 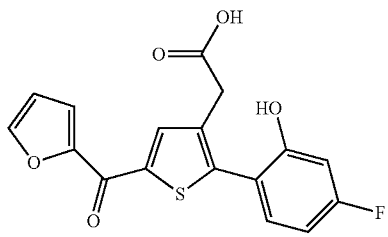 [SMILES: O=C(O)Cc1cc(C(=O)c2ccco2)sc1-c1ccc(F)cc1O] | 2-(2-(4-fluoro-2-hydroxyphenyl)-5-(furan-2-carbonyl)thiophen-3-yl)acetic acid |
| 139 | 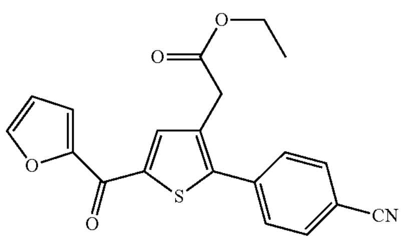 [SMILES: CCOC(=O)Cc1cc(C(=O)c2ccco2)sc1-c1ccc(C#N)cc1] | 2-(2-(4-cyanophenyl)-5-(furan-2-carbonyl)thiophen-3-yl)acetic acid |
| 140 | 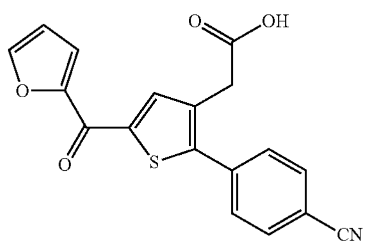 [SMILES: N#Cc1ccc(-c2sc(C(=O)c3ccco3)cc2CC(=O)O)cc1] | 2-(2-(4-cyanophenyl)-5-(furan-2-carbonyl)thiophen-3-yl)acetic acid |
| 141 | 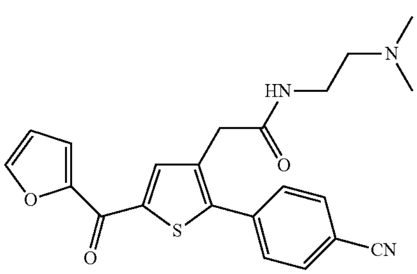 [SMILES: CN(C)CCNC(=O)Cc1cc(C(=O)c2ccco2)sc1-c1ccc(C#N)cc1] | 2-(2-(4-cyanophenyl)-5-(furan-2-carbonyl)thiophen-3-yl)-N-(2-(dimethylamino)ethyl)acetamide |
| 142 | 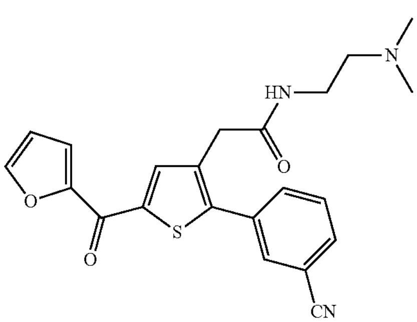 [SMILES: CN(C)CCNC(=O)Cc1cc(C(=O)c2ccco2)sc1-c1cccc(C#N)c1] | 2-(2-(3-cyanophenyl)-5-(furan-2-carbonyl)thiophen-3-yl)-N-(2-(dimethylamino)ethyl)acetamide |

TABLE 1-continued

List of the molecules for which the synthesis is exemplified

| No. | Chemical structure | Chemical name |
|---|---|---|
| 143 | 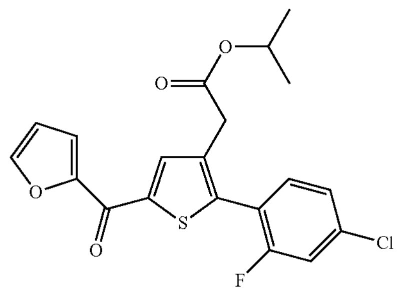 [SMILES: CC(C)OC(=O)Cc1cc(C(=O)c2ccco2)sc1-c1ccc(Cl)cc1F] | isopropyl 2-(2-(4-chloro-2-fluoro-phenyl)-5-(furan-2-carbonyl)-thiophen-3-yl)acetate |
| 144 | 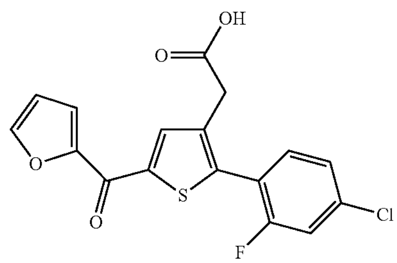 [SMILES: O=C(O)Cc1cc(C(=O)c2ccco2)sc1-c1ccc(Cl)cc1F] | 2-(2-(4-chloro-2-fluorophenyl)-5-(furan-2-carbonyl)thiophen-3-yl)acetic acid |
| 145 | 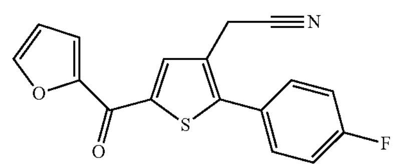 [SMILES: N#CCc1cc(C(=O)c2ccco2)sc1-c1ccc(F)cc1] | 2-(2-(4-fluorophenyl)-5-(furan-2-carbonyl)thiophen-3-yl)acetonitrile |
| 146 | 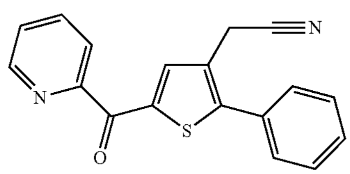 [SMILES: N#CCc1cc(C(=O)c2ccccn2)sc1-c1ccccc1] | 2-(2-phenyl-5-picolinoylthiophen-3-yl)acetonitrile |
| 147 | 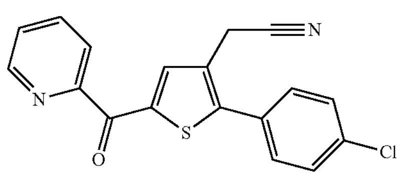 [SMILES: N#CCc1cc(C(=O)c2ccccn2)sc1-c1ccc(Cl)cc1] | 2-(2-(4-chlorophenyl)-5-picolinoylthiophen-3-yl)acetonitrile |
| 148 | 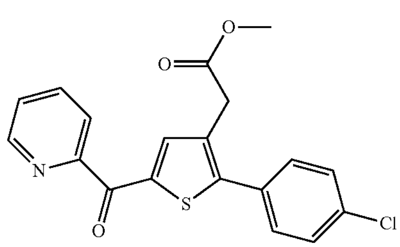 [SMILES: COC(=O)Cc1cc(C(=O)c2ccccn2)sc1-c1ccc(Cl)cc1] | methyl 2-(2-(4-chlorophenyl)-5-picolinoylthiophen-3-yl)acetate |
| 149 | 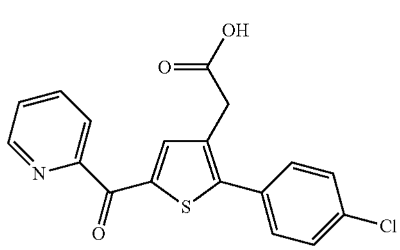 [SMILES: O=C(O)Cc1cc(C(=O)c2ccccn2)sc1-c1ccc(Cl)cc1] | 2-(2-(4-chlorophenyl)-5-picolinoylthiophen-3-yl)acetic acid |

TABLE 1-continued

List of the molecules for which the synthesis is exemplified

| No. | Chemical structure | Chemical name |
|-----|--------------------|---------------|
| 150 | 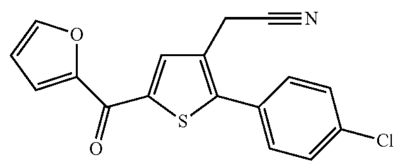 [SMILES: N#CCc1cc(C(=O)c2ccco2)sc1-c1ccc(Cl)cc1] | 2-(2-(4-chlorophenyl)-5-(furan-2-carbonyl)thiophen-3-yl)acetonitrile |
| 151 | 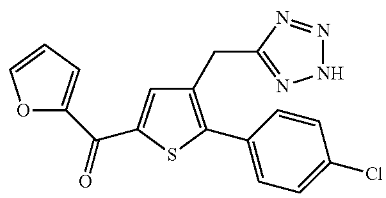 [SMILES: O=C(c1ccco1)c1cc(Cc2nn[nH]n2)c(-c2ccc(Cl)cc2)s1] | (4-((2H-tetrazol-5-yl)methyl)-5-(4-chlorophenyl)thiophen-2-yl)(furan-2-yl)methanone |
| 152 | 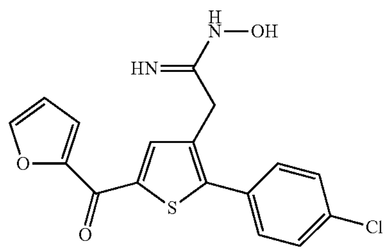 [SMILES: N=C(Cc1cc(C(=O)c2ccco2)sc1-c1ccc(Cl)cc1)NO] | 2-(2-(4-chlorophenyl)-5-(furan-2-carbonyl)thiophen-3-yl)-N-hydroxyacetimidamide |
| 153 | 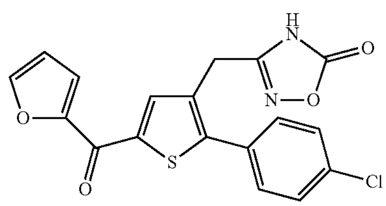 [SMILES: O=C(c1ccco1)c1cc(Cc2noc(=O)[nH]2)c(-c2ccc(Cl)cc2)s1] | 3-((2-(4-chlorophenyl)-5-(furan-2-carbonyl)thiophen-3-yl)methyl)-2,2,4-oxadiazol-5(4H)-one |
| 154 | 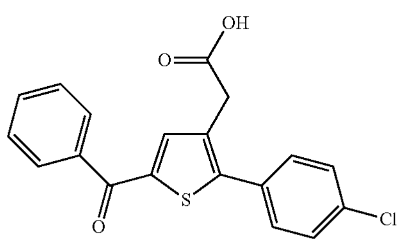 [SMILES: O=C(O)Cc1cc(C(=O)c2ccccc2)sc1-c1ccc(Cl)cc1] | 2-[5-benzoyl-2-(4-chlorophenyl)-3-thienyl]acetic acid |
| 155 | 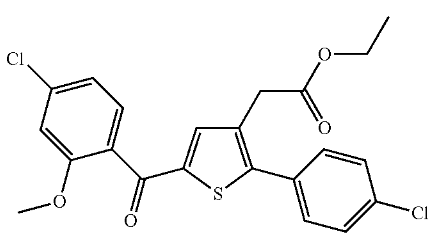 [SMILES: CCOC(=O)Cc1cc(C(=O)c2ccc(Cl)cc2OC)sc1-c1ccc(Cl)cc1] | ethyl 2-[5-(4-chloro-2-methoxy-benzoyl)-2-(4-chlorophenyl)-3-thienyl]acetate |
| 156 | 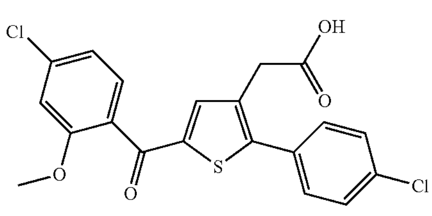 [SMILES: COc1cc(Cl)ccc1C(=O)c1cc(CC(=O)O)c(-c2ccc(Cl)cc2)s1] | 2-[5-(4-chloro-2-methoxy-benzoyl)-2-(4-chlorophenyl)-3-thienyl]acetic acid |

TABLE 1-continued

List of the molecules for which the synthesis is exemplified

| No. | Chemical structure | Chemical name |
|---|---|---|
| 157 | 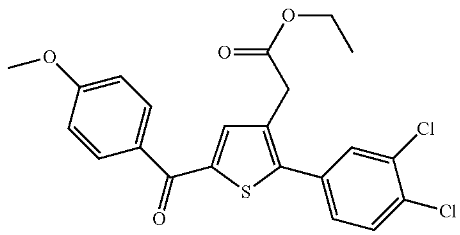 [SMILES: CCOC(=O)Cc1cc(C(=O)c2ccc(OC)cc2)sc1-c1ccc(Cl)c(Cl)c1] | ethyl 2-[2-(3,4-dichlorophenyl)-5-(4-methoxybenzoyl)-3-thienyl]acetate |
| 158 | 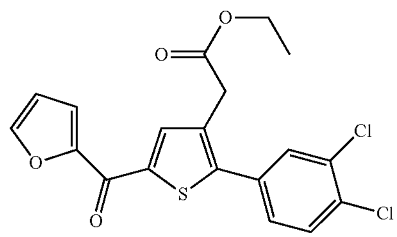 [SMILES: CCOC(=O)Cc1cc(C(=O)c2ccco2)sc1-c1ccc(Cl)c(Cl)c1] | ethyl 2-[2-(3,4-dichlorophenyl)-5-(furan-2-carbonyl)-3-thienyl]acetate |
| 159 | 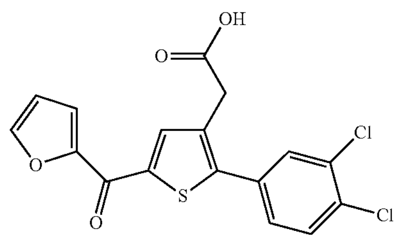 [SMILES: O=C(O)Cc1cc(C(=O)c2ccco2)sc1-c1ccc(Cl)c(Cl)c1] | 2-[2-(3,4-dichlorophenyl)-5-(furan-2-carbonyl)-3-thienyl]acetic acid |
| 160 | 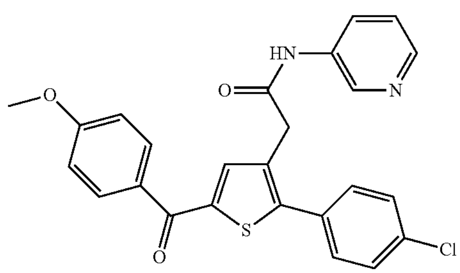 [SMILES: COc1ccc(C(=O)c2cc(CC(=O)Nc3cccnc3)c(-c3ccc(Cl)cc3)s2)cc1] | 2-[2-(4-chlorophenyl)-5-(4-methoxybenzoyl)-3-thienyl]-N-(3-pyridyl)acetamide |
| 161 | 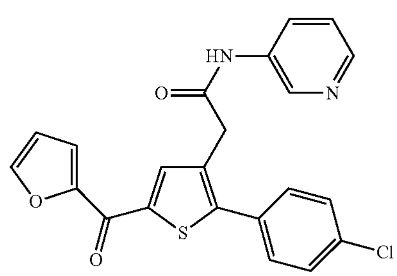 [SMILES: O=C(Cc1cc(C(=O)c2ccco2)sc1-c1ccc(Cl)cc1)Nc1cccnc1] | 2-[2-(4-chlorophenyl)-5-(furan-2-carbonyl)-3-thienyl]-N-(3-pyridyl)acetamide |
| 162 | 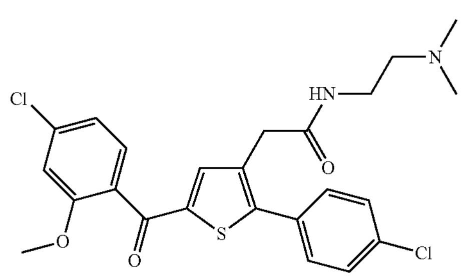 | 2-[5-(4-chloro-2-methoxy-benzoyl)-2-(4-chlorophenyl)-3-thienyl]-N-(2-dimethylaminoethyl)acetamide |

TABLE 1-continued

List of the molecules for which the synthesis is exemplified

| No. | Chemical structure | Chemical name |
|---|---|---|
| 163 | 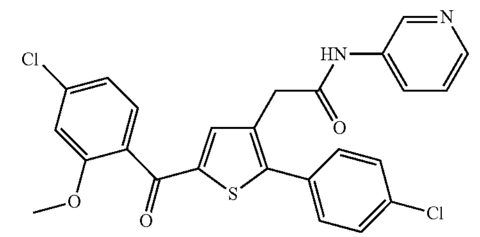 [SMILES: COc1cc(Cl)ccc1C(=O)c1cc(CC(=O)Nc2cccnc2)c(-c2ccc(Cl)cc2)s1] | 2-[5-(4-chloro-2-methoxy-benzoyl)-2-(4-chlorophenyl)-3-thienyl]-N-(3-pyridyl)acetamide |
| 164 | 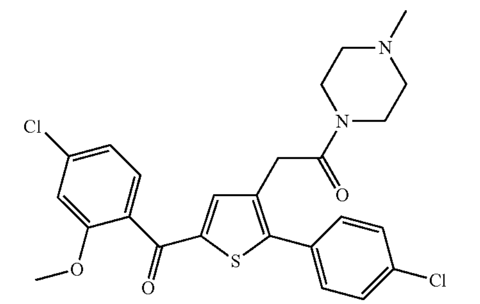 [SMILES: COc1cc(Cl)ccc1C(=O)c1cc(CC(=O)N2CCN(C)CC2)c(-c2ccc(Cl)cc2)s1] | 2-[5-(4-chloro-2-methoxy-benzoyl)-2-(4-chlorophenyl)-3-thienyl]-1-(4-methylpiperazin-1-yl)ethanone |
| 165 | 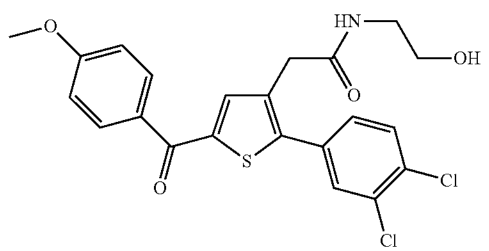 [SMILES: COc1ccc(C(=O)c2cc(CC(=O)NCCO)c(-c3ccc(Cl)c(Cl)c3)s2)cc1] | 2-[2-(3,4-dichlorophenyl)-5-(4-methoxybenzoyl)-3-thienyl]-N-(2-hydroxyethyl)acetamide |
| 166 | 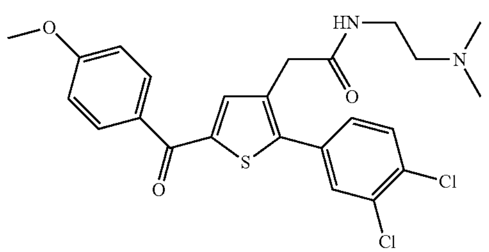 | 2-[2-(3,4-dichlorophenyl)-5-(4-methoxybenzoyl)-3-thienyl]-N-(2-dimethylaminoethyl)acetamide |
| 167 | 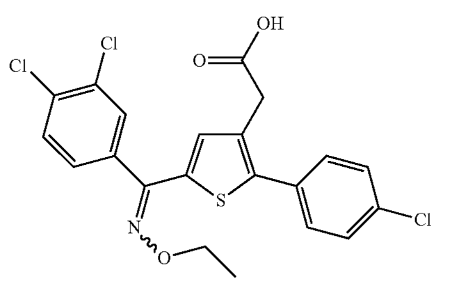 [SMILES: CCON=C(c1ccc(Cl)c(Cl)c1)c1cc(CC(=O)O)c(-c2ccc(Cl)cc2)s1] | 2-[2-(4-chlorophenyl)-5-[C-(3,4-dichlorophenyl)-N-ethoxy-carbonimidoyl]-3-thienyl]acetic acid |
| 168 | 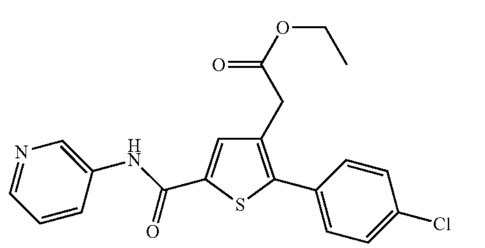 [SMILES: CCOC(=O)Cc1cc(C(=O)Nc2cccnc2)sc1-c1ccc(Cl)cc1] | ethyl 2-[2-(4-chlorophenyl)-5-(3-pyridylcarbamoyl)-3-thienyl]acetate |

TABLE 1-continued

List of the molecules for which the synthesis is exemplified

| No. | Chemical structure | Chemical name |
| --- | --- | --- |
| 169 | 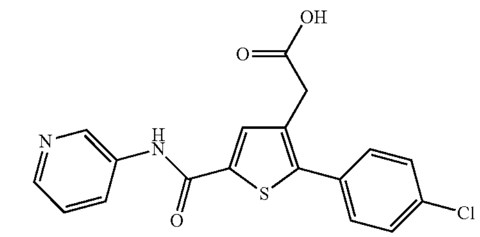 [SMILES: O=C(O)Cc1cc(C(=O)Nc2cccnc2)sc1-c1ccc(Cl)cc1] | 2-[2-(4-chlorophenyl)-5-(3-pyridylcarbamoyl)-3-thienyl]acetic acid |
| 170 | 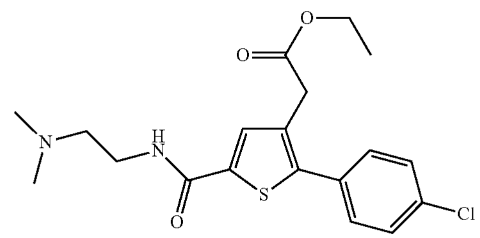 [SMILES: CCOC(=O)Cc1cc(C(=O)NCCN(C)C)sc1-c1ccc(Cl)cc1] | ethyl 2-[2-(4-chlorophenyl)-5-(2-dimethylaminoethylcarbamoyl)-3-thienyl]acetate |
| 171 | 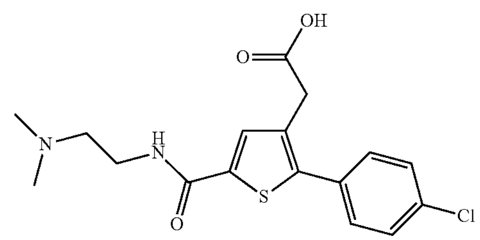 [SMILES: CN(C)CCNC(=O)c1cc(CC(=O)O)c(-c2ccc(Cl)cc2)s1] | 2-[2-(4-chlorophenyl)-5-(2-dimethylaminoethylcarbamoyl)-3-thienyl]acetic acid |
| 172 | 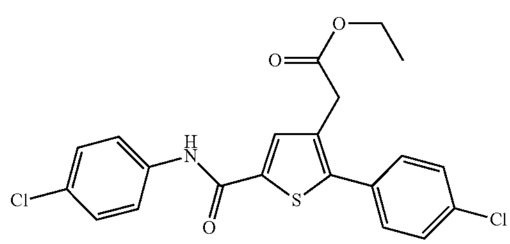 [SMILES: CCOC(=O)Cc1cc(C(=O)Nc2ccc(Cl)cc2)sc1-c1ccc(Cl)cc1] | ethyl 2-[2-(4-chlorophenyl)-5-[(4-chlorophenyl)carbamoyl]-3-thienyl]acetate |
| 173 | 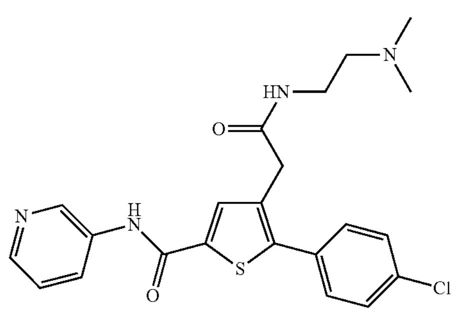 [SMILES: CN(C)CCNC(=O)Cc1cc(C(=O)Nc2cccnc2)sc1-c1ccc(Cl)cc1] | 5-(4-chlorophenyl)-4-[2-(2-dimethylaminoethylamino)-2-oxo-ethyl]-N-(3-pyridyl)thiophene-2-carboxamide |
| 174 | 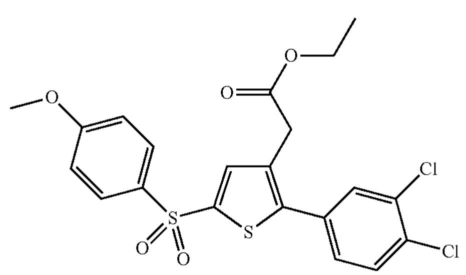 [SMILES: CCOC(=O)Cc1cc(S(=O)(=O)c2ccc(OC)cc2)sc1-c1ccc(Cl)c(Cl)c1] | ethyl 2-[2-(3,4-dichlorophenyl)-5-(4-methoxyphenyl)sulfonyl-3-thienyl]acetate |

TABLE 1-continued

List of the molecules for which the synthesis is exemplified

| No. | Chemical structure | Chemical name |
|-----|-------------------|---------------|
| 175 | 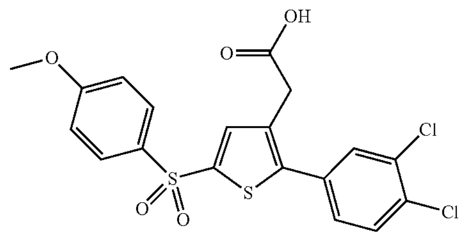 [SMILES: COc1ccc(S(=O)(=O)c2cc(CC(=O)O)c(-c3ccc(Cl)c(Cl)c3)s2)cc1] | 2-[2-(3,4-dichlorophenyl)-5-(4-methoxyphenyl)sulfonyl-3-thienyl]acetic acid |
| 176 | 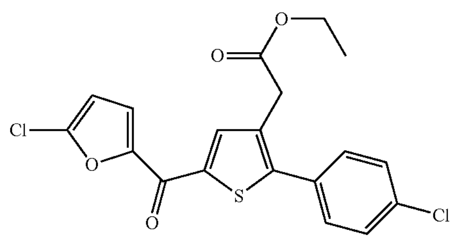 [SMILES: CCOC(=O)Cc1cc(C(=O)c2ccc(Cl)o2)sc1-c1ccc(Cl)cc1] | ethyl 2-[5-(5-chlorofuran-2-carbonyl)-2-(4-chlorophenyl)-3-thienyl]acetate |
| 177 | 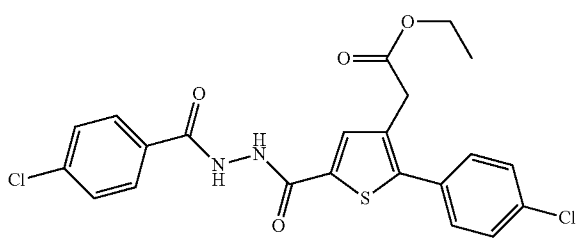 [SMILES: CCOC(=O)Cc1cc(C(=O)NNC(=O)c2ccc(Cl)cc2)sc1-c1ccc(Cl)cc1] | ethyl 2-[5-[[(4-chlorobenzoyl)-amino]carbamoyl]-2-(4-chlorophenyl)-3-thienyl]acetate |
| 178 | 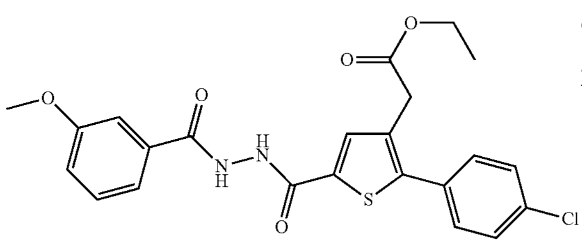 [SMILES: CCOC(=O)Cc1cc(C(=O)NNC(=O)c2cccc(OC)c2)sc1-c1ccc(Cl)cc1] | ethyl 2-[2-(4-chlorophenyl)-5-[[(3-methoxybenzoyl)-amino]carbamoyl]-3-thienyl]acetate |
| 179 | 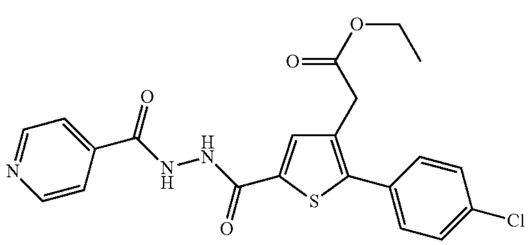 [SMILES: CCOC(=O)Cc1cc(C(=O)NNC(=O)c2ccncc2)sc1-c1ccc(Cl)cc1] | ethyl 2-[2-(4-chlorophenyl)-5-[(pyridine-4-carbonyl-amino)-carbamoyl]-3-thienyl]acetate |
| 180 | 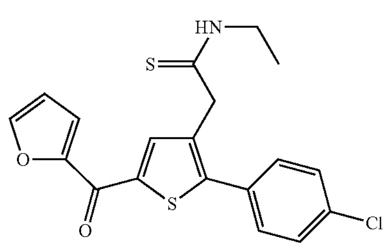 [SMILES: CCNC(=S)Cc1cc(C(=O)c2ccco2)sc1-c1ccc(Cl)cc1] | 2-[2-(4-chlorophenyl)-5-(furan-2-carbonyl)-3-thienyl]-N-ethyl-thioacetamide |

TABLE 1-continued

List of the molecules for which the synthesis is exemplified

| No. | Chemical structure | Chemical name |
|---|---|---|
| 181 | 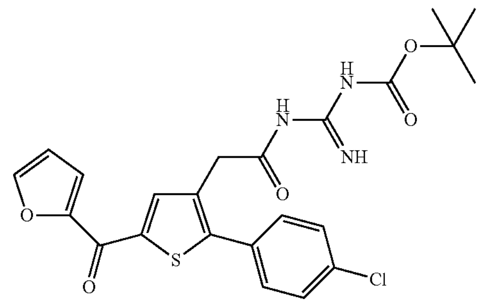 [SMILES: CC(C)(C)OC(=O)NC(=N)NC(=O)Cc1cc(C(=O)c2ccco2)sc1-c1ccc(Cl)cc1] | tert-butyl N-[N-[2-[2-(4-chloro-phenyl)-5-(furan-2-carbonyl)-3-thienyl]acetyl]carbamimidoyl]carbamate |
| 182 | 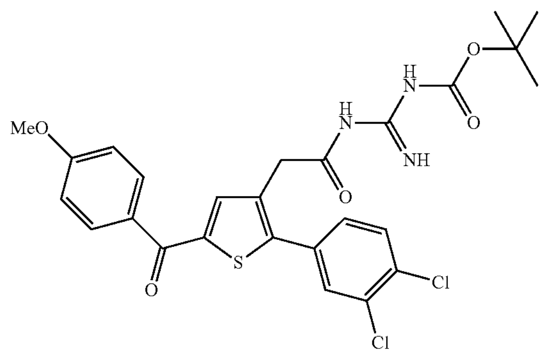 [SMILES: COc1ccc(C(=O)c2cc(CC(=O)NC(=N)NC(=O)OC(C)(C)C)c(-c3ccc(Cl)c(Cl)c3)s2)cc1] | tert-butyl N-[N-[2-[2-(3,4-dichloro-phenyl)-5-(4-methoxy-benzoyl)-3-thienyl]acetyl]-carbamimidoyl]carbamate |
| 183 | 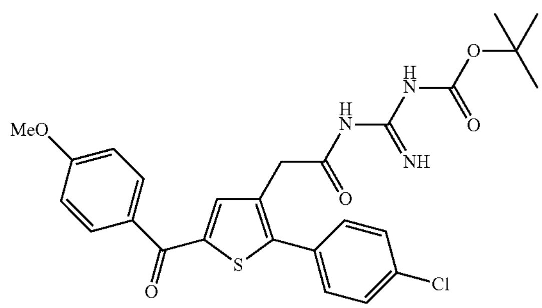 [SMILES: COc1ccc(C(=O)c2cc(CC(=O)NC(=N)NC(=O)OC(C)(C)C)c(-c3ccc(Cl)cc3)s2)cc1] | tert-butyl N-[N-[2-[2-(4-chloro-phenyl)-5-(4-methoxybenzoyl)-3-thienyl]acetyl]-carbamimidoyl]-carbamate |
| 184 | 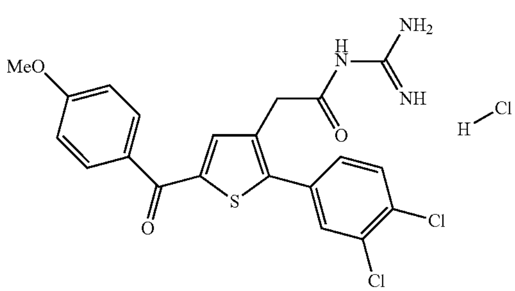 [SMILES: COc1ccc(C(=O)c2cc(CC(=O)NC(=N)N)c(-c3ccc(Cl)c(Cl)c3)s2)cc1 ; Cl] | N-carbamimidoyl-2-[2-(3,4-dichlorophenyl)-5-(4-methoxybenzoyl)-3-thienyl]acetamide hydrochloride |
| 185 | 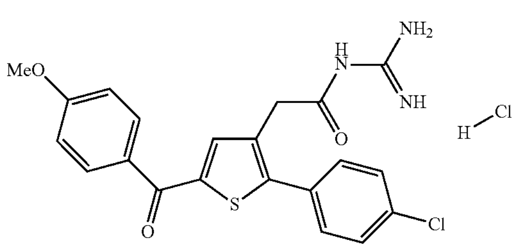 [SMILES: COc1ccc(C(=O)c2cc(CC(=O)NC(=N)N)c(-c3ccc(Cl)cc3)s2)cc1 ; Cl] | N-carbamimidoyl-2-[2-(4-chlorophenyl)-5-(4-methoxybenzoyl)-3-thienyl]acetamide hydrochloride |

TABLE 1-continued

List of the molecules for which the synthesis is exemplified

| No. | Chemical structure | Chemical name |
|---|---|---|
| 186 | 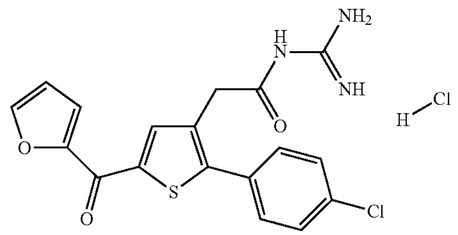 [SMILES: N=C(N)NC(=O)Cc1cc(C(=O)c2ccco2)sc1-c1ccc(Cl)cc1 ; Cl] | N-carbamimidoyl-2-[2-(4-chlorophenyl)-5-(furan-2-carbonyl)-3-thienyl]acetamide hydrochloride |
| 187 | 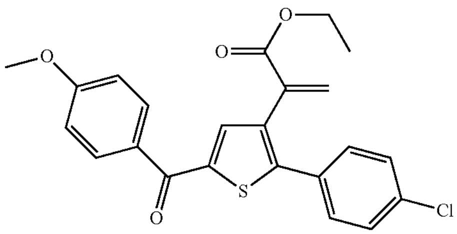 [SMILES: C=C(C(=O)OCC)c1cc(C(=O)c2ccc(OC)cc2)sc1-c1ccc(Cl)cc1] | ethyl 2-[2-(4-chlorophenyl)-5-(4-methoxybenzoyl)-3-thienyl]prop-2-enoate |

Example 1: Preparation of derivative No. 1: ethyl 2-(5-(4-methoxy benzoyl)-2-(4-methoxyphenyl) thiophen-3-yl)acetate

Step 1: Preparation of ethyl 4-methoxyphenyl-4-oxobutanoate

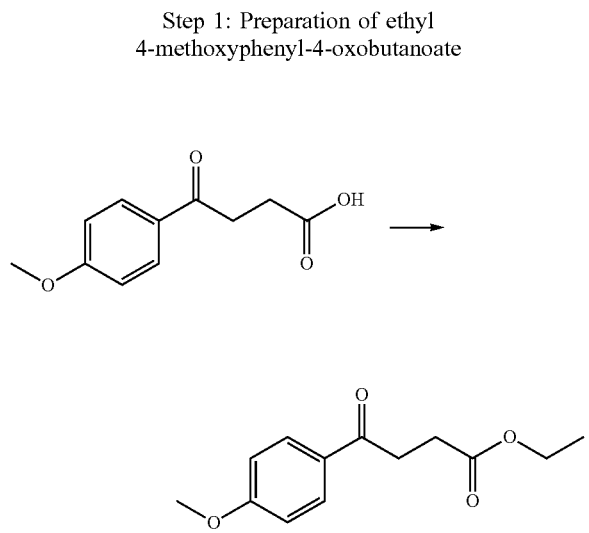

50 g (240 mmol) of a 4-methoxyphenyl-4-oxobutanoic acid were solubilized in 320 ml of ethanol, 0.64 ml (12 mmol) of sulfuric acid were added to this solution. The mixture was refluxed with heating for 16 h with magnetic stirring. After returning to r.t., the mixture was concentrated in vacuo, the crude residue was directly purified by flash chromatography on a silica gel cartridge (eluent: 100% dichloromethane). 54.04 g (yield=95%) of ethyl 4-methoxyphenyl-4-oxobutanoate were obtained as a colorless oil. LC-MS: m/z=237 (MH$^+$) UV purity at 254 nm=84%. $^1$H NMR (300 MHz, DMSO) δ 7.97 (d, J=8.9 Hz, 2H), 7.05 (d, J=8.9 Hz, 2H), 4.05 (q, J=7.1 Hz, 2H), 3.85 (s, 3H), 3.30-3.18 (m, 2H), 2.69-2.56 (m, 2H), 1.18 (t, J=7.1 Hz, 3H).

Step 2: Preparation of ethyl (Z/E)-4-chloro-3-formyl-4-(4-methoxyphenyl)but-3-enoate

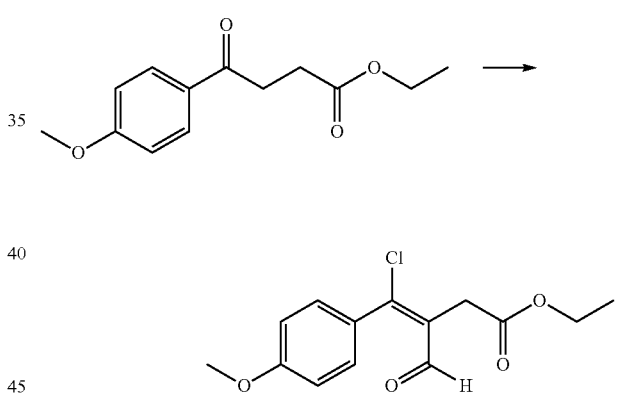

54.8 g (228 mmol) of ethyl 4-methoxyphenyl-4-oxobutanoate were solubilized in 52.9 ml of dimethylformamide (683 mmol), 53.1 ml (569 mmol) of phosphoryl trichloride were slowly added to this solution, the reaction being very exothermic. The obtained mixture was heated to 80° C. for 3 h with magnetic stirring. After returning to r.t., the mixture was poured on 1 L of a mixture consisting of water and ice. The aqueous phase was extracted with 2×200 ml of ethyl acetate. The combined organic phases were washed with 300 ml of water, and then dried on Na$_2$SO$_4$ which was then removed by filtration and the obtained filtrate was concentrated in vacuo. The crude residue was purified by flash chromatography on a silica gel cartridge (eluent: 100% dichloromethane). 57 g (yield=75%) of ethyl (Z/E)-4-chloro-3-formyl-4-(4-methoxyphenyl)but-3-enoate were obtained as an orangey oil. LC-MS: m/z=283 (MH$^+$) UV purity at 254 nm=93%. $^1$H NMR (300 MHz, DMSO) δ 9.37 (s, 1H), 7.50 (d, J=8.8 Hz, 2H), 7.08 (d, J=8.8 Hz, 2H), 4.12 (d, J=7.1 Hz, 2H), 3.84 (s, 3H), 3.55 (s, 2H), 1.19 (t, J=7.1 Hz, 3H).

Step 3: Preparation of ethyl 2-(2-(4-methoxyphenyl)thiophen-3-yl)acetate

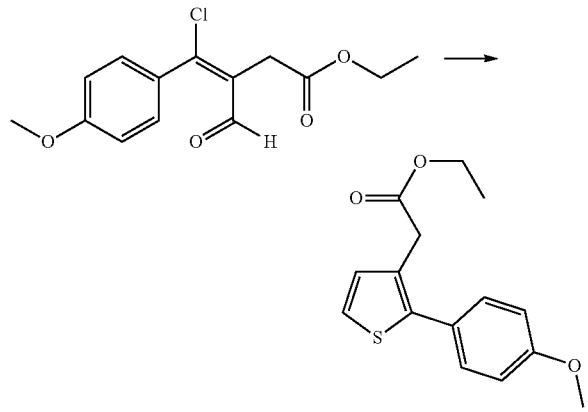

57 g (189 mmol) of ethyl (Z/E)-4-chloro-3-formyl-4-(4-methoxyphenyl)but-3-enoate were solubilized in 400 ml of tetrahydrofurane. To this solution were added 19.71 ml (284 mmol) of 2-mercapto acetic acid and 79 ml (567 mmol) of triethylamine. The obtained mixture was refluxed with heating for 6 h with magnetic stirring. After returning to r.t., the mixture was concentrated in vacuo. The residue was taken up into 200 ml of dimethylformamide and the mixture was heated to 130° C. for 2 h with magnetic stirring. After returning to r.t., the mixture was treated with 600 ml of water. The aqueous phase was extracted with 2×200 ml of ethyl acetate. The combined organic phases were washed with 2×200 ml of water, 300 ml of a saturated NaCl aqueous solution, and then dried on $Na_2SO_4$ which was then removed by filtration and the obtained filtrate was concentrated in vacuo. The crude residue was purified by flash chromatography on a silica gel cartridge (eluent: cyclohexane/dichloromethane, 3/1, v/v). 29.09 g (yield=53%) of ethyl 2-(2-(4-methoxyphenyl)thiophen-3-yl)acetate were obtained as a colorless oil. LC-MS: m/z=277 (MH+) UV purity at 254 nm=98%. $^1$H NMR (300 MHz, DMSO) δ 7.46 (d, J=5.2 Hz, 1H), 7.36 (d, J=8.7 Hz, 2H), 7.03 (t, J=6.5 Hz, 3H), 4.07 (q, J=7.1 Hz, 2H), 3.79 (s, 3H), 3.62 (s, 2H), 1.16 (t, J=7.1 Hz, 3H). NB: A different treatment is described in Example 15 (step 3) and allows isolation of the byproduct of the 1.5 type described in Scheme 1.

Step 4: Preparation of ethyl 2-(5-(4-methoxybenzoyl)-2-(4-methoxyphenyl)thiophen-3-yl)acetate (derivative No. 1)

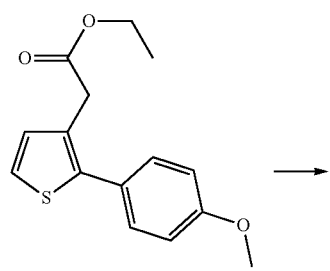

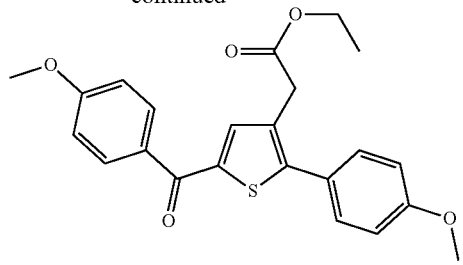

In a flask placed under an argon flow, were introduced with magnetic stirring: 5 ml of dichloromethane, 0.5 g (1.809 mmol) of ethyl 2-(2-(4-methoxyphenyl)thiophen-3-yl)acetate and 0.367 ml (2.71 mmol) of 4-methoxybenzoyl chloride. The mixture was then placed at 5° C. with magnetic stirring and 0.362 g (2.71 mmol) of aluminium chloride were added portionwise. The obtained mixture was stirred at r.t. for 5 d and then poured onto ice and stirred for 1 h. The aqueous phase was extracted with 2×20 ml of dichloromethane. The combined organic phases were dried on $Na_2SO_4$ which was then removed by filtration and the obtained filtrate was concentrated in vacuo. The crude residue was purified by flash chromatography on a silica gel cartridge (eluent: cyclohexane/dichloromethane gradient, 100% to 0% of cyclohexane, v/v). 0.652 g (yield=87%) of ethyl 2-(5-(4-methoxy benzoyl)-2-(4-methoxyphenyl)thiophen-3-yl)acetate were obtained as a pale brown oil. LC-MS: m/z=411 (MH+) UV purity at 254 nm=99%. $^1$H NMR (300 MHz, DMSO) δ 7.87 (d, J=8.8 Hz, 2H), 7.70 (s, 1H), 7.46 (d, J=8.8 Hz, 2H), 7.10 (dd, 3=13.7, 8.9 Hz, 4H), 4.06 (q, J=7.1 Hz, 2H), 3.87 (s, 3H), 3.81 (s, 3H), 3.74 (s, 2H), 1.14 (t, J=7.1 Hz, 3H).

The derivatives 2 to 43, 155, 157 and 158 were prepared according to the same sequence of steps 1 to 4:

| No. | Molecular weight g/mol | Aspect | LCMS purity UV at 254 nm | Mass spectrometry m/z MH+ | M−H+ | $^1$H NMR (300 MHz, DMSO) δ |
|---|---|---|---|---|---|---|
| 2 | 370.85 | colorless oil | 99 | 371 | | 7.75-7.85 (m, 4H), 7.60-7.67 (m, 1H), 7.45-7.55 (m, 5H), 3.79 (s, 3H), 3.59 (s, 3H) |
| 3 | 326.06 | Oil | 99 | 327 | | 8.17 (dd, J = 5.8, 5.0 Hz, 2H), 7.66-7.38 (m, 6H), 6.84 (dd, J = 3.6, 1.7 Hz, 1H), 3.81 (s, 2H), 3.62 (s, 3H). |
| 4 | 366.09 | Oil | 94.7 | 367 | | 7.76 (s, 1H), 7.58-7.11 (m, 9H), 3.84 (s, 3H), 3.79 (d, J = 2.8 Hz, 2H), 3.58 (s, 3H). |
| 5 | 366.09 | Solid | 99 | 367 | | 7.89 (d, J = 8.8 Hz, 2H), 7.73 (s, 1H), 7.52 (s, 5H), 7.13 (d, J = 8.8 Hz, 2H), 3.87 (s, 3H), 3.78 (s, 2H), 3.59 (s, 3H). |
| 6 | 342.13 | Oil | 95.6 | 343 | | 7.97 (s, 1H), 7.49 (s, 5H), 3.75 (s, 2H), 3.61 (s, 3H), 3.24 (s, 1H), 1.76 (s, 6H), 1.39 (s, 4H). |
| 7 | 336.08 | Solid | 97.5 | 337 | | 7.91-7.82 (m, 2H), 7.74 (s, 2H), 7.65-7.44 (m, 7H), 3.79 (s, 2H), 3.59 (s, 3H). |

| No. | Molecular weight g/mol | Aspect | LCMS purity UV at 254 nm | Mass spectrometry m/z MH+ / M−H+ | ¹H NMR (300 MHz, DMSO) δ |
|---|---|---|---|---|---|
| 8 | 368.09 | Oil | 98.8 | 369 | 8.09 (s, 1H), 7.49 (s, 5H), 7.34 (s, 2H), 7.16 (s, 2H), 4.31 (s, 2H), 3.76 (s, 2H), 3.62 (s, 3H). |
| 9 | 350.10 | Solid | 99 | 351 | 8.09 (s, 1H), 7.49 (s, 5H), 7.40-7.18 (m, 5H), 4.28 (s, 2H), 3.75 (s, 2H), 3.61 (s, 3H). |
| 10 | 374.04 | Oil | 92.6 | 375 | 8.19 (s, 2H), 7.58 (d, J = 3.1 Hz, 5H), 6.85 (dd, J = 3.6, 1.7 Hz, 1H), 4.07 (d, J = 7.1 Hz, 2H), 3.80 (s, 2H), 1.15 (s, 3H). |
| 11 | 418.02 | Oil | 95.8 | 419 | 7.88-7.70 (m, 4H), 7.58 (t, J = 8.1 Hz, 5H), 4.03 (d, J = 7.1 Hz, 2H), 3.77 (s, 2H), 1.11 (s, 3H). |
| 12 | 414.07 | Oil | 91.5 | 415 | 7.75 (m, 1H), 7.64-7.22 (m, 8H), 4.03 (d, J = 7.1 Hz, 2H), 3.84 (s, 3H), 3.77 (s, 2H), 1.12 (s, 3H). |
| 13 | 414.07 | Oil | 92.7 | 415 | 7.89 (d, J = 8.8 Hz, 2H), 7.74 (s, 1H), 7.58 (d, J = 4.1 Hz, 4H), 7.13 (d, J = 8.9 Hz, 2H), 4.05 (d, J = 7.1 Hz, 2H), 3.88 (s, 3H), 3.78 (s, 2H), 1.13 (s, 3H). |
| 14 | 390.11 | Oil | 95.1 | 391 | 7.97 (s, 1H), 7.54 (d, J = 9.2 Hz, 4H), 4.06 (d, J = 7.1 Hz, 2H), 3.74 (s, 2H), 3.24 (s, 1H), 1.79 (dd, J = 6.5 19.0, 5H), 1.55-1.25 (m, 5H), 1.14 (s, 3H). |
| 15 | 384.06 | solid | 96.9 | 385 | 7.90-7.81 (m, 2H), 7.77-7.66 (m, 2H), 7.60 (dd, J = 9.1, 5.7 Hz, 6H), 4.04 (d, J = 7.1 Hz, 2H), 3.78 (s, 2H), 1.12 (s, 3H). |
| 16 | 398.07 | Oil | 92.5 | 399 | 8.10 (s, 1H), 7.55 (d, J = 8.6 Hz, 4H), 7.32 (d, J = 4.1 Hz, 5H), 4.29 (s, 2H), 4.06 (d, J = 7.1 Hz, 2H), 3.75 (s, 2H), 1.14 (s, 3H). |
| 17 | 412.09 | Oil | 99 | 413 | 7.96 (s, 1H), 7.62-7.47 (m, 4H), 7.35-7.25 (m, 4H), 7.24-7.13 (m, 1H), 4.05 (q, J = 7.1 Hz, 2H), 3.72 (s, 2H), 3.29 (dd, J = 9.5, 5.6 Hz, 2H), 2.95 (t, J = 7.5 Hz, 2H), 1.13 (dd, J = 9.2, 5.0 Hz, 3H). |
| 18 | 416.44 | Solid | 99 | 417 | 7.84-7.57 (m, 2H), 7.54-7.29 (m, 4H), 7.16-6.98 (m, 2H), 4.04 (dt, J = 14.2, 6.5 Hz, 2H), 3.82 (d, J = 2.4 Hz, 3H), 3.72 (s, 2H), 1.13 (dt, J = 12.4, 7.1 Hz, 3H). |
| 19 | 416.44 | Solid | 99 | 417 | 7.76 (td, J = 8.4, 6.6 Hz, 1H), 7.65-7.41 (m, 4H), 7.38-7.23 (m, 1H), 7.13-7.01 (m, 2H), 4.04 (q, J = 7.1 Hz, 2H), 3.82 (s, 3H), 3.72 (s, 2H), 1.12 (t, J = 7.1 Hz, 3H). |
| 20 | 416.44 | Solid | 96 | 417 | 7.53 (dd, J = 39.8, 5.1 Hz, 6H), 7.08 (d, J = 8.8 Hz, 2H), 4.02 (q, J = 7.1 Hz, 2H), 3.81 (s, 3H), 3.72 (s, 2H), 1.11 (t, J = 7.1 Hz, 3H). |
| 21 | 398.45 | Oil | 99 | 399 | 7.75-7.59 (m, 2H), 7.54 (d, J = 1.5 Hz, 1H), 7.52-7.32 (m, 4H), 7.16-6.99 (m, 2H), 4.12-3.93 (m, 2H), 3.81 (s, 3H), 3.71 (s, 2H), 1.15-1.02 (m, 3H). |
| 22 | 370.09 | Solid | 96.8 | 371 | 8.16 (d, J = 8.2 Hz, 2H), 7.63-7.36 (m, 3H), 7.09 (d, J = 8.4 Hz, 2H), 6.83 (s, 1H), 4.09 (d, J = 7.0 Hz, 2H), 3.80 (d, J = 14.1 Hz, 5H), 1.16 (d, J = 7.0 Hz, 3H). |
| 23 | 412.47 | Oil | 99 | 411 | 7.54 (ddd, J = 8.5, 7.4, 1.8 Hz, 1H), 7.48-7.41 (m, 2H), 7.37 (q, J = 1.7 Hz, 2H), 7.21 (d, J = 8.2 Hz, 1H), 7.11-7.03 (m, 3H), 4.03 (q, J = 7.1 Hz, 2H), 3.81 (s, 3H), 3.77 (s, 3H), 3.68 (s, 2H), 1.11 (t, J = 7.1 Hz, 3H). |
| 24 | 416.44 | Solid | 99 | 417 | 7.77 (s, 1H), 7.67-7.56 (m, 1H), 7.55-7.42 (m, 4H), 7.16-6.98 (m, 2H), 4.05 (q, J = 7.1 Hz, 2H), 3.82 (s, 3H), 3.72 (d, J = 12.7 Hz, 2H), 1.14 (t, J = 7.1 Hz, 3H). |
| 25 | 414.07 | Oil | 99 | 415 | 7.78 (dd, J = 19.4, 10.4 Hz, 4H), 7.62 (s, 1H), 7.47 (d, J = 8.7 Hz, 2H), 7.08 (d, J = 8.8 Hz, 2H), 4.05 (d, J = 7.1 Hz, 2H), 3.81 (s, 3H), 3.75 (s, 2H), 1.14 (s, 3H). |
| 26 | 398.45 | Oil | 99 | 399 | 7.74 (s, 1H), 7.72-7.51 (m, 4H), 7.50-7.44 (m, 2H), 7.12-7.04 (m, 2H), 4.06 (q, J = 7.1 Hz, 2H), 3.82 (s, 3H), 3.75 (s, 2H), 1.14 (t, J = 7.1 Hz, 3H). |
| 27 | 428.47 | Solid | 96 | 429 | 7.84-7.63 (m, 3H), 7.52-7.43 (m, 2H), 7.38 (t, J = 8.5 Hz, 1H), 7.14-7.02 (m, 2H), 4.09 (t, J = 7.1 Hz, 2H), 3.97 (s, 3H), 3.83 (s, 3H), 3.75 (s, 2H), 1.16 (t, J = 7.1 Hz, 3H). |
| 28 | 370.42 | Oil | 99 | 371 | 8.63 (d, J = 0.9 Hz, 1H), 7.94 (dd, J = 10.6, 8.9 Hz, 2H), 7.47 (d, J = 8.8 Hz, 2H), 7.08 (d, J = 8.8 Hz, 2H), 6.96 (dd, J = 1.8, 0.7 Hz, 1H), 4.20-3.96 (m, 2H), 3.82 (s, 3H), 3.75 (s, 2H), 1.31-1.00 (m, 3H). |
| 29 | 412.47 | Solid | 99 | 413 | 7.89-7.64 (m, 3H), 7.56-7.42 (m, 2H), 7.42-7.28 (m, 1H), 7.14-6.96 (m, 2H), 4.06 (q, J = 7.1 Hz, 2H), 3.82 (s, 3H), 3.74 (s, 2H), 2.33 (d, J = 1.6 Hz, 3H), 1.14 (t, J = 7.1 Hz, 3H). |
| 30 | 410.12 | oil | 96.5 | 411 | 7.72 (s, 1H), 7.57-7.36 (m, 4H), 7.35-7.20 (m, 2H), |

| No. | Molecular weight g/mol | Aspect | LCMS purity UV at 254 nm | MH+ | M−H+ | 1H NMR (300 MHz, DMSO) δ |
|---|---|---|---|---|---|---|
| 31 | 405.47 | Oil | 99 | 406 | | 7.08 (d, J = 8.7 Hz, 2H), 4.06 (q, J = 7.1 Hz, 2H), 3.83 (d, J = 8.0 Hz, 6H), 3.75 (s, 2H), 1.14 (t, J = 7.1 Hz, 3H). |
| 32 | 398.45 | Oil | 99 | 399 | | 8.08 (d, J = 8.5 Hz, 2H), 7.97 (d, J = 8.5 Hz, 2H), 7.70 (s, 1H), 7.48 (d, J = 8.8 Hz, 2H), 7.09 (d, J = 8.8 Hz, 2H), 4.05 (q, J = 7.1 Hz, 2H), 3.82 (s, 3H), 3.74 (s, 2H), 1.22-1.02 (m, 3H). |
| 33 | 387.47 | Solid | 99 | 388 | | 8.01-7.85 (m, 2H), 7.72 (s, 1H), 7.55-7.35 (m, 4H), 7.18-7.01 (m, 2H), 4.06 (q, J = 7.1 Hz, 2H), 3.83 (s, 3H), 3.75 (s, 2H), 1.15 (t, J = 7.1 Hz, 3H). |
| 34 | 386.16 | Oil | 98.1 | 387 | | 9.34 (d, J = 2 Hz, 1H), 8.72 (d, J = 2 Hz, 1H), 8.45 (s, 1H), 7.47 (d, J = 8.8 Hz, 2H), 7.07 (d, J = 8.8 Hz, 2H), 4.07 (q, J = 7.1 Hz, 2H), 3.81 (s, 3H), 3.75 (s, 2H), 1.15 (t, J = 7.1 Hz, 3H). |
| 35 | 380.11 | Solid | 99 | 381 | | 7.93 (s, 1H), 7.42 (d, J = 8.8 Hz, 2H), 7.06 (d, J = 8.8 Hz, 2H), 4.07 (q, J = 7.1 Hz, 2H), 3.80 (s, 3H), 3.70 (s, 2H), 3.23 (s, 1H), 1.91-1.27 (m, 10H), 1.16 (t, J = 7.1 Hz, 3H). |
| 36 | 394.12 | Solid | 99 | 395 | | 7.89-7.81 (m, 2H), 7.70 (s, 2H), 7.61 (d, J = 7.6 Hz, 2H), 7.47 (d, J = 8.8 Hz, 2H), 7.08 (d, J = 8.8 Hz, 2H), 4.06 (d, J = 7.1 Hz, 2H), 3.82 (s, 3H), 3.74 (s, 2H), 1.14 (s, 3H). |
| 37 | 380.08 | Solid | 99 | 381 | | 8.06 (s, 1H), 7.42 (d, J = 8.8 Hz, 2H), 7.32 (d, J = 4.1 Hz, 5H), 7.05 (d, J = 8.8 Hz, 2H), 4.26 (s, 2H), 4.07 (d, J = 7.1 Hz, 2H), 3.80 (s, 3H), 3.71 (s, 2H), 1.15 (s, 3H). |
| 38 | 408.14 | Solid | 99 | 409 | | 7.90 (s, 1H), 7.43 (d, J = 8.8 Hz, 2H), 7.06 (d, J = 8.8 Hz, 2H), 4.07 (q, J = 7.1 Hz, 2H), 3.80 (s, 3H), 3.71 (d, J = 1.3 Hz, 4H), 3.10 (s, 2H), 2.07 (s, 2H), 1.16 (s, 3H). |
| 39 | 423.31 | Solid | >99 | 423 | | 7.93 (s, 1H), 7.42 (d, J = 8.8 Hz, 2H), 7.29 (d, J = 4.4 Hz, 4H), 7.19 (d, J = 4.5 Hz, 1H), 7.06 (d, J = 8.8 Hz, 2H), 4.06 (d, J = 7.1 Hz, 2H), 3.80 (s, 3H), 3.69 (s, 2H), 3.28 (s, 2H), 2.94 (s, 2H), 1.15 (s, 3H). |
| 40 | 463.37 | Solid | >99 | 463 | 461 | 8.18 (d, J = 10.0 Hz, 2H), 7.81 (dd, J = 10.7, 5.2 Hz, 2H), 7.64-7.50 (m, 2H), 6.86 (dd, J = 3.6, 1.7 Hz, 1H), 4.95-4.80 (m, 1H), 3.82 (s, 2H), 1.14 (d, J = 6.3 Hz, 6H). |
| 41 | 467.79 | Solid | 96 | 468 | | 7.98-7.68 (m, 5H), 7.54 (d, J = 8.4 Hz, 1H), 7.13 (d, J = 8.8 Hz, 2H), 4.86 (dt, J = 12.5, 6.2 Hz, 1H), 3.88 (s, 3H), 3.78 (s, 2H), 1.14 (d, J = 6.3 Hz, 6H). |
| 42 | 336.83 | Oil | 90 | 337 | | 8.01 (d, J = 1.9 Hz, 1H), 7.93-7.69 (m, 3H), 7.65-7.47 (m, 4H), 5.00-4.57 (m, 1H), 3.68 (d, J = 37.6 Hz, 2H), 1.11 (d, J = 6.3 Hz, 6H). |
| 43 | 428.92 | white solid | 97 | 429 | | 7.72-7.37 (m, 9H), 7.31 (s, 1H), 3.61 (s, 2H), 3.39 (t, J = 6.6 Hz, 2H), 3.30 (t, J = 6.8 Hz, 2H), 1.96-1.66 (m, 4H). |
| 155 | 449.34 | Solid | 99 | 449 | | 7.97-7.81 (m, 2H), 7.72 (s, 1H), 7.64-7.49 (m, 4H), 7.13 (d, J = 8.8 Hz, 2H), 4.96-4.73 (m, 1H), 3.88 (s, 3H), 3.74 (s, 2H), 1.13 (d, J = 6.3 Hz, 6H). |
| 157 | 449.34 | Solid | 99 | 449 | | 7.67-7.40 (m, 7H), 7.25 (d, J = 9.0 Hz, 1H), 4.01 (q, J = 7.1 Hz, 2H), 3.77 (s, 3H), 3.72 (s, 2H), 1.09 (t, J = 7.1 Hz, 3H) |
| 158 | 409.28 | Solid | 99 | 409 | 407 | 7.89 (d, J = 8.8 Hz, 2H), 7.83 (d, J = 2.1 Hz, 1H), 7.79 (d, J = 8.4 Hz, 1H), 7.75 (s, 1H), 7.53 (dd, J = 8.4, 2.1 Hz, 1H), 7.13 (d, J = 8.9 Hz, 2H), 4.05 (q, J = 7.1 Hz, 2H), 3.81 (s, 2H), 1.14 (t, J = 7.1 Hz, 3H). |

Example 2: Preparation of derivative No. 44: isopropyl 2-(2-(4-chlorophenyl)-5-(furan-2-carbonyl)thiophen-3-yl)acetate

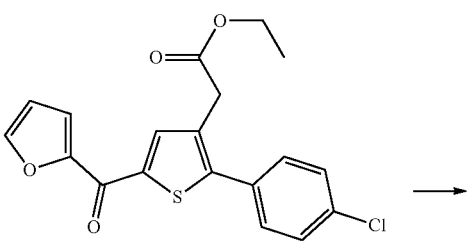

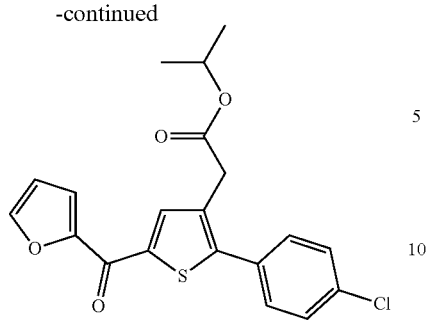

200 mg (0.518 mmol) of ethyl 2-(2-(4-chlorophenyl)-5-(furan-2-carbonyl)thiophen-3-yl)acetate were solubilized in 5 mmol of 2-propanol, a drop of sulfuric acid was added, the mixture was stirred with reflux with magnetic stirring for 17 h. The return to r.t. allowed precipitation of a solid in the reaction medium. The solid was isolated by filtration and dried in a vacuum bell jar in order to obtain 110 mg (yield=54%) of isopropyl 2-(2-(4-chlorophenyl)-5-(furan-2-carbonyl)thiophen-3-yl)acetate as a white powder. LC-MS: m/z=389 (MH$^+$) UV purity at 254 nm=99%. $^1$H NMR (300 MHz, DMSO) δ 8.15 (dd, J=6.5, 5.5 Hz, 2H), 7.58 (d, J=2.4 Hz, 5H), 6.84 (dd, J=3.6, 1.7 Hz, 1H), 5.00-4.76 (m, 1H), 3.77 (s, 2H), 1.15 (d, J=6.3 Hz, 6H).

Example 3: Preparation of derivative number 45: 2-(5-(4-methoxybenzoyl)-2-(4-methoxyphenyl)thiophen-3-yl)acetic acid

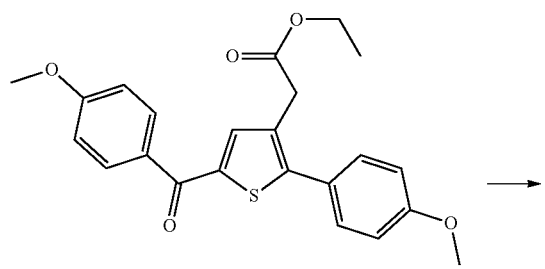

→

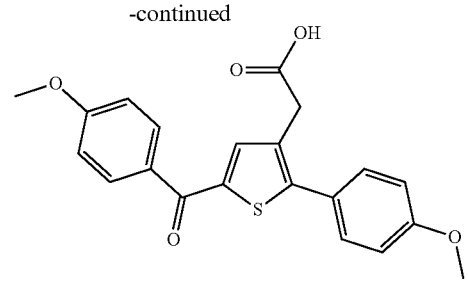

0.616 g (1.503 mmol) of ethyl 2-(5-(4-methoxybenzoyl)-2-(4-methoxyphenyl)thiophen-3-yl)acetate were solubilized in 5 ml of ethanol, to this solution were added with magnetic stirring 0.301 ml (3.01 mmol) of 30 mass % aqueous sodium hydroxide solution. The obtained mixture was stirred at r.t. for 16 h. The mixture was concentrated in vacuo, the obtained residue was taken up into 10 ml of water, the aqueous phase was extracted with 2×5 ml of ethyl acetate. The pH of the aqueous phase was then lowered by adding a 1N hydrochloric acid aqueous solution until a precipitate occurred. The solid was isolated by filtration, washed with 2×5 ml of water and dried in a vacuum bell jar in order to obtain 0.536 g (yield=92%) of 2-(5-(4-methoxybenzoyl)-2-(4-methoxyphenyl)thiophen-3-yl)acetic acid as a white solid. LC-MS: m/z=383 (MH$^+$) UV purity at 254 nm=99%. $^1$H NMR (300 MHz, DMSO) δ 12.66 (s, 1H), 7.87 (d, J=8.8 Hz, 2H), 7.69 (s, 1H), 7.48 (d, J=8.7 Hz, 2H), 7.10 (dd, J=12.0, 8.8 Hz, 4H), 3.87 (s, 3H), 3.81 (s, 3H), 3.64 (s, 2H).

The derivatives 46 to 81, 154, 156 and 159 were prepared according to the same procedure:

| No. | Molecular weight g/mol | Aspect | LCMS purity UV at 254 nm | Mass spectrometry m/z MH$^+$ | M − H$^+$ | $^1$H NMR (300 MHz, DMSO) δ |
|---|---|---|---|---|---|---|
| 46 | 358.12 | solid | 99 | 359 | | 12.64 (s, 1H), 7.93 (s, 1H), 7.44 (d, J = 8.8 Hz, 2H), 7.06 (d, J = 8.8 Hz, 2H), 3.80 (s, 3H), 3.61 (s, 2H), 3.23 (s, 1H), 1.77 (d, J = 15.3 Hz, 5H), 1.39 (t, J = 10.0 Hz, 5H). |
| 47 | 316.08 | solid | 99 | 317 | 315 | 12.67 (s, 1H), 8.05 (s, 1H), 7.44 (d, J = 8.7 Hz, 2H), 7.06 (d, J = 8.8 Hz, 2H), 3.80 (s, 3H), 3.61 (s, 2H), 2.78 (s, 1H), 1.13-0.91 (m, 4H). |
| 48 | 312.05 | solid | 97.7 | 313 | 311 | 12.65 (s, 1H), 8.27-8.07 (m, 2H), 7.65-7.39 (m, 6H), 6.84 (dd, J = 3.6, 1.7 Hz, 1H), 3.70 (s, 2H). |
| 49 | 356.03 | solid | 99 | 357 | | 12.63 (s, 1H), 7.87-7.71 (m, 4H), 7.63 (s, 1H), 7.53 (s, 5H), 3.68 (s, 2H). |

-continued

| No. | Molecular weight g/mol | Aspect | LCMS purity UV at 254 nm | Mass spectrometry m/z MH+ | M − H+ | ¹H NMR (300 MHz, DMSO) δ |
|---|---|---|---|---|---|---|
| 50 | 352.08 | oil | 95.5 | 353 | 351 | 12.74 (s, 1H), 7.76 (s, 1H), 7.58-7.16 (m, 9H), 3.85 (s, 3H), 3.67 (s, 2H). |
| 51 | 352.08 | solid | 99 | 353 | 351 | 12.61 (s, 1H), 7.88 (d, J = 8.8 Hz, 2H), 7.73 (s, 1H), 7.53 (d, J = 1.0 Hz, 5H), 7.13 (d, J = 8.8 Hz, 2H), 3.87 (s, 3H), 3.67 (s, 2H). |
| 52 | 328.11 | solid | 99 | 329 | 327 | 12.62 (s, 1H), 7.96 (s, 1H), 7.50 (s, 5H), 3.63 (s, 2H), 3.25 (s, 1H), 1.79 (dd, J = 19.5, 6.5 Hz, 5H), 1.39 (s, 4H), 1.19 (d, J = 12.0 Hz, 1H). |
| 53 | 322.07 | solid | 99 | 323 | 321 | 7.88-7.79 (m, 2H), 7.69(d, J = 7.5 Hz, 2H), 7.63-7.40 (m, 7H), 3.55 (s, 2H). |
| 54 | 354.07 | solid | 96.4 | 355 | 353 | 12.72 (s, 1H), 8.10 (s, 1H), 7.50 (s, 5H), 7.34 (d, J = 5.6 Hz, 2H), 7.15 (s, 2H), 4.31 (s, 2H), 3.63 (d, J = 11.6 Hz, 2H). |
| 55 | 336.08 | solid | 98 | 337 | | 12.65 (s, 1H), 8.11 (s, 1H), 7.68-7.17 (m, 10H), 4.29 (s, 2H), 3.65 (s, 2H). |
| 56 | 346.01 | solid | 95.8 | 347 | 345 | 12.68 (s, 1H), 8.26-8.11 (m, 2H), 7.69-7.50 (m, 5H), 6.85 (dd, J = 3.6, 1.7 Hz, 1H), 3.71 (s, 2H). |
| 57 | 425.71 | Pale yellow solid | >99 | non-ionized | | 8.00 (d, J = 1.8 Hz, 1H), 7.91-7.76 (m, 4H), 7.67 (s, 1H), 7.54 (d, J = 8.5 Hz, 2H), 3.22 (s, 2H). |
| 58 | 389.99 | solid | 97.3 | 391 | | 12.62 (s, 1H), 7.89-7.70 (m, 4H), 7.59 (s, 5H), 3.69 (s, 2H). |
| 59 | 386.04 | solid | 93.1 | 387 | 385 | 12.63 (s, 1H), 7.76 (s, 1H), 7.65-7.22 (m, 8H), 3.84 (s, 3H), 3.68 (s, 2H). |
| 60 | 386.04 | solid | 97.1 | 387 | 385 | 12.62 (s, 1H), 7.89 (d, J = 8.8 Hz, 2H), 7.73 (s, 1H), 7.58 (d, J = 3.3 Hz, 4H), 7.13 (d, J = 8.8 Hz, 2H), 3.88 (s, 3H), 3.68 (s, 2H). |
| 61 | 362.07 | solid | 99 | 363 | | 12.62 (s, 1H), 7.96 (s, 1H), 7.55 (d, J = 8.3 Hz, 4H), 3.63 (s, 2H), 3.24 (s, 1H), 1.93-1.57 (m, 5H), 1.38 (t, J = 10.3 Hz, 5H). |
| 62 | 294.75 | solid | >99 | | 293 | 12.66 (s, 1H), 7.90 (s, 1H), 7.56 (q, J = 8.7 Hz, 4H), 3.63 (s, 2H), 2.54 (s, 3H). |
| 63 | 384.06 | solid | 95.5 | 385 | | 12.63 (s, 1H), 7.97 (s, 1H), 7.55 (td, J = 8.7, 6.5 Hz, 4H), 7.29 (d, J = 4.4 Hz, 4H), 7.19 (d, J = 4.3 Hz, 1H), 3.62 (s, 2H), 3.33-3.26 (m, 3H), 2.94 (s, 2H). |
| 64 | 388.39 | solid | 99 | 389 | 387 | 13.06-11.89 (m, 1H), 7.77-7.64 (m, 1H), 7.62 (d, J = 1.5 Hz, 1H), 7.59-7.32 (m, 4H), 7.14-7.02 (m, 2H), 3.82 (d, J = 2.1 Hz, 3H), 3.61 (s, 2H). |
| 65 | 388.39 | solid | 97 | 389 | 387 | 13.08-12.07 (m, 1H), 7.76 (td, J = 8.3, 6.6 Hz, 1H), 7.65-7.39 (m, 4H), 7.29 (td, J = 8.4, 2.3 Hz, 1H), 7.18-6.96 (m, 2H), 3.82 (s, 3H), 3.61 (s, 2H). |

-continued

| No. | Molecular weight g/mol | Aspect | LCMS purity UV at 254 nm | Mass spectrometry m/z MH+ | M − H+ | ¹H NMR (300 MHz, DMSO) δ |
|---|---|---|---|---|---|---|
| 66 | 388.39 | solid | 99 | 389 | 387 | 12.83-12.21 (m, 1H), 7.71-7.34 (m, 6H), 7.08 (dd, J = 9.2, 2.6 Hz, 2H), 3.81 (s, 3H), 3.61 (s, 2H). |
| 67 | 370.39 | solid | 93 | 371 | | 12.95-12.19 (m, 1H), 7.74-7.59 (m, 2H), 7.58-7.34 (m, 5H), 7.14-7.01 (m, 2H), 3.82 (s, 3H), 3.62 (s, 2H). |
| 68 | 342.06 | solid | 99 | 343 | 341 | 12.66 (s, 1H), 8.16 (d, J = 5.8 Hz, 2H), 7.53 (dd, J = 23.6, 6.0 Hz, 3H), 7.09 (d, J= 8.6 Hz, 2H), 6.93-6.74 (m, 1H), 3.82 (s, 3H), 3.68 (s, 2H). |
| 69 | 382.43 | solid | 99 | 383 | 381 | 7.52 (dd, J = 7.2, 1.3 Hz, 1H), 7.49-7.41 (m, 2H), 7.41-7.32 (m, 2H), 7.20 (d, J = 8.3 Hz, 1H), 7.07 (dt, J = 3.5, 2.5 Hz, 3H), 3.81 (s, 3H), 3.77 (s, 3H), 3.55 (d, J = 14.3 Hz, 2H). |
| 70 | 388.39 | solid | 99 | 389 | 387 | 13.06-12.16 (m, 1H), 7.77 (s, 1H), 7.72-7.41 (m, 5H), 7.08 (dd, J = 9.4, 2.6 Hz, 2H), 3.82 (s, 3H), 3.65 (s, 2H). |
| 71 | 386.04 | solid | 99 | 387 | 385 | 12.60 (s, 1H), 7.85-7.69 (m, 4H), 7.62 (s, 1H), 7.49 (d, J = 8.7 Hz, 2H), 7.09 (d, J = 8.8 Hz, 2H), 3.82 (s, 3H), 3.66 (s, 2H). |
| 72 | 370.39 | oil | 97 | 371 | 369 | 12.95-12.12 (m, 1H), 7.78-7.43 (m, 7H), 7.10 (d, J = 8.8 Hz, 2H), 3.83 (s, 3H), 3.66 (s, 2H). |
| 73 | 400.42 | solid | 97 | 401 | 399 | 7.71 (dt, J = 11.9, 4.7 Hz, 3H), 7.48 (d, J = 8.7 Hz, 2H), 7.37 (t, J = 8.5 Hz, 1H), 7.08 (d, J = 8.8 Hz, 2H), 3.96 (s, 3H), 3.82 (s, 3H), 3.65 (s, 2H). |
| 74 | 384.42 | solid | 99 | 385 | 383 | 7.90-7.65 (m, 3H), 7.56-7.41 (m, 2H), 7.41-7.26 (m, 1H), 7.15-6.96 (m, 2H), 3.81 (s, 3H), 3.61 (d, J = 22.1 Hz, 2H), 2.31 (dd, J = 12.0, 5.1 Hz, 3H). |
| 75 | 382.09 | oil | 99 | 383 | 381 | 7.72 (s, 1H), 7.44 (ddd, J = 45.8, 19.3, 2.0 Hz, 6H), 7.09 (d, J = 8.8 Hz, 2H), 3.84 (s, 3H), 3.82 (s, 3H), 3.65 (s, 2H). |
| 76 | 377.41 | solid | 92 | | 376 | 7.93 (t, J = 9.4 Hz, 2H), 7.82 (t, J = 8.3 Hz, 2H), 7.59 (d, J = 4.7 Hz, 1H), 7.48-7.37 (m, 2H), 7.07-6.90 (m, 2H), 3.87 (s, 3H), 3.70 (s, 2H). |
| 77 | 370.94 | solid | 99 | 371 | 369 | 8.04-7.85 (m, 2H), 7.71 (s, 1H), 7.58-7.30 (m, 4H), 7.08 (dd, J = 8.8, 3.2 Hz, 2H), 3.82 (s, 3H), 3.64 (s, 2H). |
| 78 | 352.08 | solid | 99 | 353 | 351 | 12.58 (s, 1H), 7.88-7.81 (m, 2H), 7.70 (s, 2H), 7.61 (d, J = 7.6 Hz, 2H), 7.49 (d, J = 8.8 Hz, 2H), 7.09 (d, J = 8.8 Hz, 2H), 3.82 (s, 3H), 3.65 (s, 2H). |
| 79 | 366.09 | solid | 95.1 | 367 | 365 | 12.64 (s, 1H), 8.07 (s, 1H), 7.44 (d, J = 8.7 Hz, 2H), 7.38-7.20 (m, 5H), 7.06 |

-continued

| No. | Molecular weight g/mol | Aspect | LCMS purity UV at 254 nm | Mass spectrometry m/z MH⁺ | M − H⁺ | ¹H NMR (300 MHz, DMSO) δ |
|---|---|---|---|---|---|---|
| 80 | 380.11 | oil | 99 | 381 | 379 | (d, J = 8.8 Hz, 2H), 4.27 (s, 2H), 3.80 (s, 3H), 3.62 (s, 2H). 12.62 (s, 1H), 7.93 (s, 1H), 7.44 (d, J = 8.7 Hz, 2H), 7.29 (d, J = 4.3 Hz, 4H), 7.19 (dq, J = 8.7, 4.2 Hz, 1H), 7.06 (d, J = 8.8 Hz, 2H), 3.80 (s, 3H), 3.59 (s, 2H), 3.28 (s, 2H), 2.94 (s, 4H). |
| 81 | 421.29 | solid | 97 | 421 | | 12.61 (s, 1H), 7.52 (m, 6H), 7.33 (s, 1H), 6.99 (d, J = 8.8 Hz, 2H), 3.80 (s, 3H), 3.59 (s, 2H). |
| 154 | 356.82 | grey solid | 97 | 357 | | 12.63 (s, 1H), 7.93-7.80 (m, 2H), 7.74 (s, 2H), 7.67-7.51 (m, 6H), 3.68 (s, 2H). |
| 156 | 421.29 | solid | 99 | 421 | | 7.57 (q, J = 9.0 Hz, 5H), 7.47 (d, J = 2.6 Hz, 2H), 7.25 (d, J = 9.0 Hz, 1H), 3.77 (s, 3H), 3.62 (s, 2H) |
| 159 | 381.22 | solid | 97 | 381 | | 12.70 (s, 1H), 8.18 (d, J = 8.4 Hz, 2H), 7.90-7.74 (m, 2H), 7.58 (dd, J = 17.4, 5.9 Hz, 2H), 6.85 (d, J = 5.2 Hz, 1H), 3.73 (s, 2H) |

Example 4: Preparation of derivative No. 82: sodium 2-(2-(4-chlorophenyl)-5-(furan-2-carbonyl)thiophen-3-yl)acetate

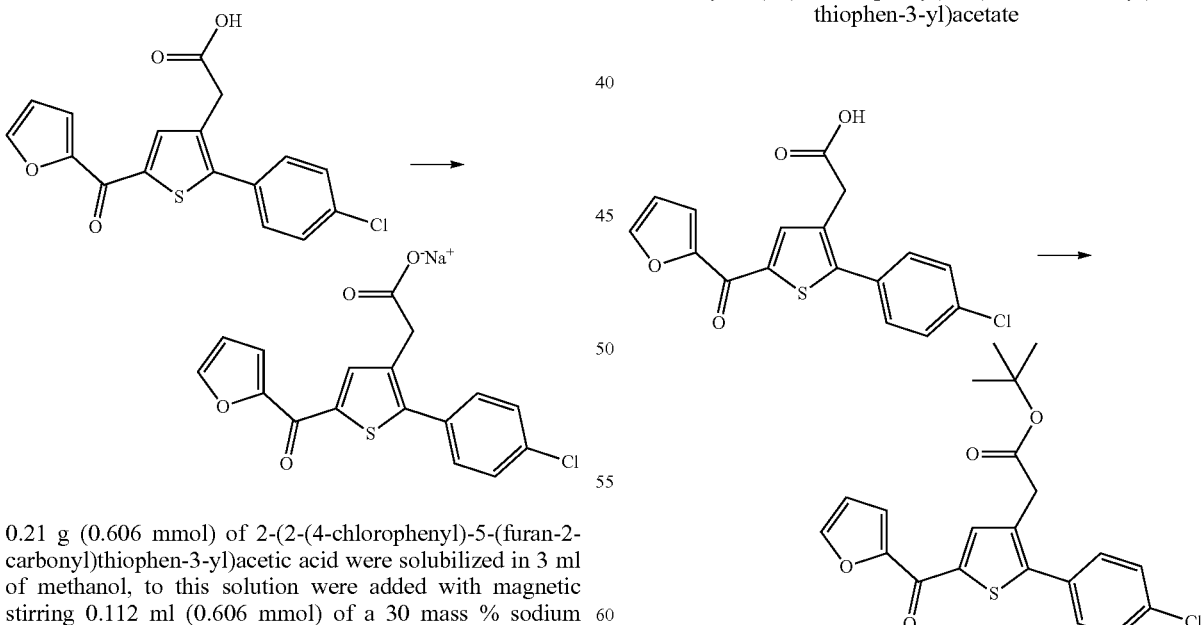

0.21 g (0.606 mmol) of 2-(2-(4-chlorophenyl)-5-(furan-2-carbonyl)thiophen-3-yl)acetic acid were solubilized in 3 ml of methanol, to this solution were added with magnetic stirring 0.112 ml (0.606 mmol) of a 30 mass % sodium methoxide solution. The obtained mixture was stirred at r.t. for 1 h. The mixture was treated with 10 ml of water and the methanol was evaporated in vacuo. The remaining aqueous phase was freeze-dried in order to obtain 0.222 g (yield=97%) of sodium 2-(2-(4-chlorophenyl)-5-(furan-2-carbonyl)thiophen-3-yl)acetate as a yellow solid. LC-MS: m/z=347 (MH⁺) UV purity at 254 nm=98%. ¹H NMR (300 MHz, DMSO) δ 8.13 (dd, J=3.4, 2.4 Hz, 2H), 7.89-7.74 (m, 2H), 7.58-7.47 (m, 3H), 6.81 (dd, J=3.6, 1.7 Hz, 1H), 3.30 (s, 2H).

Example 5: Preparation of derivative No. 83: tert-butyl 2-(2-(4-chlorophenyl)-5-(furan-2-carbonyl)thiophen-3-yl)acetate 280 mg (0.783 mmol) of 2-(2-(4-chlorophenyl)-5-(furan-2-carbonyl)thiophen-3-yl)acetic acid were solubilized in 5 ml of dichloromethane, to this solution were added with magnetic stirring 0.205 ml (2.35 mmol) of oxalyl chloride and a drop of dimethylformamide. The mixture was stirred at r.t.

for 2 h before being concentrated in vacuo. This product was added dropwise with magnetic stirring to a solution at 5° C. of 0.225 ml (2.349 mmol) of tert-butanol in 5 ml of dichloromethane. The mixture was maintained for 15 min at 5° C. and then the bath was removed and the mixture was stirred at r.t. for 40 h. The reaction medium was poured into 30 ml of water, the aqueous phase was extracted with 3×20 ml of dichloromethane. The combined organic phases were washed with 30 ml of a saturated aqueous NaHCO₃ solution, 30 ml of water, 30 ml of a saturated aqueous NaCl solution, and then dried on Na₂SO₄ which was then removed by filtration and the obtained filtrate was concentrated in vacuo. The crude residue was purified by flash chromatography on a silica gel cartridge (eluent: heptane/ethyl acetate gradient, 95% to 90% of heptane, v/v). 0.2 g (yield=62%) of tert-butyl 2-(2-(4-chlorophenyl)-5-(furan-2-carbonyl)thiophen-3-yl) acetate were obtained as a pale yellow oil. LC-MS: m/z=403 (MH$^+$) UV purity at 254 nm=97%. 1H NMR (300 MHz, DMSO) δ 8.29-7.99 (m, 2H), 7.77-7.40 (m, 5H), 6.84 (dd, J=3.6, 1.7 Hz, 1H), 3.72 (s, 2H), 1.35 (s, 9H).

The derivative 84 was prepared according to the same procedure:

| No. | Molecular weight g/mol | Aspect | LCMS purity UV at 254 nm | Mass spectrometry m/z MH$^+$ | M−H$^+$ | $^1$H NMR (300 MHz, DMSO) δ |
|---|---|---|---|---|---|---|
| 84 | 442.85 | pale yellow solid | 97 | 443 | | 7.88 (d, J = 8.8 Hz, 2H), 7.70 (s, 1H), 7.65-7.49 (m, 4H), 7.12 (d, J = 8.9 Hz, 2H), 3.87 (s, 3H), 3.69 (s, 2H), 1.33 (s, 9H). |

Example 6: Preparation of derivative number 85: 1,2-3,4-di-O-isopropylidene-α-.D-galactopyranose 2-(5-(3-methoxybenzoyl)-2-(4-methoxyphenyl)thiophen-3-yl)acetate

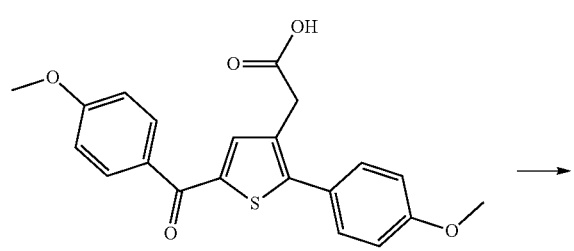

-continued

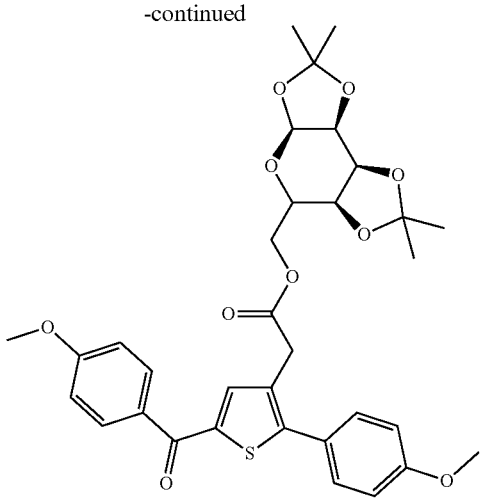

0.314 g (0.812 mmol) of 2-(5-(4-methoxybenzoyl)-2-(4-methoxyphenyl)thiophen-3-yl)acetic acid were solubilized in 4 ml of dichloromethane, with magnetic stirring 0.145 g (0.894 mmol) of carbonyl diimidazole were added, the mixture was stirred at r.t. for 2 h. A solution of 211 mg (0.812 mmol) of 1,2-3,4-di-O-isopropylidene-α-.D-galactopyranose in 4 ml of dichloromethane was added with magnetic stirring and the mixture was stirred at r.t. for 16 h. The reaction medium was concentrated in vacuo and the crude residue was directly purified by flash chromatography on a silica gel cartridge (eluent: heptane/ethyl acetate, 9/1, v/v). 386 mg (yield=75%) of 1,2-3,4-di-O-isopropylidene-α-D-galactopyranose 2-(5-(3-methoxybenzoyl)-2-(4-methoxyphenyl)thiophen-3-yl)acetate were obtained as a pale yellow solid. LC-MS: m/z=625 (MH$^+$), UV purity at 254 nm=>99%. $^1$H NMR (300 MHz, DMSO) δ $^1$H NMR (300 MHz, DMSO) δ 7.71 (s, 26H), 7.60-7.37 (m, 104H), 7.37-7.21 (m, 52H), 7.16-7.03 (m, 51H), 5.41 (d, J=5.0 Hz, 25H), 4.58 (dd, J=7.9, 2.4 Hz, 26H), 4.35 (dd, J=5.0, 2.4 Hz, 26H), 4.22-3.99 (m, 80H), 3.89 (d, J=2.8 Hz, 19H), 3.85 (t, J=7.9 Hz, 160H), 3.75 (s, 50H), 1.99 (s, 3H), 1.33 (s, 78H), 1.29 (s, 79H), 1.25 (d, J=4.6 Hz, 160H), 1.17 (s, 6H), 0.84 (d, J=6.6 Hz, 5H).

Example 7: Preparation of derivative number 86: 2-(2-(4-chlorophenyl)-5-(4-methoxybenzoyl)thiophen-3-yl)acetamide

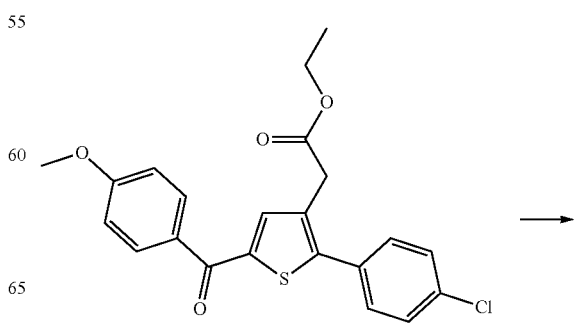

-continued

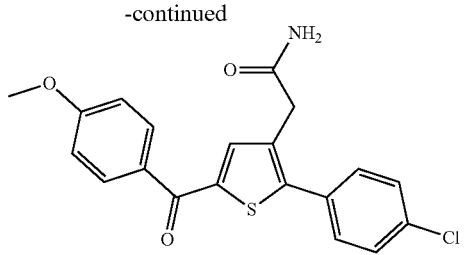

0.25 g (0.603 mmol) of ethyl 2-(2-(4-chlorophenyl)-5-(4-methoxybenzoyl)thiophen-3-yl)acetate were suspended in 2.15 ml (15.06 mmol) of a 7 M ammoniacal methanol solution. The reaction medium was stirred at r.t. with magnetic stirring for 5 d before being poured into 25 ml of water. Magnetic stirring for 10 min allowed precipitation of a solid which was isolated by filtration, washed with 2×5 ml of water and recrystallized from ethanol. 0.137 g (yield=58%) of 2-(2-(4-chlorophenyl)-5-(4-methoxybenzoyl)-thiophen-3-yl) acetamide were obtained as a white solid. LC-MS: m/z=386 (MH+), UV purity at 254 nm=98%. $^1$H NMR (300 MHz, DMSO) δ 7.88 (d, J=8.8 Hz, 2H), 7.75 (s, 1H), 7.72-7.52 (m, 5H), 7.13 (d, J=8.9 Hz, 2H), 7.05 (s, 1H), 3.88 (s, 3H), 3.47 (s, 2H).

Example 8: Preparation of derivative No. 87: ethyl 2-(2-(5-(4-methoxybenzoyl)-2-phenylthiophen-3-yl)-N-methylacetamido) acetate

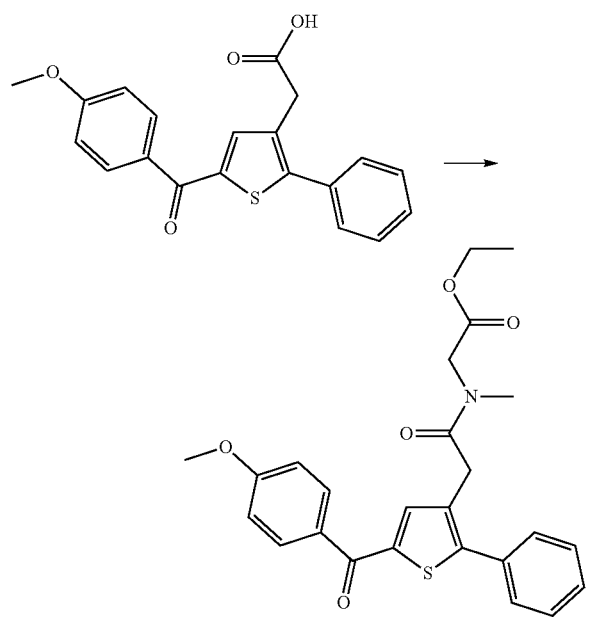

0.091 g (0.593 mmol) of sarcosine ethyl ester hydrochloride were solubilized in 3 ml of tetrahydrofurane. To this solution, were added with magnetic stirring, 0.149 g (1.079 mmol) of potassium carbonate and 0.2 g (0.593 mmol) of 2-(5-(4-methoxybenzoyl)-2-phenylthiophen-3-yl)acetic acid. The mixture was stirred at r.t. for 16 h before being poured into 20 ml of water. The aqueous phase was extracted with 2×20 ml of dichloromethane. The combined organic phases were dried on $Na_2SO_4$ which was then removed by filtration and the obtained filtrate was concentrated in vacuo. The crude residue was purified by flash chromatography on a silica gel cartridge (eluent: dichloromethane/ethyl acetate gradient, 100% to 75% of dichloromethane, v/v). 0.133 g (yield=54%) of ethyl 2-(2-(5-(4-methoxybenzoyl)-2-phenylthiophen-3-yl)-N-methylacetamido)acetate were obtained as a pale brown oil. LC-MS: m/z=452 (MH+), UV purity at 254 nm=98%. $^1$H NMR (300 MHz, DMSO) δ 7.88 (d, J=8.8 Hz, 2H), 7.66-7.39 (m, 6H), 7.12 (d, J=8.8 Hz, 2H), 4.15 (d, J=40.5 Hz, 4H), 3.87 (s, 3H), 3.74 (d, J=35.2 Hz, 2H), 2.92 (d, J=51.8 Hz, 3H), 1.15 (dd, J=13.1, 6.0 Hz, 3H).

Example 9: Preparation of derivative No. 88: 2-(2-(5-(4-methoxybenzoyl)-2-phenylthiophen-3-yl)-N-methylacetamido) acetic acid

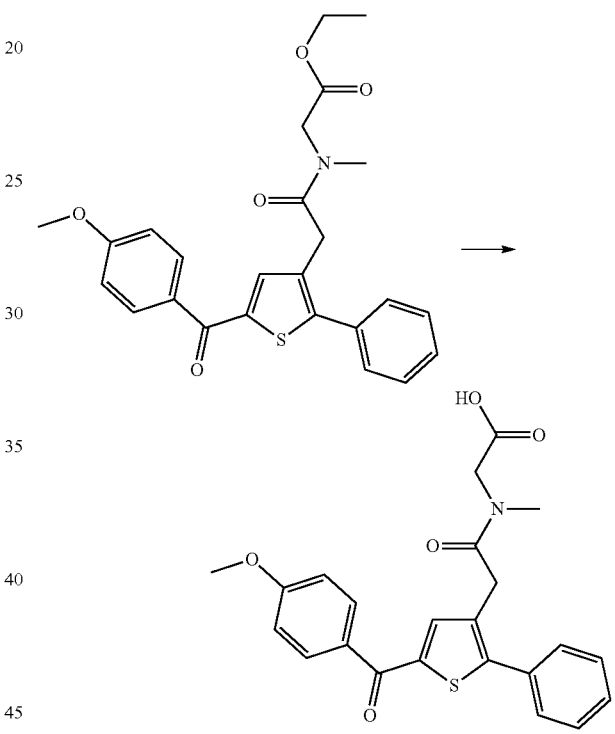

0.099 g (0.203 mmol) of ethyl 2-(2-(5-(4-methoxybenzoyl)-2-phenylthiophen-3-yl)-N-methylacetamido) acetate were solubilized in 3 ml of ethanol, to this solution were added with magnetic stirring 0.02 ml (0.203 mmol) of a 30 mass % aqueous sodium hydroxide solution. The obtained mixture was stirred at r.t. for 16 h. The mixture was concentrated in vacuo, the obtained residue was taken up into 5 ml of water, the aqueous phase was extracted with 5 ml of ethyl acetate. The pH of the aqueous phase was then lowered by adding a 1N hydrochloric acid solution until a precipitate occurred. The solid was isolated by filtration, washed with 2×3 ml of water and dried in a vacuum bell jar in order to obtain 0.01 g (yield=12%) of 2-(2-(5-(4-methoxybenzoyl)-2-phenylthiophen-3-yl)-N-methylacetamido)acetic acid as a white solid. LC-MS: m/z=424 (MH+), UV purity at 254 nm=99%. $^1$H NMR (300 MHz, DMSO) δ 12.85 (s, 1H), 7.89 (d, J=8.8 Hz, 2H), 7.70-7.42 (m, 6H), 7.18-7.08 (m, 2H), 4.04 (d, J=21.1 Hz, 2H), 3.87 (s, 3H), 3.73 (d, J=34.0 Hz, 2H), 2.91 (d, J=49.4 Hz, 3H).

Example 10: Preparation of derivative No. 89: 2-(2-(4-chlorophenyl)-5-(4-methoxybenzoyl)thiophen-3-yl)-N-(2-(dimethylamino)ethyl) acetamide

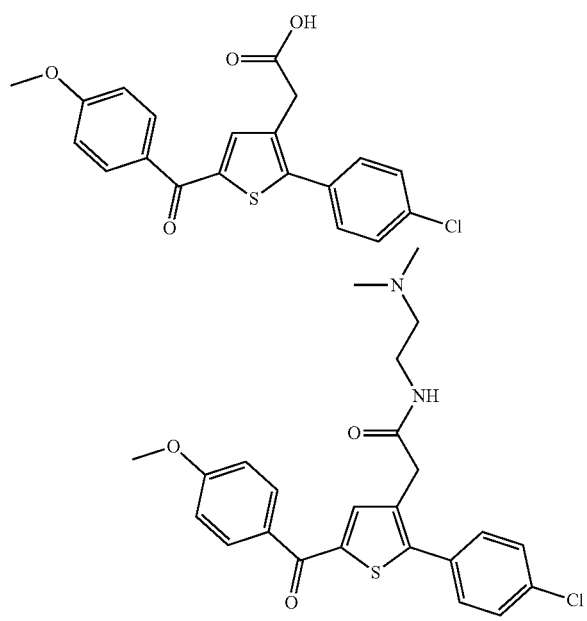

0.1 g (0.258 mmol) of 2-(2-(4-chlorophenyl)-5-(4-methoxybenzoyl)thiophen-3-yl)acetic acid were solubilized in 2 ml of dichloromethane. To this solution were added with magnetic stirring, 0.059 g (0.310 mmol) of EDC, 0.047 g (0.310 mmol) of HOBt and 0.108 ml (0.775 mmol) of triethylamine. The mixture was stirred at r.t. for 15 min and then 0.034 ml (0.310 mmol) of N,N-dimethylethane-1,2-diamine were added and the mixture was stirred at r.t. for 16 h. 20 ml of dichloromethane were added to the reaction mixture. The mixture was washed with 2×20 ml of water. The organic phase was dried on $Na_2SO_4$ which was then removed by filtration and the obtained filtrate was concentrated in vacuo. The crude residue was purified by flash chromatography on a silica gel cartridge (eluent: dichloromethane/methanol gradient, 100% to 90% of dichloromethane, v/v). 49 mg (yield=39%) of 2-(2-(4-chlorophenyl)-5-(4-methoxybenzoyl)thiophen-3-yl)-N-(2-(dimethylamino)ethyl)acetamide were obtained as a white solid. LC-MS: m/z=457 ($MH^+$), UV purity at 254 nm=94%. $^1H$ NMR (300 MHz, DMSO) δ 8.06 (t, J=5.5 Hz, 1H), 7.87 (d, J=8.8 Hz, 2H), 7.78-7.65 (m, 3H), 7.58 (d, J=8.5 Hz, 2H), 7.13 (d, J=8.9 Hz, 2H), 3.88 (s, 3H), 3.49 (s, 2H), 3.14 (dd, J=12.3, 6.4 Hz, 2H), 2.25 (t, J=6.6 Hz, 2H), 2.11 (s, 6H).

The derivatives 160 to 166 were prepared according to the same procedure:

| No. | Molecular weight g/mol | Aspect | LCMS purity UV at 254 nm | Mass spectrometry m/z MH+ | M − H+ | $^1H$ NMR (300 MHz, DMSO) δ |
|---|---|---|---|---|---|---|
| 160 | 462.95 | Yellow solid | 94.4 | 463 | 461 | 10.41 (s, 1H), 8.71 (d, J = 2.5 Hz, 1H), 8.27 (dd, J = 4.6, 1.2 Hz, 1H), 8.07-7.96 (m, 1H), 7.94-7.78 (m, 3H), 7.64 (dd, J = 19.5, 8.5 Hz, 4H), 7.34 (dd, J = 8.3, 4.7 Hz, 1H), 7.13 (d, J = 8.7 Hz, 2H), 3.88 (s, 3H), 3.80 (s, 2H). |
| 161 | 422.88 | Grey solid | 98.9 | 423 | 421 | 10.44 (s, 1H), 8.72 (d, J = 2.3 Hz, 1H), 8.26 (dd, J = 4.0, 2.1 Hz, 2H), 8.14 (dd, J = 1.7, 0.7 Hz, 1H), 8.02 (ddd, J = 8.4, 2.5, 1.5 Hz, 1H), 7.74-7.51 (m, 5H), 7.34 (dd, J = 8.2, 4.6 Hz, 1H), 6.84 (dd, J = 3.6, 1.7 Hz, 1H), 3.82 (s, 2H). |
| 162 | 491.43 | Solid | 99 | 491 | | 8.09 (s, 1H), 7.71 (d, J = 8.5 Hz, 2H), 7.57 (d, J = 8.4 Hz, 3H), 7.51-7.38 (m, 2H), 7.25 (d, J = 9.0 Hz, 1H), 3.77 (s, 3H), 3.11 (d, J = 5.9 Hz, 2H), 2.20 (t, J = 6.5 Hz, 2H), 2.09 (s, 6H). |
| 163 | 497.39 | Solid | 97 | 497 | 495 | 10.40 (s, 1H), 8.68 (s, 1H), 8.26 (d, J = 3.8 Hz, 1H), 7.98 (d, J = 8.4 Hz, 1H), 7.63 (dd, J = 20.0, 7.9 Hz, 6H), 7.49 (d, J = 2.6 Hz, 1H), 7.33 (d, J = 12.9 Hz, 1H), 7.24 (d, J = 8.9 Hz, 1H), 3.73 (s, 5H) |
| 164 | 503.44 | Solid | 99 | 503 | | (in CDCl3) δ 7.43-7.26 (m, 7H), 6.87 (d, J = 8.8 Hz, 1H), 3.74 (s, 3H), 3.55 (d, J = 8.2 Hz, 4H), 3.26-3.16 (m, 2H), 2.31-2.23 (m, 2H), 2.21 (s, 3H), 2.18-2.09 (m, 2H) |
| 165 | 464.36 | Solid | 99 | 464 | | 8.32-7.57 (m, 7H), 7.13 (d, J = 7.9 Hz, 2H), 4.72 (s, 1H), 3.88 (s, 3H), 3.51 (s, 2H), 3.14 (s, 2H) |
| 166 | 491.43 | Solid | 91 | 491 | | 8.13 (s, 1H), 8.03 (d, J = 1.9 Hz, 1H), 7.88 (d, J = 8.7 Hz, 2H), 7.82-7.72 (m, 2H), 7.66 (d, J = 6.4 Hz, 1H), 7.13 (d, J = 8.7 Hz, 2H), 3.88 (s, 3H), 3.51 (s, 2H), 3.14 (dd, J = 12.3, 6.3 Hz, 2H), 2.24 (t, J = 6.6 Hz, 2H), 2.10 (s, 6H) |

Example 11: Preparation of derivative No. 90: 2-(5-(4-methoxybenzoyl)-2-phenylthiophen-3-yl)-1-(pyrrolidin-1-yl) ethanone

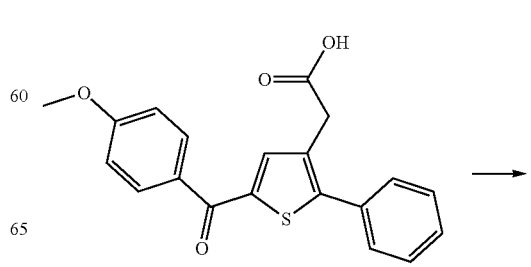

-continued

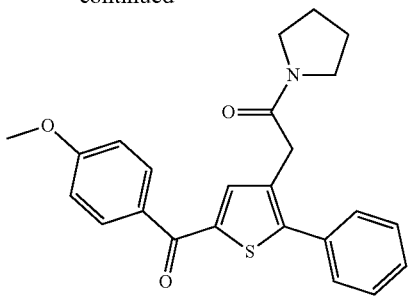

0.095 g (0.270 mmol) of 2-(5-(4-methoxybenzoyl)-2-phenylthiophen-3-yl)acetic acid were solubilized in 3 ml of dichloromethane, to this solution were added with magnetic stirring, 0.047 ml (0.540 mmol) of oxalyl chloride and a drop of dimethylformamide. The mixture was stirred at r.t. for 2 h before being concentrated in vacuo. This product was solubilized in 2 ml of tetrahydrofurane so as to be next added dropwise with magnetic stirring to a solution of 0.049 ml (0.593 mmol) of pyrrolidine in 2 ml of tetrahydrofurane. The mixture was stirred at r.t. for 16 h. The reaction medium was poured into 20 ml of water, the aqueous phase was extracted with 2×10 ml of dichloromethane. The combined organic phases were dried on $Na_2SO_4$ which was then removed by filtration and the obtained filtrate was concentrated in vacuo. The crude residue was purified by flash chromatography on a silica gel cartridge (eluent: dichloromethane/ethyl acetate, 3/1, v/v). 0.077 g (yield=65%) of 2-(5-(4-methoxybenzoyl)-2-phenylthiophen-3-yl)-1-(pyrrolidin-1-yl)ethanone were obtained as a pale brown oil. LC-MS: m/z=406 (MH⁺), UV purity at 254 nm=93%. ¹H NMR (300 MHz, DMSO) δ 7.87 (d, J=8.8 Hz, 2H), 7.64 (s, 1H), 7.57-7.42 (m, 5H), 7.13 (d, J=8.9 Hz, 2H), 3.87 (s, 3H), 3.68 (s, 2H), 3.46-3.23 (m, 4H), 1.91-1.68 (m, 4H).

The derivatives 91 to 100 were prepared according to the same procedure:

| No. | Molecular weight g/mol | Aspect | LCMS purity UV at 254 nm | Mass spectrometry m/z MH⁺ | M − H⁺ | ¹H NMR (300 MHz, DMSO) δ |
|---|---|---|---|---|---|---|
| 91 | 415.89 | orangey oil | 96.9 | 416 | 415 | 8.17-8.11 (m, 1H), 8.08 (s, 1H), 7.63-7.51 (m, 5H), 6.84 (dd, J = 3.6, 1.7 Hz, 1H), 3.80 (s, 2H), 3.55 (s, 4H), 3.47 (d, J = 5.0 Hz, 4H). |
| 92 | 455.95 | pale yellow oil | 97 | 456 | | 7.96-7.77 (m, 2H), 7.72-7.46 (m, 5H), 7.25-7.03 (m, 2H), 3.87 (s, 3H), 3.76 (s, 2H), 3.52 (s, 4H), 3.44 (d, J = 4.9 Hz, 4H). |
| 93 | 468.99 | colorless oil | >99 | 469 | | 7.87 (d, J = 8.8 Hz, 2H), 7.65-7.48 (m, 5H), 7.12 (d, J = 8.8 Hz, 2H), 3.87 (s, 3H), 3.75 (s, 2H), 3.39 (d, J = 17.5 Hz, 4H), 2.19 (d, J = 12.5 Hz, 4H), 2.16 (s, 3H). |
| 94 | 485.04 | white solid | >99 | 485 | | 7.96 (t, J = 5.5 Hz, 1H), 7.92-7.82 (m, 2H), 7.77-7.64 (m, 3H), 7.62-7.48 (m, 2H), 7.24-7.02 (m, 2H), 3.88 (s, 3H), 3.49 (s, 2H), 3.10 (dd, J = 13.1, 6.3 Hz, 2H), 2.48-2.29 (m, 6H), 0.89 (t, J = 7.1 Hz, 6H). |
| 95 | 416.92 | yellow solid | >99 | 417 | | 8.24-8.12 (m, 2H), 8.08 (s, 1H), 7.69 (d, J = 8.6 Hz, 2H), 7.64-7.47 (m, 3H), 6.84 (dd, J = 3.6, 1.7 Hz, 1H), 3.53 (s, 2H), 3.17 (dd, J = 12.3, 6.4 Hz, 2H), 2.29 (t, J = 6.5 Hz, 2H), 2.15 (s, 6H). |
| 96 | 429.92 | yellow solid | 96.2 | 430 | | 8.18 (t, J = 5.5 Hz, 1H), 7.88 (d, J = 8.8 Hz, 2H), 7.80-7.65 (m, 3H), 7.58 (d, J = 8.6 Hz, 2H), 7.13 (d, J = 8.9 Hz, 2H), 4.70 (t, J = 5.3 Hz, 1H), 3.88 (s, 3H), 3.50 (s, 2H), 3.45-3.36 (m, 2H), 3.13 (q, J = 5.8 Hz, 2H). |
| 97 | 413.92 | white solid | 97.2 | 414 | | 8.12 (s, 1H), 7.87 (d, J = 8.7 Hz, 2H), 7.78-7.48 (m, 5H), 7.13 (d, J = 8.8 Hz, 2H), 3.88 (s, 3H), 3.47 (s, 2H), 3.07 (dd, J = 7.1, 5.7 Hz, 2H), 1.00 (t, J = 7.2 Hz, 3H). |

| No. | Molecular weight g/mol | Aspect | LCMS purity UV at 254 nm | Mass spectrometry m/z MH+ | M − H+ | 1H NMR (300 MHz, DMSO) δ |
|---|---|---|---|---|---|---|
| 98 | 389.85 | beige solid | 97 | 390 | 388 | 11.21 (s, 1H), 8.26-8.07 (m, 2H), 7.76-7.49 (m, 5H), 6.85 (dd, J = 3.6, 1.7 Hz, 1H), 3.80 (q, J = 7.0 Hz, 2H), 3.44 (s, 2H), 1.14 (t, J = 7.0 Hz, 3H). |
| 99 | 361.8 | white solid | >99 | | 360 | 10.73 (s, 1H), 8.93 (s, 1H), 8.22-8.08 (m, 2H), 7.72 (d, J = 8.5 Hz, 2H), 7.57 (dd, J = 8.4, 6.0 Hz, 4H), 6.85 (dd, J = 3.6, 1.6 Hz, 1H), 3.41 (s, 2H). |
| 100 | 401.86 | yellow solid | >99 | 402 | 400 | 10.71 (s, 1H), 8.91 (s, 1H), 7.87 (d, J = 8.8 Hz, 2H), 7.71 (d, J = 7.0 Hz, 3H), 7.63-7.54 (m, 2H), 7.13 (d, J = 8.8 Hz, 2H), 3.88 (s, 3H), 3.38 (s, 2H). |

Example 12: Preparation of derivative No. 101: ethyl 2-(5-(hydroxy(phenyl)methyl)-2-(4-methoxyphenyl)thiophen-3-yl)acetate

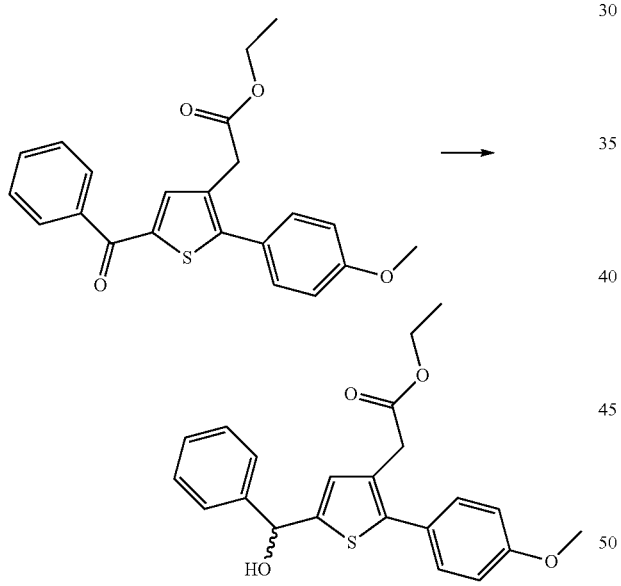

2.8 g (7.36 mmol) of ethyl 2-(5-benzoyl-2-(4-methoxyphenyl)thiophen-3-yl) acetate were solubilized in 50 ml of ethanol. Under magnetic stirring, this mixture was placed in a bath at 0° C., and then 0.557 g (14.72 mmol) of sodium borohydride were added. The mixture was maintained for 15 min at 0° C. and then the bath was removed and the mixture was stirred at r.t. for 72 h. The reaction medium was poured into 400 ml of a mixture consisting of water and ice, the aqueous phase was extracted with 2×200 ml of ethyl acetate. The combined organic phases were washed with 2×50 ml of a saturated NaCl aqueous solution, and then dried on Na$_2$SO$_4$ which was then removed by filtration and the obtained filtrate was concentrated in vacuo. The crude residue was purified by flash chromatography on a silica gel cartridge (eluent: dichloromethane/acetone gradient, 100% to 95% of dichloromethane, v/v). 1.05 g (yield=37%) of ethyl 2-(5-(hydroxy(phenyl)methyl)-2-(4-methoxy phenyl) thiophen-3-yl)acetate were obtained as a pale yellow oil. LC-MS: m/z=non-ionized. $^1$H NMR (300 MHz, DMSO) δ 7.40 (d, 2H), 7.20-7.35 (m, 5H), 6.80 (d, 2H), 6.75 (s, 1H), 5.92 (s, 1H), 4.07 (q, 2H), 3.75 (s, 3H), 3.44 (s, 2H), 2.45 (s, 1H), 1.15 (t, 3H).

Example 13: Preparation of derivative number 102: ethyl 2-(2-(4-chlorophenyl)-5-((ethoxyimino)(4-methoxyphenyl)methyl) thiophen-3-yl)-acetate

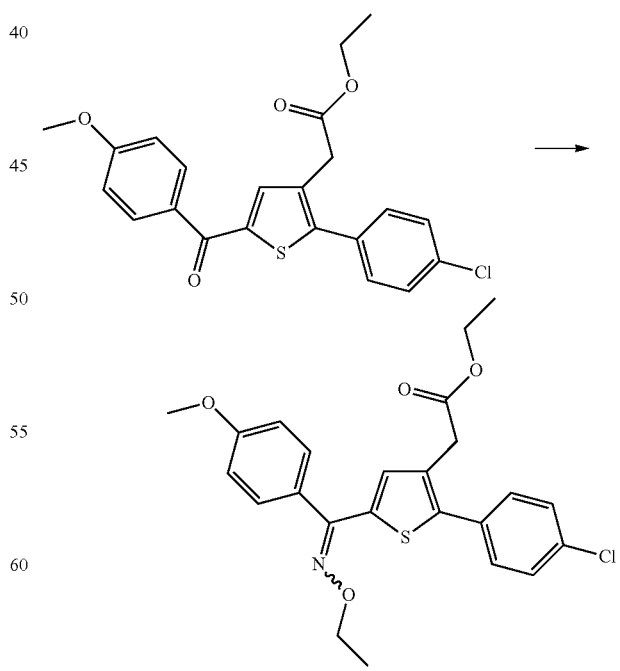

0.3 g (0.701 mmol) of ethyl 2-(2-(4-chlorophenyl)-5-(4-methoxybenzoyl)thiophen-3-yl)acetate were solubilized in 1.5 ml of ethanol, with magnetic stirring. To this solution, 0.342 g (3.51 mmol) of O-ethylhydroxylammonium chloride and 0.187 ml (2.315 mmol) of pyridine were then added. The mixture was stirred at 50° C. for 24 h. After returning to r.t., the mixture was poured into 5 ml of water. The aqueous phase was extracted with 2×5 ml of ethyl acetate. The combined organic phases were washed with 5 ml of a saturated NaHCO$_3$ aqueous solution, 5 ml of a saturated NaCl aqueous solution, and then dried on Na$_2$SO$_4$ which was then removed by filtration and the obtained filtrate was concentrated in vacuo. The crude residue was purified by flash chromatography on a silica gel cartridge (eluent: heptane/ethyl acetate, 9/1, v/v). 0.242 g (yield=73%) of ethyl 2-(2-(4-chlorophenyl)-5-((ethoxyimino)(4-methoxyphenyl)methyl)thiophen-3-yl) acetate were obtained as a colorless oil. LC-MS: m/z=458 (MH$^+$); UV purity at 254 nm=97%. 1H NMR (300 MHz, DMSO) δ 7.62-7.31 (m, 6H), 7.12 (s, 1H), 7.10-6.98 (m, 2H), 4.30 (q, J=7.0 Hz, 1,6H), 4.11 (q, J=7.0 Hz, 0.4H), 4.01 (p, J=7.1 Hz, 2H), 3.82 (s, 3H), 3.64 (d, J=12.6 Hz, 2H), 1.33 (t, J=7.0 Hz, 2,4H), 1.26-1.15 (m, 0.6H), 1.09 (t, J=7.1 Hz, 3H).

The derivatives 103 to 107 were prepared according to the same procedure:

Example 14: Preparation of derivative No. 108: 2-(2-(4-chloro phenyl)-5-((ethoxyimino)(4-methoxyphenyl)methyl) thiophen-3-yl)acetic acid

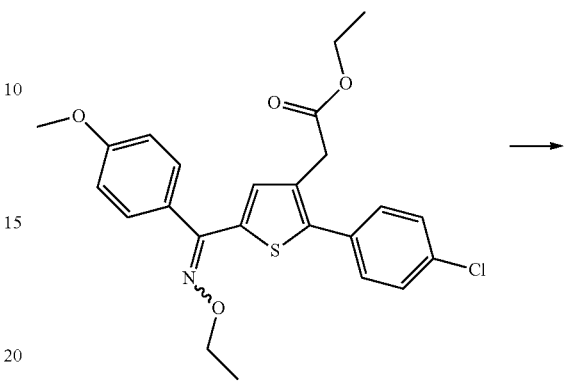

| No. | Molecular weight g/mol | Aspect | LCMS purity UV at 254 nm | Mass spectrometry m/z MH$^+$ M − H$^+$ | $^1$H NMR (300 MHz, DMSO) δ |
|---|---|---|---|---|---|
| 103 | 510.86 | white solid | 92 | 512 | 7.78 (dd, J = 5.1, 3.1 Hz, 2H), 7.65-7.37 (m, 5H), 7.10 (s, 1H), 4.80 (dt, J = 12.5, 6.3 Hz, 1H), 4.34 (q, J = 7.0 Hz, 2H), 3.64 (s, 2H), 1.34 (t, J = 7.0 Hz, 3H), 1.08 (d, J = 6.3 Hz, 6H). |
| 104 | 429.92 | pale yellow solid | 97 | 430 | 12.29 (s, 1H), 7.60-7.30 (m, 6H), 7.12-6.96 (m, 3H), 4.07-3.93 (m, 2H), 3.81 (s, 3H), 3.65 (s, 2H), 1.09 (t, J = 7.1 Hz, 3H). |
| 105 | 472 | solid | 99 | 472 | 12.19 (s, 1H), 11.28 (d, J = 6.3 Hz, 1H), 7.96 (t, J = 5.5 Hz, 1H), 7.65 (ddd, J = 8.5, 4.4, 2.3 Hz, 2H), 7.57-7.48 (m, 2H), 7.46-7.31 (m, 2H), 7.07-6.97 (m, 2H), 3.82 (s, 3H), 3.39 (s, 2H), 3.09 (dd, J = 12.5, 6.5 Hz, 2H), 2.19 (t, J = 6.7 Hz, 2H), 2.09 (t, J = 3.2 Hz, 6H) |
| 106 | 443.94 | yellow oil | 97 | 444 | 7.57-7.32 (m, 5H), 7.14 (s, 1H), 6.96 (ddt, J = 7.7, 4.9, 2.4 Hz, 3H), 4.20-4.03 (m, 2H), 3.90 (d, J = 25.8 Hz, 3H), 3.53 (d, J = 12.5 Hz, 2H), 1.31-1.12 (m, 3H). |
| 107 | 441.97 | oil | 98 | 442 | 7.50 (q, J = 8.6 Hz, 4H), 7.38 (d, J = 7.2 Hz, 6H), 5.15 (s, 2H), 4.93-4.79 (m, 1H), 3.63 (s, 2H), 2.22 (s, 3H), 1.14 (d, J = 6.3 Hz, 6H). |

-continued

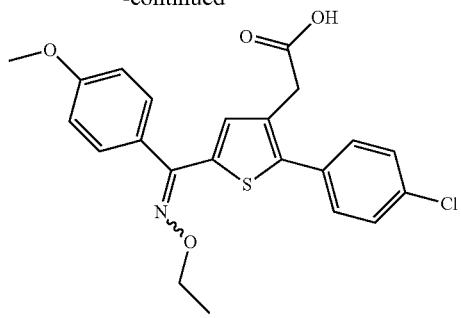

0.238 g (0.505 mmol) of ethyl 2-(2-(4-chlorophenyl)-5-((ethoxyimino)(4-methoxyphenyl)methyl) thiophen-3-yl)acetate were solubilized with magnetic stirring in 1.1 ml of a methanol-tetrahydrofurane mixture (1/1, v/v), 0.545 ml (0.545 mmol) of a 1 M sodium hydroxide aqueous solution were added. The mixture was stirred at r.t. for 16 h. The mixture was neutralized by adding a 1N aqueous hydrochloric acid solution until occurrence of a precipitate. The mixture was concentrated in vacuo, the obtained residue was taken up into isopropanol, the inorganic salts were removed by filtration, the obtained filtrate was concentrated in vacuo before being taken up into 2 ml of water and stirred with magnetic stirring at 80° C. for 1 h. The mixture was concentrated in vacuo in order to obtain 0.191 g (yield=82%) of 2-(2-(4-chlorophenyl)-5-((ethoxyimino)(4-methoxyphenyl)methyl)thiophen-3-yl) acetic acid as a white solid. LC-MS: m/z=430 (MH$^+$); UV purity at 254 nm=97%. $^1$H NMR (300 MHz, DMSO) (un mélange d'isomères Z/E est observé) δ 7.65-7.29 (m, 6H), 7.16-6.97 (m, 3H), 4.30 (q, J=7.0 Hz, 1,5H), 4.17-4.04 (m, 0.5H), 3.82 (s, 3H), 3.53 (d, J=13.9 Hz, 2H), 1.40-1.29 (m, 1,5H), 1.20 (dd, J=13.0, 6.0 Hz, 0.5H).

The derivatives 109 to 111 were prepared according to the same procedure:

Example 15: Preparation of derivative No. 112: 5-(4-chloro phenyl)-4-(2-isopropoxy-2-oxoethyl) thiophene-2-carboxylic acid Step 1: Preparation of isopropyl 4-chlorophenyl-4-oxobutanoate

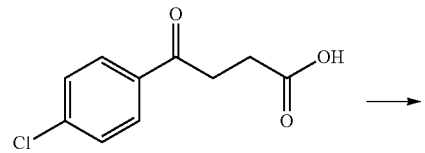

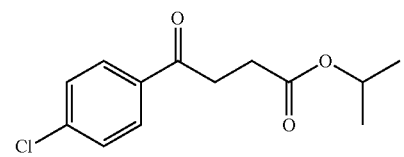

50 g (235 mmol) of 4-chlorophenyl-4-oxobutanoic acid were solubilized in 300 ml of isopropanol, 0.63 ml (11.76 mmol) of sulfuric acid were added to this solution. The mixture was refluxed with heating for 6 d with magnetic stirring. After returning to r.t., the mixture was concentrated in vacuo, the crude residue was directly purified by flash chromatography on a silica gel cartridge (eluent: 100% dichloromethane). 59.83 g (yield=>99%) of isopropyl 4-chlorophenyl-4-oxobutanoate were obtained as a colorless oil. LC-MS: m/z=255 (MH$^+$) UV purity at 254 nm=95%. $^1$H NMR (300 MHz, DMSO) δ 8.13-7.85 (m, 2H), 7.70-7.47 (m, 2H), 4.86 (dt, J=12.5, 6.3 Hz, 1H), 3.29-3.22 (m, 2H), 2.65-2.54 (m, 2H), 1.16 (d, J=6.3 Hz, 6H).

| No. | Molecular weight g/mol | Aspect | LCMS purity UV at 254 nm | Mass spectrometry m/z MH$^+$ | M − H$^+$ | $^1$H NMR (300 MHz, DMSO) δ |
|---|---|---|---|---|---|---|
| 109 | 401.86 | white solid | 97 | 402 | | 12.31 (s, 0.7H), 11.34 (s, 0.3H), 7.98-7.65 (m, 2H), 7.64-7.20 (m, 4H), 7.20-6.84 (m, 3H), 3.81 (s, 3H), 3.14 (d, J = 17.0 Hz, 2H). |
| 110 | 415.89 | white solid | 97 | 416 | | 7.46 (ddd, J = 38.2, 30.9, 8.0 Hz, 6H), 7.21-6.84 (m, 3H), 4.02 (s, 3H), 3.81 (s, 3H), 3.35 (d, J = 15.1 Hz, 2H). |
| 111 | 399.89 | solid | 95 | 400 | | 7.51 (q, J = 8.7 Hz, 4H), 7.44-7.25 (m, 6H), 5.16 (s, 2H), 3.56 (s, 2H), 2.22 (s, 3H). |
| 167 | 468.77 | white solid | 94.6 | 468 | | 7.76 (dd, J = 5.1, 3.1 Hz, 2H), 7.63-7.43 (m, 5H), 7.13 (s, 1H), 4.33 (q, J = 7.0 Hz, 2H), 3.57 (s, 2H), 1.33 (q, J = 7.0 Hz, 3H). |

Step 2: Preparation of isopropyl (Z/E)-4-chloro-3-formyl-4-(4-chlorophenyl)but-3-enoate

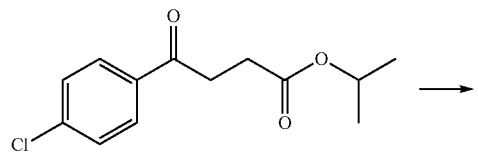

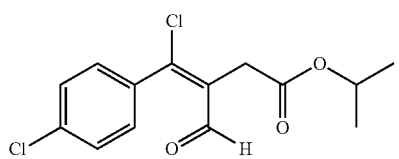

59.8 g (235 mmol) of isopropyl 4-chlorophenyl-4-oxobutanoate were solubilized in 54.5 ml of dimethylformamide (704 mmol), 54.7 ml (587 mmol) of phosphoryl trichloride were slowly added to this solution, the reaction being very exothermic. The obtained mixture was then heated to 80° C. for 2 h with magnetic stirring. After returning to r.t., the mixture was poured onto 1 L of a mixture consisting of water and ice, magnetic stirring was set up and the mixture was stirred at r.t. for 16 h. The aqueous phase was extracted with 300 ml and then 2×150 ml of ethyl acetate. The combined organic phases were washed with 2×200 ml of water, 300 ml of a saturated NaCl aqueous solution, and then dried on $Na_2SO_4$ which was then removed by filtration and the obtained filtrate was concentrated in vacuo. The crude residue was purified by flash chromatography on a silica gel cartridge (eluent: heptane/dichloromethane gradient, from 50 to 100% of dichloromethane, v/v). 47.4 g (yield=62%) of isopropyl (Z/E)-4-chloro-3-formyl-4-(4-chlorophenyl)but-3-enoate were obtained as an orangey oil. LC-MS: m/z=301 (MH+) UV purity at 254 nm=92%. $^1$H NMR (300 MHz, DMSO) δ 10.29-9.28 (m, 1H), 7.71-7.38 (m, 4H), 4.87 (dq, J=25.0, 6.3 Hz, 1H), 3.53 (s, 19H), 3.18-1.16 (m, 2H).

Step 3: Preparation of isopropyl 2-(2-(4-chlorophenyl)thiophen-3-yl)acetate and of 5-(4-chlorophenyl)-4-(2-isopropoxy-2-oxoethyl)thiophene-2-carboxylic acid (derivative No. 112)

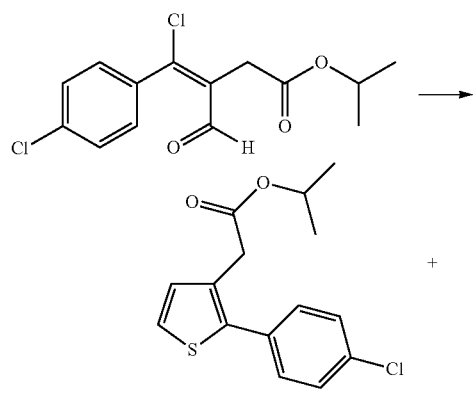

47.4 g (157 mmol) of isopropyl (Z/E)-4-chloro-3-formyl-4-(4-chlorophenyl)but-3-enoate were solubilized in 250 ml of tetrahydrofurane, to this solution were added 16.40 ml (236 mmol) of 2-mercapto acetic acid and 65.8 ml (472 mmol) of triethylamine. The obtained mixture was refluxed with heating for 4 h with magnetic stirring. After returning to r.t., the mixture was concentrated in vacuo. The residue was taken up into 175 ml of dimethylformamide and the mixture was heated to 130° C. for 2 h with magnetic stirring. After returning to r.t., the mixture was treated with 500 ml of water. The aqueous phase was extracted with 300 ml and then with 2×150 ml of ethyl acetate. The combined organic phases were washed with 2×200 ml of water, 300 ml of a saturated NaCl aqueous solution, and then dried on $Na_2SO_4$ which was then removed by filtration and the obtained filtrate was concentrated in vacuo. The crude residue was taken up and triturated in heptane. A solid precipitated and was isolated by filtration in order to obtain 22.8 g (yield=30%) of 5-(4-chlorophenyl)-4-(2-isopropoxy-2-oxoethyl)thiophene-2-carboxylic acid. The filtrate was concentrated in vacuo and purified by flash chromatography on a silica gel cartridge (eluent: heptane/dichloromethane, 2/1, v/v). 16.18 g (yield=34%) of isopropyl 2-(2-(4-chlorophenyl)thiophen-3-yl)acetate were obtained as a pale brown oil. 5-(4-chlorophenyl)-4-(2-isopropoxy-2-oxoethyl)thiophene-2-carboxylic acid: LC-MS: non-ionized. $^1$H NMR (300 MHz, DMSO) δ 13.19 (s, 1H), 7.69 (s, 1H), 7.53 (q, J=8.7 Hz, 4H), 4.86 (dt, J=12.5, 6.2 Hz, 1H), 3.69 (s, 2H), 1.13 (d, J=6.3 Hz, 6H).

Isopropyl 2-(2-(4-chlorophenyl)thiophen-3-yl)acetate: LC-MS: m/z=294 (M) UV purity at 254 nm=96%. $^1$H NMR (300 MHz, DMSO) δ 7.51 (dt, J=19.3, 6.9 Hz, 5H), 7.08 (d, J=5.2 Hz, 1H), 4.87 (dt, J=12.5, 6.3 Hz, 1H), 3.63 (s, 2H), 1.15 (d, J=6.3 Hz, 6H).

Derivative number 113 was prepared according to the same sequence of steps 1 to 3

| No. | Molecular weight g/mol | Aspect | LCMS purity UV at 254 nm | Mass spectrometry m/z MH+ | M−H+ | $^1$H NMR (300 MHz, DMSO) δ |
|---|---|---|---|---|---|---|
| 113 | 324.78 | solid | 93 | | 323 | 13.17 (s, 1H), 7.70 (s, 1H), 7.63-7.45 (m, 4H), 4.05 (q, J = 7.1 Hz, 2H), 3.71 (s, 2H), 1.14 (t, J = 7.1 Hz, 3H). |

Example 16: Preparation of derivative No. 114: ethyl 2-(2-(4-chloro phenyl)-5-(morpholine-4-carbonyl)thiophen-3-yl)acetate

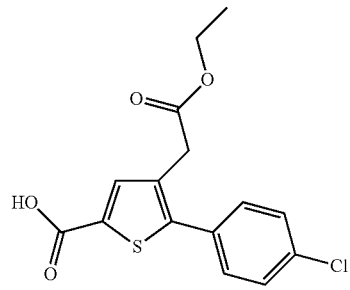

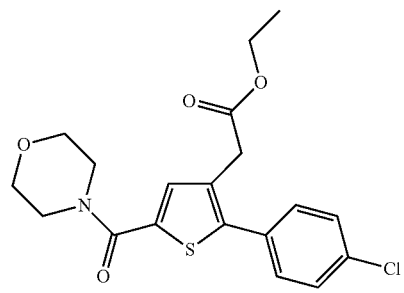

0.44 g (1.244 mmol) of 5-(4-chlorophenyl)-4-(2-ethoxy-2-oxoethyl)thiophene-2-carboxylic acid were solubilized in 5 ml of dichloromethane, to this solution were added with magnetic stirring, 0.327 ml (3.73 mmol) of oxalyl chloride and a droplet of dimethylformamide. The mixture was stirred at r.t. for 2 h before being concentrated in vacuo. This product was added dropwise with magnetic stirring to a solution of 0.542 ml (6.22 mmol) of morpholine in 5 ml of dichloromethane. The mixture was stirred at r.t. for 16 h. The reaction medium was poured into 20 ml of water, the aqueous phase was extracted with 3×25 ml of dichloromethane. The combined organic phases were washed with 20 ml of a saturated NaHCO$_3$ aqueous solution, 20 ml of water, 20 ml of a saturated NaCl aqueous solution, and then dried on Na$_2$SO$_4$ which was then removed by filtration and the obtained filtrate was concentrated in vacuo. The crude residue was purified by flash chromatography on a silica gel cartridge (eluent: dichloromethane/methanol gradient, 98/2, v/v). 0.359 g (yield=68%) ethyl 2-(2-(4-chlorophenyl)-5-(morpholine-4-carbonyl)thiophen-3-yl) acetate were obtained as a yellow orangey oil. LC-MS: m/z=394 (MH$^+$); UV purity at 254 nm=98%. $^1$H NMR (300 MHz, DMSO) δ 7.63-7.44 (m, 4H), 7.41 (s, 1H), 4.16-3.95 (m, 2H), 3.66 (dd, J=11.0, 7.8 Hz, 10H), 1.14 (t, J=7.1 Hz, 3H).

Example 17: Preparation of derivative No. 115: ethyl 2-(2-(4-chloro phenyl)-5-(morpholine-4-carbonyl)thiophen-3-yl)acetate

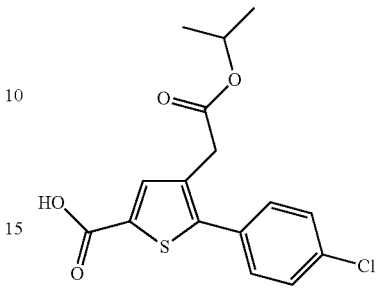

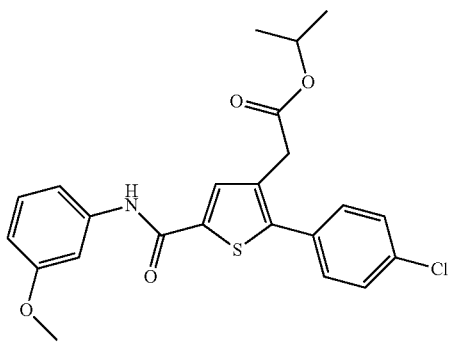

0.5 g (1.476 mmol) of 5-(4-chlorophenyl)-4-(2-isopropoxy-2-oxoethyl)thiophene-2-carboxylic acid were solubilized in 10 ml of dimethylformamide, to this solution were added with magnetic stirring, 0.311 g (1.623 mmol) of EDC, 0.249 g (1.623 mmol) of HOBt and 0.411 mol (2.95 mmol) of triethylamine. The mixture was stirred at r.t. for 30 min before adding 0.205 ml (1.77 mmol) of 3-methoxyaniline, the mixture was then stirred at r.t. for 3 h. The reaction medium was diluted with 20 ml of ethyl acetate and washed with 2×20 ml of a saturated NaCl aqueous solution. The aqueous phase was extracted with 20 ml of ethyl acetate, the combined organic phases were washed with 20 ml of a saturated NaCl aqueous solution and then dried on Na$_2$SO$_4$ which was then removed by filtration and the obtained filtrate was concentrated in vacuo. The crude residue was purified by trituration in 10 ml of diisopropyl ether, a brown solid was isolated by filtration in order to obtain 0.529 g (yield=80%) of ethyl 2-(2-(4-chlorophenyl)-5-(morpholine-4-carbonyl)thiophen-3-yl)acetate. LC-MS: m/z=444 (MH$^+$); UV purity at 254 nm >99%. $^1$H NMR (300 MHz, DMSO) δ 10.27 (s, 1H), 8.00 (s, 1H), 7.55 (q, J=8.6 Hz, 4H), 7.42 (d, J=2.1 Hz, 1H), 7.34 (d, J=8.3 Hz, 1H), 7.26 (t, J=8.1 Hz, 1H), 6.70 (dd, J=7.8, 1.8 Hz, 1H), 4.90 (dt, J=12.5, 6.2 Hz, 1H), 3.76 (s, 3H), 3.70 (s, 2H), 1.16 (d, J=6.3 Hz, 6H).

The derivatives of numbers 116 to 118, 168 and 170 were prepared according to the same procedure

| No. | Molecular weight g/mol | Aspect | LCMS purity UV at 254 nm | Mass spectrometry m/z MH+ | M − H+ | 1H NMR (300 MHz, DMSO) δ |
|---|---|---|---|---|---|---|
| 116 | 457.97 | Pale brown solid | 97 | 458 | | 9.12 (t, J = 6.0 Hz, 1H), 7.77 (s, 1H), 7.53 (q, J = 8.6 Hz, 4H), 7.25 (t, J = 8.1 Hz, 1H), 6.98-6.75 (m, 3H), 4.88 (dt, J = 12.5, 6.2 Hz, 1H), 4.42 (d, J = 5.9 Hz, 2H), 3.74 (s, 3H), 3.64 (s, 2H), 1.15 (d, J = 6.3 Hz, 6H). |
| 117 | 457.97 | Brown solid | 96 | 458 | | 9.07 (t, J = 5.9 Hz, 1H), 7.75 (s, 1H), 7.53 (dd, J = 19.6, 8.5 Hz, 4H), 7.24 (d, J = 8.6 Hz, 2H), 6.89 (d, J = 8.6 Hz, 2H), 4.87 (dt, J = 12.5, 6.3 Hz, 1H), 4.37 (d, J = 5.9 Hz, 2H), 3.73 (s, 3H), 3.64 (s, 2H), 1.15 (d, J = 6.2 Hz, 6H). |
| 118 | 443.94 | Brown solid | 99 | 444 | 442 | 9.07 (t, J = 5.9 Hz, 1H), 7.75 (s, 1H), 7.53 (dd, J = 19.6, 8.5 Hz, 4H), 7.24 (d, J = 8.6 Hz, 2H), 6.89 (d, J = 8.6 Hz, 2H), 4.87 (dt, J = 12.5, 6.3 Hz, 1H), 4.37 (d, J = 5.9 Hz, 2H), 3.73 (s, 3H), 3.64 (s, 2H), 1.15 (d, J = 6.2 Hz, 6H). |
| 168 | 400.88 | Solid | 96% | 401 | 399 | 10.55 (s, 1H), 8.90 (s, 1H), 8.32 (d, J = 3.9 Hz, 1H), 8.15 (d, J = 9.0 Hz, 1H), 8.03 (s, 1H), 7.56 (q, J = 8.7 Hz, 4H), 7.41 (d, J = 12.9 Hz, 1H), 4.09 (q, J = 7.1 Hz, 2H), 3.74 (s, 2H), 1.17 (t, J = 7.1 Hz, 3H) |
| 170 | 394.91 | Solid | 99% | 395 | | (CDCl3) 7.42 (s, 1H), 7.34 (s, 4H), 4.11 (q, J = 7.1 Hz, 2H), 3.52 (s, 2H), 3.45 (dd, J = 11.3, 5.2 Hz, 2H), 2.53-2.43 (m, 2H), 2.23 (s, 6H), 1.20 (t, J = 7.2 Hz, 3H) |

Example 18: Preparation of derivative No. 119: 2-(2-(4-chlorophenyl)-5-((3-methoxyphenyl)carbamoyl)thiophen-3-yl)acetic acid

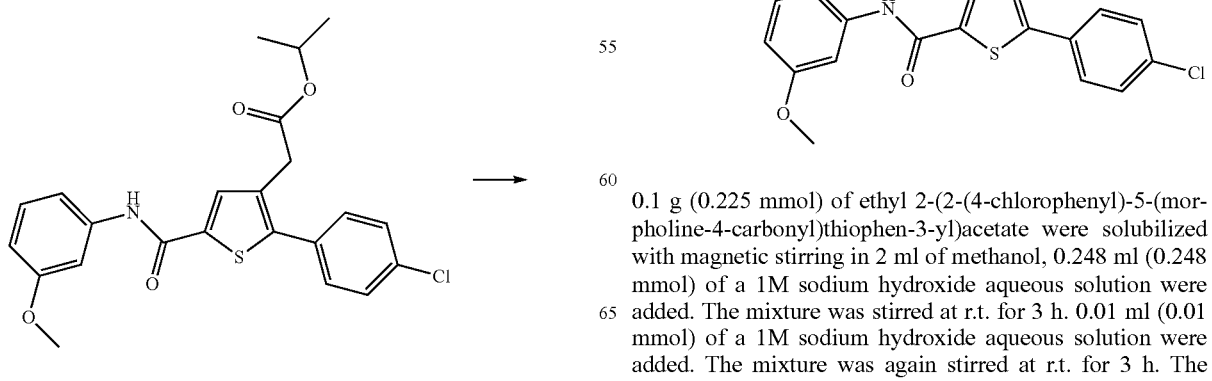

0.1 g (0.225 mmol) of ethyl 2-(2-(4-chlorophenyl)-5-(morpholine-4-carbonyl)thiophen-3-yl)acetate were solubilized with magnetic stirring in 2 ml of methanol, 0.248 ml (0.248 mmol) of a 1M sodium hydroxide aqueous solution were added. The mixture was stirred at r.t. for 3 h. 0.01 ml (0.01 mmol) of a 1M sodium hydroxide aqueous solution were added. The mixture was again stirred at r.t. for 3 h. The reaction medium was neutralized by adding a solution of 0.019 ml (0.338 mmol) of acetic acid in 5 ml of water. The mixture was extracted with 2×10 ml of ethyl acetate, the combined organic phases were washed with 10 ml of a saturated NaCl aqueous solution and then dried on Na$_2$SO$_4$ which was then removed by filtration. The obtained filtrate was concentrated in vacuo in order to obtain 0.082 g (yield=86%) of 2-(2-(4-chlorophenyl)-5-((3-methoxyphenyl)carbamoyl)thiophen-3-yl)acetic acid as a white solid. LC-MS: m/z=402 (MH$^+$); UV purity at 254 nm=95%. $^1$H NMR (300 MHz, DMSO) δ 12.69 (s, 1H), 10.29 (s, 1H), 8.03 (s, 1H), 7.66-7.49 (m, 4H), 7.42 (t, J=2.1 Hz, 1H), 7.34 (d, J=8.4 Hz, 1H), 7.25 (t, J=8.1 Hz, 1H), 6.69 (dd, J=8.0, 2.1 Hz, 1H), 3.75 (s, 3H), 3.62 (s, 2H).

The derivatives of numbers 120 to 122, 169, 171 and 172 were prepared according to the same procedure Example 19: Preparation of derivative number 123: ethyl 2-(2-(4-chlorophenyl)-5-(4-methoxybenzoyl)thiophen-3-yl)propanoate

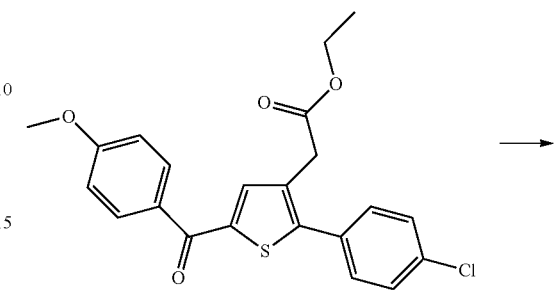

| No. | Molecular weight g/mol | Aspect | LCMS purity UV at 254 nm | Mass spectrometry m/z MH$^+$ | M − H$^+$ | $^1$H NMR (300 MHz, DMSO) δ |
|---|---|---|---|---|---|---|
| 120 | 415.89 | Brown foam | 96 | 416 | | 12.62 (s, 1H), 9.13 (t, J = 6.0 Hz, 1H), 7.79 (s, 1H), 7.53 (q, J = 8.6 Hz, 4H), 7.24 (t, J = 8.1 Hz, 1H), 6.95-6.75 (m, 3H), 4.41 (d, J = 5.9 Hz, 2H), 3.73 (s, 3H), 3.57 (s, 2H). |
| 121 | 401.86 | Pale brown solid | 95 | 402 | | 12.68 (s, 1H), 10.22 (s, 1H), 7.98 (s, 1H), 7.58 (dt, J = 14.0, 8.9 Hz, 6H), 6.93 (d, J = 9.1 Hz, 2H), 3.74 (s, 3H), 3.61 (s, 2H). |
| 122 | 415.89 | Pale brown solid | 96 | 416 | | 12.62 (s, 1H), 9.09 (t, J = 5.9 Hz, 1H), 7.78 (s, 1H), 7.54 (q, J = 8.6 Hz, 4H), 7.24 (d, J = 8.6 Hz, 2H), 6.90 (d, J = 8.6 Hz, 2H), 4.37 (d, J = 5.8 Hz, 2H), 3.73 (s, 3H), 3.57 (s, 2H). |
| 169 | 372.82 | solid | 99 | 373 | | 9.15 (s, 1H), 8.59-8.35 (m, 2H), 8.08 (s, 1H), 7.84-7.69 (m, 1H), 7.56 (q, J = 8.5 Hz, 4H) |
| 171 | 366.86 | white solid | 93 | 367 | | 8.48 (s, 1H), 7.79 (d, J = 8.5 Hz, 2H), 7.72 (s, 1H), 7.48 (d, J = 8.5 Hz, 2H), 2.36 (t, J = 6.7 Hz, 2H), 2.15 (s, 6H), 1.69 (s, 2H) |
| 172 | 434.33 | solid | 91 | 434 | 432 | 10.45 (s, 1H), 8.00 (s, 1H), 7.78 (d, J = 8.9 Hz, 2H), 7.56 (q, J = 8.8 Hz, 4H), 7.42 (d, J = 8.9 Hz, 2H), 4.09 (q, J = 7.1 Hz, 2H), 3.73 (s, 2H), 1.17 (t, J = 7.1 Hz, 3H) |

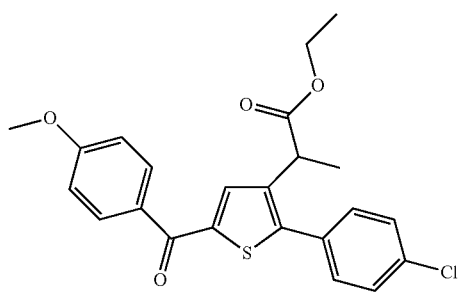

0.25 g (0.597 mmol) of ethyl 2-(2-(4-chlorophenyl)-5-(4-methoxybenzoyl)thiophen-3-yl)acetate were solubilized in 5 ml of tetrahydrofurane with magnetic stirring. The mixture was cooled to −20° C. and 0.663 ml (1.193 mmol) of a 2M solution of lithium diisopropylamide in tetrahydrofurane were added dropwise. The mixture was stirred for 1 h at −20° C. before adding 0.039 ml (0.626 mmol) of methyl iodide. The mixture was stirred for a further 1 h at −20° C. Without waiting for it to return to r.t., the mixture was poured into 10 ml of water. The aqueous phase was extracted with 3×10 ml of ethyl acetate, the combined organic phases were washed with 15 ml of a saturated NaCl aqueous solution and then dried on $Na_2SO_4$ which was then removed by filtration. The obtained filtrate was concentrated in vacuo. The crude residue was purified by flash chromatography on a silica gel cartridge (eluent: dichloromethane/petroleum ether gradient, from 50 to 70% of dichloromethane, v/v). 0.145 g (yield=55%) of ethyl 2-(2-(4-chlorophenyl)-5-(4-methoxybenzoyl)-thiophen-3-yl)propanoate were obtained as a pale yellow oil. LC-MS: m/z=429 ($MH^+$); UV purity at 254 nm=97%. $^1H$ NMR (300 MHz, DMSO) δ 0.92-7.83 (m, 2H), 7.68 (s, 1H), 7.65-7.51 (m, 4H), 7.19-7.08 (m, 2H), 4.05 (dt, J=7.2, 3.4 Hz, 2H), 3.92-3.80 (m, 4H), 1.43 (d, J=7.1 Hz, 3H), 1.13 (t, J=7.1 Hz, 3H).

The derivative number 124 was prepared according to the same procedure

| No. | Molecular weight g/mol | Aspect | LCMS purity UV at 254 nm | Mass spectrometry m/z $MH^+$ | $M − H^+$ | $^1H$ NMR (300 MHz, DMSO) δ |
|---|---|---|---|---|---|---|
| 124 | 458.95 | Solid | 92 | 459 | | 7.87 (d, J = 8.8 Hz, 2H), 7.73 (s, 1H), 7.61 (q, J = 8.7 Hz, 4H), 7.14 (d, J = 8.8 Hz, 2H), 4.19-3.56 (m, 8H), 3.20 (s, 3H), 1.15 (t, J = 7.1 Hz, 3H). |

Example 20: Preparation of derivative number 125: isopropyl 2-(2-(4-chlorophenyl)-5-(4-methoxybenzoyl)thiophen-3-yl) propanoate

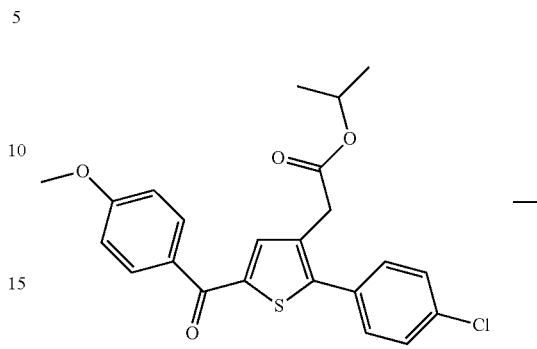

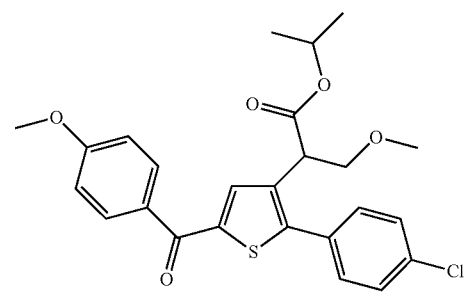

0.2 g (0.382 mmol) of isopropyl 2-(2-(4-chlorophenyl)-5-(4-methoxybenzoyl)thiophen-3-yl)acetate were solubilized in 3 ml of tetrahydrofurane with magnetic stirring. The mixture was cooled to −80° C. and 0.765 ml (0.765 mmol) of a 1N lithium bis-trimethylsilylamide solution in tetrahydrofurane were added dropwise. The mixture was stirred for 30 min at −50° C. before being again cooled to −80° C. and adding 0.058 ml (0.765 mmol) of methoxymethane chloride. The bath was removed and the mixture was stirred for 1 further hour while leaving it to return to r.t. The reaction medium was poured into 20 ml of a saturated ammonium chloride solution. The aqueous phase was extracted with 2×15 ml of ethyl acetate, the combined organic phases were washed with 15 ml of a saturated NaCl aqueous solution and then dried on $Na_2SO_4$ which was then removed by filtration. The obtained filtrate was concentrated in vacuo. The crude residue was purified by flash chromatography on a silica gel cartridge (eluent: petroleum ether/diisopropyl ether gradient, from 100% to 0% of petroleum ether, v/v). 0.062 g (yield=33%) of ethyl 2-(2-(4-chlorophenyl)-5-(4-methoxybenzoyl)thiophen-3-yl)propanoate were obtained as a solid. LC-MS: m/z=473 ($MH^+$); UV purity at 254 nm=96%. $^1H$ NMR (300 MHz, DMSO) δ 7.87 (d, J=8.6 Hz, 2H), 7.72 (s, 1H), 7.61 (d, J=8.5 Hz, 4H), 7.14 (d, J=8.6 Hz, 2H), 4.90 (dt, J=12.4, 6.1 Hz, 1H), 4.02-3.76 (m, 5H), 3.72-3.60 (m, 1H), 3.20 (s, 3H), 1.15 (dd, J=14.8, 6.1 Hz, 6H).

Example 21: Preparation of derivative number 126: isopropyl 2-(2-(4-chlorophenyl)-5-(cyclohexanecarbonyl)thiophen-3-yl)-3-phenyl propanoate Step 1: Preparation of ethyl 2-(2-(4-chlorophenyl)thiophen-3-yl)-3-phenylpropanoate

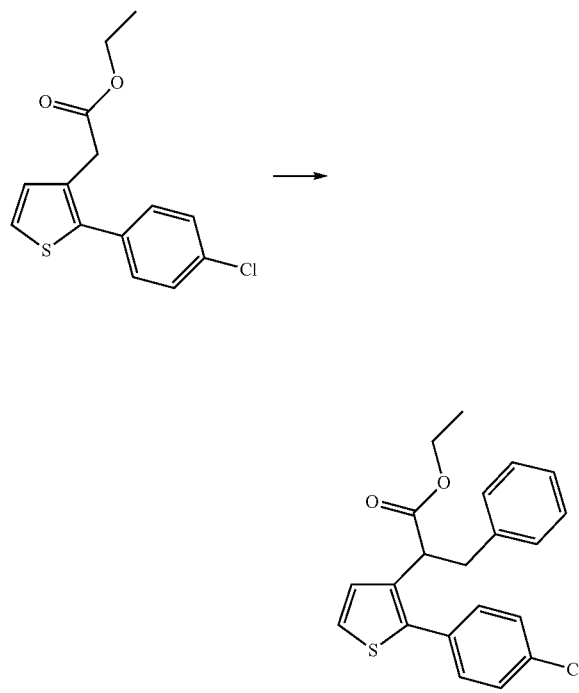

1 g (3.56 mmol) of ethyl 2-(2-(4-chlorophenyl)thiophen-3-yl)acetate were solubilized under argon in 5 ml of tetrahydrofurane. The mixture was cooled to −50° C. and 0.663 ml (3.56 mmol) of a 2M lithium diisopropyl amide solution in tetrahydrofurane were added dropwise with magnetic stirring. The reaction mixture was stirred for 5 min at −20° C. before being cooled to −50° C. 1.272 ml (10.68 mmol) of benzyl bromide were added dropwise. The mixture was stirred at −50° C. for 15 min before removing the bath and then the mixture was stirred for 1 h while letting it return to r.t. The reaction medium was poured into 30 ml of a mixture consisting of water and ice. The aqueous phase was extracted with 2×20 ml of dichloromethane, the combined organic phases were washed with 30 ml of a 1N hydrochloric acid aqueous solution, 30 ml of water and then dried on MgSO4 which was then removed by filtration. The obtained filtrate was concentrated in vacuo in order to obtain 1.285 g (yield=94%) of ethyl 2-(2-(4-chlorophenyl)thiophen-3-yl)-3-phenyl-propanoate as an orangey oil. LC-MS: m/z=non-ionized. ¹H NMR (300 MHz, DMSO) δ 7.54 (d, J=5.3 Hz, 1H), 7.43 (d, J=8.5 Hz, 2H), 7.24 (d, J=5.3 Hz, 1H), 7.13 (d, J=7.8 Hz, 6H), 6.99-6.86 (m, 2H), 4.04-3.91 (m, 2H), 3.85 (t, J=7.8 Hz, 1H), 3.23 (dd, J=13.5, 7.6 Hz, 1H), 2.95 (dd, J=13.5, 8.0 Hz, 1H), 1.03 (t, J=7.1 Hz, 3H).

Step 2: Preparation of 2-(2-(4-chlorophenyl)thiophen-3-yl)-3-phenylpropanoic acid

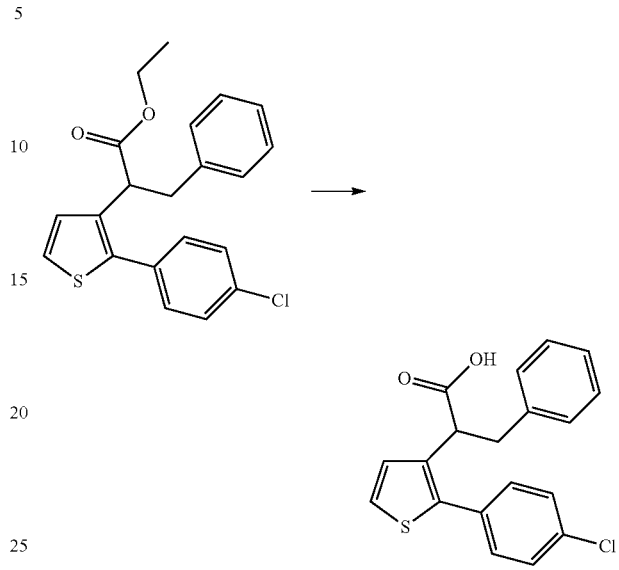

1 g (3.56 mmol) of ethyl 2-(2-(4-chlorophenyl)thiophen-3-yl)-3-phenyl propanoate were solubilized in 10 ml of ethanol with magnetic stirring. 0.311 ml (3.11 mmol) of a 10M sodium hydroxide aqueous solution were added. The mixture was stirred at r.t. for 3 d before being concentrated in vacuo. A 1N hydrochloric acid aqueous solution was added until occurrence of a precipitate, the aqueous phase was extracted with 2×25 ml of ethyl acetate. The combined organic phases were washed with 40 ml of water, 40 ml of a saturated NaCl aqueous solution and then dried on MgSO4 which was then removed by filtration. The obtained filtrate was concentrated in vacuo. The residue was purified by trituration in 15 ml of a mixture of petroleum ether and of diisopropyl ether (1/1, v/v). The solid was isolated by filtration, washed with 10 ml of petroleum ether and dried in a vacuum bell jar in order to obtain 0.681 g (yield=70%) of 2-(2-(4-chlorophenyl)thiophen-3-yl)-3-phenylpropanoic acid. LC-MS: m/z=340 (M-H⁺); UV purity at 254 nm >99%. ¹H NMR (300 MHz, DMSO) δ 12.56 (s, 1H), 7.58 (d, J=5.3 Hz, 1H), 7.46 (d, J=8.4 Hz, 2H), 7.27 (d, J=5.3 Hz, 1H), 7.17 (dd, J=10.7, 7.7 Hz, 5H), 6.94 (dd, J=7.3, 1.9 Hz, 2H), 3.83 (t, J=7.7 Hz, 1H), 2.93 (dd, J=13.6, 8.1 Hz, 1H).

Step 3: Preparation of isopropyl 2-(2-(4-chlorophenyl)thiophen-3-yl)-3-phenylpropanoate

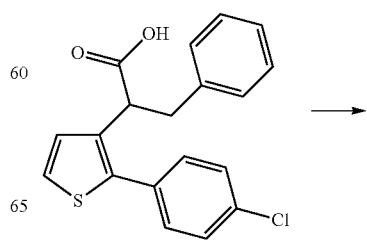

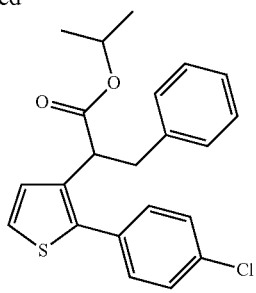

0.55 g (1.604 mmol) of 2-(2-(4-chlorophenyl)thiophen-3-yl)-3-phenylpropanoic acid were solubilized in 25 ml of isopropanol, a drop of sulfuric acid was added to this solution. The mixture was refluxed with heating for 16 h with magnetic stirring. After returning to r.t., the mixture was concentrated in vacuo, the crude residue was taken up into 25 ml and the mixture was stirred at r.t. for 16 h. A precipitate was isolated by filtration; washed with a mixture consisting of 10 ml of water and of 0.5 ml of petroleum ether and dried in a vacuum bell jar in order to obtain 0.46 g (yield=71%) of isopropyl 2-(2-(4-chlorophenyl)thiophen-3-yl)-3-phenylpropanoate as a white solid. LC-MS: m/z=non-ionized. $^1$H NMR (300 MHz, DMSO) δ 7.57 (d, J=5.3 Hz, 1H), 7.46 (d, J=8.5 Hz, 2H), 7.34-7.05 (m, 6H), 6.96 (d, J=5.4 Hz, 2H), 4.78 (dt, J=12.5, 6.2 Hz, 1H), 3.84 (t, J=7.8 Hz, 1H), 3.24 (dd, J=13.5, 8.1 Hz, 1H), 2.96 (dd, J=13.5, 7.6 Hz, 1H), 1.02 (dd, J=6.2, 3.4 Hz, 6H).

Step 4: Preparation of isopropyl 2-(2-(4-chlorophenyl)-5-(cyclohexane-carbonyl)thiophen-3-yl)-3-phenylpropanoate (derivative number 126)

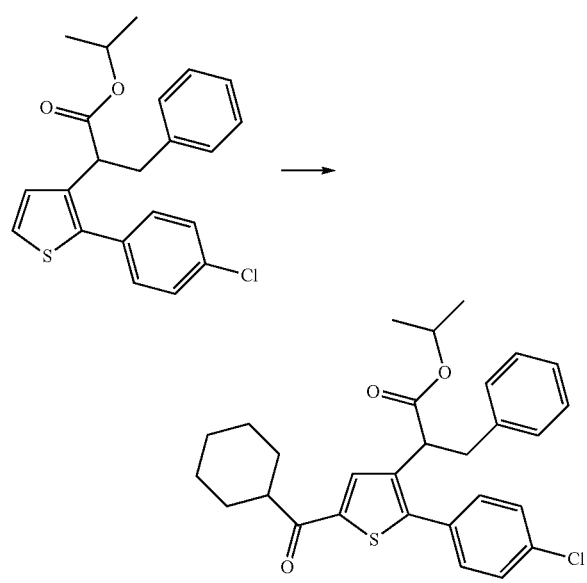

In a flask placed under an argon flow, were introduced with magnetic stirring: 2 ml of dichloromethane, 0.285 g (2.14 mmol) of trialuminium chloride, 0.173 g (1.77 mmol) of cyclohexane carbonyl chloride and a solution of 0.429 g (1.07 mmol) of isopropyl 2-(2-(4-chlorophenyl)thiophen-3-yl)-3-phenylpropanoate in 3 ml of dichloromethane. The obtained mixture was stirred at r.t. for 16 h and then poured into 25 ml of a mixture consisting of water and ice and stirred for 30 min. The aqueous phase was extracted with 2×15 ml of ethyl acetate. The combined organic phases were washed with 15 ml of a saturated NaHCO₃ aqueous solution, 15 ml of water and then dried on MgSO₄ which was then removed by filtration. The obtained filtrate was concentrated in vacuo which was then removed by filtration and the obtained filtrate was concentrated in vacuo. The crude residue was purified by flash chromatography on a silica gel cartridge (eluent: diisopropyl ether/petroleum ether, 1/9, v/v). 0.108 g (yield=20%) of isopropyl 2-(2-(4-chlorophenyl)-5-(cyclohexanecarbonyl)thiophen-3-yl)-3-phenylpropanoate were obtained as a solid. LC-MS: m/z=495 (MH⁺); UV purity at 254 nm=97%. $^1$H NMR (300 MHz, DMSO) δ 8.07 (s, 1H), 7.51 (d, J=8.3 Hz, 2H), 7.20 (dd, J=18.0, 7.5 Hz, 5H), 7.00 (d, J=7.2 Hz, 2H), 4.81 (dt, J=12.5, 6.2 Hz, 1H), 3.85 (t, J=7.8 Hz, 1H), 3.10 (dd, J=13.4, 8.0 Hz, 1H), 1.76 (t, J=23.5 Hz, 5H), 1.58-1.11 (m, 6H), 1.04 (t, J=6.0 Hz, 6H).

Example 22: Preparation of derivative No. 127: 2-(2-(4-chlorophenyl)-5-(4-methoxybenzoyl)thiophen-3-yl)propanoic acid

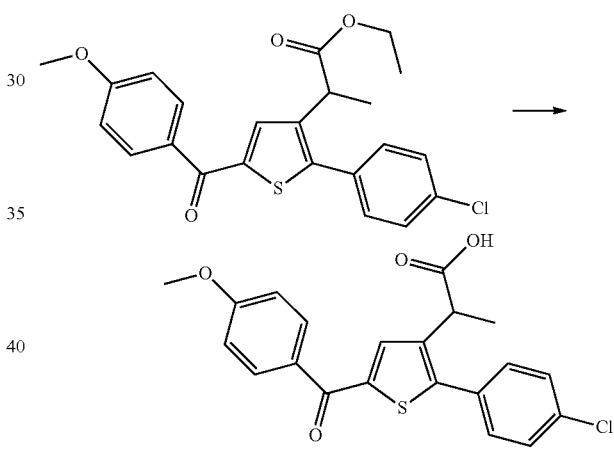

0.087 g (0.197 mmol) of ethyl 2-(2-(4-chlorophenyl)-5-(4-methoxybenzoyl)thiophen-3-yl)-propanoate were solubilized in 1 ml of a mixture of tetrahydrofurane and of ethanol (1/1, v/v), to this solution were added with magnetic stirring 0.197 ml (0.197 mmol) of a 1N sodium hydroxide aqueous solution. The obtained mixture was stirred at r.t. for 16 h. The mixture was concentrated in vacuo, the obtained residue was taken up into 10 ml of water, the aqueous phase was extracted with 10 ml of methyl tert-butyl ether. The aqueous phase was then acidified down to a pH=3-4 by adding a 1N hydrochloric acid aqueous solution. The aqueous phase was extracted with 3×10 ml of ethyl acetate, the combined organic phases were washed with 20 ml of a saturated NaCl aqueous solution and then dried on Na₂SO₄ which was then removed by filtration. The obtained filtrate was concentrated in vacuo in order to obtain 0.077 g (yield=95%) of 2-(2-(4-chlorophenyl)-5-(4-methoxybenzoyl)thiophen-3-yl)propanoic acid as a white solid. LC-MS: m/z=401 (MH⁺); UV purity at 254 nm=97%. $^1$H NMR (300 MHz, DMSO) δ 7.97-7.79 (m, 4H), 7.73 (s, 1H), 7.57 (t, J=10.0 Hz, 2H), 7.13 (d, J=8.8 Hz, 2H), 3.88 (s, 3H), 3.46 (d, J=7.1 Hz, 2H), 1.25 (d, J=7.0 Hz, 3H).

The derivative 128 was prepared according to the same procedure:

| No. | Molecular weight g/mol | Aspect | LCMS purity UV at 254 nm | Mass spectrometry m/z MH+ | M – H+ | 1H NMR (300 MHz, CDCl3) δ |
|---|---|---|---|---|---|---|
| 128 | 430.90 | oil | 91 | 431 | | 7.97-7.85 (m, 2H), 7.53-7.37 (m, 5H), 7.09-6.92 (m, 2H), 4.16-4.03 (m, 1H), 3.90 (s, 3H), 3.64-3.54 (m, 2H), 3.32 (s, 3H). |

Example 23: Preparation of derivative No. 129: ethyl 2-(2-(4-fluoro-2-methoxyphenyl)-5-(furan-2-carbonyl)thiophen-3-yl)-acetate Step 1: Preparation of ethyl 2-(thiophen-3-yl)acetate

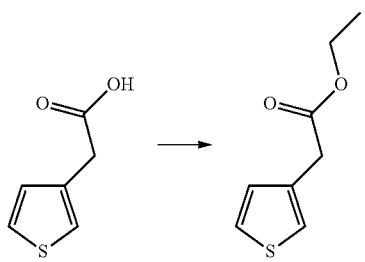

10.75 g (74.1 mmol) of 2-(thiophen-3-yl)acetic acid were solubilized in 100 ml of ethanol, 6 ml (72 mmol) of sulfuric acid were added to this solution. The mixture was heated with magnetic stirring with reflux for 24 h. After returning to r.t., the mixture was concentrated in vacuo, the crude residue was treated with 100 ml of a mixture consisting of water and ice. The aqueous phase was extracted with 2×100 ml of ethyl acetate. The combined organic phases were washed with 100 ml of water, 100 ml of a saturated NaHCO3 aqueous solution and 100 ml of a saturated NaCl aqueous solution and then dried on MgSO4 which was then removed by filtration. The obtained filtrate was concentrated in vacuo in order to obtain 12.27 g (yield=97%) of ethyl 2-(thiophen-3-yl)acetate as a colorless oil. LC-MS: m/z=non-ionized. 1H NMR (300 MHz, CDCl3) δ 7.24 (dd, J=6.0, 3.0 Hz, 1H), 7.16-7.07 (m, 1H), 7.02 (dd, J=4.9, 1.1 Hz, 1H), 4.13 (q, J=7.1 Hz, 2H), 3.62 (s, 2H), 1.23 (t, J=7.1 Hz, 3H).

Step 2: Preparation of ethyl 2-(2-bromothiophen-3-yl)acetate

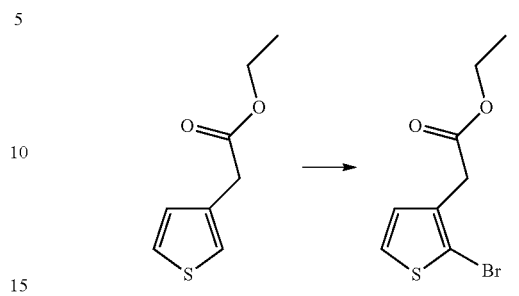

12.2 g (71.7 mmol) of ethyl 2-(thiophen-3-yl)acetate were solubilized in 100 ml of tetrahydrofurane with magnetic stirring, 121.7 mmol of N-bromosuccinimide were added and the mixture was stirred with reflux for 3 h. After returning to r.t., the mixture was concentrated in vacuo, the crude residue was taken up into a minimum of petroleum ether so as to be filtered on silica gel (eluent: dichloromethane 100%) and in order to obtain 18.38 g (yield=88%) of ethyl 2-(2-bromothiophen-3-yl)acetate as a pale yellow oil. LC-MS: m/z=non-ionized. 1H NMR (300 MHz, CDCl3) δ 7.27-7.16 (m, 1H), 7.03-6.86 (m, 1H), 4.12 (qd, J=7.1, 3.2 Hz, 2H), 3.64-3.48 (m, 2H), 1.22 (td, J=7.1, 1.4 Hz, 3H).

Step 3: Preparation of ethyl 2-(2-(4-fluoro-2-methoxyphenyl)thiophen-3-yl)acetate

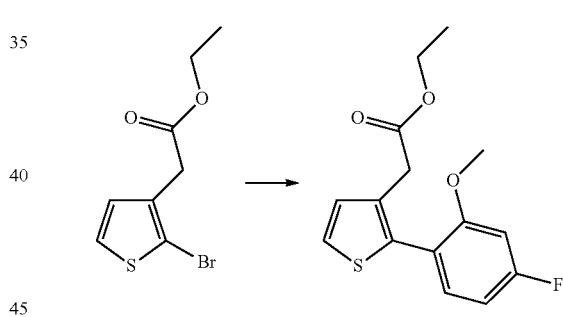

0.7 g (2.53 mmol) of ethyl 2-(2-bromothiophen-3-yl)acetate were solubilized under argon in 10 ml of a mixture consisting of toluene and ethanol (1/1, v/v), were added with magnetic stirring, 0.645 g (3.79 mmol) of 4-fluoro-2-methoxyphenylboronic acid, 8.85 ml (17.7 mmol) of a 2M Na2CO3 aqueous solution and 0.148 g (0.126 mmol) of palladium[0] tetrakis(triphenylphosphine). The mixture was stirred with reflux for 3 h. After returning to r.t., the mixture was poured, diluted with 15 ml of water and 15 ml of ethyl acetate before being filtered on celite. After separation, the aqueous phase was extracted with 20 ml of ethyl acetate. The combined organic phases were washed with 10 ml of water, 10 ml of a saturated NaCl aqueous solution and then dried on MgSO4 which was then removed by filtration. The obtained filtrate was concentrated in vacuo. The crude residue was purified by flash chromatography on a silica gel cartridge (eluent: petroleum ether/ethyl acetate gradient, from 100 to 90% of petroleum ether, v/v). 0.529 g (yield=70%) of ethyl 2-(2-(4-fluoro-2-methoxyphenyl)thiophen-3-yl)acetate were obtained as a pale yellow foam. LC-MS: m/z=295 (MH+); UV purity at 254 nm=83%. 1H NMR (300 MHz, CDCl₃) δ 7.51 (d, J=5.2 Hz, 1H), 7.26 (dd, J=8.4, 6.9 Hz, 1H), 7.09-7.00 (m, 2H), 6.84 (td, J=8.4, 2.5 Hz, 1H), 4.01 (q, J=7.1 Hz, 2H), 3.74 (s, 3H), 3.41 (s, 2H), 1.13 (t, J=7.1 Hz, 3H).

Step 4: Preparation of ethyl 2-(2-(4-fluoro-2-methoxyphenyl)-5-(furan-2-carbonyl)thiophen-3-yl)acetate (derivative number 129)

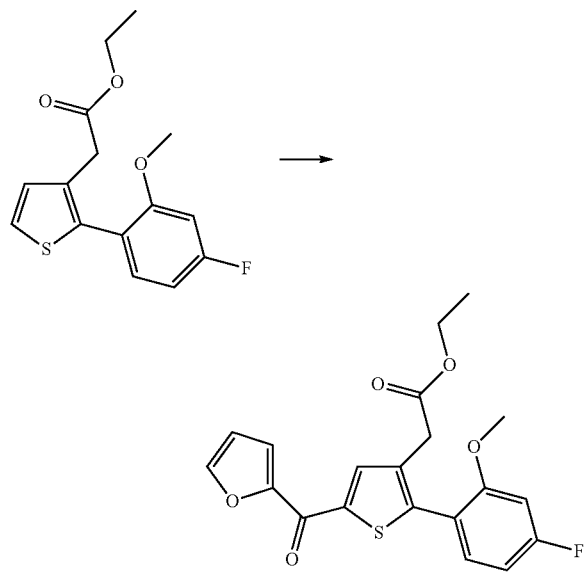

In a flask placed under an argon flow, were introduced with magnetic stirring: 5 ml of dichloromethane, 0.583 g (4.37 mmol) of trialuminium chloride, a solution of 0.19 ml (1.924 mmol) of 2-furoyl chloride in 2 ml of dichloromethane and a solution of 0.52 g (1.749 mmol) of ethyl 2-(2-(4-fluoro-2-methoxyphenyl)thiophen-3-yl)-acetate in 2 ml of dichloromethane. The obtained mixture was stirred with reflux for 3 h and then at r.t. for 16 h before being poured into 15 ml of a mixture consisting of water and ice and being stirred for 30 min. 15 ml of dichloromethane were added and the mixture was filtered on celite. After separation, the aqueous phase was extracted with 20 ml of dichloromethane. The combined organic phases were washed with 20 ml of water and then dried on MgSO₄ which was then removed by filtration. The obtained filtrate was concentrated in vacuo. The crude residue was purified by flash chromatography on a silica gel cartridge (eluent: petroleum ether/diisopropyl ether gradient, from 100 to 0% of petroleum ether, v/v). 0.287 g (yield=41%) of ethyl 2-(2-(4-fluoro-2-methoxyphenyl)-5-(furan-2-carbonyl)thiophen-3-yl)acetate were obtained as a solid. LC-MS: m/z=389 (MH⁺); UV purity at 254 nm=98%. ¹H NMR (300 MHz, DMSO) δ 8.19-8.11 (m, 2H), 7.56 (d, J=3.6 Hz, 1H), 7.37 (dd, J=8.5, 6.8 Hz, 1H), 7.11 (dd, J=11.4, 2.4 Hz, 1H), 6.91 (td, J=8.4, 2.5 Hz, 1H), 6.84 (dd, J=3.6, 1.7 Hz, 1H), 4.04 (q, J=7.1 Hz, 2H), 3.78 (s, 3H), 3.53 (s, 2H), 1.14 (t, J=7.1 Hz, 3H).

The derivatives of numbers 130 to 134 were prepared according to the same sequence of 4 steps.

| No. | Molecular weight g/mol | Aspect | LCMS purity UV at 254 nm | Mass spectrometry m/z MH⁺ | M − H⁺ | ¹H NMR (300 MHz, DMSO) δ |
|---|---|---|---|---|---|---|
| 130 | 376.37 | oil | 98 | 377 | | 8.24 (s, 1H), 8.17 (d, J = 1.0 Hz, 1H), 7.67-7.53 (m, 2H), 7.42-7.30 (m, 2H), 6.86 (dd, J = 3.6, 1.7 Hz, 1H), 4.02 (q, J = 7.1 Hz, 2H), 3.70 (s, 2H), 1.11 (t, J = 7.1 Hz, 3H). |
| 131 | 37.42 | pale brown oil | 92 | 371 | | 8.19 (s, 1H), 8.15 (d, J = 1.0 Hz, 1H), 7.59 (dd, J = 3.6, 0.6 Hz, 1H), 7.49-7.38 (m, 1H), 7.13-7.02 (m, 3H), 6.84 (dd, J = 3.6, 1.7 Hz, 1H), 4.08 (q, J = 7.1 Hz, 2H), 3.81 (s, 5H), 1.15 (t, J = 7.1 Hz, 3H). |
| 132 | 384.40 | oil | 96 | 385 | | 8.21-8.10 (m, 2H), 7.57 (d, J = 4.0 Hz, 1H), 7.15-6.96 (m, 3H), 6.84 (dd, J = 3.6, 1.7 Hz, 1H), 6.12 (s, 2H), 4.08 (q, J = 7.1 Hz, 2H), 3.78 (s, 2H), 1.16 (t, J = 7.1 Hz, 3H). |
| 133 | 416.44 | white solid | 90 | 417 | | 7.91 (d, J = 8.9 Hz, 2H), 7.79 (s, 1H), 7.61 (s, 1H), 7.42-7.29 (m, 2H), 7.14 (d, J = 8.9 Hz, 2H), 4.01 (q, J = 7.1 Hz, 2H), 3.88 (s, 3H), 3.67 (s, 2H), 1.11 (t, J = 7.1 Hz, 3H). |

-continued

| No. | Molecular weight g/mol | Aspect | LCMS purity UV at 254 nm | Mass spectrometry m/z MH+ M − H+ | ¹H NMR (300 MHz, DMSO) δ |
|---|---|---|---|---|---|
| 134 | 370.42 | oil | 92 | 371 | 8.10 (d, J = 1.7 Hz, 1H), 7.84 (d, J = 8.9 Hz, 2H), 7.55 (d, J = 5.2 Hz, 1H), 7.02 (t, J = 7.1 Hz, 3H), 6.86 (d, J = 1.7 Hz, 1H), 3.99 (q, J = 7.1 Hz, 2H), 3.83 (s, 3H), 3.52 (s, 2H), 1.09 (t, J = 7.1 Hz, 3H). |

Example 24: Preparation of derivative number 135: 2-(2-(4-chlorophenyl)-5-(4-methoxybenzoyl)thiophen-3-yl)propanoic acid

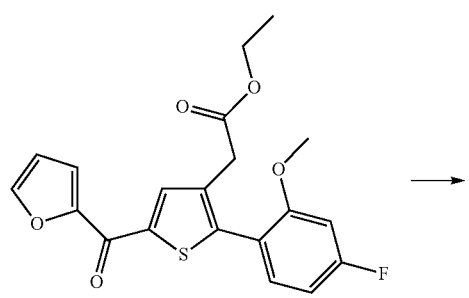

0.207 g (0.522 mmol) of ethyl 2-(2-(4-fluoro-2-methoxyphenyl)-5-(furan-2-carbonyl)thiophen-3-yl)acetate were solubilized in 3 ml of a mixture consisting of tetrahydrofurane and ethanol (1/2, v/v), to this solution were added with magnetic stirring 0.057 ml (0.575 mmol) of a 10N sodium hydroxide aqueous solution. The obtained mixture was stirred at r.t. for 3 h. The mixture was concentrated in vacuo, the obtained residue was taken up into 10 ml of water, the aqueous phase was acidified down to pH=2-3 by adding a 12N hydrochloric acid aqueous solution. 2 ml of petroleum ether were added and the mixture was vigorously stirred for 15 min. A precipitate was isolated by filtration, washed with 5 ml of water and 5 ml of petroleum ether before being dried in a vacuum bell jar in order to obtain 0.136 g (yield=70%) of 2-(2-(4-chlorophenyl)-5-(4-methoxybenzoyl)thiophen-3-yl) propanoic acid. LC-MS: m/z=361 (MH+); UV purity at 254 nm=98%. ¹H NMR (300 MHz, DMSO) δ 12.44 (s, 1H), 8.15 (s, 2H), 7.56 (d, J=3.6 Hz, 1H), 7.38 (dd, J=8.4, 6.8 Hz, 1H), 7.11 (dd, J=11.4, 2.4 Hz, 1H), 6.91 (td, J=8.4, 2.4 Hz, 1H), 6.86-6.77 (m, 1H), 3.78 (s, 3H), 3.44 (s, 2H).

The derivatives 136 and 137 were prepared according to the same procedure.

| No. | Molecular weight g/mol | Aspect | LCMS purity UV at 254 nm | Mass spectrometry m/z MH+ M − H+ | ¹H NMR (300 MHz, DMSO) δ |
|---|---|---|---|---|---|
| 136 | 348.32 | solid | 99 | 349 | 12.57 (s, 1H), 8.22 (s, 1H), 8.17 (dd, J = 1.6, 0.6 Hz, 1H), 7.68-7.52 (m, 2H), 7.36 (dd, J = 6.6, 3.2 Hz, 2H), 6.86 (dd, J = 3.7, 1.7 Hz, 1H), 3.59 (s, 2H). |
| 137 | 388.39 | solid | 94 | 389 | δ 12.52 (s, 1H), 7.91 (d, J = 8.8 Hz, 2H), 7.78 (s, 1H), 7.68-7.52 (m, 1H), 7.45-7.27 (m, 2H), 7.14 (d, J = 8.8 Hz, 2H), 3.88 (s, 3H), 3.58 (s, 2H). |

-continued

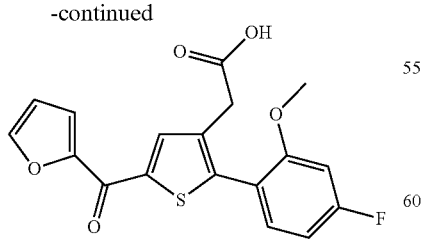

Example 25: Preparation of derivative number 138: 2-(2-(4-fluoro-2-hydroxyphenyl)-5-(furan-2-carbonyl)thiophen-3-yl)acetic acid

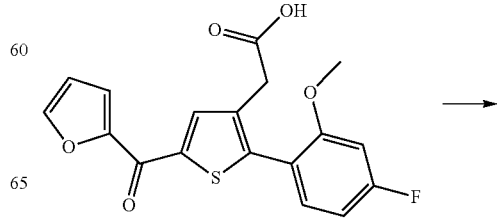

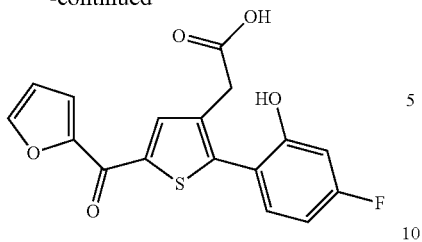

0.122 g (0.816 mmol) of D,L-methionine were solubilized in 0.882 ml (13.69 mmol) of methanesulfonic acid with magnetic stirring. To this solution were added 0.1 g (0.272 mmol) of 2-(2-(4-chlorophenyl)-5-(4-methoxybenzoyl)thiophen-3-yl)propanoic acid. The mixture was heated to 80° C. for 4 d during which 0.041 g (0.272 mmol) of D,L-methionine were added every 24 h (i.e. 3 additions in 4 d). After returning to r.t., the mixture was poured into 15 ml of a mixture consisting of water and ice. The aqueous phase was extracted with 15 ml of isobutanol. The organic phase was washed with 15 ml of water and 15 ml of a saturated NaCl aqueous solution and then dried on MgSO$_4$ which was then removed by filtration. The obtained filtrate was concentrated in vacuo and purified by preparative HPLC/MS in order to obtain 0.02 g (yield=21%) of 2-(2-(4-fluoro-2-hydroxyphenyl)-5-(furan-2-carbonyl)thiophen-3-yl)acetic acid as a pale yellow solid. LC-MS: m/z=347 (MH$^+$); UV purity at 254 nm=97%. $^1$H NMR (300 MHz, DMSO) 511.66 (s, 1H), 8.14 (s, 2H), 7.55 (d, J=4.0 Hz, 1H), 7.29 (dd, J=8.9, 6.9 Hz, 1H), 6.83 (dd, J=3.6, 1.7 Hz, 1H), 6.75 (t, J=8.1 Hz, 2H), 3.51 (s, 2H).

Example 26: Preparation of derivative number 139: ethyl 2-(2-(4-cyanophenyl)-5-(furan-2-carbonyl) thiophen-3-yl)acetate Step 1: Preparation of ethyl 2-(5-(furan-2-carbonyl)thiophen-3-yl)acetate

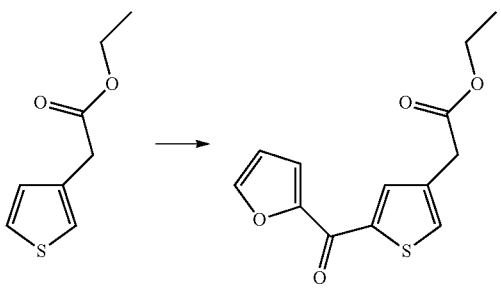 [SMILES: CCOC(=O)Cc1ccsc1 ; CCOC(=O)Cc1csc(C(=O)c2ccco2)c1]

In a flask placed under argon flow, were introduced with magnetic stirring: 25 ml of dichloromethane, 7.84 g (0.585 mmol) of trialuminium chloride, a solution of 3.35 ml (32.3 mmol) of 2-furoyl chloride in 10 ml of dichloromethane and a solution of 5 g (29.35 mmol) of ethyl 2-(thiophen-3-yl) acetate in 10 ml of dichloromethane. The obtained mixture was stirred with reflux for 1 h before being poured into 75 ml of a mixture consisting of water and ice and being stirred at r.t. for 1 h. The aqueous phase was extracted with 2×50 ml of dichloromethane. The combined organic phases were washed with 75 ml of water and then dried on MgSO$_4$ which was then removed by filtration. The obtained filtrate was concentrated in vacuo. The crude residue was purified by flash chromatography on a silica gel cartridge (eluent: petroleum ether/ethyl acetate gradient, from 100 to 80% of petroleum ether, v/v). 5.9 g (yield=72%) of ethyl 2-(5-(furan-2-carbonyl)thiophen-3-yl)acetate were obtained as a solid. LC-MS: m/z=265 (MH$^+$); UV purity at 254 nm=95%. $^1$H NMR (300 MHz, DMSO) δ 8.12 (s, 2H), 7.88 (s, 1H), 7.54 (d, J=3.6 Hz, 1H), 6.82 (dd, J=3.6, 1.7 Hz, 1H), 4.11 (q, J=7.1 Hz, 2H), 3.79 (s, 2H), 1.21 (t, J=7.1 Hz, 3H).

Step 2: Preparation of ethyl 2-(2-(4-cyanophenyl)-5-(furan-2-carbon yl)thiophen-3-yl)acetate (derivative number 139)

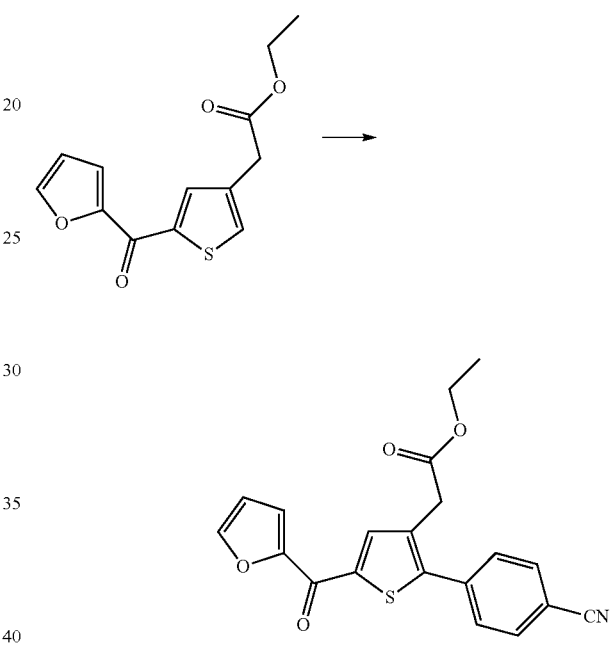

1.189 g (4.27 mmol) of ethyl 2-(5-(furan-2-carbonyl)thiophen-3-yl)acetate were solubilized in 20 ml of DMSO with magnetic stirring, and then 0.999 g (4.27 mmol) of 4-iodobenzonitrile, 0.497 g (8.55 mmol) of potassium fluoride, 0.6 g (0.855 mmol) of Pd(Cl)$_2$(PPh$_3$)$_2$ and 1.452 g (8.55 mmol) of silver nitrate were added. The mixture was stirred at 130° C. for 10 min. After returning to r.t. the mixture was poured into 100 ml of a mixture consisting of water and ice. The aqueous phase was extracted with 2×50 ml of ethyl acetate. The combined organic phases were washed with 50 ml of water and 50 ml of a saturated NaCl aqueous solution and then dried on MgSO$_4$ which was then removed by filtration. The obtained filtrate was concentrated in vacuo, taken up into 20 ml of dichloromethane and filtered on silica gel (eluent dichloromethane 100%). The obtained filtrate was concentrated in vacuo and purified by flash chromatography on a silica gel cartridge (eluent: petroleum ether/diisopropyl ether gradient, from 100 to 0% petroleum ether, v/v). 254 mg (yield=15%) of ethyl 2-(2-(4-cyanophenyl)-5-(furan-2-carbonyl)thiophen-3-yl)acetate were obtained as a pale yellow oil. LC-MS: m/z=366 (MH$^+$); UV purity at 254 nm=94%. $^1$H NMR (300 MHz, DMSO) 58.18 (d, J=15.8 Hz, 2H), 7.99 (d, J=8.3 Hz, 2H), 7.75 (d, J=8.3 Hz, 2H), 7.61 (d, J=3.6 Hz, 1H), 6.85 (dd, J=3.6, 1.6 Hz, 1H), 4.06 (q, J=7.1 Hz, 2H), 3.85 (s, 2H), 1.14 (t, J=7.1 Hz, 3H).

Example 27: Preparation of derivative number 140: 2-(2-(4-cyanophenyl)-5-(furan-2-carbonyl)thiophen-3-yl)acetic acid

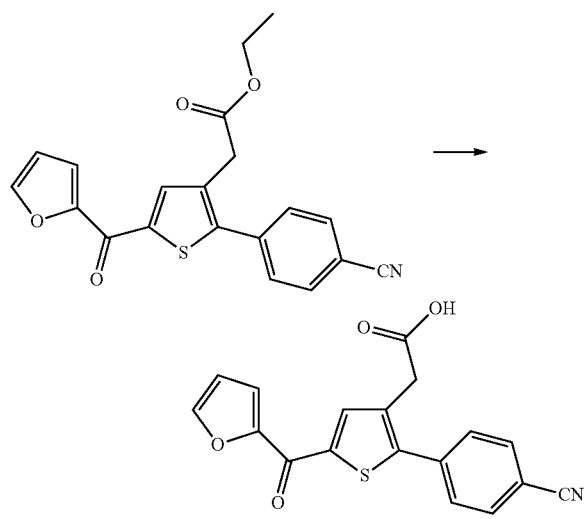

0.189 g (0.491 mmol) of ethyl 2-(2-(4-cyanophenyl)-5-(furan-2-carbonyl)thiophen-3-yl)acetate were solubilized in 1.5 ml of a mixture of tetrahydrofurane and ethanol (1/2, v/v), to this solution were added with magnetic stirring 0.054 ml (0.541 mmol) of a 10N sodium hydroxide aqueous solution. The obtained mixture was stirred at r.t. for 1 h. The mixture was concentrated in vacuo, the obtained residue was taken up into 10 ml of water, the aqueous phase was acidified down to pH=2-3 by adding a 4N hydrochloric acid aqueous solution. The aqueous phase was extracted with 2×10 ml of ethyl acetate, the combined organic phases were washed with 20 ml of water and 20 ml of a saturated NaCl aqueous solution and then dried on MgSO$_4$ which was then removed by filtration. The residue was taken up into 10 ml of water, stirred at r.t. for 1 h, the obtained solid was isolated by filtration and washed with water in order to obtain 166 mg (yield=68%) of 2-(2-(4-cyanophenyl)-5-(furan-2-carbonyl)thiophen-3-yl)acetic acid. LC-MS: m/z=non-ionized. $^1$H NMR (300 MHz, DMSO) δ 12.69 (s, 1H), 8.21 (s, 1H), 8.16 (d, J=0.8 Hz, 1H), 8.00 (d, J=8.2 Hz, 2H), 7.76 (d, J=8.3 Hz, 2H), 7.61 (d, J=3.6 Hz, 1H), 6.85 (dd, J=3.6, 1.6 Hz, 1H), 3.75 (s, 2H).

Example 28: Preparation of derivative number 141: 2-(2-(4-cyanophenyl)-5-(furan-2-carbonyl)thiophen-3-yl)-N-(2-(dimethylamino)ethyl)acetamide

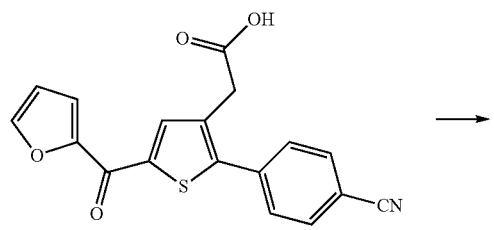

-continued

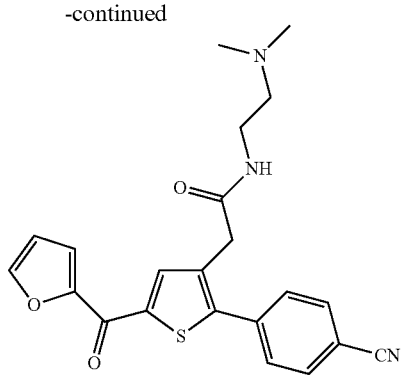

0.125 g (0.371 mmol) of 2-(2-(4-cyanophenyl)-5-(furan-2-carbonyl)thiophen-3-yl)acetic acid were solubilized in a mixture of 5 ml of dichloromethane and 0.1 ml of dimethylformamide. To this solution, were added with magnetic stirring at 0° C., 0.045 ml (0.408 mmol) of N,N-dimethylethane-1,2-diamine, 0.178 g (0.926 mmol) of EDC.HCl and 0.055 g (0.408 mmol) of HOBt. The mixture was stirred at r.t. for 16 h. 30 ml of water were added to the reaction mixture. The aqueous phase was extracted with 30 ml of dichloromethane, the organic phase was washed with 10 ml of a saturated NaHCO$_3$ aqueous solution, 10 ml of water and 10 ml of a saturated NaCl aqueous solution and then dried on Na$_2$SO$_4$ which was then removed by filtration and the obtained filtrate was concentrated in vacuo. 0.16 g (yield=30%) of 2-(2-(4-cyanophenyl)-5-(furan-2-carbonyl)thiophen-3-yl)-N-(2-(dimethylamino)ethyl)acetamide were obtained as a white solid. LC-MS: m/z=408 (MH$^+$); UV purity at 254 nm=98%. $^1$H NMR (300 MHz, DMSO) δ 8.20 (s, 1H), 8.15 (d, J=1.0 Hz, 2H), 7.98 (d, J=8.4 Hz, 2H), 7.88 (d, J=8.4 Hz, 2H), 7.58 (d, J=3.5 Hz, 1H), 6.86 (dd, J=3.6, 1.7 Hz, 1H), 3.56 (s, 2H), 3.16 (dd, J=12.3, 6.4 Hz, 2H), 2.27 (t, J=6.6 Hz, 2H), 2.13 (s, 6H).

Example 29: Preparation of derivative number 142: 2-(2-(4-cyanophenyl)-5-(furan-2-carbonyl)thiophen-3-yl)-N-(2-(dimethylamino)ethyl)acetamide Step 1: Preparation of 2-(5-(furan-2-carbonyl)thiophen-3-yl)acetic acid

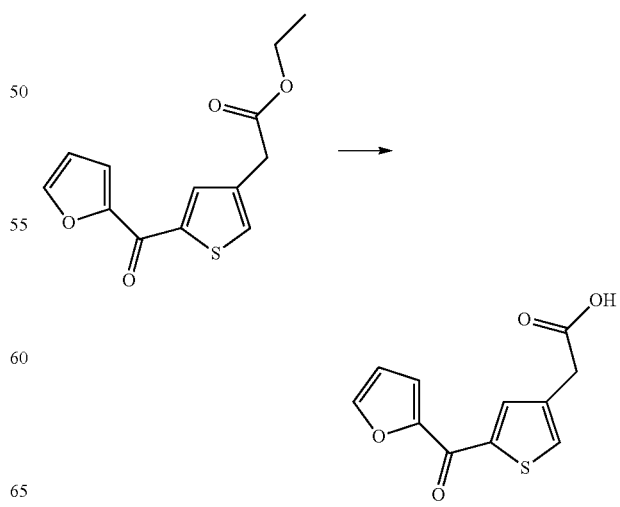

2 g (7.57 mmol) of ethyl 2-(5-(furan-2-carbonyl)thiophen-3-yl)acetate were solubilized in 10 ml of ethanol, to this solution were added with magnetic stirring 0.832 ml (8.32 mmol) of a 10N sodium hydroxide aqueous solution. The obtained mixture was stirred at r.t. for 2 h. The mixture was concentrated in vacuo, the obtained residue was taken up into 15 ml of water, the aqueous phase was washed with 2×15 ml of ethyl acetate and then acidified down to pH=1-2 by adding a 12N hydrochloric acid aqueous solution. The aqueous phase was extracted with 2×15 ml of ethyl acetate, the combined organic phases were washed with 15 ml of water and 15 ml of a saturated NaCl aqueous solution and then dried on MgSO$_4$ which was then removed by filtration. 1.715 g (yield=96%) of 2-(5-(furan-2-carbonyl)thiophen-3-yl)acetic acid were obtained were obtained as an orangey oil. LC-MS: m/z=non-ionized. $^1$H NMR (300 MHz, DMSO) δ 12.43 (s, 1H), 8.11 (s, 2H), 7.86 (s, 1H), 7.54 (d, J=3.6 Hz, 1H), 6.81 (dd, J=3.6, 1.7 Hz, 1H), 3.70 (s, 2H).

Step 2: Preparation of N-(2-(dimethylamino)ethyl)-2-(5-(furan-2-carbonyl)thiophen-3-yl)acetamide 0.416 g (1.761 mmol) of 2-(5-(furan-2-carbonyl)thiophen-3-yl)acetic acid were solubilized in a mixture of 5 ml of dichloromethane and 0.1 ml of dimethylformamide. To this solution, were added with magnetic stirring at 0° C., 0.212 ml (1.937 mmol) of N,N-dimethylethane-1,2-diamine, 0.844 g (4.4 mmol) of EDC.HCl and 0.262 g (1.937 mmol) of HOBt. The mixture was stirred at r.t. for 16 h. 30 ml of water were added to the reaction mixture. The aqueous phase was extracted with 30 ml of dichloromethane, the organic phase was washed with 10 ml of a saturated NaHCO$_3$ aqueous solution, 10 ml of water and 10 ml of a saturated NaCl aqueous solution and then dried on Na$_2$SO$_4$ which was then removed by filtration and the obtained filtrate was concentrated in vacuo. 0.16 g (yield=30%) of 2-(2-(4-cyanophenyl)-5-(furan-2-carbonyl)thiophen-3-yl)-N-(2-(dimethylamino)ethyl)acetamide were obtained as a white solid. LC-MS: m/z=non-ionized. $^1$H NMR (300 MHz, DMSO) δ 8.07 (dd, J=3.8, 1.2 Hz, 2H), 7.77 (s, 1H), 7.51 (d, J=3.2 Hz, 1H), 6.79 (dd, J=3.6, 1.7 Hz, 1H), 3.50 (s, 2H), 3.15 (t, J=6.6 Hz, 2H), 2.31 (t, J=6.6 Hz, 2H), 2.13 (s, 6H).

Step 3: Preparation of 2-(2-(3-cyanophenyl)-5-(furan-2-carbonyl)thiophen-3-yl)-N-(2-(dimethylamino)ethyl)acetamide (derivative number 142)

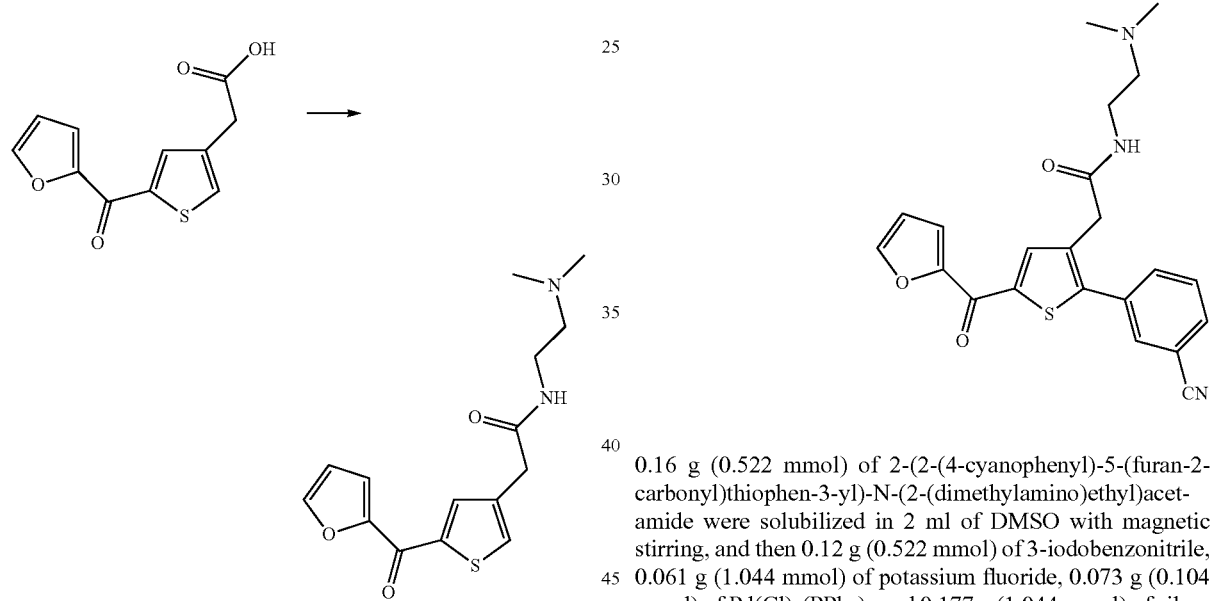

0.16 g (0.522 mmol) of 2-(2-(4-cyanophenyl)-5-(furan-2-carbonyl)thiophen-3-yl)-N-(2-(dimethylamino)ethyl)acetamide were solubilized in 2 ml of DMSO with magnetic stirring, and then 0.12 g (0.522 mmol) of 3-iodobenzonitrile, 0.061 g (1.044 mmol) of potassium fluoride, 0.073 g (0.104 mmol) of Pd(Cl)$_2$(PPh$_3$)$_2$ and 0.177 g (1.044 mmol) of silver nitrate were added. The mixture was stirred at 130° C. for 10 min. After returning to r.t. the mixture was poured into 100 ml of a mixture consisting of water and ice. The aqueous phase was extracted with 2×50 ml of ethyl acetate. The combined organic phases were washed with 50 ml of water and 50 ml of a saturated NaCl aqueous solution and then dried on MgSO$_4$ which was then removed by filtration. The obtained filtrate was concentrated in vacuo, taken up into 20 ml of dichloromethane and filtered on silica gel (eluent dichloromethane 100%). The obtained filtrate was concentrated in vacuo and purified by flash chromatography on a silica gel cartridge (eluent: petroleum ether/diisopropyl ether gradient, from 100 to 0% of petroleum ether, v/v). 45 mg (yield=21%) of ethyl 2-(2-(4-cyanophenyl)-5-(furan-2-carbonyl)thiophen-3-yl)acetate were obtained as a pale yellow solid. LC-MS: m/z=408 (MH$^+$); UV purity at 254 nm=99%. $^1$H NMR (300 MHz, DMSO) 58.18 (s, 1H), 8.12 (d, J=6.4 Hz, 2H), 7.94 (t, J=7.7 Hz, 2H), 7.71 (t, J=7.8 Hz, 1H), 7.57 (d, J=3.6 Hz, 1H), 6.83 (dd, J=3.6, 1.7 Hz, 1H), 3.18 (t, J=6.6 Hz, 2H), 2.20 (s, 6H).

Example 30: Preparation of derivative number 143: isopropyl 2-(2-(4-chloro-2-fluorophenyl)-5-(furan-2-carbonyl)thiophen-3-yl)acetate

Step 1: Preparation of isopropyl 2-(5-(furan-2-carbonyl)thiophen-3-yl)acetate

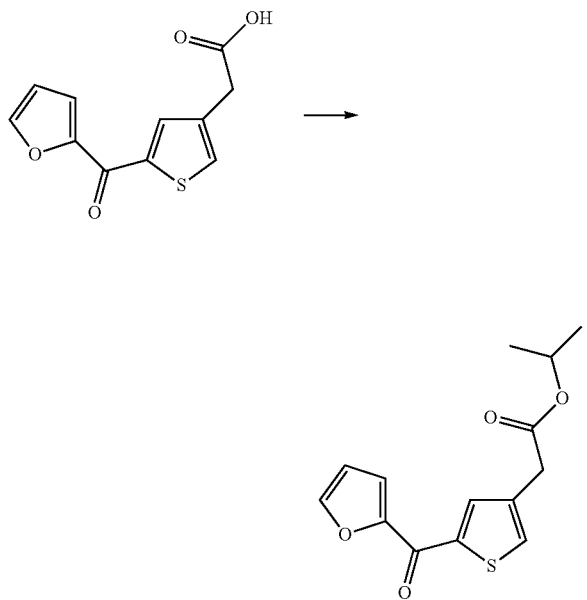

1 g (4.23 mmol) of 2-(5-(furan-2-carbonyl)thiophen-3-yl)acetic acid were solubilized in 10 ml of isopropanol, 1 drop of sulfuric acid was added to this solution. The mixture was heated with magnetic stirring with reflux for 24 h. After returning to r.t., the mixture was concentrated in vacuo, the crude residue was taken up into 15 ml of dichloromethane, the organic phase was washed with 10 ml of a saturated NaHCO₃ aqueous solution and 10 ml of water and then dried on MgSO₄ which was then removed by filtration. The obtained filtrate was concentrated in vacuo in order to obtain 0.667 g (yield=53%) of isopropyl 2-(5-(furan-2-carbonyl)thiophen-3-yl)acetate as an orangey oil. LC-MS: m/z=279 (MH⁺); UV purity at 254 nm=94%

Step 2: Preparation of isopropyl 2-(2-(4-chloro-2-fluorophenyl)-5-(furan-2-carbonyl)thiophen-3-yl)acetate (derivative number 143)

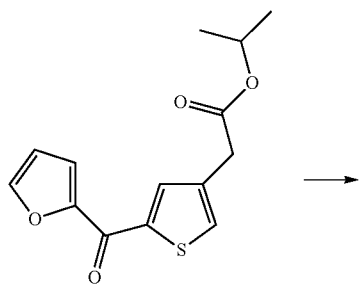

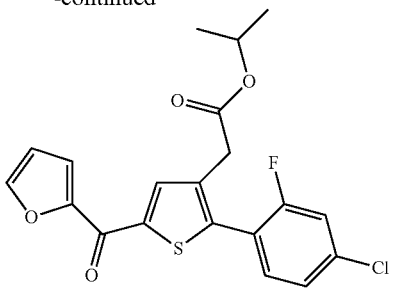

0.66 g (2.29 mmol) of isopropyl 2-(5-(furan-2-carbonyl)thiophen-3-yl)acetate were solubilized in 10 ml of DMSO with magnetic stirring, and then 0.572 g (2.29 mmol) of 4-chloro-2-fluoro-1-iodobenzene, 0.259 g (4.46 mmol) of potassium fluoride, 0.313 g (0.446 mmol) of Pd(Cl)₂(PPh₃)₂ and 0.757 g (4.46 mmol) of silver nitrate were added. The mixture was stirred at 130° C. for 10 min. After returning to r.t., the mixture was poured into 100 ml of a mixture consisting of water and ice. The aqueous phase was extracted with 2×50 ml of ethyl acetate. The combined organic phases were washed with 50 ml of water and 50 ml of a saturated NaCl aqueous solution and then dried on MgSO₄ which was then removed by filtration. The obtained filtrate was concentrated in vacuo, taken up into 20 ml of dichloromethane and filtered on silica gel (eluent: dichloromethane 100%). The obtained filtrate was concentrated in vacuo and purified by flash chromatography on a silica gel cartridge (eluent: petroleum ether/dichloromethane gradient, from 100 to 0% of petroleum ether gradient, v/v). 135 mg (yield=1%) of isopropyl 2-(2-(4-chloro-2-fluorophenyl)-5-(furan-2-carbonyl)thiophen-3-yl)acetate were obtained as a pale yellow solid. LC-MS: m/z=407 (MH⁺); UV purity at 254 nm=97%. ¹H NMR (300 MHz, DMSO) δ 8.18 (d, J=16.2 Hz, 2H), 7.82-7.29 (m, 5H), 6.85 (s, 1H), 4.83 (dt, J=12.2, 6.0 Hz, 1H), 3.64 (s, 2H), 1.12 (d, J=6.1 Hz, 6H).

Example 31: Preparation of derivative number 144: 2-(2-(4-chloro-2-fluorophenyl)-5-(furan-2-carbonyl)thiophen-3-yl)acetic acid

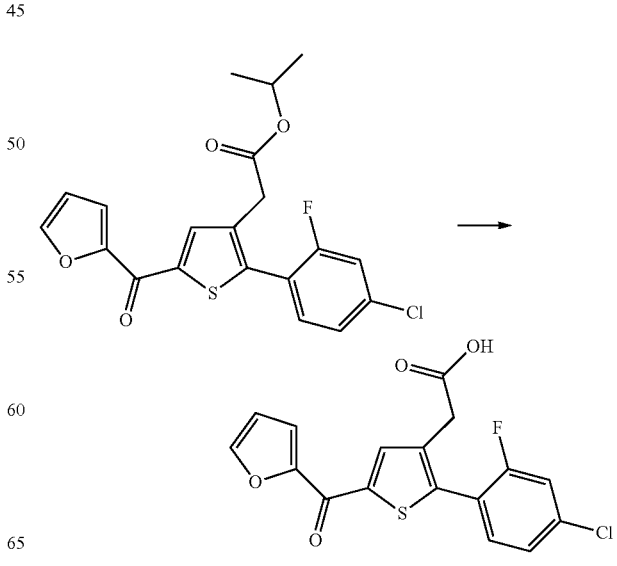

0.115 g (0.283 mmol) of isopropyl 2-(2-(4-chloro-2-fluorophenyl)-5-(furan-2-carbonyl)thiophen-3-yl)acetate were solubilized in 3 ml of isopropanol, to this solution were added with magnetic stirring 0.028 ml (0.283 mmol) of a 10N sodium hydroxide aqueous solution. The obtained mixture was stirred at r.t. for 24 h. The mixture was concentrated in vacuo, the obtained residue was taken up into 15 ml of water, the aqueous phase was washed with 15 ml of methyl tert-butyl ether, and then acidified down to pH=1-2 by adding a 4N hydrochloric acid aqueous solution. The aqueous phase was extracted with 2×10 ml of ethyl acetate, the combined organic phases were washed with 15 ml of water and 15 ml of a saturated NaCl aqueous solution and then dried on MgSO₄ which was then removed by filtration. The residue was taken up into 10 ml of water, stirred at r.t. for 1 h, an obtained solid was isolated by filtration and washed with water in order to obtain 71 mg (yield=63%) of 2-(2-(4-chloro-2-fluorophenyl)-5-(furan-2-carbonyl)-thiophen-3-yl)acetic acid. LC-MS: m/z=365 (MH⁺); UV purity at 254 nm=91%. ¹H NMR (300 MHz, DMSO) δ 12.54 (s, 1H), 8.18 (d, J=14.1 Hz, 2H), 7.68 (d, J=10.0 Hz, 1H), 7.58 (dd, J=13.0, 5.8 Hz, 2H), 7.46 (d, J=10.3 Hz, 1H), 6.91-6.75 (m, 1H), 3.57 (s, 2H).

Example 32: Preparation of derivative number 145: 2-(2-(4-fluorophenyl)-5-(furan-2-carbonyl)thiophen-3-yl)acetonitrile Step 1: Preparation of 2-(4-fluorophenyl)-3-methylthiophene

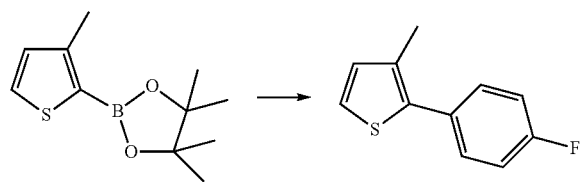

1 g (4.46 mmol) of 4,4,5,5-tetramethyl-2-(3-methylthiophen-2-yl)-1,3,2-dioxaborolane were solubilized under argon in 15 ml of toluene, were added with magnetic stirring, 0.781 g (4.46 mmol) of 1-bromo-4-fluorobenzene, 15.62 ml (31.2 mmol) of a 2M Na₂CO₃ aqueous solution and 0.26 g (0.223 mmol) of palladium[0] tetrakis(triphenylphosphine). The mixture was stirred with reflux for 3 h. After returning to r.t., the mixture was filtered on celite. The aqueous phase was extracted with 20 ml of ethyl acetate. The organic phase was washed with 10 ml of water, 10 ml of a saturated NaCl aqueous solution and then dried on MgSO₄ which was then removed by filtration. The obtained filtrate was concentrated in vacuo. The crude residue was purified by flash chromatography on a silica gel cartridge (eluent: petroleum ether 100%). 0.509 g (yield=51%) of 2-(4-fluorophenyl)-3-methylthiophene were obtained as an oil and directly engaged into the following step.

Step 2: Preparation of (5-(4-fluorophenyl)-4-methylthiophen-2-yl)(furan-2-yl)methanone

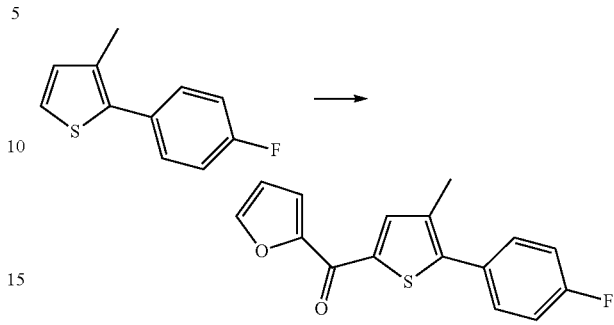

In a flask placed under an argon flow, were introduced with magnetic stirring: 20 ml of dichloromethane, 0.5 g (2.237 mmol) of 2-(4-fluorophenyl)-3-methylthiophene, 0.265 ml (2.68 mmol) of 2-furoyl chloride. The obtained mixture was cooled to 5° C. before adding portion wise 0.328 g (2.46 mmol) of trialuminium chloride. The mixture was stirred at r.t. for 16 h before being poured onto 150 ml of a mixture consisting of water and of dichloromethane (2/1, v/v) and being stirred at r.t. for 30 min. This mixture was filtered on celite. After separation, the aqueous phase was extracted with 50 ml of dichloromethane, the combined organic phases were washed with 50 ml of water and then dried on MgSO₄ which was then removed by filtration. The obtained filtrate was concentrated in vacuo. The crude residue was purified by flash chromatography on a silica gel cartridge (eluent: petroleum ether/ethyl acetate gradient), from 100 to 75% of petroleum ether, v/v). 0.58 g (yield=89%) of (5-(4-fluorophenyl)-4-methylthiophen-2-yl)(furan-2-yl)methanone as a foam. LC-MS: m/z=287 (MH⁺); UV purity at 254 nm=88%. ¹H NMR (300 MHz, DMSO) δ 8.13 (dd, J=1.6, 0.7 Hz, 1H), 8.09 (s, 1H), 7.62 (ddd, J=6.3, 4.2, 3.0 Hz, 3H), 7.36 (t, J=8.9 Hz, 2H), 6.83 (dd, J=3.6, 1.7 Hz, 1H), 2.34 (s, 3H).

Step 3: Preparation of (4-(bromomethyl)-5-(4-fluorophenyl)thiophen-2-yl)(furan-2-yl)methanone

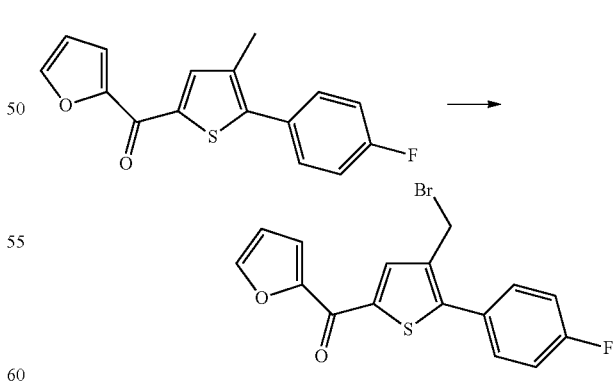

0.56 g (1.741 mmol) of (5-(4-fluorophenyl)-4-methylthiophen-2-yl)(furan-2-yl)methanone were solubilized in 15 ml of carbon tetrachloride with magnetic stirring, were then added 0.286 g (1.741 mmol) of AIBN and 0.31 g (1.741 mmol) of N-bromosuccinimide. The mixture was stirred with reflux under a 300 watt light for 9 h during which 0.043 g (0.26 mmol) of AIBN and 0.047 g (0.26 mmol) of N-bromosuccinimide were added at 3 and 6 h. The reaction medium was concentrated in vacuo, the obtained residue was taken up into 50 ml of a mixture consisting of water and ice, the aqueous phase was extracted with 3×50 ml of ethyl acetate. The combined organic phases were washed with 100 ml of a saturated NaCl aqueous solution and then dried on MgSO$_4$ which was then removed by filtration. The obtained filtrate was concentrated in vacuo. The crude residue was purified by flash chromatography on a silica gel cartridge (eluent: petroleum ether/diisopropyl ether gradient, from 100 to 66% of petroleum ether, v/v). 0.308 g (yield=36%) of (4-(bromomethyl)-5-(4-fluorophenyl)thiophen-2-yl)(furan-2-yl)methanone as a solid. LC-MS: m/z=367 (MH$^+$); UV purity at 254 nm=75%. $^1$H NMR (300 MHz, DMSO) δ 7.98 (s, 1H), 7.89 (dd, J=12.5, 8.0 Hz, 3H), 7.74 (d, J=7.7 Hz, 1H), 7.67 (d, J=5.2 Hz, 1H), 7.26 (d, J=5.2 Hz, 1H), 4.70 (s, 2H), 1.74-1.51 (m, 6H), 1.43 (s, 3H).

Step 4: Preparation of 2-(2-(4-fluorophenyl)-5-(furan-2-carbonyl)thiophen-3-yl)acetonitrile (derivative number 145)

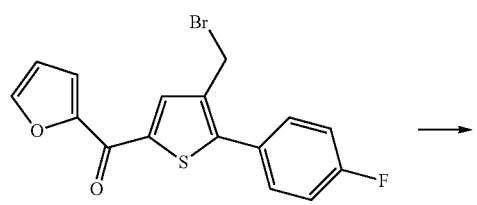

0.3 g (0.616 mmol) of (4-(bromomethyl)-5-(4-fluorophenyl)thiophen-2-yl)(furan-2-yl)methanone were solubilized in 10 ml of tetrahydrofurane with magnetic stirring, were then added 0.044 g (0.678 mmol) of potassium cyanide and 1 ml of water. The mixture was stirred with reflux for 16 h. The reaction medium was poured into 15 ml of water, the aqueous phase was extracted with 2×15 ml of ethyl acetate, the combined organic phases were washed with 15 ml of water and 15 ml of a saturated NaCl aqueous solution and then dried on MgSO$_4$ which was then removed by filtration. The obtained filtrate was concentrated in vacuo. The crude residue was purified by preparative HPLC/MS. 0.024 g (yield=11%) of 2-(2-(4-fluorophenyl)-5-(furan-2-carbonyl)thiophen-3-yl)acetonitrile as a pale yellow solid. LC-MS: m/z=312 (MH$^+$); UV purity at 254 nm=94%. $^1$H NMR (300 MHz, DMSO) δ. 8.25 (s, 1H), 8.18 (s, 1H), 7.74-7.57 (m, 3H), 7.41 (t, J=8.8 Hz, 2H), 6.86 (dd, J=3.6, 1.7 Hz, 1H), 4.13 (s, 2H).

Example 33: Preparation of derivative number 146: 2-(2-phenyl-5-picolinoylthiophen-3-yl)acetonitrile Step 1: Preparation of 5-bromo-4-methylthiophene-2-carboxylic acid

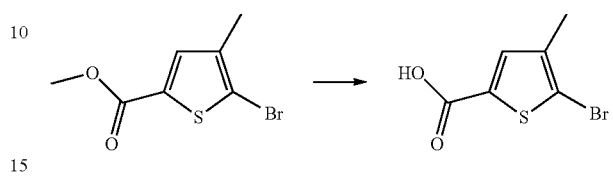

5 g (21.27 mmol) of methyl 5-bromo-4-methylthiophene-2-carboxylate were solubilized in 250 ml of ethanol, to this solution were added with magnetic stirring 106 ml (106 mmol) of a 1N sodium hydroxide aqueous solution. The obtained mixture was stirred at 80° C. for 2 h. The mixture was concentrated in vacuo, the obtained residue was taken up into 250 ml of water and 100 ml of a 1N hydrochloric acid aqueous solution were added. A precipitate was isolated by filtration, washed with a minimum of water and 10 ml of pentane. The white solid was dried in a vacuum bell jar and 3.63 g (yield=76%) of 5-bromo-4-methylthiophene-2-carboxylic acid were obtained. LC-MS: m/z=219 (M-H$^+$); UV purity at 254 nm >99%. $^1$H NMR (300 MHz, DMSO) δ 13.34 (s, 1H), 7.53 (s, 1H), 2.15 (s, 3H).

Step 2: Preparation of 5-bromo-N-methoxy-N,4-dimethylthiophene-2-carboxamide

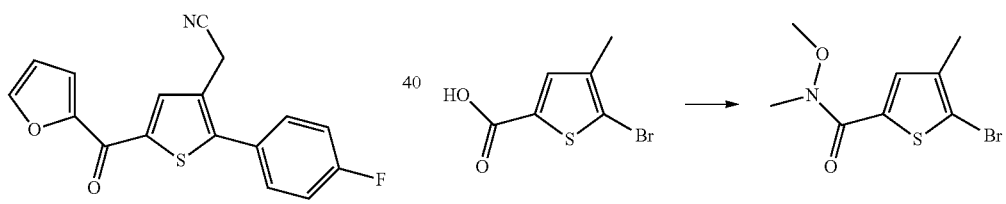

3.63 g (16.26 mmol) of 5-bromo-4-methylthiophene-2-carboxylic acid were solubilized in dichloromethane with magnetic stirring, next were added 4.27 ml (48.8 mmol) of oxalyl chloride and a droplet of dimethylformamide. The mixture was stirred at r.t. for 2 h before being concentrated in vacuo. The residue was taken up into 75 ml of a dichloromethane/pyridine mixture (2/1, v/v) and then 2.427 g (24.38 mmol) of N,O-dimethylhydroxylamine hydrochloride were added. The mixture was stirred at r.t. for 3 h before being poured into 300 ml of water. The aqueous phase was extracted with 3×150 ml of ethyl acetate. The combined organic phases were washed with 2×150 ml of a 1N hydrochloric acid aqueous solution, 150 ml of water and 150 ml of a saturated NaCl aqueous solution and then dried on Na$_2$SO$_4$ which was then removed by filtration. The obtained filtrate was concentrated in vacuo. 4.32 g (yield=100%) of 5-bromo-N-methoxy-N,4-dimethylthiophene-2-carboxamide were obtained as a brown oil. LC-MS: m/z=265 (MH$^+$); UV purity at 254 nm >99%. $^1$H NMR (300 MHz, DMSO) δ 7.64 (s, 1H), 3.76 (s, 3H), 3.26 (s, 3H), 2.17 (s, 3H).

Step 3: Preparation of (5-bromo-4-methylthiophene-2-yl)(pyridin-2-yl)methanone

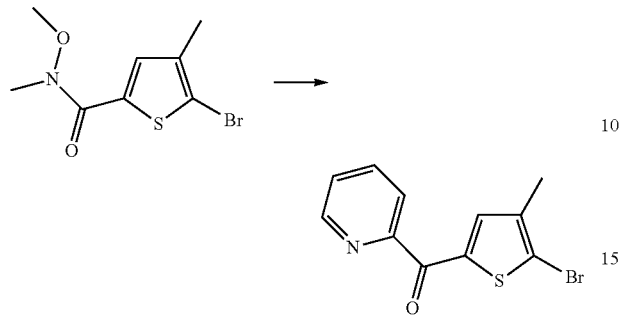

In a flask placed under argon, were introduced at 0° C.: 25 ml of tetrahydrofurane, 0.407 ml (3.75 mmol) of 2-iodopyridine and 3.75 ml (3.75 mmol) of ethyl magnesium bromide, the cold bath was withdrawn and the mixture was stirred at r.t. for 30 min. Next, a solution of 1 g (3.75 mmol) of 5-bromo-N-methoxy-N,4-dimethylthiophene-2-carboxamide in 25 ml of tetrahydrofurane was added dropwise. The mixture was stirred at r.t. for 3 h before being poured into 75 ml of a saturated ammonium chloride aqueous solution. The organic phase was extracted with 3×100 ml of ethyl acetate, 100 ml of a saturated NaHCO$_3$ aqueous solution, 100 ml of water, 100 ml of a saturated NaCl aqueous solution, and then dried on Na$_2$SO$_4$ which was then removed by filtration and the obtained filtrate was concentrated in vacuo. The crude residue was purified by flash chromatography on a silica gel cartridge (eluent: heptane/ethyl acetate gradient, from 95% to 75% of heptane, v/v). 0.357 g (yield=33%) of (5-bromo-4-methylthiophen-2-yl)(pyridin-2-yl)methanone were obtained as a white solid. LC-MS: m/z=283 (MH$^+$); UV purity at 254 nm >99%. $^1$H NMR (300 MHz, DMSO) δ 8.79 (s, 1H), 8.08 (d, J=26.9 Hz, 3H), 7.73 (s, 1H), 2.22 (s, 3H).

Step 4: Preparation of (4-methyl-5-phenylthiophen-2-yl)(pyridin-2-yl)methanone

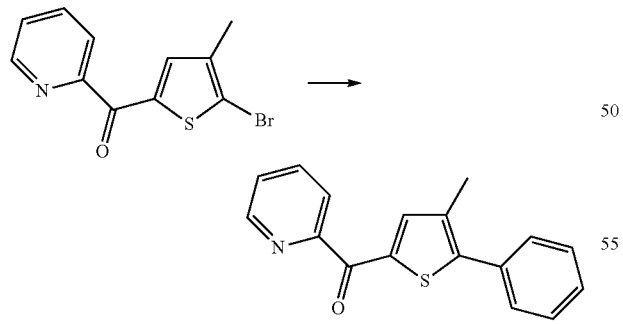

In a reactor suitable for microwaves, were introduced with magnetic stirring: 3 ml of a mixture consisting of dimethyl ether, ethanol and water (1/1/1, v/v/v), 0.357 g (1.253 mmol) of 5-bromo-4-methylthiophen-2-yl)(pyridin-2-yl)methanone, 0.816 g (2.505 mmol) of cesium carbonate and 0.229 g (1.879 mmol) of phenylboronic acid. The mixture was irradiated at 150° C. for 15 min. Once it had returned to r.t., the reaction medium was extracted with 3×10 ml of ethyl acetate. The combined organic phases were washed with 10 ml of a saturated NaCl aqueous solution, and then dried on Na$_2$SO$_4$ which was then removed by filtration and the obtained filtrate was concentrated in vacuo. The crude residue was purified by flash chromatography on a silica gel cartridge (eluent: heptane/ethyl acetate gradient, from 100% to 95% of heptane, v/v). 0.321 g (yield=91%) of (4-methyl-5-phenylthiophen-2-yl)(pyridin-2-yl)methanone were obtained as a pale yellow solid. LC-MS: m/z=280 (MH$^+$); UV purity at 254 nm >99%. $^1$H NMR (300 MHz, DMSO) δ. 8.85-8.77 (m, 1H), 8.19 (s, 1H), 8.17-8.02 (m, 2H), 7.78-7.67 (m, 1H), 7.65-7.39 (m, 5H), 2.35 (s, 3H).

Step 5: Preparation of (4-(bromomethyl)-5-phenylthiophen-2-yl)(pyridin-2-yl)methanone

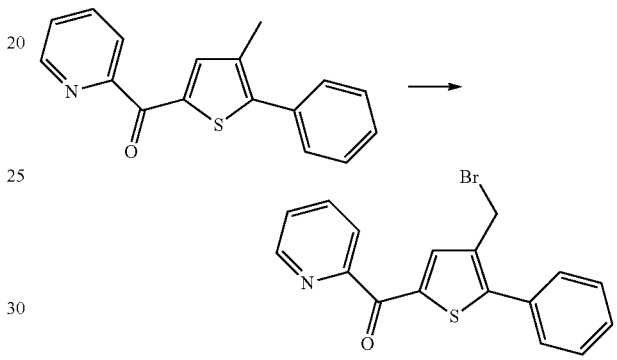

0.157 g (0.556 mmol) of (4-methyl-5-phenylthiophen-2-yl)(pyridin-2-yl)methanone were solubilized in 4.5 ml of carbon tetrachloride with magnetic stirring, were then added 0.091 g (0.556 mmol) of AIBN and 0.099 g (0.556 mmol) of N-bromosuccinimide. The mixture was stirred with reflux for 6 h. The reaction medium was poured into 30 ml of a mixture consisting of water and ice, the aqueous phase was extracted with 3×20 ml of ethyl acetate. The combined organic phases were washed with 50 ml of a saturated NaCl aqueous solution and then dried on Na$_2$SO$_4$ which was then removed by filtration. The obtained filtrate was concentrated in vacuo. The crude residue was purified by flash chromatography on a silica gel cartridge (eluent: heptane/ethyl acetate, 95% of heptane, v/v). 0.199 g (yield=56%) of (4-(bromomethyl)-5-phenylthiophen-2-yl)(pyridin-2-yl)methanone were obtained as a pale yellow solid. LC-MS: m/z=359 (MH$^+$); UV purity at 254 nm=82%. $^1$H NMR (300 MHz, DMSO) δ 8.89-8.74 (m, 1H), 8.23-7.98 (m, 4H), 7.82-7.34 (m, 5H), 4.76 (s, 2H).

Step 6: Preparation of 2-(2-phenyl-5-picolinoylthiophen-3-yl)acetonitrile (derivative number 146)

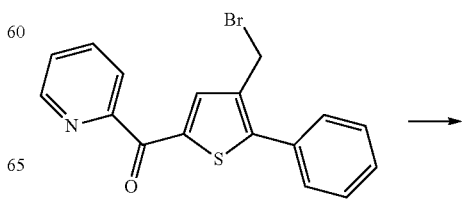

-continued

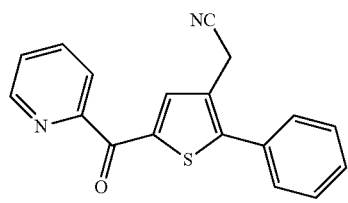

0.135 g (0.309 mmol) of (4-(bromomethyl)-5-phenylthiophen-2-yl)(pyridin-2-yl)methanone were solubilized in 6 ml of ethanol with magnetic stirring, were then added 0.024 g (0.361 mmol) of potassium cyanide and 0.5 ml of water. The mixture was stirred at r.t. for 2 h before being stirred at 55° C. for 90 min. The reaction medium was concentrated in vacuo and the obtained residue was taken up into 20 ml of a mixture consisting of water and of ethyl acetate (1/1, v/v). After separation, the aqueous phase was extracted with 2×15 ml of ethyl acetate, the combined organic phases were washed with 2×15 ml of water and then dried on $Na_2SO_4$ which was then removed by filtration. The obtained filtrate was concentrated in vacuo. The crude residue was purified by flash chromatography on a silica gel cartridge (eluent: heptane/ethyl acetate gradient, from 95 to 90% of heptane, v/v). 0.033 g (yield=36%) of 2-(2-phenyl-5-picolinoylthiophen-3-yl)acetonitrile were obtained as a white solid. LC-MS: m/z=305 ($MH^+$); UV purity at 254 nm=99%. $^1$H NMR (300 MHz, DMSO) δ 8.91-8.76 (m, 1H), 8.36 (s, 1H), 8.25-8.03 (m, 2H), 7.75 (ddd, J=7.2, 4.7, 1.6 Hz, 1H), 7.66-7.41 (m, 5H), 4.14 (s, 2H).

The compound 147 was prepared according to the same sequence of steps 1 to 6.

| No. | Molecular weight g/mol | Aspect | LCMS purity UV at 254 nm | Mass spectrometry m/z $MH^+$ | $M - H^+$ | $^1$H NMR (300 MHz, DMSO) δ |
|---|---|---|---|---|---|---|
| 147 | 338.81 | Solid | 98 | 339 | | 8.88-8.77 (m, 1H), 8.34 (s, 1H), 8.14 (ddd, J = 9.0, 4.3, 1.3 Hz, 2H), 7.83-7.71 (m, 1H), 7.63 (s, 4H), 4.16 (s, 2H). |

Example 34: Preparation of derivative number 148: Preparation of ethyl 2-(2-(4-chlorophenyl)-5-picolinoylthiophen-3-yl)acetate

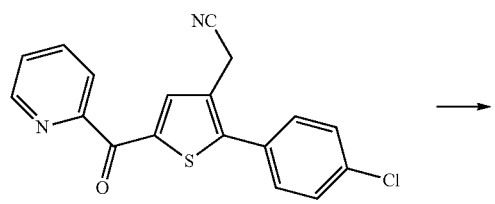

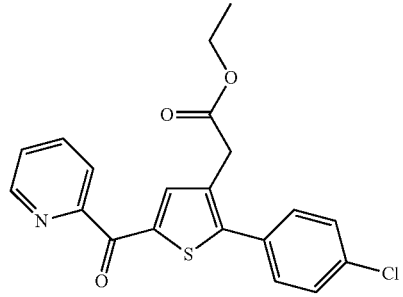

0.2 g (0.578 mmol) of 2-(2-(4-chlorophenyl)-5-picolinoylthiophen-3-yl)acetonitrile were solubilized with magnetic stirring in 5 ml of methanol, a whitish suspension was obtained and 0.1 ml (1.876 mmol) of sulfuric acid were added. The mixture was stirred with reflux for 8 d. The reaction medium was concentrated in vacuo and the obtained residue was taken up into 20 ml of a mixture consisting of water and of ethyl acetate (1/1, v/v). After separation, the aqueous phase was extracted with 2×15 ml of ethyl acetate, the combined organic phases were washed with 20 ml of a saturated NaCl aqueous solution and then dried on $Na_2SO_4$ which was then removed by filtration. The obtained filtrate was concentrated in vacuo. The crude residue was purified by flash chromatography on a silica gel cartridge (eluent: heptane/ethyl acetate gradient, from 85% to 70% of heptane, v/v). 0.215 g (yield=60%) of ethyl 2-(2-(4-chlorophenyl)-5-picolinoylthiophen-3-yl)acetate were obtained as a white solid. LC-MS: m/z=372 ($MH^+$); UV purity at 254 nm=99%. $^1$H NMR (300 MHz, DMSO) δ 8.86-8.77 (m, 1H), 8.26 (s, 1H), 8.19-8.04 (m, 2H), 7.73 (s, 1H), 7.58 (d, J=3.0 Hz, 4H), 3.80 (s, 2H), 3.61 (s, 3H).

Example 35: Preparation of derivative number 149: Preparation of 2-(2-(4-chlorophenyl)-5-picolinoylthiophen-3-yl)acetic acid

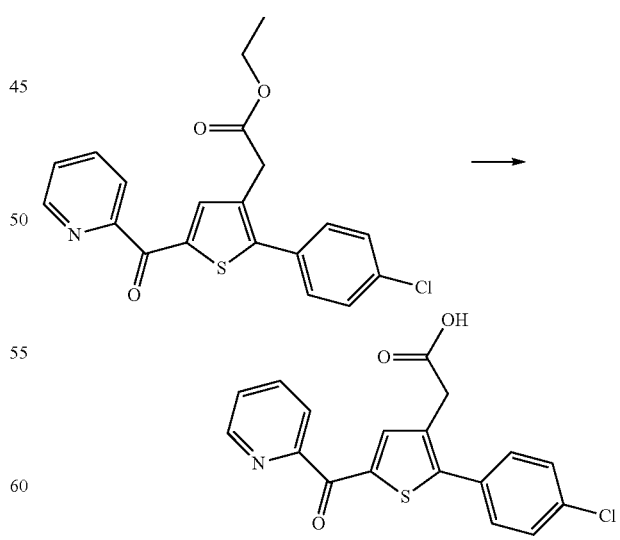

0.099 g (0.264 mmol) of ethyl 2-(2-(4-chlorophenyl)-5-picolinoylthiophen-3-yl)acetate were solubilized in 6 ml of methanol with magnetic stirring. To this solution were added 0.527 ml (0.527 mmol) of a 1N NaOH aqueous solution. The mixture was stirred at r.t. for 16 h before being concentrated in vacuo. The residue was taken up into 5 ml of water and a 1N hydrochloric acid aqueous solution was added until a precipitate occurred which was isolated by filtration and dried in a vacuum bell jar. 0.07 g (yield=73%) of 2-(2-(4-chlorophenyl)-5-picolinoylthiophen-3-yl)acetic acid were obtained. LC-MS: m/z=358 (M-H$^+$); UV purity at 254 nm=99%. $^1$H NMR (300 MHz, DMSO) δ 12.57 (s, 1H), 8.81 (d, J=4.4 Hz, 1H), 8.27 (s, 1H), 8.19-8.04 (m, 2H), 7.73 (m, 1H), 7.59 (m, 4H), 3.68 (s, 2H).

Example 36: Preparation of derivative number 150: (2-(4-chlorophenyl)-5-(furan-2-carbonyl)thiophen-3-yl)acetonitrile Step 1: Preparation of 2-(2-bromothiophen-3-yl)acetonitrile

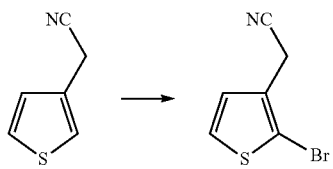 [SMILES: N#CCc1ccsc1 ; N#CCc1ccsc1Br]

5.9 g (46 mmol) of 2-(thiophen-3-yl)acetonitrile were solubilized in 25 ml of carbon tetrachloride with magnetic stirring and 8.27 g (46 mmol) of N-bromosuccinimide were added. Under vigorous stirring, 0.04 ml (0.460 mmol) of perchloric acid were added and the mixture was stirred at r.t. for 4.5 h. 0.155 g (1.839 mmol) of sodium bicarbonate were added to the reaction mixture. The solid was removed by filtration and the filtrate was concentrated in vacuo. The crude residue was purified by flash chromatography on a silica gel cartridge (eluent: heptane/ethyl acetate, 9/1, v/v). 8.47 g (yield=57%) of 2-(2-bromothiophen-3-yl)acetonitrile were obtained as a pale yellow oil. LC-MS: m/z=non-ionized. $^1$H NMR (300 MHz, DMSO) δ $^1$H NMR (300 MHz, DMSO) δ 7.67 (d, J=5.6 Hz, 1H), 7.08 (d, J=5.6 Hz, 1H), 3.93 (s, 2H).

Step 2: Preparation of 2-(2-bromo-5-(furan-2-carbonyl)thiophen-3-yl)acetonitrile

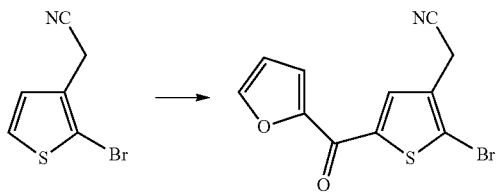 [SMILES: N#CCc1ccsc1Br ; N#CCc1cc(C(=O)c2ccco2)sc1Br]

In a flask placed under an argon flow, were introduced with magnetic stirring: 4 ml of 1,2-dichloroethane, 0.2 g (0.99 mmol) of 2-(2-bromothiophen-3-yl)acetonitrile and 0.145 g (1.089 mmol) of trialuminium chloride. The mixture was placed at 0° C. with magnetic stirring and a solution of 0.113 ml (1.089 mmol) of 2-furoyl chloride in 1 ml of 1,2-dichloroethane was added dropwise. The obtained mixture was stirred at r.t. for 4 d and then 0.073 g (0.455 mmol) of trialuminium chloride and 0.057 ml (0.455 mmol) of 2-furoyl chloride were added and stirring at r.t. was continued for 24 h. The reaction medium was poured into 30 ml of water. The aqueous phase was extracted with 2×25 ml of ethyl acetate. The combined organic phases were washed with 30 ml of a saturated NaHCO$_3$ aqueous solution, 30 ml of a saturated NaCl aqueous solution dried on Na$_2$SO$_4$ which was then removed by filtration and the obtained filtrate was concentrated in vacuo. 0.211 g (yield=71%) of 2-(2-bromo-5-(furan-2-carbonyl)thiophen-3-yl)acetonitrile were obtained as a yellow solid. LC-MS: m/z=296 (MH$^+$); UV purity at 254 nm >99%. $^1$H NMR (300 MHz, DMSO) δ $^1$H NMR (300 MHz, DMSO) δ 8.17 (d, J=0.9 Hz, 1H), 8.14 (s, 1H), 7.61 (d, J=3.7 Hz, 1H), 6.85 (dd, J=3.6, 1.7 Hz, 1H), 4.05 (s, 2H).

Step 3: Preparation of 2-(2-(4-chlorophenyl)-5-(furan-2-carbonyl)thiophen-3-yl)acetonitrile (derivative number 150)

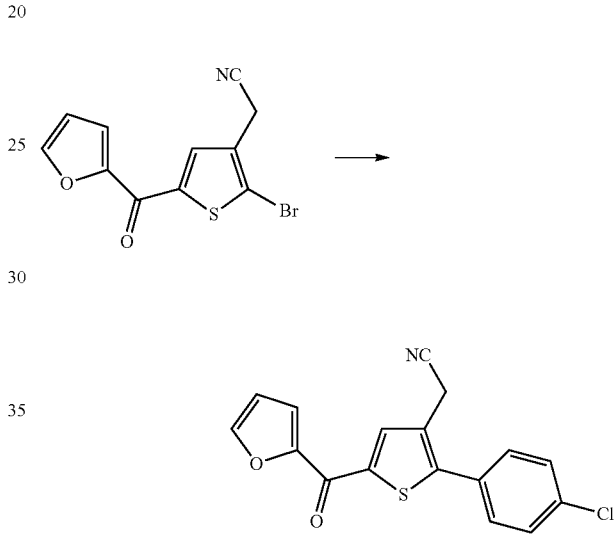

0.207 g (0.699 mmol) of 2-(2-bromo-5-(furan-2-carbonyl)thiophen-3-yl)acetonitrile were solubilized under argon in 6 ml of a mixture consisting of toluene and ethanol (7/5, v/v), were added with magnetic stirring, 0.173 g (1.048 mmol) of 4-chlorophenylboronic acid, 2.342 ml (4.68 mmol) of a 2 M Na$_2$CO$_3$ aqueous solution and 0.040 g (0.035 mmol) of palladium[0] tetrakis(triphenylphosphine). The mixture was stirred with reflux for 2.5 h. After returning to r.t., the mixture was diluted with 30 ml of water. The aqueous phase was extracted with 2×30 ml of ethyl acetate. The combined organic phases were washed with 10 ml of a saturated NaCl aqueous solution and then dried on Na$_2$SO$_4$ which was then removed by filtration. The obtained filtrate was concentrated in vacuo. The crude residue was purified by flash chromatography on a silica gel cartridge (eluent: heptane/ethyl acetate, 8/2, v/v). 0.169 g (yield=72%) of 2-(2-(4-chlorophenyl)-5-(furan-2-carbonyl)thiophen-3-yl)acetonitrile were obtained as a pale yellow solid. LC-MS: m/z=328 (MH$^+$); UV purity at 254 nm=98%. $^1$H NMR (300 MHz, DMSO) δ 8.25 (s, 1H), 8.19 (s, 1H), 7.63 (d, J=3.2 Hz, 5H), 6.86 (dd, J=3.6, 1.7 Hz, 1H), 4.16 (s, 2H).

Example 37: Preparation of derivative number 151: Preparation of (4-((2H-tetrazol-5-yl)methyl)-5-(4-chlorophenyl)thiophen-2-yl)(furan-2-yl)methanone

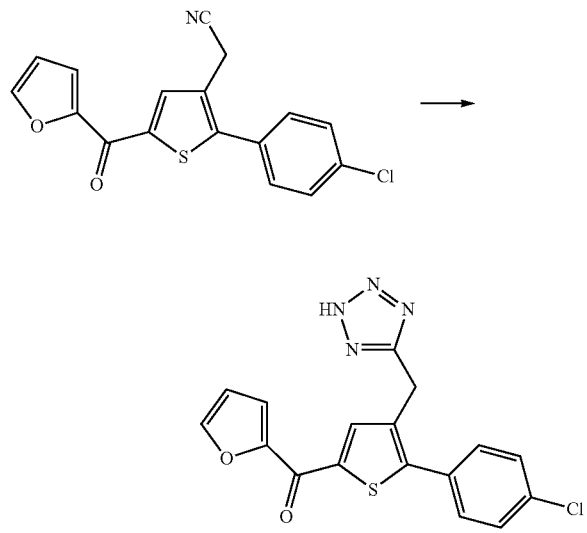 [SMILES: N#CCc1cc(C(=O)c2ccco2)sc1-c1ccc(Cl)cc1 ; O=C(c1ccco1)c1cc(Cc2nn[nH]n2)c(-c2ccc(Cl)cc2)s1]

0.149 g (0.45 mmol) of 2-(2-(4-chlorophenyl)-5-(furan-2-carbonyl)thiophen-3-yl)acetonitrile were solubilized in 3 ml of dimethylformamide with magnetic stirring. To this solution, were added: 0.088 g (1.35 mmol) of sodium azide and 0.096 g (1.8 mmol) of ammonium chloride. The mixture was stirred at 160° C. for 5 h. After returning to r.t., the reaction medium was diluted with 5 ml of water, the pH was adjusted to 2 by adding a 1N hydrochloric acid aqueous solution. The aqueous phase was extracted with 3×15 ml of ethyl acetate. The combined organic phases were washed with 30 ml of a saturated NaCl aqueous solution and then dried on $Na_2SO_4$ which was then removed by filtration. The obtained filtrate was concentrated in vacuo. The crude residue was purified by flash chromatography on a silica gel cartridge (eluent: dichloromethane/methanol gradient, from 100 to 95% of dichloromethane, v/v). 0.015 g (yield=8%) of (4-((2H-tetrazol-5-yl)methyl)-5-(4-chlorophenyl)thiophen-2-yl)(furan-2-yl)methanone were obtained as a pale yellow solid. LC-MS: m/z=370 (MH+); UV purity at 254 nm=97%. $^1$H NMR (300 MHz, DMSO) δ 12.12 (s, 1H), 7.94 (s, 1H), 7.60 (q, J=8.6 Hz, 4H), 7.20 (d, J=16.2 Hz, 2H), 6.42-6.22 (m, 1H), 4.35 (s, 2H).

Example 38: Preparation of derivative number 152: Preparation of 2-(2-(4-chlorophenyl)-5-(furan-2-carbonyl)thiophen-3-yl)-N-hydroxyacetimidamide

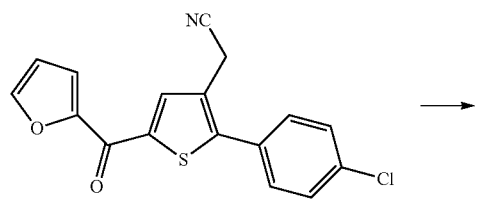

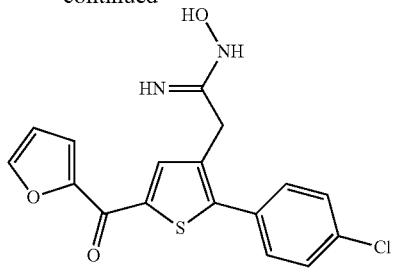

0.1 g (0.299 mmol) of 2-(2-(4-chlorophenyl)-5-(furan-2-carbonyl)thiophen-3-yl)acetonitrile were solubilized in 3 ml of methanol with magnetic stirring. To this solution, were added 0.028 g (0.404 mmol) of hydroxylamine hydrochloride and 0.043 g (0.314 mmol) of potassium carbonate. The mixture was stirred at r.t. for 1 h, and then refluxed for 5 h. The reaction medium was poured into 20 ml of water. The aqueous phase was extracted with 2×20 ml of ethyl acetate. The combined organic phases were washed with 30 ml of a saturated NaCl aqueous solution and then dried on $Na_2SO_4$ which was then removed by filtration. The obtained filtrate was concentrated in vacuo. The crude residue was purified by flash chromatography on a silica gel cartridge (eluent: heptane/ethyl acetate, 4/6, v/v). 0.023 g (yield=21%) of 2-(2-(4-chlorophenyl)-5-(furan-2-carbonyl)thiophen-3-yl)-N-hydroxyacetimidamide were obtained as a pale yellow solid. LC-MS: m/z=361 (MH+); UV purity at 254 nm >99%. $^1$H NMR (300 MHz, DMSO) δ 9.11 (s, 1H), 8.19 (s, 1H), 8.14 (s, 1H), 7.69 (d, J=8.5 Hz, 2H), 7.65-7.50 (m, 3H), 6.84 (dd, J=3.5, 1.6 Hz, 1H), 5.66 (s, 2H), 3.39 (s, 2H).

Example 39: Preparation of derivative number 153: Preparation of 3-((2-(4-chlorophenyl)-5-(furan-2-carbonyl)thiophen-3-yl)-methyl)-1,2,4-oxadiazol-5(2H)-one

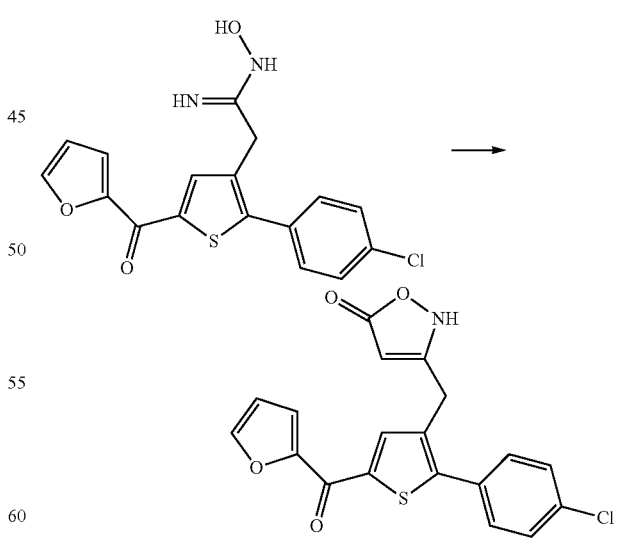

0.05 g (0.139 mmol) of 2-(2-(4-chlorophenyl)-5-(furan-2-carbonyl)thiophen-3-yl)-N-hydroxyacetimidamide were solubilized in 1 ml of 1,4-dioxane with magnetic stirring. To this solution were added: 0.028 g (0.173 mmol) of carbonyl diimidazole and 0.023 ml (0.152 ml) of DBU. The mixture was stirred at 105° C. for 30 min. The reaction medium was poured into 10 ml of water. The aqueous phase was washed with 5 ml of ethyl acetate, the pH of the aqueous phase was adjusted to 2 by adding a 1N hydrochloric acid aqueous solution. The aqueous phase was extracted with 2×10 ml of ethyl acetate. The combined organic phases were washed with 10 ml of a saturated NaCl aqueous solution and then dried on $Na_2SO_4$ which was then removed by filtration. 0.02 g (yield=36%) of 3-((2-(4-chlorophenyl)-5-(furan-2-carbonyl)thiophen-3-yl)methyl)-1,2,4-oxadiazol-5(2H)-one were obtained as a pale yellow solid. LC-MS: m/z=387 ($MH^+$); UV purity at 254 nm=96%. $^1H$ NMR (300 MHz, DMSO) δ 12.40 (s, 1H), 8.19 (s, 1H), 8.16 (d, J=1.1 Hz, 1H), 7.66-7.57 (m, 5H), 6.85 (dd, J=3.6, 1.7 Hz, 1H), 3.99 (s, 2H).

Example 40: Preparation of derivative No. 173: 5-(4-chlorophenyl)-4-[2-(2-dimethylaminoethylamino)-2-oxo-ethyl]-N-(3-pyridyl)thiophene-2-carboxamide

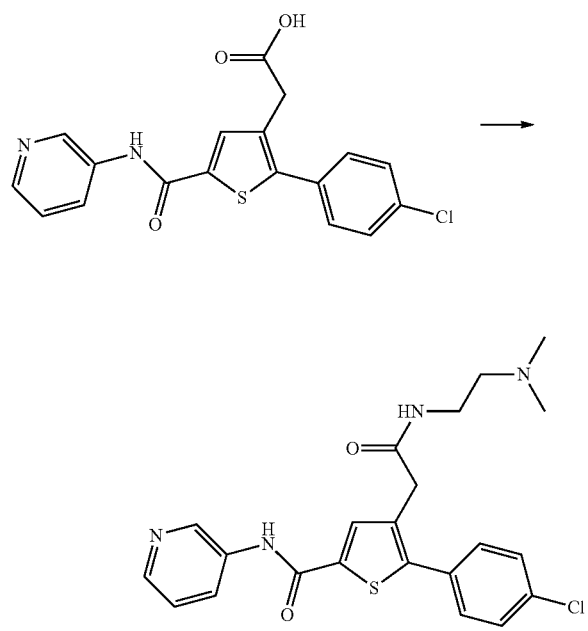

80 mg (0.215 mmol) of 2-[2-(4-chlorophenyl)-5-(3-pyridylcarbamoyl)-3-thienyl]acetic acid and 0.049 mL (0.429 mmol) of N,N-dimethylethane-1,2-diamine were solubilized in 2 ml of DMPU. To this solution were added with magnetic stirring, 0.045 ml (0.322 mol) of triethylamine and 112 mg (0.215 mmol) of PyBOP. The mixture was stirred at r.t. for 4 hours. 10 ml of water were added, the stirring was maintained for 30 min, and the obtained solid was filtered on a frit, washed with water and dried in vacuo. 0.053 g (yield=53%) of 5-(4-chlorophenyl)-4-[2-(2-dimethylaminoethylamino)-2-oxo-ethyl]-N-(3-pyridyl)thiophene-2-carboxamide were obtained as a solid. LC-MS: m/z=443 (MH+), UV purity at 254 nm=95%. $^1H$ NMR (300 MHz, DMSO) δ 10.58 (s, 1H), 8.90 (s, 1H), 8.32 (d, J=4.6 Hz, 1H), 8.16 (d, J=8.5 Hz, 2H), 8.02 (s, 1H), 7.59 (q, J=8.6 Hz, 4H), 7.40 (d, J=12.9 Hz, 1H), 3.51 (s, 2H), 2.31 (s, 6H)

Example 41: Preparation of derivative No. 174: ethyl 212-(3,4-dichlorophenyl)-5-(4-methoxyphenyl)sulfonyl-3-thienyl)acetate

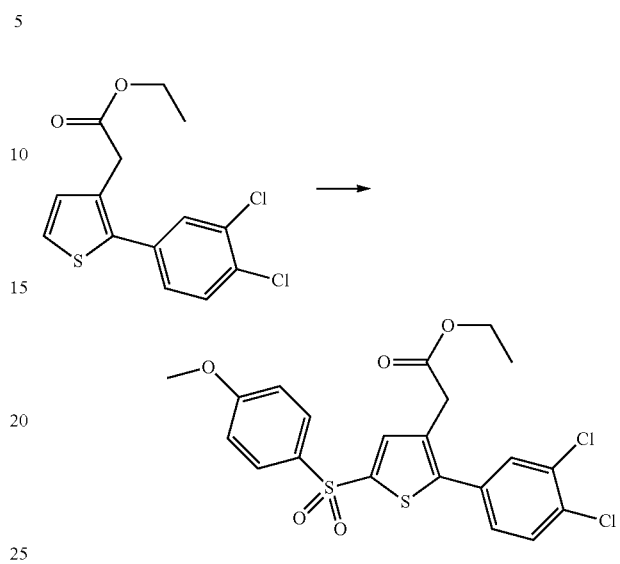

In a flask placed under an argon flow, were introduced with magnetic stirring: 2 ml of dichloromethane, 0.1 g (0.317 mmol) of ethyl 2-(2-(3,4-dichlorophenyl)thiophen-3-yl)acetate and 0.131 g (0.634 mmol) of 4-methoxybenzene-1-sulfonyl chloride. The mixture was placed at 5° C. with magnetic stirring and 0.085 g (0.634 mmol) of aluminium chloride were added portion wise. The obtained mixture was stirred at r.t. for 24 hours and then poured onto ice and stirred for 1 hour. The aqueous phase was extracted with 2×5 ml of dichloromethane. The combined organic phases were dried on $Na_2SO_4$ which was then removed by filtration and the obtained filtrate was concentrated in vacuo. The crude residue was purified by flash chromatography on a silica gel cartridge (eluent: petroleum/dichloromethane gradient, 100% to 0% of petroleum ether, v/v). 0.120 g (yield=76%) of ethyl 2-[2-(3,4-dichlorophenyl)-5-(4-methoxyphenyl)sulfonyl-3-thienyl]acetate were obtained as a pale brown oil. LC-MS: m/z=486 ($MH^+$) UV purity at 254 nm=98%. $^1H$ NMR (300 MHz, DMSO) δ 7.93 (d, J=8.9 Hz, 2H), 7.82-7.72 (m, 3H), 7.45 (dd, J=8.3, 2.1 Hz, 1H), 7.18 (d, J=9.0 Hz, 2H), 4.01 (q, J=7.1 Hz, 2H), 3.85 (s, 3H), 3.74 (s, 2H), 1.10 (t, J=7.1 Hz, 3H)

Example 42: Preparation of derivative No. 175: 2-[2-(3,4-dichlorophenyl)-5-(4-methoxyphenyl)sulfonyl-3-thienyl]acetic acid

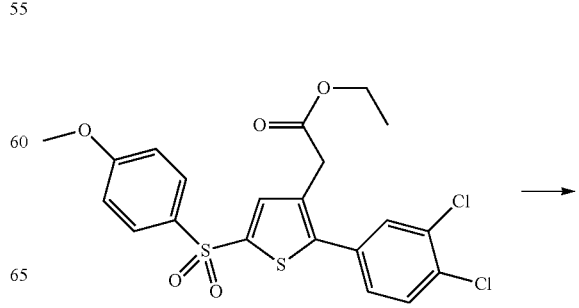

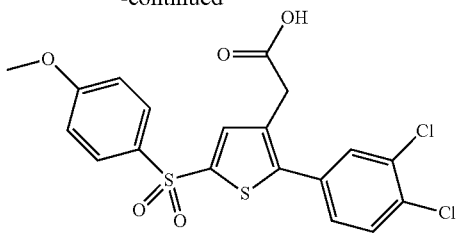

0.090 g (0.185 mmol) of ethyl 2-[2-(3,4-dichlorophenyl)-5-(4-methoxyphenyl)sulfonyl-3-thienyl]-acetate were solubilized in 2 ml of ethanol and 2 ml of THF, to this solution were added with magnetic stirring 0.020 ml (0.204 mmol) of a 30% by mass sodium hydroxide aqueous solution. The obtained mixture was stirred at r.t. for 16 hours. The mixture was concentrated in vacuo, the obtained residue was taken up into 10 ml of water. The pH of the aqueous phase was then lowered by adding a 1N hydrochloric acid aqueous solution until a precipitate occurred. The solution was stirred for 2 h after having added 1 ml of diisopropyl ether. The solid was isolated by filtration, washed with 2×5 ml of water and 1 ml of diisopropyl ether and dried in a vacuum bell jar in order to obtain 0.072 g (yield=84%) of 2-[2-(3,4-dichlorophenyl)-5-(4-methoxyphenyl)sulfonyl-3-thienyl]acetic acid as a white solid. UV purity at 254 nm=99%. $^1$H NMR (300 MHz, DMSO) δ 12.69 (s, 1H), 7.93 (d, J=8.9 Hz, 2H), 7.76 (d, J=9.6 Hz, 3H), 7.46 (dd, J=8.3, 2.1 Hz, 1H), 7.18 (d, J=8.9 Hz, 2H), 3.85 (s, 3H), 3.63 (s, 2H)

Example 43: Preparation of derivative No. 176: ethyl 2-[5-(5-chlorofuran-2-carbonyl)-2-(4-chlorophenyl)-3-thienyl]acetate

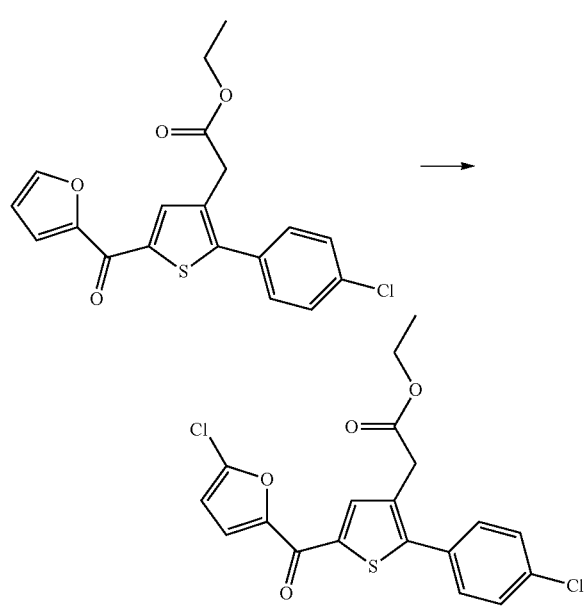

200 mg (0.534 mmol) of ethyl 2-[2-(4-chlorophenyl)-5-(furan-2-carbonyl)-3-thienyl]acetate were dissolved in 3 ml of acetonitrile, before adding 142.4 mg (1.068 mmol) of N-chloro-succinimide. The reaction was refluxed for 15 h. The mixture is washed with 5 ml of water, dried on Na$_2$SO$_4$ which was then removed by filtration and the obtained filtrate was concentrated in vacuo. The crude residue was purified by flash chromatography on a silica gel cartridge (eluent: heptane/dichloromethane gradient, 100 to 0% of heptane, v/v). 78 mg (yield=31%) of ethyl 2-[5-(5-chlorofuran-2-carbonyl)-2-(4-chlorophenyl)-3-thienyl]acetate were obtained as a not very colored oil. LC-MS: m/z=409 (MW) UV purity at 254 nm=99%. $^1$H NMR (300 MHz, DMSO) δ 8.14 (s, 1H), 7.69 (d, J=3.7 Hz, 1H), 7.64-7.43 (m, 4H), 6.93 (d, J=3.7 Hz, 1H), 4.11-4.00 (m, 2H), 3.82 (d, J=12.5 Hz, 2H), 1.14 (t, J=7.1 Hz, 3H)

Example 44: Preparation of derivative No. 177: ethyl 2-[5-[[(4-chlorobenzoyl)amino]carbamoyl]-2-(4-chlorophenyl)-3-thienyl]acetate

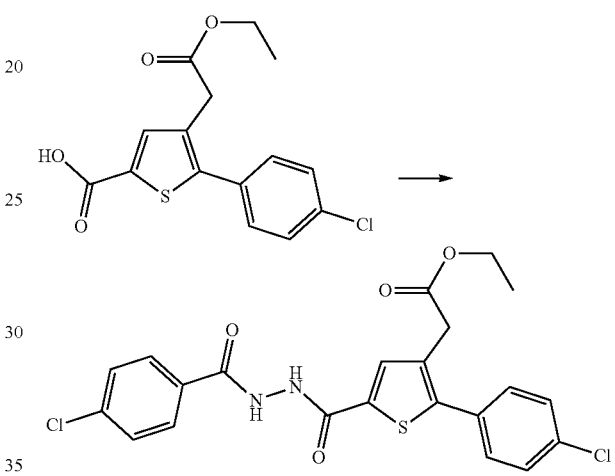

100 mg (0.308 mmol) of 5-(4-chlorophenyl)-4-(2-ethoxy-2-oxo-ethyl)thiophene-2-carboxylic acid, 0.172 ml (0.985 mmol) of triethylamine and 52.5 mg (0.308 mmol) of 4-chlorobenzohydrazide are loaded in 2 ml of DMF. The solution is cooled to 0° C. and 240 mg (0.462 mmol) of PyBOP are added. The mixture is stirred at r.t. for 4 h. The solution is poured on 10 ml of water added with 1 ml of diisopropyl ether. After 30 minutes of vigorous stirring, the obtained solid is filtered and then washed with water and diisopropyl ether. 123 mg (yield=78%) of ethyl 2-[5-[[(4-chloro-benzoyl)amino]carbamoyl]-2-(4-chlorophenyl)-3-thienyl]acetate were obtained as a solid. LC-MS: m/z=477 (MH$^+$) UV purity at 254 nm=93%. $^1$H NMR (300 MHz, DMSO) δ 10.68 (s, 2H), 7.93 (d, J=8.5 Hz, 2H), 7.86 (s, 1H), 7.57 (dt, J=17.0, 8.6 Hz, 6H), 4.09 (q, J=7.1 Hz, 2H), 3.72 (s, 2H), 1.17 (t, J=7.1 Hz, 3H)

The derivatives 178 and 179 were prepared according to the same procedure:

| No. | Molecular weight g/mol | Aspect | LCMS purity UV at 254 nm | Mass spectrometry m/z MH$^+$ | M − H$^+$ | $^1$H NMR (300 MHz, DMSO) δ |
|---|---|---|---|---|---|---|
| 178 | 472.94 | solid | 99 | 473 | 471 | 10.61 (d, J = 32.2 Hz, 2H), 7.87 (s, 1H), 7.66-7.35 (m, 7H), 7.17 (d, J = 7.8 Hz, 1H), 4.10 (q, J = 7.1 Hz, |

-continued

| No. | Molecular weight g/mol | Aspect | LCMS purity UV at 254 nm | Mass spectrometry m/z MH+ | M − H+ | $^1$H NMR (300 MHz, DMSO) δ |
|---|---|---|---|---|---|---|
| 179 | 443.90 | solid | 95 | 444 | 442 | 2H), 3.82 (s, 3H), 3.72 (s, 2H), 1.18 (t, J = 7.1 Hz, 3H) 10.84 (d, J = 33.9 Hz, 2H), 8.80 (d, J = 6.0 Hz, 2H), 7.97-7.73 (m, 3H), 7.56 (q, J = 8.6 Hz, 4H), 4.09 (q, J = 7.1 Hz, 2H), 3.73 (s, 2H), 1.17 (t, J = 7.1 Hz, 3H) |

Example 45: Preparation of derivative No. 180: 2-[2-(4-chlorophenyl)-5-(furan-2-carbonyl)-3-thienyl]-N-ethyl-thioacetamide Step 1: Preparation of 2-[2-(4-chlorophenyl)-3-thienyl]acetic acid

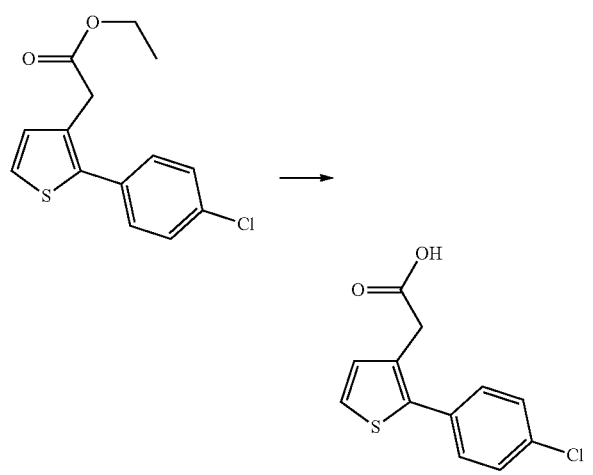

1.5 g (5.34 mmol) of ethyl 2-[2-(4-chlorophenyl)-3-thienyl] acetate were loaded in 8 ml of ethanol before adding 0.588 ml (5.88 mmol) of a 30% by mass sodium hydroxide aqueous solution. The solution was stirred at r.t. for 18 hours. The mixture was concentrated in vacuo, the obtained residue was taken up into 15 ml of water. The pH of the aqueous phase was then lowered by adding a 1N hydrochloric acid aqueous solution until a precipitate occurred. The solid was isolated by filtration, washed with 2×5 ml of water and dried in a vacuum bell jar. 1.227 g (yield=88%) of 2-[2-(4-chlorophenyl)-3-thienyl]acetic acid were obtained as a solid. LC-MS: m/z=251 (MH⁻) UV purity at 254 nm=93%.

Step 2: Preparation of 2-[2-(4-chlorophenyl)-3-thienyl]-N-ethyl-acetamide

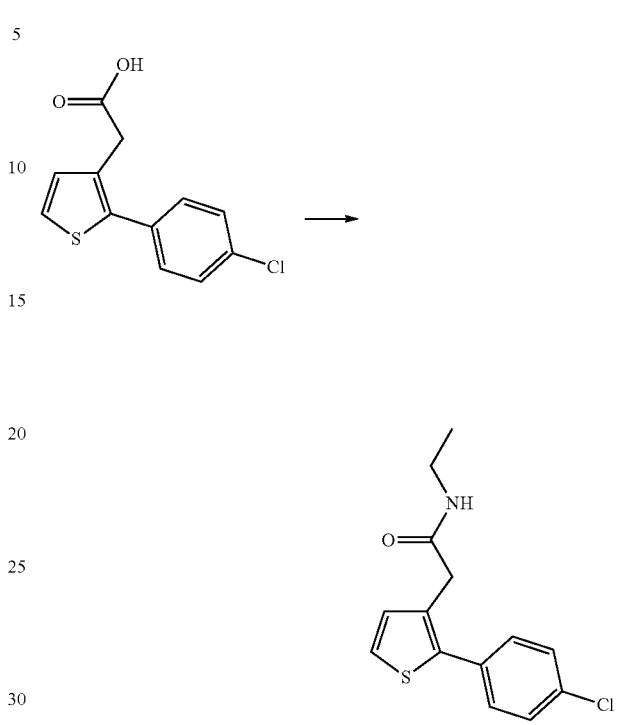

0.6 g (2.374 mmol) of 2-[2-(4-chlorophenyl)-3-thienyl]acetic acid, 0.290 g (3.55 mmol) of ethanamine hydrochloride, 1.236 g (2.374 mmol) of PyBOP and 0.827 ml (5.94 mmol) of triethylamine were loaded in 2 ml of DMF. The solution was then stirred at r.t. for 18 hours. The mixture was concentrated in vacuo, the obtained residue was taken up into 10 ml of a 1N hydrochloric acid aqueous solution, and then stirred for 1 hour. The solid was isolated by filtration, washed with 2×5 ml of water and dried in a vacuum bell jar. 0.559 g (yield=79%) of 2-[2-(4-chlorophenyl)-3-thienyl]-N-ethyl-acetamide were obtained as a solid. LC-MS: m/z=280 (MH⁺) UV purity at 254 nm=94%. $^1$H NMR (300 MHz, DMSO) δ 8.11 (s, 1H), 7.62 (d, J=8.5 Hz, 2H), 7.57-7.46 (m, 3H), 7.08 (d, J=5.2 Hz, 1H), 3.39 (s, 2H), 3.14-3.02 (m, 2H), 1.01 (t, J=7.2 Hz, 3H).

Step 3: Preparation of 2-[1-(4-chlorophenyl)-3-thienyl]-N-ethyl-thioacetamide

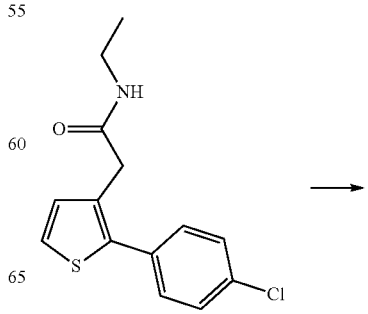

-continued

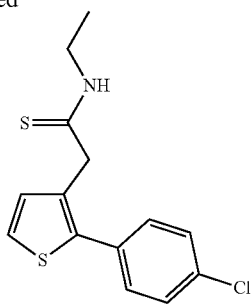

559 mg (1.998 mmol) of 2-[2-(4-chlorophenyl)-3-thienyl]-N-ethyl-acetamide and 808 mg (1.998 mmol) of Lawesson's reagent were added to 5 ml of toluene. The solution was stirred and refluxed with heating for 4 h. 10 ml of water was added, and the mixture was extracted with 2×15 ml of ethyl acetate. The collected organic phases were washed with 10 ml of water and 10 ml of brine, dried on $Na_2SO_4$ which was then removed by filtration and the obtained filtrate was concentrated in vacuo. The crude residue was purified by flash chromatography on a silica gel cartridge (eluent: petroleum ether/diisopropyl ether gradient, 100% to 0% of petroleum ether, v/v). 476 mg (yield=77%) were obtained as an oil. LC-MS: m/z=296 (MH$^+$) UV purity at 254 nm=95%. $^1$H NMR (300 MHz, DMSO) δ 10.22 (s, 1H), 7.66 (d, J=8.6 Hz, 2H), 7.56-7.47 (m, 3H), 7.02 (d, J=5.2 Hz, 1H), 3.86 (s, 2H), 3.59-3.47 (m, 2H), 1.14 (t, J=7.3 Hz, 3H).

Step 4: Preparation of 2-[2-(4-chlorophenyl)-5-(furan-2-carbonyl)-3-thienyl]-N-ethyl-thioacetamide (derivative number 180)

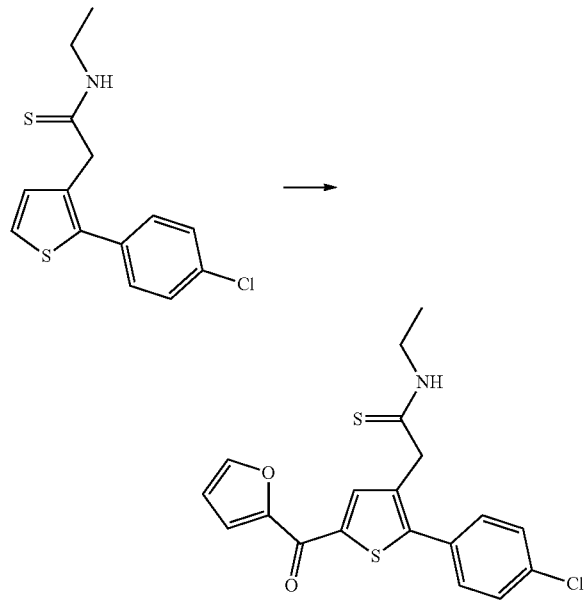

215 mg (0.727 mmol) of 2-[2-(4-chlorophenyl)-3-thienyl]-N-ethyl-thioacetamide were dissolved in 3 ml of dichloromethane. At +5° C., 0.107 ml (1.090 mmol) of 2-furane-carbonyl chloride were added, and then, still at +5° C., 97 mg (0.727 mmol) of aluminium chloride were added. The solution was stirred at r.t. for 18 h. The mixture was poured into 200 ml of water, stirred for 3 h and filtered on celite, and then the solution was extracted twice with 15 ml of dichloromethane. The collected organic phases were washed with 10 ml of water, dried on $Na_2SO_4$ which was then removed by filtration and the obtained filtrate was concentrated in vacuo. The crude residue was purified by flash chromatography on a silica gel cartridge (eluent: petroleum ether/dichloromethane gradient, 100% to 0% of petroleum ether, v/v). 51 mg (yield=17%) of 2-[2-(4-chlorophenyl)-5-(furan-2-carbonyl)-3-thienyl]-N-ethyl-thioacetamide were obtained as a solid. LC-MS: m/z=390 (MH$^+$) UV purity at 254 nm=94%. $^1$H NMR (300 MHz, DMSO) δ 10.27 (s, 1H), 8.14 (d, J=6.6 Hz, 2H), 7.70 (d, J=8.6 Hz, 2H), 7.62-7.49 (m, 3H), 6.89-6.81 (m, 1H), 3.94 (s, 2H), 3.67-3.46 (m, 2H), 1.15 (t, J=7.2 Hz, 3H).

Example 46: Preparation of derivative No. 182: N—(N-(tert-butoxycarbonyl)carbamimidoyl)-2-(2-(4-chlorophenyl)-5-(4-methoxybenzoyl)thiophen-3-yl)acetamide

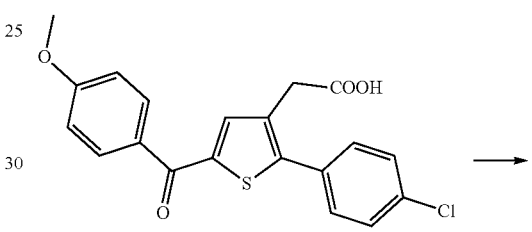

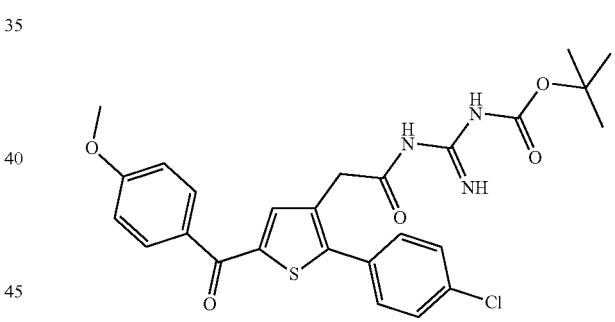

142 mg (0.337 mmol) of 2-(2-(4-chlorophenyl)-5-(4-methoxybenzoyl)thiophen-3-yl)acetic acid, 175 mg (0.337 mmol) of PyBOP and 64.4 mg (0.404 mmol) of Boc-guanidine were added to 1 ml of DMF. 0.141 ml (1.011 mmol) of triethylamine were then added. The mixture was stirred at r.t. for 4 h. The solution was poured on 10 ml of water and 5 ml of diisopropyl ether with strong stirring. The obtained solid was filtered and then washed with water and diisopropyl ether. 172 mg (yield=90%) of N—(N-(tert-butoxycarbonyl)carbamimidoyl)-2-(2-(4-chlorophenyl)-5-(4-methoxybenzoyl)-thiophen-3-yl)acetamide were obtained as a white solid. LC-MS: m/z=462 (MH$^+$) UV purity at 254 nm=99%. $^1$H NMR (300 MHz, DMSO) δ 11.05 (s, 1H), 8.70 (s, 2H), 7.93-7.77 (m, 5H), 7.57 (d, J=8.4 Hz, 1H), 7.13 (d, J=8.8 Hz, 2H), 3.88 (s, 3H), 3.75 (s, 2H), 1.39 (s, 9H).

The derivatives 181 and 183 were prepared according to the same procedure

| No. | Molecular weight g/mol | Aspect | LCMS purity 254 nm | Mass spectrometry m/z MH+ | M − H+ | 1H NMR (300 MHz, DMSO) δ |
|---|---|---|---|---|---|---|
| 181 | 487.96 | White solid | 99 | 388 [M + 1 − BOC] | 486 | 11.15 (s, 1H), 8.70 (s, 2H), 8.33-8.03 (m, 2H), 7.64-7.55 (m, 5H), 6.83 (dd, J = 3.6, 1.7 Hz, 1H), 3.75 (s, 2H), 1.39 (s, 9H) |
| 183 | 528.02 | Pale yellow solid | 95 | 428 [M + 1 − BOC] | 526 | 11.08 (s, 1H), 8.77 (d, J = 42.4 Hz, 2H), 7.94-7.82 (m, 2H), 7.76 (s, 1H), 7.59 (s, 4H), 7.19-7.03 (m, 2H), 3.86 (s, 3H), 3.72 (s, 2H), 1.38 (s, 9H) |

Example 47: Preparation of derivative No. 185: N-carbamimidoyl-2-(2-(4-chlorophenyl)-5-(4-methoxybenzoyl)thiophen-3-yl) acetamide hydrochloride

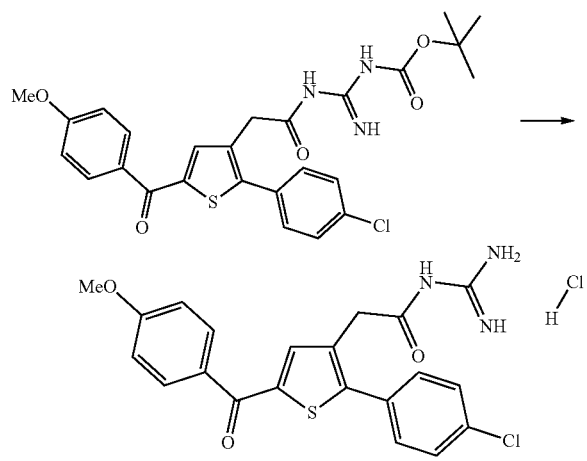

481 mg (0.911 mmol) of N—(N-(tert-butoxycarbonyl)carbamimidoyl)-2-(2-(4-chlorophenyl)-5-(4-methoxybenzoyl) thiophen-3-yl)acetamide were dissolved in 2 ml of dichloromethane and then 2 ml (26 mmol) of trifluoroacetic acid were added. The mixture was stirred at r.t. for 2 h. 0.25 ml (1 mmol) of a hydrochloric acid solution with 4 moles per liter in dioxane was added before evaporating the solvents in vacuo. The obtained solid was triturated in 5 ml of boiling propan-2-ol, and after cooling of the solution, the solid was filtered and washed with 1 ml of propan-2-ol and then dried in vacuo. 421 mg (yield=99%) of N-carbamimidoyl-2-(2-(4-chlorophenyl)-5-(4-methoxybenzoyl)thiophen-3-yl)acetamide hydrochloride was obtained as a yellow solid. LC-MS: m/z=428 (MH+) UV purity at 254 nm=99%. 1H NMR (300 MHz, DMSO) δ 11.78 (s, 1H), 8.36 (s, 4H), 7.88 (d, J=8.8 Hz, 2H), 7.81 (s, 1H), 7.66-7.45 (m, 4H), 7.12 (d, J=8.9 Hz, 2H), 3.88 (d, J=7.2 Hz, 5H).

The derivatives 184 and 186 were prepared according to the same procedure

| No. | Molecular weight g/mol | Aspect | LCMS purity UV at 254 nm | Mass spectrometry m/z MH+ | M − H+ | 1H NMR (300 MHz, DMSO) δ |
|---|---|---|---|---|---|---|
| 184 | 498.80 | White solid | 97 | 462 | | 11.88 (s, 1H), 8.25 (d, J = 45.7 Hz, 4H), 7.95-7.81 (m, 4H), 7.78 (d, J = 8.3 Hz, 1H), 7.54 (dd, J = 8.3, 2.1 Hz, 1H), 7.12 (d, J = 8.9 Hz, 2H), 3.91 (s, 2H), 3.87 (s, 3H) |
| 186 | 424.30 | Grey solid | 95 | 388 | 386 | 11.89 (s, 1H), 8.43 (s, 3H), 8.25 (s, 1H), 8.15 (d, J = 1.0 Hz, 1H), 7.59 (d, J = 5.9 Hz, 5H), 7.02 (s, 1H), 6.85 (dd, J = 3.6, 1.7 Hz, 1H), 3.93 (s, 2H) |

Example 48: Preparation of derivative No. 187: ethyl 2-(2-(4-chlorophenyl)-5-(4-methoxybenzoyl)thiophen-3-yl)acrylate

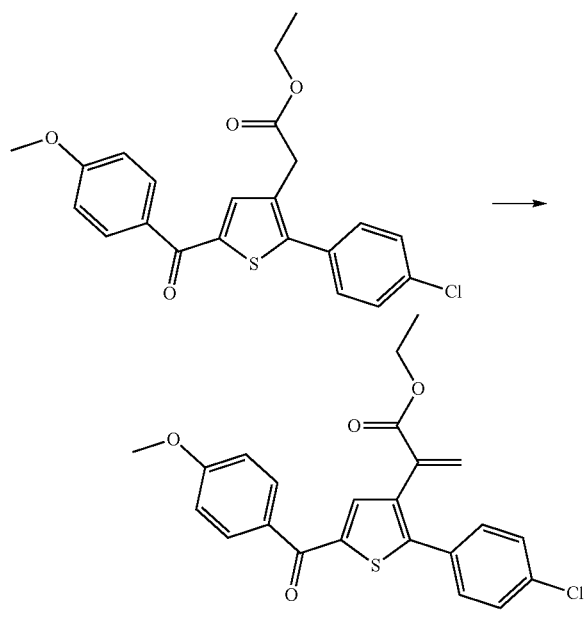

Under an argon atmosphere, 1.5 g (3.62 mmol) of ethyl 2-(2-(4-chlorophenyl)-5-(4-methoxybenzoyl)thiophen-3-yl)acetate was dissolved in 20 ml of tetrahydrofurane, and after cooling to −78° C., 10.85 ml (10.85 mmol) of a lithium bis(trimethylsilyl)amide solution at one mole per liter in tetrahydrofurane was poured dropwise. The solution was stirred at −78° C. for 30 min before slowly adding 0.984 ml (10.85 mmol) of bromo(methoxy)methane. The mixture was stirred by letting the temperature rise to r.t. for 16 h. The mixture was then poured on 50 ml of water, extracted with 3 fractions of 15 ml of dichloromethane, the collected organic phases were washed with 20 ml of water, dried on $Na_2SO_4$ which was then removed by filtration and the obtained filtrate was concentrated in vacuo. The crude residue was purified by flash chromatography on a silica gel cartridge (eluent: heptane/ethyl acetate gradient, 100 to 0% heptane, v/v). 0.696 g (yield=41%) of ethyl 2-(2-(4-chlorophenyl)-5-(4-methoxybenzoyl)thiophen-3-yl)acrylate were obtained as a solid. LC-MS: m/z=427 (MH$^+$) UV purity at 254 nm=90.6%. $^1$H NMR (300 MHz, DMSO) δ 7.93 (d, J=8.9 Hz, 2H), 7.70 (s, 1H), 7.56-7.51 (m, 2H), 7.48-7.41 (m, 2H), 7.11 (d, J=8.9 Hz, 2H), 6.39 (d, J=0.8 Hz, 1H), 6.11 (d, J=0.7 Hz, 1H), 3.93-3.78 (m, 5H), 0.91 (t, J=7.1 Hz, 3H).

Stimulation Test of Insulin Secretion by INS-1 Cells

The different compounds were tested on an INS-1 beta-pancreatic line in order to evaluate their capability of potentializing the insulin secretion in response to glucose. Very briefly, the cells are cultivated in a culture medium, RPMI 1640 with 10 mM glucose containing 1 mM of sodium pyruvate, 50 μM of 2-mercaptoethanol, 2 mM of glutamine, 10 mM of HEPES, 100 IU/mL of penicillin, 100 μg/mL of streptomycin and 10% of inactivated fetal calf serum, as described by Asfari et al. [13]. For the insulin secretion test, the INS-1 cells are sown and cultivated in 96-well plates. After 3 days of cultivation at 37° C. in a humid atmosphere (95% air/5% $CO_2$), the medium is removed and the cells are incubated for 16 h in a medium containing 5 mM of glucose and 1% of inactivated fetal calf serum. On the day of the test, the cells are washed with a Krebs buffer (pH 7.4) containing 0.1% of bovine albumin and then pre-incubated for 30 min at 37° C. in this same buffer containing 2.8 mM of glucose. Finally, the cells are again washed with Krebs buffer and then incubated for 1 h in the buffer of the secretion test (Krebs, pH 7.4 containing 0.1% of bovine albumin and 3.5 mM of glucose and molecules to be evaluated). At the end of the test, the cell supernatant is recovered in order to measure therein the secreted insulin, by means of an ELISA kit using a rat anti-insulin antibody (ELISA Alpco Cat no. 80-INSRTH-E10). Each condition is tested in triplicate. The 3.5 mM glucose, the $10^{-7}$M GLP-1 and the Forskoline $10^{-7}$/IBMX $10^{-5}$M mixtures are used as positive controls of the test. A compound stimulates the secretion of insulin if this factor is greater than or equal to 130% of the control for a given glucose dose.

| No. | INS-1 % of ctrl @ 50 μM | INS-1 % of ctrl @ 10 μM |
|---|---|---|
| 3 | 318 | 152 |
| 10 | 210 | 144 |
| 13 |  | 155 |
| 14 | 165 | 152 |
| 15 | 160 | 150 |
| 22 | 207 | 152 |
| 28 | 138 | 136 |
| 30 |  | 157 |
| 33 | 280 | 199 |
| 35 | 148 | 128 |
| 37 | 107 | 157 |
| 39 | 389 | 143 |
| 44 | 223 | 180 |
| 52 | 140 | 127 |
| 84 | 153 | 139 |
| 85 |  | 146 |
| 89 |  | 171 |
| 91 | 152 | 184 |
| 93 |  | 149 |
| 95 | 147 | 144 |
| 96 |  | 177 |
| 104 | 203 | 153 |
| 106 | 151 | 148 |
| 108 |  | 135 |
| 114 |  | 150 |
| 123 | 166 | 168 |
| 124 | 169 | 177 |
| 125 | 126 | 154 |
| 130 | 323 | 179 |
| 136 | 158 | 120 |
| 139 | 247 | 183 |
| 140 | 188 | 123 |
| 142 | 175 | 117 |
| 143 | 233 | 127 |
| 145 | 145 | 125 |
| 148 | 189 | 134 |
| 155 | 143 |  |
| 157 | 140 |  |
| 158 | 201 | 132 |
| 175 | 145 | 106 |
| 176 | 246 | 144 |
| 187 | 120 | 152 |

The tested derivatives of formula I therefore have a significant effect on the potentialization of the insulin secretion in response to glucose by the INS-1β pancreatic cells. The values are comprised between 132% and more than 300% of activation regardless of the relevant dose.

Test of Inhibition of Hepatic Production of Glucose

The hepatocytes are isolated from Wistar rat liver having fasted for 24 h after perfusion of collagenase in the portal vein. The freshly isolated hepatocytes are sown in 6-well plates coated with collagen and containing an adhesion medium (Williams Medium). After adhesion, the medium is replaced with RPMI 1640 medium without any glucose, containing hydrocortisone ($7.10^{-5}$M) for a duration from 16 to 18 h. The next day, the glucose hepatic production test is conducted in a Krebs medium for 3 h. The basal conditions are cells incubated with only Krebs, the stimulated conditions are the cells placed in Krebs+lactate+pyruvate, the produced conditions are the cells exposed to chemical compounds in a Krebs/lactate/pyruvate medium. In the case when the compounds are dissolved in DMSO, all the conditions of the tests are met in the presence of a final concentration of 0.1% DMSO. The positive control of the test is the mercaptopicolinate known for its inhibitory action on hepatic production of glucose via the phosphoenolpyruvate carboxykinase. For short term treatments, the compounds are incubated for 3 h. For long term treatments, the compounds are incubated for 20 h at the moment when the hepatocytes are cultivated in RPMI and then added during the hepatic production test for 3 h. At the end of the 3 hours of incubation, the supernatant is recovered for measurement of glucose with a colorimetric method using glucose oxidase. The cells are lysed with a 0.1% NaOH aqueous solution in order to measure the amount of protein with the Lowry method. The results are expressed in mmols of glucose per mg of protein. A compound inhibits hepatic production of glucose if this factor is less than or equal to 75% of the control for a given glucose dose.

3 h Incubation

| No. | HGP % of ctrl @ 100 μM | HGP % of ctrl @ 50 μM |
| --- | --- | --- |
| 2 | 62 | 83 |
| 3 | 74 | 82 |
| 4 | 75 | 77 |
| 5 | 50 | 68 |
| 6 | 55 | 72 |
| 7 | 70 | 84 |
| 10 | 39 | 64 |
| 12 | 53 | 70 |
| 13 | 69 | 84 |
| 14 | 73 | 91 |
| 16 | 63 | 69 |
| 17 | 73 | 76 |
| 23 | 73 | 79 |
| 26 | 71 | 86 |
| 38 | 70 | 74 |
| 43 | 73 | 82 |
| 44 | 69 | 83 |
| 45 | 73 | 82 |
| 46 | 55 | 74 |
| 48 | 73 | 91 |
| 49 | 38 | 57 |
| 50 | 75 | 97 |
| 51 | 54 | 90 |
| 52 | 44 | 61 |
| 54 | 74 | 85 |
| 56 | 70 | 94 |
| 57 | 51 | 77 |
| 58 | 25 | 51 |
| 59 | 35 | 67 |
| 60 | 53 | 74 |
| 61 | 66 | 78 |
| 63 | 28 | 56 |
| 65 | 66 | 93 |
| 69 | 60 | 86 |
| 80 | 67 | 83 |
| 81 | 54 | 106 |
| 82 | 26 | 67 |
| 86 | 72 | 77 |
| 87 | 73 | 77 |
| 98 | 74 | 88 |
| 108 | 26 | 88 |
| 109 | 27 | 69 |
| 110 | 33 | 72 |
| 115 | 75 | 66 |
| 116 | 67 | 62 |
| 121 | 66 | 80 |
| 123 | 63 | 101 |
| 127 | 23 | 54 |
| 143 | 72 | 89 |
| 144 | 52 | 74 |
| 148 | 49 | 80 |
| 153 | 38 | 95 |
| 154 | 63 | 81 |
| 155 | 54 | 65 |
| 156 | 7 | 21 |
| 157 | 74 | 97 |
| 158 |  | 59 |
| 159 |  | 40 |
| 166 | 65 | 71 |
| 167 | 23 | 20 |
| 174 | 77 | 73 |
| 175 | 20 | 51 |
| 176 | 36 | 76 |
| 178 | 72 | 92 |
| 179 | 69 | 91 |
| 184 | 80 | 68 |
| 185 | 28 | 54 |
| 186 | 60 | 69 |
| V | 63 | 81 |
| Y | 15 | 26 |
| Z | 19 | 67 |

The tested derivatives of formula I have a significant effect on the inhibition of hepatic production of glucose. The strongest inhibitions are obtained with the derivatives 49, 58, 63, 127, 156, 167, 175, 185 and Y with two doses and the derivatives 158 and 159 at the dose of 50 μM.

20 h Incubation

| No. | HGP % of ctrl @ 100 μM | HGP % of ctrl @ 50 μM |
| --- | --- | --- |
| 13 | 35 | 58 |
| 15 | 32 | 63 |
| 35 | 70 | 100 |
| 44 | 61 | 71 |
| 84 | 40 | 85 |
| 100 | 20 | 43 |
| 104 | 50 | 76 |
| 106 | 45 | 74 |
| 124 | 60 | 92 |
| 128 | 16 | 41 |
| 130 | 40 | 53 |
| 136 | 43 | 64 |
| 149 | 13 | 47 |

The tested derivatives of formula I have a significant effect on the inhibition of hepatic production of glucose. The strongest inhibitions are obtained with two doses with derivatives 13, 100, 128, 130 and 149.

Study of the Effect of the Compounds on the Insulin Secretion in Response to Glucose at Isolated Perfused Pancreases of N0STZ Diabetic Rats Equipment and Method:

The pancreas was taken on rats made to be diabetic by injection of Streptozotocin on the day of birth [14] and anesthetized with Pentobarbital (Nembutal©: 45 mg/kg; intraperitoneal route). These rats have a specific deficiency of the insulin response to glucose [15], as observed in humans with diabetes of type II. The isolation and the perfusion of the pancreas were achieved according to a modification [16] of the procedure described by Sussman et al. [17]. The effect of the compounds or reference substances is tested for 35 minutes (from t=20 min to t=55 min) in Krebs buffer in the absence (G0) or in the presence of glucose at 2.8 mM (G2.8 mM), and then 20 minutes (from t=55 min to t=75 min) in the presence of glucose 16.5 mM. The concentration of insulin secreted into the medium is measured by an Elisa assay (ELISA Alpco Cat no. 80-IN-SRTH-E10). The results are expressed as an average+/−SEM (Standard Error of the Mean) of several experiments.

Table of results:

| No. | Tested concentration (µM) | Insulin secretion peak at G16.5 mM | |
|---|---|---|---|
| | | Tested product (µU/min.) | Control group (µU/min.) |
| 10 | 10 | 2 028 ± 278 | 560 ± 71 |
| 10 | 1 | 1 052 ± 187 | 560 ± 71 |
| 13 | 10 | 1 489 | 560 ± 71 |
| 56 | 10 | 845 ± 133 | 454 ± 52 |
| 124 | 10 | 1 278 ± 66 | 454 ± 52 |
| 157 | 10 | 989 ± 86 | 560 ± 71 |

The tested derivatives of formula I have a significant effect on restoring insulin secretion in response to glucose at isolated perfused pancreases of N0STZ diabetic rats. The strongest secretions are obtained with the compounds 10, 13 and 124.

Study of the Antidiabetic Activity of Compound 10 in GK (Goto-Kakisaki) Rats

The antidiabetic activity of compound 10 was evaluated in GK rats, a non-obese model of diabetes of type II. This model was obtained by cross-breeding of Wistar rats selected on the basis of a slight intolerance to glucose [18]. These rats have the majority of dysfunctions observed in diabetes of type II in humans [19]: hyperglycemia, intolerance to glucose, insulin-resistance, and deteriorated insulin response to glucose. These animals were bred at Metabrain and were housed in an animal housing facility with a regulated temperature (22±2° C.) under constant humidity (50±20%) with a day/night cycle of 12 h (light from 7 h-19 h) and have access ad libitum to food and drink. The housing and experimentation conditions comply with the European directives relating to health and ethical treatment of laboratory animals (ETS123). In this study, the rats used are female 16-week old GK rats having fasted for 2 hours before beginning the study (postabsorptive condition). A glucose tolerance test is carried out via an intravenous route (IVGTT) on 2 groups of rats: One group treated with the compound 10 orally at the single dose of 20 mg/kg and a control group treated orally with the carrier. The tolerance test is carried out 1 h after oral administration of compound 10 on the animals anesthetized beforehand with pentobarbital (45 mg/kg via an intraperitoneal route). A blood sample was taken at T0 just before administration of the glucose load (0.5 g/kg via an intravenous route) and at x T5, T10, T15, T20 and T30 min after the glucose load. The blood samples are centrifuged in order to collect the plasma for determining glycemia. The results shown above are expressed as a percentage of the decrease of glycemia at T0 for the group treated with the compound 10, compared with the control group.

as a percentage of the decrease of AUC (area under the curve of glycemia versus time) for the group treated with the compound 10 as compared with the control group.

| Compound 10 | % of activity | Statistical significance (Student t test) |
|---|---|---|
| Glycemia at T0 | −11% | p = 0.0499 |
| AUC | −35% | P = 0.0326 |

These results show that the compound 10 administered as a single dose at 20 mg/kg is capable of reducing basal hyperglycemia and intolerance to glucose of a diabetic animal of type II.

BIBLIOGRAPHY

[1] WO 2008051197;
[2] Park et al., Bioorganic & Medicinal Chemistry (2006), 14(2), 395-408;
[3] Shengwu Jishu Tongxun (2007), 18(4), 625-627;
[4] US 20090163545;
[5] Floquet et al., Bioorganic & Medicinal Chemistry Letters (2007), 17(7), 1966-1970;
[6] Khimiko-Farmatsevticheskii Zhurnal (1987), 21(11), 1320-6;
[7] WO 2002095361;
[8] Pang et al., PLoS ONE (2010), 5(4), e10129;
[9] Tang et al., PLoS ONE (2007) 2(8), e761;
[10] US 20120114696
[11] Merino et al., Bioorganic & Medicinal Chemistry (2006), 14(2), 3583-3591;
[12] Pang et al., PLoS ONE (2009), 4(11), e7730;
[13] Asfari et al., Endocrinology 130: 167-178, 1992;
[14] Portha et al., Diabetes, 23, (1974), 889-895;
[15] Giroix et al., Diabetes, 32, (1983), 445-451;
[16] Assan et al., Nature, 239, (1972), 125-126;
[17] Sussman et al., Diabetes, 15, (1966), 466-472;
[18] Goto et al, Proc. Jpn. Acad. 51, 80-85, 1975;
[19] Portha et al., Mol. Cell. Endocrinol., 297: 73-85, 2009.

The invention claimed is:

1. A thiophene derivative of the following general formula I:

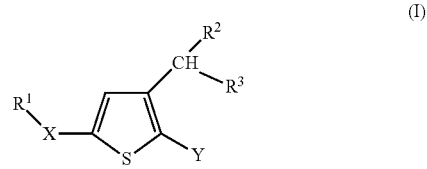

wherein:
Y represents an aryl group, or a heteroaryl group, wherein the aryl or heteroaryl group is optionally substituted with one or more groups selected from:
—CN;
a halogen atom;
—O($C_1$-$C_6$ alkyl), the alkyl group being optionally substituted with one or more halogen atoms or a —O($C_1$-$C_6$ alkyl) group;
a $C_1$-$C_6$ alkyl substituted with one or more halogen atoms, a —O($C_1$-$C_6$ alkyl) group or a —OH group;
—$SO_2$($C_1$-$C_6$ alkyl);

—CONRaRb, wherein Ra represents a hydrogen atom or a $C_1$-$C_6$ alkyl group and Rb represents a $C_1$-$C_6$ alkyl group;
and —OH;

X represents a —$SO_2$ group or a

group, wherein

represents a bond and W represents an oxygen atom or the —$NOR^4$ group, wherein $R^4$ represents a hydrogen atom, a $C_1$-$C_6$ alkyl group or a ($C_1$-$C_6$ alkyl)aryl group, wherein the aryl group is optionally substituted with one or more groups selected from:
—CN;
a halogen atom;
—O($C_1$-$C_6$ alkyl), the alkyl group being optionally substituted with one or more halogen atoms or a —O($C_1$-$C_6$ alkyl) group;
a $C_1$-$C_6$ alkyl substituted with one or more halogen atoms, a —O($C_1$-$C_6$ alkyl) group or a OH group;
—$SO_2$($C_1$-$C_6$ alkyl);
—CONRa'Rb', wherein Ra' represents a hydrogen atom or a $C_1$-$C_6$ alkyl group and Rb' represents a $C_1$-$C_6$ alkyl group;
and —OH or

is absent and W represents —OH;
$R^1$ represents
a $C_1$-$C_6$ alkyl group, the alkyl group being optionally substituted with a halogen atom;
a $C_3$-$C_6$ cycloalkyl group;
a ($C_1$-$C_6$ alkyl)O($C_1$-$C_6$ alkyl) group;
a ($C_1$-$C_6$ alkyl)NR($C_1$-$C_6$ alkyl) group, wherein R represents a hydrogen atom or a $C_1$-$C_6$ alkyl group;
an aryl group, the aryl group being optionally substituted with one or more groups selected from:
—CN;
a halogen atom;
—O($C_1$-$C_6$ alkyl), the alkyl group being optionally substituted with one or more halogen atoms or a —O($C_1$-$C_6$ alkyl) group,
—$SO_2$($C_1$-$C_6$ alkyl);
—CONRa"Rb", wherein Ra" represents a hydrogen atom or a $C_1$-$C_6$ alkyl group and Rb" represents a $C_1$-$C_6$ alkyl group;
and $C_1$-$C_6$ alkyl, the alkyl group being optionally substituted with one or more halogen atoms, a —O($C_1$-$C_6$ alkyl) group or an —OH group;
a ($C_1$-$C_6$ alkyl)aryl group, the aryl group being optionally substituted with one or more groups selected from: —CN; a halogen atom; —O($C_1$-$C_6$ alkyl); and $C_1$-$C_6$ alkyl;

an —NH-aryl group, the aryl group being optionally substituted with one or more groups selected from: —CN; a halogen atom; —O($C_1$-$C_6$ alkyl) and $C_1$-$C_6$ alkyl;
an —NH($C_1$-$C_6$ alkyl)aryl group, the aryl group being optionally substituted with one or more groups selected from: —CN; a halogen atom; —O($C_1$-$C_6$ alkyl); and $C_1$-$C_6$ alkyl;
a heteroaryl group, optionally substituted with a halogen atom;
an —OH group;
a morpholine group;
an N-phenylpiperazine group;
an NH—NH—CO-aryl group, wherein the aryl group is optionally substituted with one or more groups selected from a halogen atom, and a —O($C_1$-$C_6$ alkyl) group, or
an NH—NH—CO-heteroaryl group,
$R^2$ represents a hydrogen atom, a $C_1$-$C_6$ alkyl group, a ($C_1$-$C_6$ alkyl)aryl group or a ($C_1$-$C_6$ alkyl)O($C_1$-$C_6$ alkyl) group,
$R^3$ represents
a —$COOR^5$ group, wherein $R^5$ represents a hydrogen atom, a $C_1$-$C_6$ alkyl group or glucopyranose group;
a —$COSR^6$ group, wherein $R^6$ represents a hydrogen atom or a $C_1$-$C_6$ alkyl group;
a —$CONR^7R^8$ group, wherein $R^7$ represents a hydrogen atom or a $C_1$-$C_6$ alkyl group and $R^8$ represents a hydrogen atom, a $C_1$-$C_6$ alkyl group optionally substituted with an —OH group, an —OH group, an —O($C_1$-$C_6$ alkyl) group, an —$NH_2$ group, a —($C_1$-$C_6$ alkyl)$NR^9R^{10}$ group, wherein $R^9$ and $R^{10}$ both represent a $C_1$-$C_6$ alkyl group, a —($C_1$-$C_6$ alkyl)COOH group, a —($C_1$-$C_6$ alkyl)COO($C_1$-$C_6$ alkyl) group, an aryl group or a heteroaryl group;
a —$CSNR^{11}R^{12}$ group, wherein $R^1$ and $R^{12}$ represent independently of each other a hydrogen atom or a $C_1$-$C_6$ alkyl group;
a —CN group;
a —C(=NH)NHOH group;
a —COmorpholine group;
a —COpyrolidine group;
a —CON-Me-piperazine group;
a —COguanidine or —COguanidine-BOC group;
a tetrazole group; or
a oxadiazolone group;
or an enantiomer, a diastereoisomer, hydrate, solvate, tautomer, racemic mixture or pharmaceutically acceptable salt thereof,
except for the compounds (a) to (z1) of the following formulae:

(a)

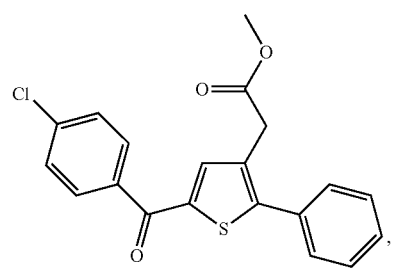

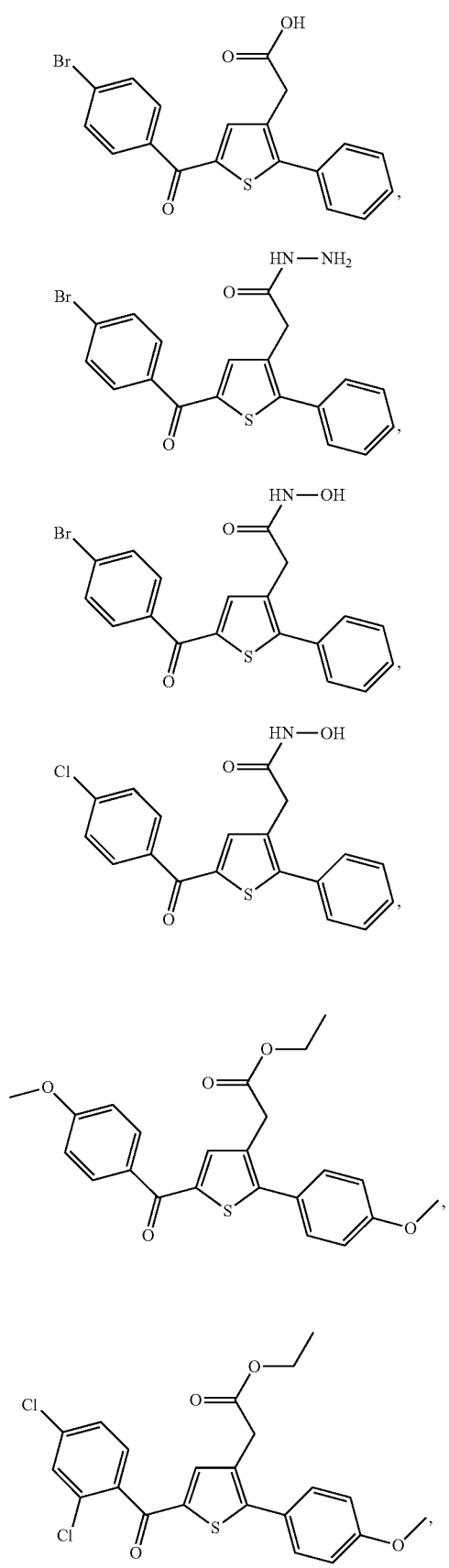
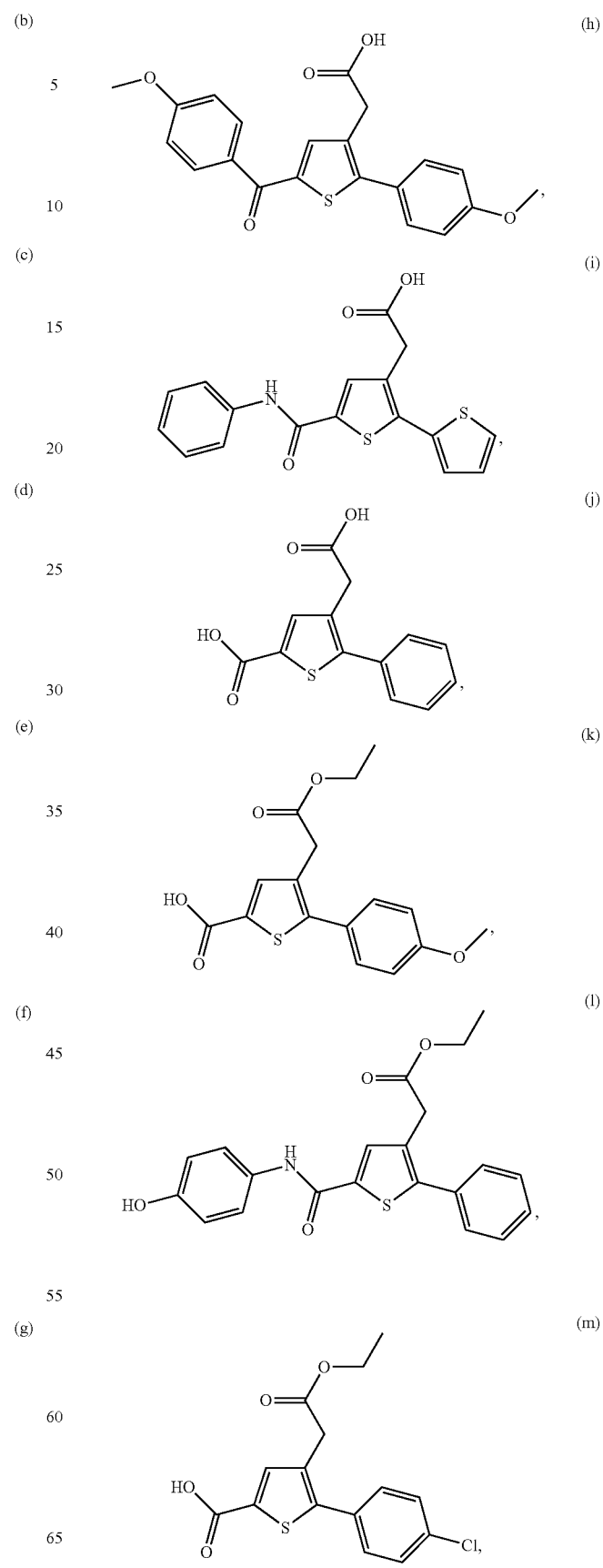

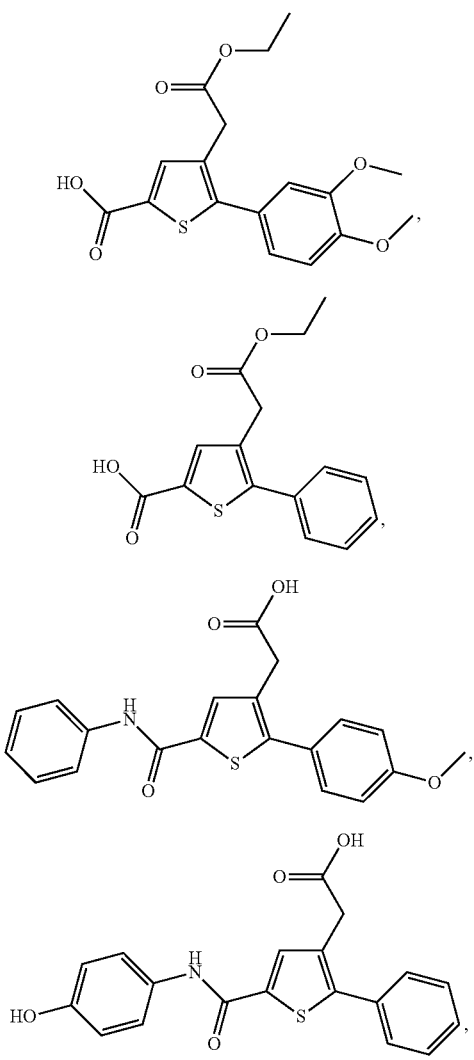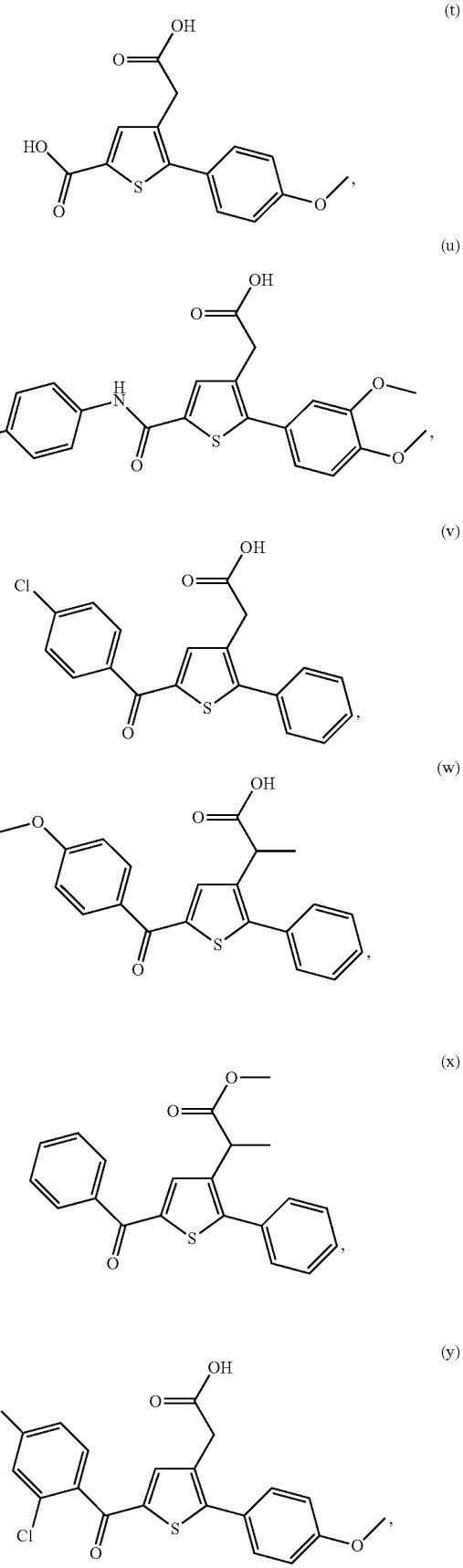

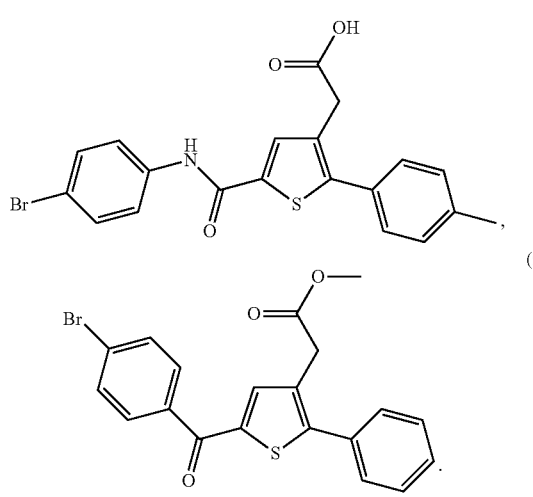

2. The thiophene derivative according to claim 1, wherein X represents

and

represents a bond and W represents an oxygen atom or the —NOR⁴ group, wherein R⁴ represents a hydrogen atom or a $C_1$-$C_6$ alkyl group.

3. The thiophene derivative according to claim 1, wherein $R^3$ represents
a —COguanidine group;
a —COOR⁵ group, wherein R⁵ represents a hydrogen atom or a $C_1$-$C_6$ alkyl group;
a —CONR⁷R⁸ group, wherein R⁷ represents a hydrogen atom and R⁸ represents a hydrogen atom;
a $C_1$-$C_6$ alkyl group optionally substituted with an —OH group; an —OH group; an —O($C_1$-$C_6$ alkyl) group or a —($C_1$-$C_6$ alkyl)NR⁹R¹⁰ group wherein R⁹ and R¹⁰ both represent a $C_1$-$C_6$ alkyl group; or
a —COmorpholine group.

4. The thiophene derivative according to claim 1, wherein Y represents an aryl group, the aryl group being optionally substituted, with one or more groups selected from —CN; a halogen atom; and —O($C_1$-$C_6$ alkyl).

5. The thiophene derivative according to claim 4, wherein Y represents a phenyl group, the phenyl group being substituted with one or more halogen atoms.

6. The thiophene derivative according to claim 1, wherein $R^1$ represents
a $C_3$-$C_6$ cycloalkyl group;
an aryl group, the aryl group being optionally substituted with one or more groups selected from —CN; a halogen atom; —O($C_1$-$C_6$ alkyl); and $C_1$-$C_6$ alkyl,
a heteroaryl group optionally substituted with a halogen atom; or
a morpholine group.

7. The thiophene derivative according to claim 6, wherein $R^1$ represents
a phenyl group, the phenyl group being optionally substituted with one or more —O($C_1$-$C_6$ alkyl) groups, or
a furanyl, pyridyl or thiazolyl group, the furanyl group being optionally substituted with a halogen atom.

8. The thiophene derivative according to claim 1, which is selected from the following compounds:
2-(2-(4-chlorophenyl)-5-((ethoxyimino)(4-methoxyphenyl)methyl) thiophen-3-yl) acetic acid (108);
2-(2-(4-chlorophenyl)-5-((hydroxyimino)(4-methoxyphenyl)methyl) thiophen-3-yl) acetic acid (109);
2-(2-(4-chlorophenyl)-5-((methoxyimino)(4-methoxyphenyl)methyl) thiophen-3-yl) acetic acid (110);
ethyl 2-(2-(4-chlorophenyl)-5-((ethoxyimino)(4-methoxyphenyl)methyl) thiophen-3-yl) acetate (102);
ethyl 2-(2-(4-chlorophenyl)-5-((hydroxyimino)(4-methoxyphenyl)methyl)-thiophen-3-yl)acetate (104);
ethyl 2-(2-(4-chlorophenyl)-5-((methoxyimino)(4-methoxyphenyl)methyl) thiophen-3-yl)acetate (106);
2-(2-(2,3-difluorophenyl)-5-(4-methoxybenzoyl)thiophen-3-yl) acetic acid (137);
2-(2-(2,3-difluorophenyl)-5-(furan-2-carbonyl)thiophen-3-yl) acetic acid (136);
2-(2-(3,4-dichlorophenyl)-5-(4-methoxybenzoyl)thiophen-3-yl) acetic acid (81);
2-(2-(3-cyanophenyl)-5-(furan-2-carbonyl)thiophen-3-yl)-N-(2-(dimethyl amino)ethyl)acetamide (142);
2-(2-(4-chloro-2-fluorophenyl)-5-(furan-2-carbonyl)thiophen-3-yl) acetic acid (144);
2-(2-(4-chlorophenyl)-5-(3-methoxybenzoyl)thiophen-3-yl) acetic acid (59);
2-(2-(4-chlorophenyl)-5-(4-methoxybenzoyl)thiophen-3-yl)-3-methoxy-propanoic acid (128);
2-(2-(4-chlorophenyl)-5-(4-methoxybenzoyl)thiophen-3-yl)acetamide (86);
2-(2-(4-chlorophenyl)-5-(4-methoxybenzoyl)thiophen-3-yl) acetic acid (60);
2-(2-(4-chlorophenyl)-5-(4-methoxybenzoyl)thiophen-3-yl)-N-(2-(dimethyl amino)ethyl)acetamide (89);
2-(2-(4-chlorophenyl)-5-(4-methoxybenzoyl)thiophen-3-yl)-N-(2-hydroxy ethyl)acetamide (96);
2-(2-(4-chlorophenyl)-5-(4-methoxybenzoyl)thiophen-3-yl)-N-hydroxy acetamide (100);
2-(2-(4-chlorophenyl)-5-(4-methoxybenzoyl)thiophen-3-yl) propanoic acid (127);
2-(2-(4-chlorophenyl)-5-(cyclohexanecarbonyl)thiophen-3-yl)acetic acid (61);
2-(2-(4-chlorophenyl)-5-(furan-2-carbonyl)thiophen-3-yl)-1-morpholino ethanone (91);
2-(2-(4-chlorophenyl)-5-(furan-2-carbonyl)thiophen-3-yl) acetic acid (56)
2-(2-(4-chlorophenyl)-5-(furan-2-carbonyl)thiophen-3-yl)-N-(2-(dimethyl amino)ethyl)acetamide (95);
2-(2-(4-chlorophenyl)-5-(furan-2-carbonyl)thiophen-3-yl)-N-ethoxy acetamide (98);
2-(2-(4-chlorophenyl)-5-picolinoylthiophen-3-yl) acetic acid (149);
2-(5-(2,3-difluorobenzoyl)-2-(4-methoxyphenyl)thiophen-3-yl) acetic acid (64);
2-(5-(2,4-difluorobenzoyl)-2-(4-methoxyphenyl)thiophen-3-yl) acetic acid (65);
2-(5-(2-fluorobenzoyl)-2-(4-methoxyphenyl)thiophen-3-yl) acetic acid (67);
2-(5-(3,5-difluorobenzoyl)-2-(4-methoxyphenyl)thiophen-3-yl) acetic acid (70);

2-(5-(3-chlorobenzoyl)-2-(4-methoxyphenyl)thiophen-3-yl) acetic acid (71);
2-(5-(3-chlorobenzoyl)-2-(4-chlorophenyl)thiophen-3-yl) acetic acid (58);
2-(5-(3-fluoro-4-methoxybenzoyl)-2-(4-methoxyphenyl) thiophen-3-yl) acetic acid (73);
2-(5-(3-fluorobenzoyl)-2-(4-methoxyphenyl)thiophen-3-yl) acetic acid (72);
2-(5-(3-methoxybenzoyl)-2-(4-methoxyphenyl)thiophen-3-yl) acetic acid (75);
2-(5-(4-cyanobenzoyl)-2-(4-methoxyphenyl)thiophen-3-yl) acetic acid (76);
2-(5-(4-fluoro-3-methylbenzoyl)-2-(4-methoxyphenyl) thiophen-3-yl) acetic acid (74);
2-(5-(4-fluorobenzoyl)-2-(4-methoxyphenyl)thiophen-3-yl) acetic acid (77);
2-(5-(4-methoxybenzoyl)-2-phenylthiophen-3-yl) acetic acid (51);
2-(5-(cyclohexanecarbonyl)-2-phenylthiophen-3-yl) acetic acid (52);
2-(5-(furan-2-carbonyl)-2-(4-methoxyphenyl)thiophen-3-yl) acetic acid (68);
2-(5-(furan-2-carbonyl)-2-phenylthiophen-3-yl) acetic acid (48);
2-(5-benzoyl-2-(4-chlorophenyl)thiophen-3-yl) acetic acid (63);
2-(5-benzoyl-2-(4-methoxyphenyl)thiophen-3-yl) acetic acid (78);
ethyl 2-(2-(2,3-difluorophenyl)-5-(4-methoxybenzoyl) thiophen-3-yl)acetate (133);
ethyl 2-(2-(2,3-difluorophenyl)-5-(furan-2-carbonyl)thiophen-3-yl)acetate (130);
ethyl 2-(2-(4-chlorophenyl)-5-(3-methoxybenzoyl)thiophen-3-yl)acetate (12);
ethyl 2-(2-(4-chlorophenyl)-5-(4-methoxybenzoyl)thiophen-3-yl)-3-methoxy-propanoate (124);
ethyl 2-(2-(4-chlorophenyl)-5-(4-methoxybenzoyl)thiophen-3-yl)acetate (13);
ethyl 2-(2-(4-chlorophenyl)-5-(4-methoxybenzoyl)thiophen-3-yl) propanoate (123);
ethyl 2-(2-(4-chlorophenyl)-5-(cyclohexanecarbonyl) thiophen-3-yl)acetate (14);
ethyl 2-(2-(4-chlorophenyl)-5-(furan-2-carbonyl)thiophen-3-yl)acetate (10);
ethyl 2-(2-(4-chlorophenyl)-5-(morpholine-4-carbonyl) thiophen-3-yl)acetate (114);
ethyl 2-(2-(4-cyanophenyl)-5-(furan-2-carbonyl)thiophen-3-yl)acetate (139);
ethyl 2-(2-(4-methoxyphenyl)-5-(thiazole-4-carbonyl) thiophen-3-yl)acetate (33);
ethyl 2-(5-(2,3-difluorobenzoyl)-2-(4-methoxyphenyl) thiophen-3-yl)acetate (18);
ethyl 2-(5-(2,4-difluorobenzoyl)-2-(4-methoxyphenyl) thiophen-3-yl)acetate (19);
ethyl 2-(5-(2-fluorobenzoyl)-2-(4-methoxyphenyl)thiophen-3-yl)acetate (21);
ethyl 2-(5-(3,5-difluorobenzoyl)-2-(4-methoxyphenyl) thiophen-3-yl)acetate (24);
ethyl 2-(5-(3-chlorobenzoyl)-2-(4-chlorophenyl)thiophen-3-yl)acetate (11);
ethyl 2-(5-(3-chlorobenzoyl)-2-(4-methoxyphenyl)thiophen-3-yl)acetate (25);
ethyl 2-(5-(3-fluoro-4-methoxybenzoyl)-2-(4-methoxyphenyl)thiophen-3-yl) acetate (27);
ethyl 2-(5-(3-fluorobenzoyl)-2-(4-methoxyphenyl)thiophen-3-yl)acetate (26);
ethyl 2-(5-(3-methoxybenzoyl)-2-(4-methoxyphenyl) thiophen-3-yl)acetate (30);
ethyl 2-(5-(4-cyanobenzoyl)-2-(4-methoxyphenyl)thiophen-3-yl)acetate (31);
ethyl 2-(5-(4-fluoro-3-methylbenzoyl)-2-(4-methoxyphenyl)thiophen-3-yl) acetate (29);
ethyl 2-(5-(4-fluorobenzoyl)-2-(4-methoxyphenyl)thiophen-3-yl)acetate (32);
ethyl 2-(5-(furan-2-carbonyl)-2-(4-methoxyphenyl)thiophen-3-yl)acetate (22);
ethyl 2-(5-benzoyl-2-(4-chlorophenyl)thiophen-3-yl)acetate (15);
ethyl 2-(5-benzoyl-2-(4-methoxyphenyl)thiophen-3-yl) acetate (35);
isopropyl 2-(2-(3,4-dichlorophenyl)-5-(4-methoxybenzoyl)thiophen-3-yl) acetate (40);
isopropyl 2-(2-(3,4-dichlorophenyl)-5-(furan-2-carbonyl) thiophen-3-yl) acetate (39);
isopropyl 2-(2-(4-chloro-2-fluorophenyl)-5-(furan-2-carbonyl)thiophen-3-yl)acetate (143);
isopropyl 2-(2-(4-chlorophenyl)-5-(4-methoxybenzoyl) thiophen-3-yl)-3-methoxypropanoate (125);
methyl 2-(2-(4-chlorophenyl)-5-picolinoylthiophen-3-yl) acetate (148);
methyl 2-(5-(4-methoxybenzoyl)-2-phenylthiophen-3-yl) acetate (5);
methyl 2-(5-(cyclohexanecarbonyl)-2-phenylthiophen-3-yl)acetate (6);
methyl 2-(5-(furan-2-carbonyl)-2-phenylthiophen-3-yl) acetate (3);
isopropyl 2-(2-(4-chlorophenyl)-5-(4-methoxybenzoyl) thiophen-3-yl) acetate (43);
isopropyl 2-(2-(4-chlorophenyl)-5-(furan-2-carbonyl) thiophen-3-yl)acetate (44);
tert-butyl 2-(2-(4-chlorophenyl)-5-(4-methoxybenzoyl) thiophen-3-yl) acetate (84);
tert-butyl 2-(2-(4-chlorophenyl)-5-(furan-2-carbonyl) thiophen-3-yl)acetate (83);
N—(N-(tert-butoxycarbonyl)carbamimidoyl)-2-(2-(4-chlorophenyl)-5-(4-methoxybenzoyl)thiophen-3-yl)acetamide (46);
2-(5-(3-chlorobenzoyl)-2-phenylthiophen-3-yl)acetic acid (49);
2-(5-(3-methoxybenzoyl)-2-phenylthiophen-3-yl) acetic acid (50);
2-(2-(4-chlorophenyl)-5-(4-methoxybenzoyl)thiophen-3-yl)-1-(4-methyl piperazin-1-yl)ethanone (93);
2-(2-(4-cyanophenyl)-5-(furan-2-carbonyl)thiophen-3-yl) acetic acid (140);
2-[5-benzoyl-2-(4-chlorophenyl)-3-thienyl] acetic acid (154);
ethyl 2-[5-(4-chloro-2-methoxy-benzoyl)-2-(4-chlorophenyl)-3-thienyl] acetate (155);
2-[5-(4-chloro-2-methoxy-benzoyl)-2-(4-chlorophenyl)-3-thienyl] acetic acid (156);
ethyl 2-[2-(3,4-dichlorophenyl)-5-(4-methoxybenzoyl)-3-thienyl]acetate (157);
ethyl 2-[2-(3,4-dichlorophenyl)-5-(furan-2-carbonyl)-3-thienyl]acetate (158);
2-[2-(3,4-dichlorophenyl)-5-(furan-2-carbonyl)-3-thienyl] acetic acid (159);
2-[2-(3,4-dichlorophenyl)-5-(4-methoxybenzoyl)-3-thienyl]-N-(2-hydroxyethyl)acetamide (165);
2-[2-(3,4-dichlorophenyl)-5-(4-methoxybenzoyl)-3-thienyl]-N-(2-dimethylaminoethyl)acetamide (166);
2-[2-(4-chlorophenyl)-5-[C-(3,4-dichlorophenyl)-N-ethoxy-carbonimidoyl]-3-thienyl] acetic acid (167);

2-[2-(3,4-dichlorophenyl)-5-(4-methoxyphenyl)sulfonyl-3-thienyl]acetic acid (175);

ethyl 2-[5-(5-chlorofuran-2-carbonyl)-2-(4-chlorophenyl)-3-thienyl]acetate (176).

9. A pharmaceutical composition comprising a derivative according to claim 1 and a pharmaceutically acceptable excipient.

10. The pharmaceutical composition according to claim 9, further comprising another antidiabetic agent.

11. A method for treating diabetes and/or hyperglycemia, for reducing hyperglycemia, for delaying the occurrence of diabetes, for inhibiting hepatic glucose production, for restoring insulin secretion in response to glucose, and/or for treating complications of diabetes and/or pathologies associated with diabetes selected from functional and quantitative abnormalities of endocrine pancreatic cells, insulin resistance, inflammation, obesity, hypertension, myocardial infarction, cardiovascular strokes, diabetic neuropathy, diabetic nephropathy, diabetic retinopathy, neurological problems and wound healing problems, comprising the administration of an effective amount of a derivative according to claim 1 or selected from compounds of formulae (a) to (z1), as defined in claim 1 to a patient in need thereof.

12. The method according to claim 11, wherein diabetes is diabetes of type II.

13. The method according to claim 11, wherein the method is for treating hyperglycemia.

14. The derivative according to claim 1, wherein X represents

15. The derivative according to claim 1, wherein W represents an oxygen atom.

16. The derivative according to claim 4, wherein the aryl group is a phenyl group.

17. The derivative according to claim 4, wherein the $O(C_1\text{-}C_6$ alkyl) group is —OMe.

18. The derivative according to claim 5, wherein the halogen atom is Cl.

19. The derivative according to claim 7, wherein the $O(C_1\text{-}C_6$ alkyl) group is —OMe.

20. The pharmaceutical composition according to claim 10, wherein the other antidiabetic agent is metformin.

* * * * *